US008067219B2

(12) United States Patent
Hayden et al.

(10) Patent No.: US 8,067,219 B2
(45) Date of Patent: *Nov. 29, 2011

(54) POLYNUCLEOTIDE ENCODING AN ATP BINDING CASSETTE TRANSPORTER 1 (ABC1) POLYPEPTIDE

(75) Inventors: Michael R. Hayden, Vancouver (CA); Angela R. Brooks-Wilson, Richmond (CA); Simon N. Pimstone, Vancouver (CA)

(73) Assignees: Xenon Pharmaceuticals Inc., Burnaby, B.C. (CA); University of British Columbia, Vancouver, B.C. (CA)

(*) Notice: Subject to any disclaimer, the term of this patent is extended or adjusted under 35 U.S.C. 154(b) by 0 days.

This patent is subject to a terminal disclaimer.

(21) Appl. No.: 12/807,775

(22) Filed: Sep. 14, 2010

(65) Prior Publication Data
US 2011/0065147 A1  Mar. 17, 2011

Related U.S. Application Data

(60) Continuation of application No. 10/452,510, filed on Jun. 2, 2003, now abandoned, which is a division of application No. 09/526,193, filed on Mar. 15, 2000, now Pat. No. 6,617,122.

(60) Provisional application No. 60/124,702, filed on Mar. 15, 1999, provisional application No. 60/138,048, filed on Jun. 8, 1999, provisional application No. 60/139,600, filed on Jun. 17, 1999, provisional application No. 60/151,977, filed on Sep. 1, 1999.

(51) Int. Cl.
| C12N 9/16 | (2006.01) |
| C12N 15/00 | (2006.01) |
| C12N 5/02 | (2006.01) |
| C12N 1/20 | (2006.01) |
| C12N 1/00 | (2006.01) |
| C07H 21/04 | (2006.01) |

(52) U.S. Cl. .................... 435/196; 435/320.1; 435/325; 435/252.3; 435/254.11; 536/23.2; 536/23.5; 536/24.3; 536/24.31

(58) Field of Classification Search .................. None
See application file for complete search history.

(56) References Cited

U.S. PATENT DOCUMENTS

| 5,260,275 A | 11/1993 | Cooper et al. |
| 5,744,310 A | 4/1998 | Reed |
| 5,859,037 A | 1/1999 | Whitcomb |
| 5,972,973 A | 10/1999 | Whitcomb |
| 6,030,806 A | 2/2000 | Landes et al. |
| 6,100,053 A | 8/2000 | Bech et al. |
| 6,555,323 B2 | 4/2003 | Bamberger et al. |
| 6,617,122 B1 * | 9/2003 | Hayden et al. ............ 435/19 |
| 6,713,300 B1 | 3/2004 | Allikmets et al. |
| 6,821,774 B1 | 11/2004 | Lawn et al. |
| 7,166,584 B1 | 1/2007 | Attie et al. |
| 7,785,886 B2 * | 8/2010 | Hayden et al. ............ 435/455 |

FOREIGN PATENT DOCUMENTS

| WO | WO 97/17359 | 5/1997 |
| WO | WO 98/03548 | 1/1998 |
| WO | WO 98/24818 | 6/1998 |
| WO | WO 98/37764 | 9/1998 |
| WO | WO 98/51351 | 9/1998 |
| WO | WO 98/48784 | 11/1998 |
| WO | WO 99/31133 | 6/1999 |
| WO | WO 00/18912 | 4/2000 |
| WO | WO 00/24390 | 5/2000 |
| WO | WO 00/34461 | 6/2000 |
| WO | WO 00/71710 | 11/2000 |
| WO | WO 00/78970 | 12/2000 |
| WO | WO 00/78971 | 12/2000 |
| WO | WO 00/78972 | 12/2000 |
| WO | WO 01/32184 | 5/2001 |
| WO | WO 01/41704 | 6/2001 |
| WO | WO 01/66098 | 9/2001 |
| WO | WO 01/83746 | 11/2001 |

OTHER PUBLICATIONS

Voet et al., "Biochemistry", 2nd Ed., John Wiley and Sons, Inc., New York, 1995, p. 1053.*
Costet et al., J. Biol. Chem. 275:28240-28245, 2000.*
Wang et al., J. Biol. Chem. 275:33053-33058, 2000.*
Juengst, BMJ 326:1410, 2003.*
GenBank Accession No. NM_005502, GI:21536375; Jun. 2002, 8 pages.*
Allikmets et al., "Organization of the ABCR Gene: Analysis of Promoter and Splice Junction Sequences." Gene. vol. 215, pp. 111-122 (1998).
Allikmets et al., "Characterization of the Human ABC Superfamily: Isolation and Mapping of 21 New Genes Using the Expressed Sequence Tags Database." Human Mol. Genet., 5:1649-1655 (1996).
Arakawa et al Arterioscler. Thromb. Vasc. Biol. 25:1193-1197 (2005).
Becq et al., "ABC1, an ATP Binding Cassette Transporter Required for Phagocytosis of Apoptotic Cells, Generates a Regulated Anion Flux after Expression in *Xenopus laevis* Ooocytes." J. Biol. Chem. 272(5):2695-2699 (1997).
Bellosta et al., "Direct Vascular Effects of HMG-CoA Reductase Inhibitors." Atherosclerosis 137:S101-109 (1998) (Abstract).
Blom et al., Nucleic Acids Res., 26,384-386 (1998). Bodzioch et al., "The Gene Encoding ATP-Binding Cassette Transporter-1 is Mutated in Tangier Disease." Nat. Genet. 22:347-351 (1999).
Borst. P. "Multidrug Resistant Proteins," Semin. Cancer. Biol. 8:131-134 (1997).
Brinton et al., Phalan. Res., vol, 15(3). pp. 386-398 (1998).
Broach et al., Nature 384 (Supp.): 14-16 (1996).
Brooks-Wilson et al.. "Mutations in ABC1 in Tangier Disease and Familial High-Density Lipoprotein Deficiency," Nat. Genet. 22:336-345 (1999).
Brown, "Hybridization Analysis of DNA Blots" in Curr. Protocols in Mol. Biol., John Wiley & Sons, Inc. (2003).
Burbaum et al., Curr. Opin. Chem. Biol. 1:72-78 (1997).
Dean et al., "Evolution of ATP-Binding Cassette Transporter Genes." Curr. Opin. Gen. Dev. 5:779-785 (1995).
Drobnik et al., "Activation of Phosphatidylinositol-Specific Phospholipase C in Response to HDI. Sub 3 and LDL is Markedly Reduced in Cultured Fibroblasts from Tangier Patients," Arterioscler. Thromb. Vasc. Biol. 15 1369-1377 (1995).

(Continued)

Primary Examiner — David J Steadman
(74) Attorney, Agent, or Firm — Elliot M. Olstein; Alan J. Grant

(57) ABSTRACT

The invention features ABC1 nucleic acids and polypeptides for the diagnosis and treatment of abnormal cholesterol regulation. The invention also features methods for identifying compounds for modulating cholesterol levels in an animal (e.g., a human).

9 Claims, 76 Drawing Sheets

OTHER PUBLICATIONS

Fischer et al., FASEB Journal, vol. 10. pp. 126-136 (1996).
Fitzgerald et al., J. Biol. Chem., vol. 279, pp. 18477-48485 (2004).
Frikke-Schmidt et al., JAMA, vol. 299(21), pp. 2524-2532 (2008).
Guo et al., PNAS, vol. 101, pp. 9205-9210 (2004).
Hahmann et al., Am. J. Cardiol. 67:957-961 (1991).
Hamon et al., "Interleukin-1β Secretion is Impaired by Inhibitors of the ATP Binding Cassette Transporter, ABC1." Blood 90(8):2911-2915 (1997).
Hansen et al., "Familial Defective Apolipoprotein B-100." Danish Medical Bulletin 45:370-382 (1998) (Abstract).
Hull et al., Curr. Opin. Biotech., vol. 14. pp. 395-400 (2003).
Kamei et al. Psychopharmacology 113:318-321 (1994).
Kim-Schultze et al., "Estrogen Stimulates Delayed Mitogen-activated Protein Kinase Activity in Human Endothelial Cells Via an Autocrine Loop That Involves Basic Fibroblast Growth Factor." Circulation 98(5):413-421 (1998) (Abstract).
Kronqvist et al. Eur. J. Biochem., 262:939-946 (1999).
Kuivenhoven et al., "Heterogeneity at the CETP Gene Locus: Influence on Plasma CETP Concentrations and HDL Cholesterol Levels," Arterioscler. Thromb. Vasc. Biol. 17:560-568 (1997).
Lange et al., J. Biol. Chem.. 264:3786-3793 (1989).
Langmann et al., "Molecular Cloning of the Human ATP-Binding Cassette Transporter 1 (hABC1): Evidence for Sterol-Dependent Regulation in Macrophages," Biochem. Biophys. Res. Comm. 257:29-33 (1999).
Lawn et al., "The Tangier Disease Gene Product ABC1 Controls the Cellular Apolipoprotein-mediated Lipid Removal Pathway," J Cin. Invest. 104:R25-R31 (1999).
Lehmann et al., J. Biol. Chem. vol. 272:3137-3140 (1997).
Luciani et al., "Cloning of Two Novel ABC Transporters Mapping on Human Chromosome 9," Genomics 21:150-159 (1994).
Luciani et al., The ATP Binding Cassette Transporter ABC1 is Required for the Engulfment of Corpses Generated by Apoptotic Cell Death, EMBO Journal 15(2):2053-2059 (1994).
Mack et al., Am. J. Public Health. 81:1180-1184 (1991).
Marcil et al., "Cellular Cholesterol Transport and Efflux in Fibroblasts are Abnormal in Subjects with Familial HDL Deficiency." Arterioscler. Thromb. Vasc. Biol. 19:159-169 (1999).
McElreavy et al., PNAS, vol. 89, pp. 11016-11020 (1992).
Mendez, J. Biol. Chem. 270:5891-5900 (1995).
Neve et al., Trends in Neuroscience, vol. 21. pp. 15-19 (1998).
Nieland et al. J. Lipid Res. 45:1256-1265 (2004).
Nofer et al. Cell Mol Life Sci 62:2150-2160, 2005.
Olivier et al., Atherosclerosis 70:107-114 (1988).
Orso et al. Nature Genetics 24:192-96 (2000).
Pullinger et al. Biochem. Biophys. Res. Comm., vol. 271, pp. 451-455 (2000).
Remaley et al., "Human ATP-Binding Cassette Transporter 1 (ABC1): Genomic Organization and Identification of the Genetic Defect in the Original Tangier Disease Kindred," Proc. Nat. Acad. Sci. (USA) 96:12685-12690 (1999).
Rogler et al., "HDL-Mediated Efflux of Intracellular Cholesterol is Impaired in Fibroblasts from Tangier Disease Patients." Arterioscler. Thromb. Vasc. Biol. 15:683-690 (1995).
Rust et al., "Assignment of Tangier Disease to Chromosome 9q31 by a Graphical Linkage Exclusion Strategy." Nature Genetics 20:96-98 (1998).
Rust et al., "Tangier Disease is Caused by Mutations in the Gene Encoding ATP-Binding Cassette Transporter 1," Nature Genetics 22:352-355 (1999).
Santamariana-Fojo et al., PNAS, vol. 97, pp. 7987-7992 (2000).
Savary et al., "Isolation and Chromosomal Mapping of a Novel ATP-Binding Cassette Transporter Conserved in Mouse and Human," Genomics 41:275-278 (1997).
Schmitz et al., "ATP-Binding Cassette Transporter A1 (ABCA1) in Macrophages: A Duel Function in Inflammation and Lipid Metabolism?" Pathobiology 67:236-240 (1999).
Schrayer et al., "Hypercatabolism of Lipoprotein-free Apolipoprotein A-1 in HDL-Deficient Mutant Chickens." Arteriosclerosis and Thrombosis 14:2053-2059 (1994).
Schwartz et al., Biochem. Biophys. Res. Comm., vol. 272: 794=802 (2000).
Smud et al., Curr. Med. Res. Opin. 10:612-624 (1987).
Staels et al., Circulation, 98:2088-2093 (1998).
Steiner et al., Diabetologia 39:1655-1661 (1996).
Toti et al., Biochem. Biophys. Res. Comm., vol. 241, pp. 548-552 (1997).
Urban et al. EMBO Journal, 18:512-521 (1999).
Wang et al., J. Lipid Res., vol. 48, pp. 1062-1068 (2007).
Williams et al., Biochemistry, vol. 37, pp. 7096-7102 (1998).
Wilson et al., "2.2 Mb of Contiguous Nucleotide Sequence from Chromosome III of C. clegans." Nature 368:32-38 (1994).
Witkowski et al., Biochemistry, vol. 38, pp. 11643-11650 (1999(.
Chimini et al., GenBank Accession No. X75926 (Mar. 19, 1998).
Langman et al., GenBank Accession No. CAA10005 (Apr. 12, 1999).
Langmann et al., GenBank Accession No. AJ012376 (Jan. 7, 1999).
Luciani et al., GenBank Accession No. P41233 (Oct. 1, 2000).
Luciani et al., GenBank Accesion No. NM_005502 (Aug. 3, 2000).
Luciani et al., GenBank Accesion No. A54774 (Mar. 17, 1999).
Rust et al., GenBank Accession No. AF165281 (Aug. 17, 1999).
Wilson et al., GenBank Accession No. AAC69223 (Mar. 5, 1999).
GenBank Accession No. O95477, Mar. 2010, 37 pages.
GenBank Accession No. NP_989476, ATP-binding cassette, subfamily A (ABC1), member 1 [Gallus gallus], Jun. 2007.
GenBank Accession No. P41233, G1:51338775. Sep. 2005. 10 pages.

* cited by examiner

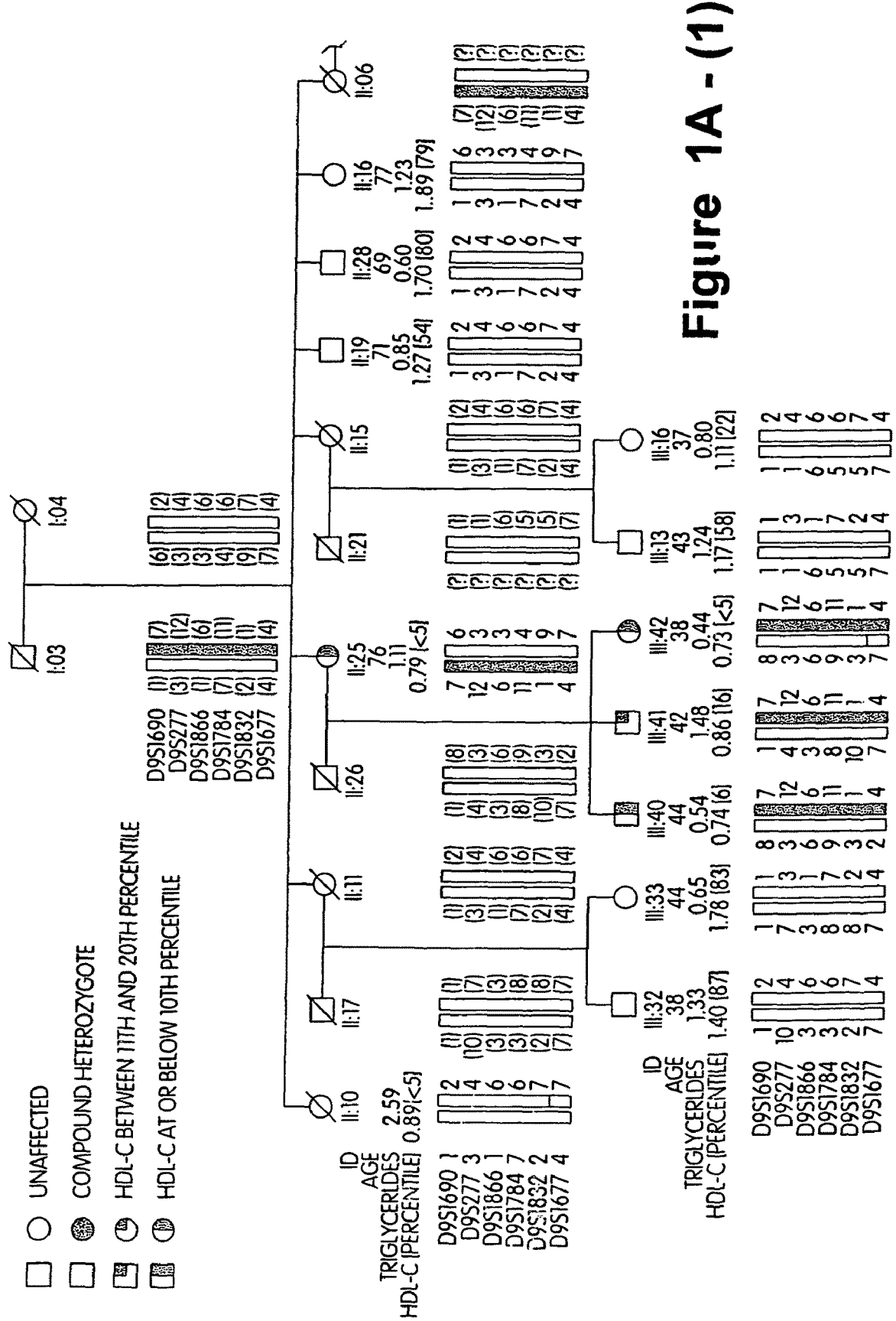
Figure 1A - (1)

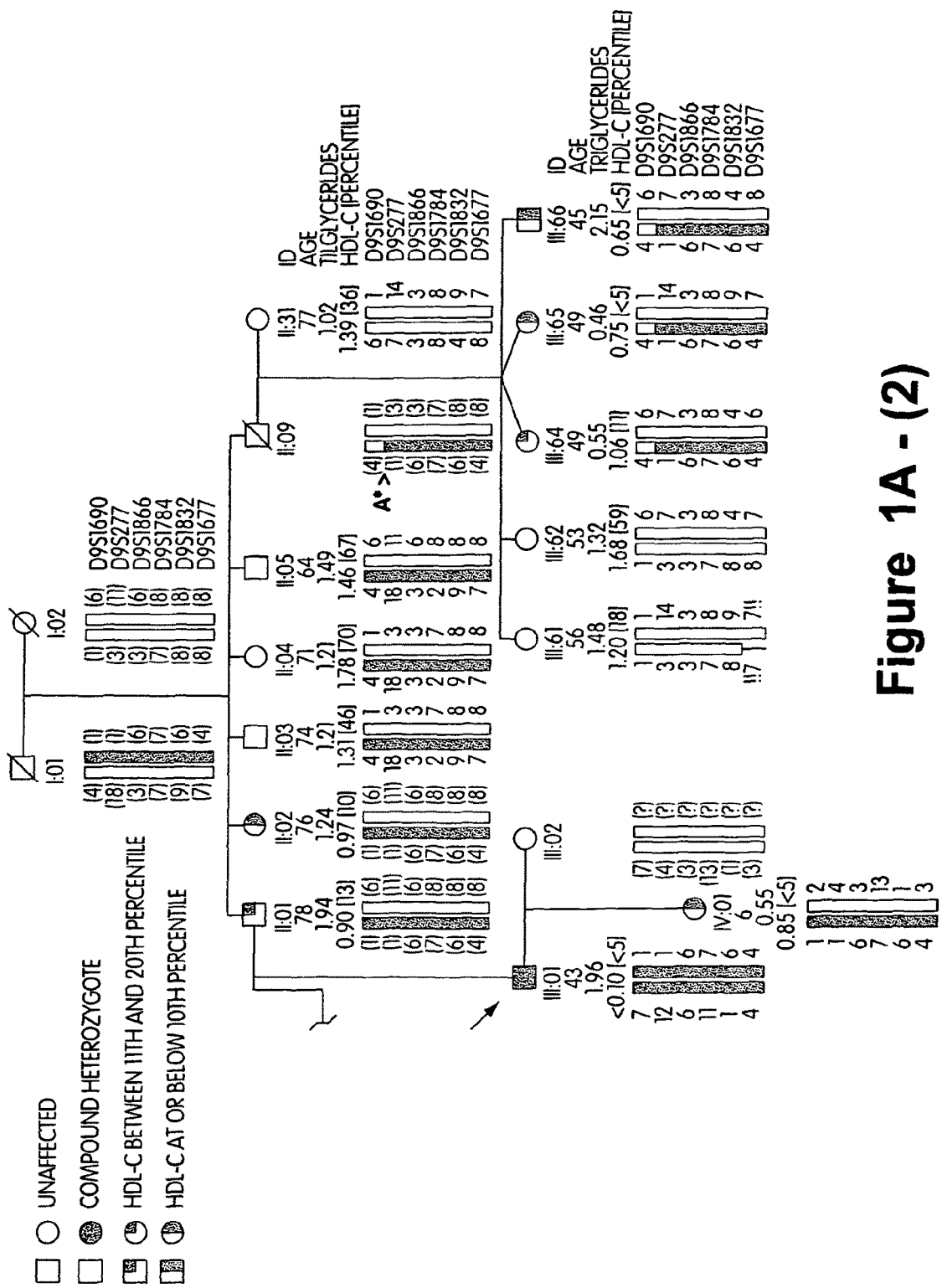
Figure 1A - (2)

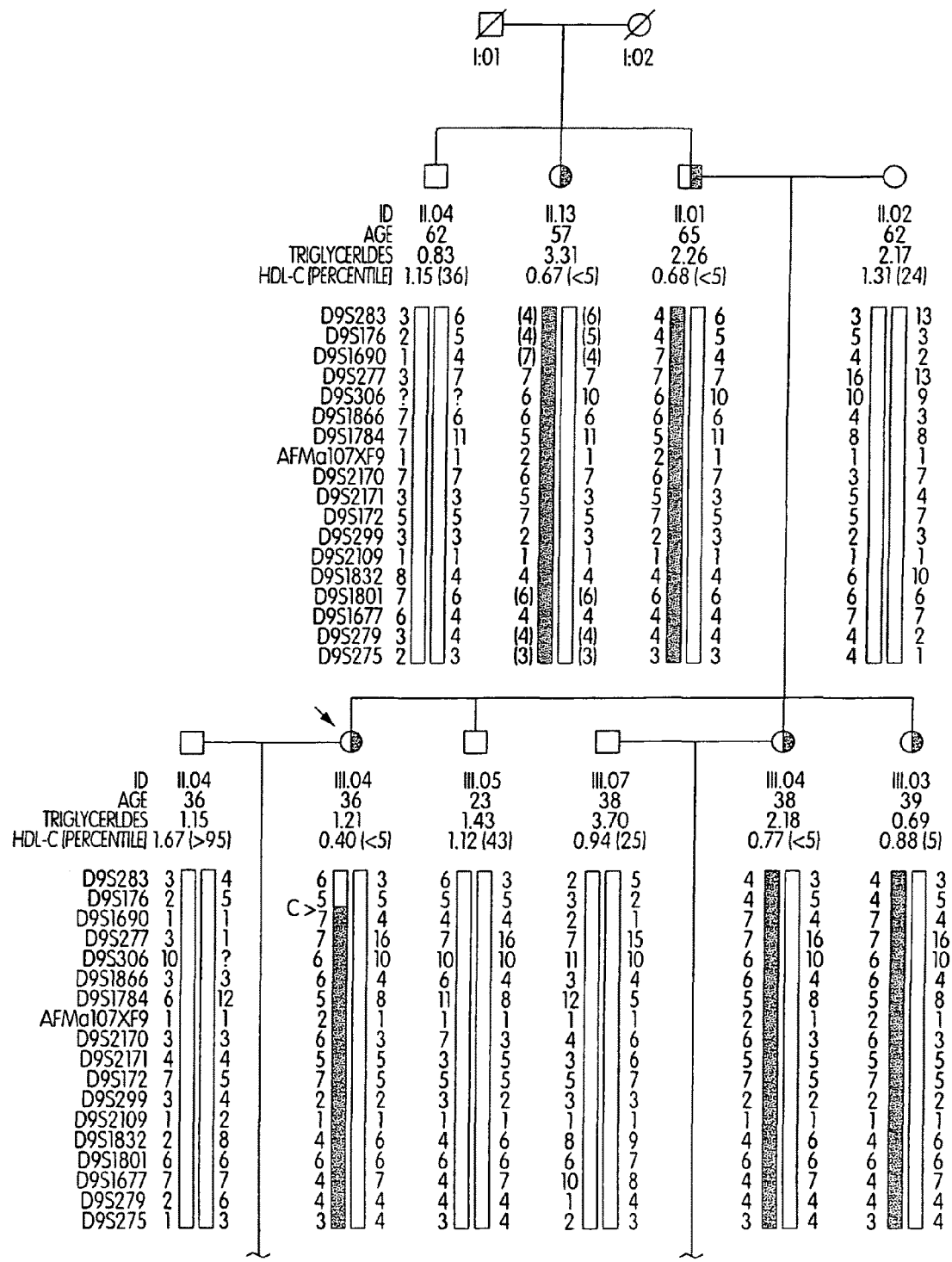
Figure 2A – (1)

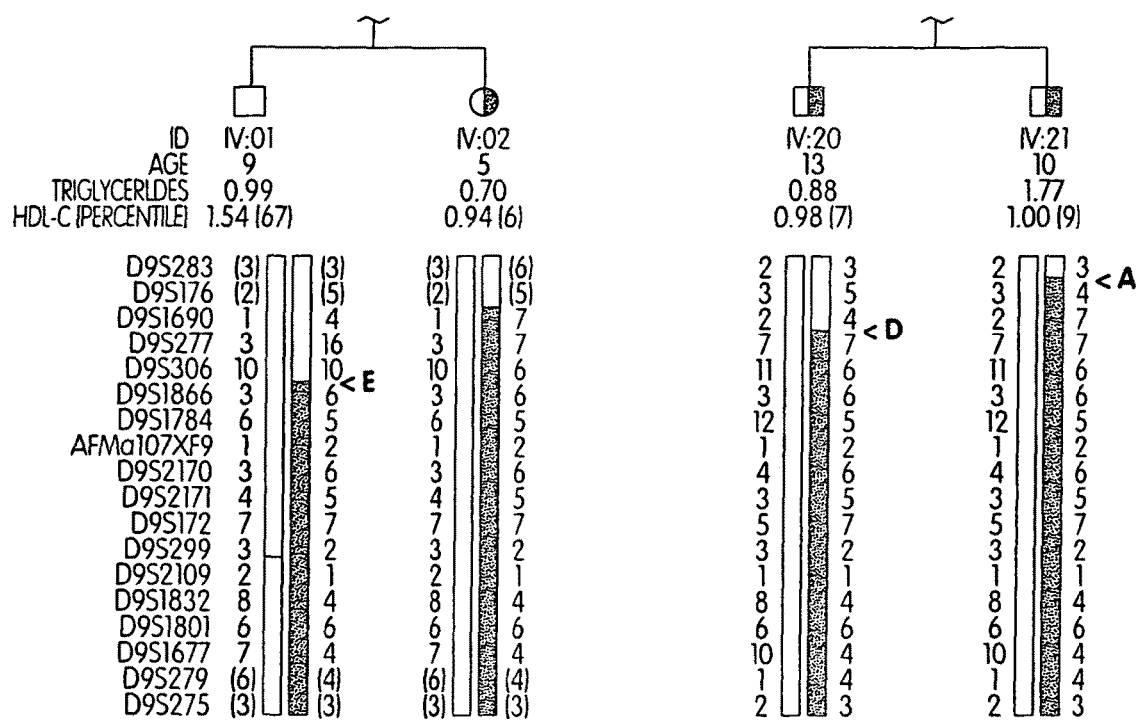
Figure 2A – (2)

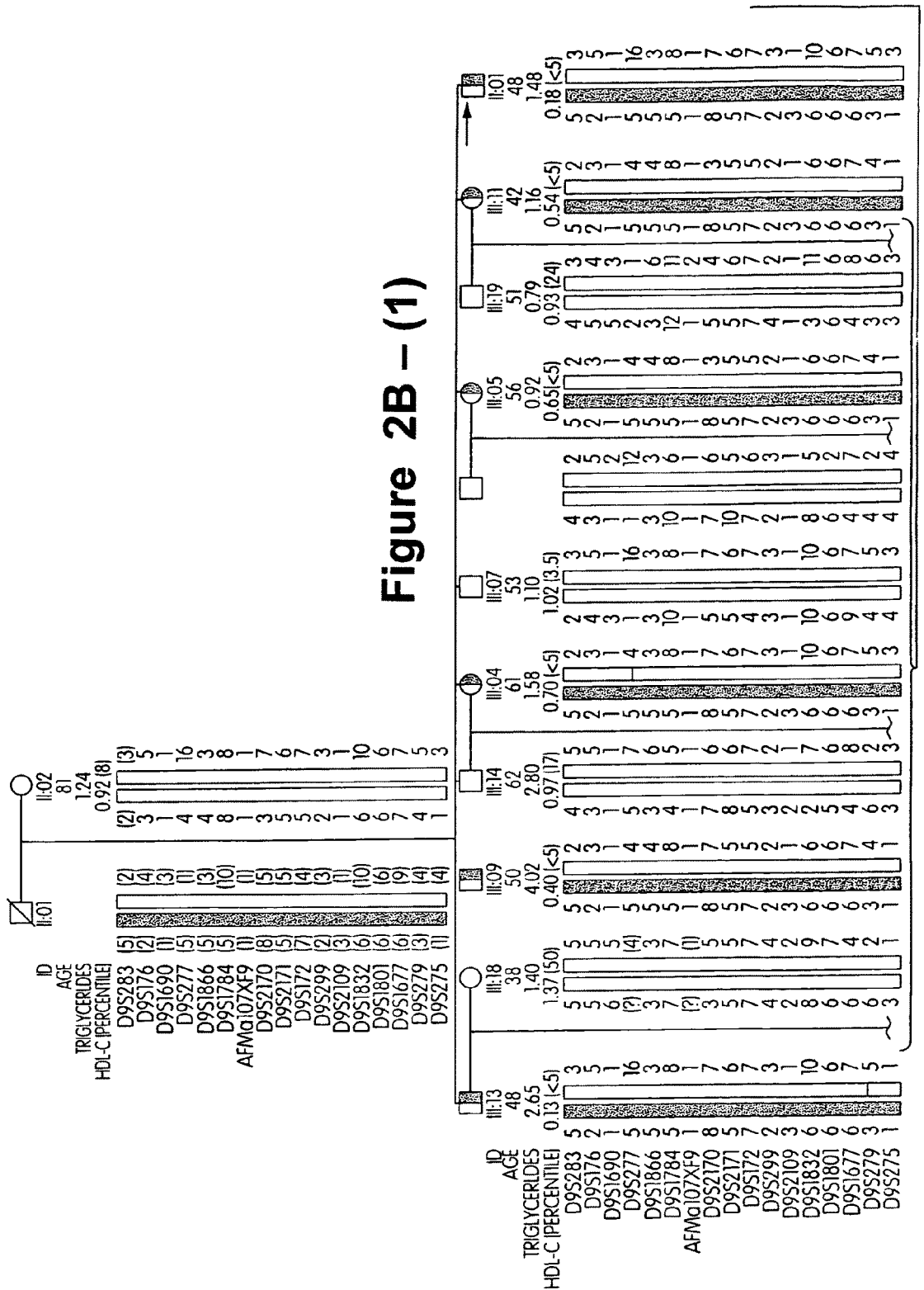
Figure 2B – (1)

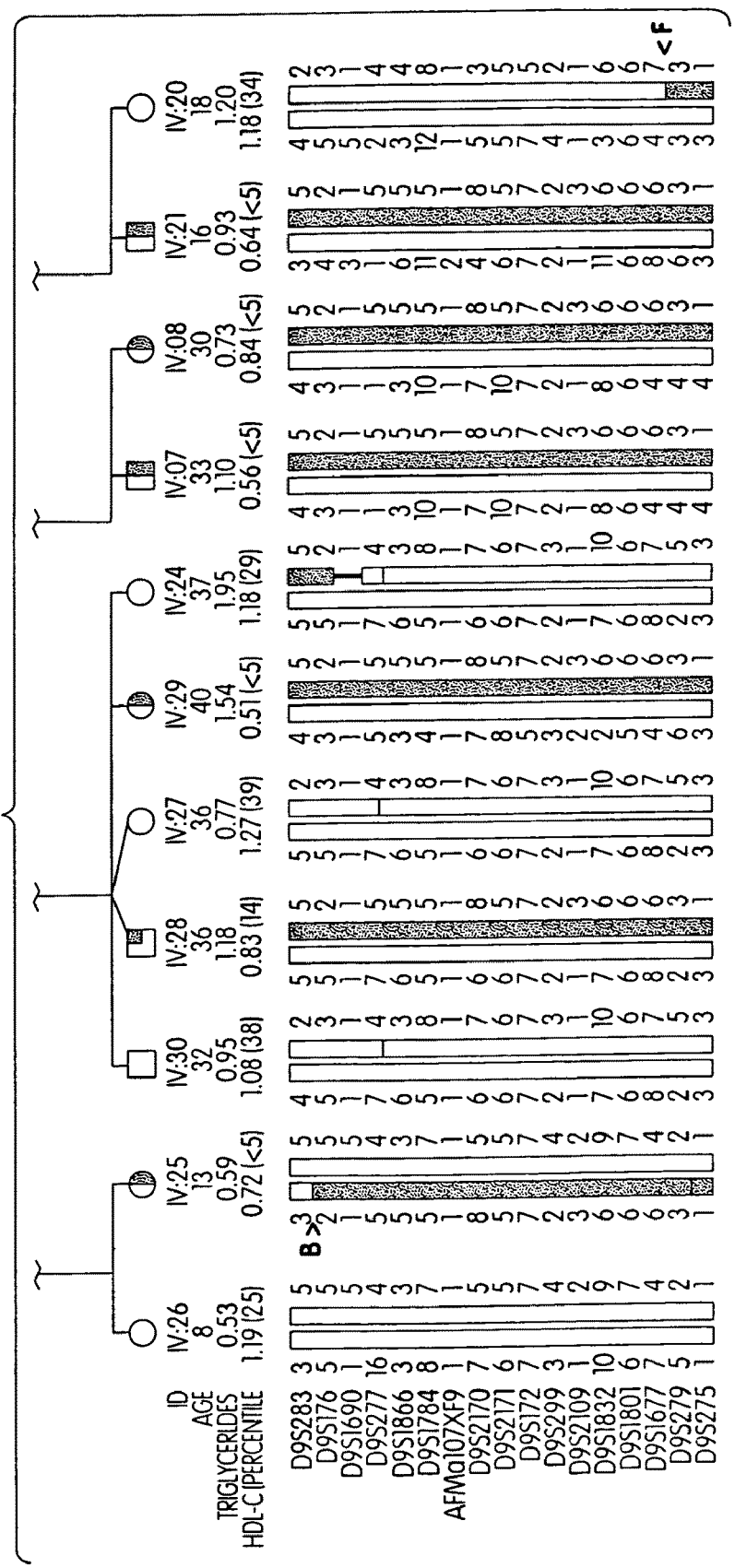
Figure 2B – (2)

EXON 20
TD-1

```
                    4485                  4503                            4529
                     |                      |                               |
wt sequence    aagaagatgctgcctgtgTgtcccccagggggcagggggggctgcct
HUMAN_ABC1      K   K   M   L   P   V   C   P   P   G   A   G   G   L   P
MOUSE_ABC1      K   K   M   L   P   V   C   P   P   G   A   G   G   L   P
Patient         K   K   M   L   P   V   R   P   P   G   A   G   G   L   P
CAEEL_ABC       -   -   L   L   -   -   -   -   -   -   -   G   G   S   -
Patient        aagaagatgctgcctgtgCgtcccccagggggcagggggggctgcct
```

Fig. 4B

EXON 13
TD-2

```
                    1842                    1864                    1886
                      |                       |                       |
wt sequence         tggggggggcttcgcctacttgcAggatgtggtggagcaggcaatc
HUMAN_ABC1            N  G  G  F  A  Y  L  Q  D  V  V  E  Q  A  I
MOUSE_ABC1            N  G  G  F  A  Y  L  Q  D  V  V  E  Q  A  I
Patient               N  G  G  F  A  Y  L  R  D  V  V  E  Q  A  I
CAEEL_ABC             -  -  -  F  M  T  V  Q  R  A  V  D  V  A  I
Patient             tggggggggcttcgcctacttgcGggatgtggtggagcaggcaatc
```

Fig. 5B

EXON 14
FHA-1

```
                 2136             2151                              2180
                   |                |                                 |
wt sequence      agtagcctcattcctCTTcttgtgagcgctggcctgctagtggtc
HUMAN_ABC1        S  S  L  I  P  L  L  V  S  A  G  L  L  V  V
MOUSE_ABC1        S  S  L  I  P  L  L  V  S  A  G  L  L  V  V
Patient           S  S  L  I  P  L  -  V  S  A  G  L  L  V  V
CAEEL_ABC         I  N  Y  A  K  L  T  F  A  V  I  V  L  T  I
Patient          agtagcctcattcct---cttgtgagcgctggcctgctagtggtc
                                 ↑
                          3 bp deletion
```

Fig. 6B

Exon 48 mutation:
Control
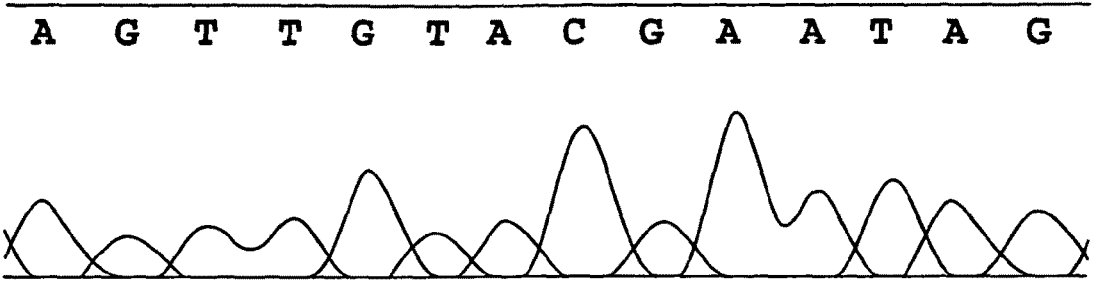
Family FHA - 2, patient III:01
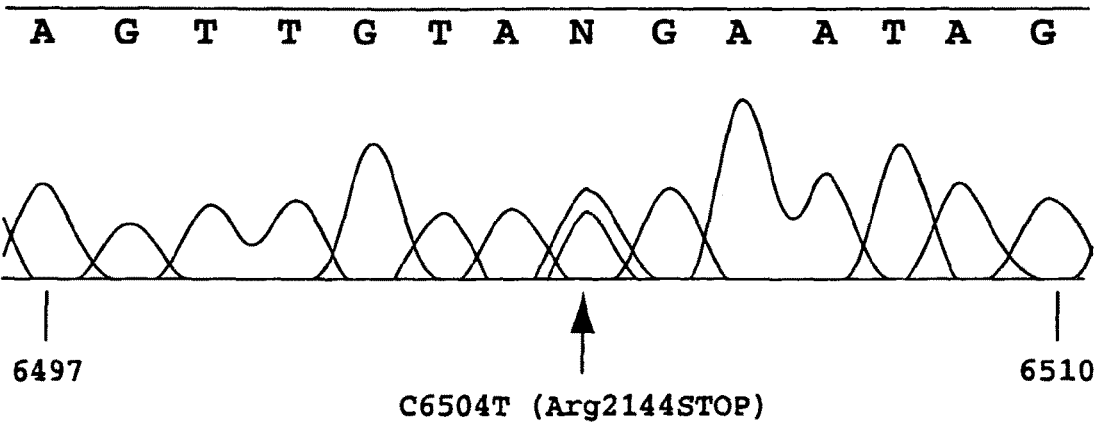
6497                    C6504T (Arg2144STOP)                    6510
Fig. 6F

SEQ ID NO: 1

```
MACWPQLRLLLWKNLTFRRRQTCQLLLEVAWPLFIFLILISVRLSYPPYEQHECHFPNKAMPSAGTLPWVQ
GIICNANNPCFRYPTPGEAPGVVGNFNKSIVARLFSDARRLLLYSQKDTSMKDMRKVLRTLQQIKKSSSNL
KLQDFLVDNETFSGFLYHNLSLPKSTVDKMLRADVILHKVFLQGYQLHLTSLCNGSKSEEMIQLGDQEVSE
LCGLPREKLAAAERVLRSNMDILKPILRTLNSTSPFPSKELAEATKTLLHSLGTLAQELFSMRSWSDMRQE
VMFLTNVNSSSSSTQIYQAVSRIVCGHPEGGGLKIKSLNWYEDNNYKALFGGNGTEEDAETFYDNSTTPYC
NDLMKNLESSPLSRIIWKALKPLLVGKILYTPDTPATRQVMAEVNKTFQELAVFHDLEGMWEELSPKIWTF
MENSQEMDLVRMLLDSRDNDHFWEQQLDGLDWTAQDIVAFLAKHPEDVQSSNGSVYTWREAFNETNQAIRT
ISRFMECVNLNKLEPIATEVWLINKSMELLDERKFWAGIVFTGITPGSIELPHHVKYKIRMDIDNVERTNK
IKDGYWDPGPRADPFEDMRYVWGGFAYLQDVVEQAIIRVLTGTEKKTGVYMQQMPYPCYVDDIFLRVMSRS
MPLFMTLAWIYSVAVIIKGIVYEKEARLKETMRIMGLDNSILWFSWFISSLIPLLVSAGLLVVILKLGNLL
PYSDPSVVFVFLSVFAVVTILQCFLISTLFSRANLAAACGGIIYFTLYLPYVLCVAWQDYVGFTLKIFASL
LSPVAFGFGCEYFALFEEQGIGVQWDNLFESPVEEDGFNLTTSVSMMLFDTFLYGVMTWYIEAVFPGQYGI
PRPWYFPCTKSYWFGEESDEKSHPGSNQKRISEICMEEEPTHLKLGVSIQNLVKVYRDGMKVAVDGLALNF
YEGQITSFLGHNGAGKTTTMSILTGLFPPTSGTAYILGKDIRSEMSTIRQNLGVCPQHNVLFDMLTVEEHI
WFYARLKGLSEKHVKAEMEQMALDVGLPSSKLKSKTSQLSGGMQRKLSVALAFVGGSKVVILDEPTAGVDP
YSRRGIWELLLKYRQGRTIILSTHHMDEADVLGDRIAIISHGKLCCVGSSLFLKNQLGTGYYLTLVKKDVE
SSLSSCRNSSSTVSYLKKEDSVSQSSSDAGLGSDHESDTLTIDVSAISNLIRKHVSEARLVEDIGHELTYV
LPYEAAKEGAFVELFHEIDDRLSDLGISSYGISETTLEEIFLKVAEESGVDAETSDGTLPARRNRRAFGDK
QSCLRPFTEDDAADPNDSDIDPESRETDLLSGMDGKGSYQVKGWKLTQQQFVALLWKRLLIARRSRKGFFA
QIVLPAVFVCIALVFSLIVPPFGKYPSLELQPWMYNEQYTFVSNDAPEDTGTLELLNALTKDPGFGTRCME
GNPIPDTPCQAGEEEWTTAPVPQTIMDLFQNGNWTMQNPSPACQCSSDKIKKMLPVCPPGAGGLPPPQRKQ
NTADILQDLTGRNISDYLVKTYVQIIAKSLKNKIWVNEFRYGGFSLGVSNTQALPPSQEVNDAIKQMKKHL
KLAKDSSADRFLNSLGRFMTGLDTRNNVKVWFNNKGWHAISSFLNVINNAILRANLQKGENPSHYGITAFN
HPLNLTKQQLSEVALMTTSVDVLVSICVIFAMSFVPASFVVFLIQERVSKAKHLQFISGVKPVIYWLSNFV
WDMCNYVVPATLVIIIFICFQQKSYVSSTNLPVLALLLLLYGWSITPLMYPASFVFKIPSTAYVVLTSVNL
FIGINGSVATFVLELFTDNKLNNINDILKSVFLIFPHFCLGRGLIDMVKNQAMADALERFGENRFVSPLSW
DLVGRNLFAMAVEGVVFFLITVLIQYRFFIRPRPVNAKLSPLNDEDEDVRRERQRILDGGGQNDILEIKEL
TKIYRRKRKPAVDRICVGIPPGECFGLLGVNGAGKSSTFKMLTGDTTVTRGDAFLNKNSILSNIHEVHQNM
GYCPQFDAITELLTGREHVEFFALLRGVPEKEVGKVGEWAIRKLGLVKYGEKYAGNYSGGNKRKLSTAMAL
IGGPPVVFLDEPTTGMDPKARRFLWNCALSVVKEGRSVVLTSHSMEECEALCTRMAIMVNGRFRCLGSVQH
LKNRFGDGYTIVVRIAGSNPDLKPVQDFFGLAFPGSVLKEKHRNMLQYQLPSSLSSLARIFSILSQSKKRL
HIEDYSVSQTTLDQVFVNFAKDQSDDDHLKDLSLHKNQTVVDVAVLTSFLQDEKVKESYV*
```

Fig. 9A

SEQ ID NO: 2

```
GTCCCTGCTGTGAGCTCTGGCCGCTGCCTTCCAGGGCTCCCGAGCCACACGCTGGGGGTG
CTGGCTGAGGGAACATGGCTTGTTGGCCTCAGCTGAGGTTGCTGCTGTGGAAGAACCTCA
CTTTCAGAAGAAGACAAACATGTCAGCTGTTACTGGAAGTGGCCTGGCCTCTATTTATCT
TCCTGATCCTGATCTCTGTTCGGCTGAGCTACCCACCCTATGAACAACATGAATGCCATT
TTCCAAATAAAGCCATGCCCTCTGCAGGAACACTTCCTTGGGTTCAGGGGATTATCTGTA
ATGCCAACAACCCCTGTTTCCGTTACCCGACTCCTGGGGAGGCTCCCGGAGTTGTTGGAA
ACTTTAACAAATCCATTGTGGCTCGCCTGTTCTCAGATGCTCGGAGGCTTCTTTTATACA
GCCAGAAAGACACCAGCATGAAGGACATGCGCAAAGTTCTGAGAACATTACAGCAGATCA
AGAAATCCAGCTCAAACTTGAAGCTTCAAGATTTCCTGGTGGACAATGAAACCTTCTCTG
GGTTCCTGTATCACAACCTCTCTCTCCCAAAGTCTACTGTGGACAAGATGCTGAGGGCTG
ATGTCATTCTCCACAAGGTATTTTTGCAAGGCTACCAGTTACATTTGACAAGTCTGTGCA
ATGGATCAAAATCAGAAGAGATGATTCAACTTGGTGACCAAGAAGTTTCTGAGCTTTGTG
GCCTACCAAGGGAGAAACTGGCTGCAGCAGAGCGAGTACTTCGTTCCAACATGGACATCC
TGAAGCCAATCCTGAGAACACTAAACTCTACATCTCCCTTCCCGAGCAAGGAGCTGGCTG
AAGCCACAAAAACATTGCTGCATAGTCTTGGGACTCTGGCCCAGGAGCTGTTCAGCATGA
GAAGCTGGAGTGACATGCGACAGGAGGTGATGTTTCTGACCAATGTGAACAGCTCCAGCT
CCTCCACCCAAATCTACCAGGCTGTGTCTCGTATTGTCTGCGGGCATCCCGAGGGAGGGG
GGCTGAAGATCAAGTCTCTCAACTGGTATGAGGACAACAACTACAAAGCCCTCTTTGGAG
GCAATGGCACTGAGGAAGATGCTGAAACCTTCTATGACAACTCTACAACTCCTTACTGCA
ATGATTTGATGAAGAATTTGGAGTCTAGTCCTCTTTCCCGCATTATCTGGAAAGCTCTGA
AGCCGCTGCTCGTTGGGAAGATCCTGTATACACCTGACACTCCAGCCACAAGGCAGGTCA
TGGCTGAGGTGAACAAGACCTTCCAGGAACTGGCTGTGTTCCATGATCTGGAAGGCATGT
GGGAGGAACTCAGCCCCAAGATCTGGACCTTCATGGAGAACAGCCAAGAAATGGACCTTG
TCCGGATGCTGTTGGACAGCAGGGACAATGACCACTTTTGGGAACAGCAGTTGGATGGCT
TAGATTGGACAGCCCAAGACATCGTGGCGTTTTTGGCCAAGCACCCAGAGGATGTCCAGT
CCAGTAATGGTTCTGTGTACACCTGGAGAGAAGCTTTCAACGAGACTAACCAGGCAATCC
GGACCATATCTCGCTTCATGGAGTGTGTCAACCTGAACAAGCTAGAACCCATAGCAACAG
AAGTCTGGCTCATCAACAAGTCCATGGAGCTGCTGGATGAGAGGAAGTTCTGGGCTGGTA
TTGTGTTCACTGGAATTACTCCAGGCAGCATTGAGCTGCCCCATCATGTCAAGTACAAGA
TCCGAATGGACATTGACAATGTGGAGAGGACAAATAAAATCAAGGATGGGTACTGGGACC
CTGGTCCTCGAGCTGACCCCTTTGAGGACATGCGGTACGTCTGGGGGGCTTCGCCTACT
TGCAGGATGTGGTGGAGCAGGCAATCATCAGGGTGCTGACGGGCACCGAGAAGAAAACTG
```

Fig. 9B

```
GTGTCTATATGCAACAGATGCCCTATCCCTGTTACGTTGATGACATCTTTCTGCGGGTGA
TGAGCCGGTCAATGCCCCTCTTCATGACGCTGGCCTGGATTTACTCAGTGGCTGTGATCA
TCAAGGGCATCGTGTATGAGAAGGACGGCACGGCTGAAAGAGACCATGCGGATCATGGCC
TGGACAACAGCATCCTCTGGTTTAGCTGGTTCATTAGTAGCCTCATTCCTCTTCTTGTGA
GCGCTGGCCTGCTAGTGGTCATCCTGAAGTTAGGAAACCTGCTGCCCTACAGTGATCCCA
GCGTGGTGTTTGTCTTCCTGTCCGTGTTTGCTGTGGTGACAATCCTGCAGTGCTTCCTGA
TTAGCACACTCTTCTCCAGAGCCAACCTGGCAGCAGCCTGTGGGGCATCATCTACTTCA
CGCTGTACCTGCCCTACGTCCTGTGTGTGGCATGGCAGGACTACGTGGGCTTCACACTCA
AGATCTTCGCTAGCCTGCTGTCTCCTGTGGCTTTTGGGTTTGGCTGTGAGTACTTTGCCC
TTTTTGAGGAGCAGGGCATTGGAGTGCAGTGGGACAACCTGTTTGAGAGTCCTGTGGAGG
AAGATGGCTTCAATCTCACCACTTCGGTCTCCATGATGCTGTTTGACACCTTCCTCTATG
GGGTGATGACCTGGTACATTGAGGCTGTCTTTCCAGGCCAGTACGGAATTCCCAGGCCCT
GGTATTTTCCTTGCACCAAGTCCTACTGGTTTGGCGAGGAAAGTGATGAGAAGAGCCACC
CTGGTTCCAACCAGAAGAGAATATCAGAAATCTGCATGGAGGAGGAACCCACCCACTTGA
AGCTGGGCGTGTCCATTCAGAACCTGGTAAAAGTCTACCGAGATGGGATGAAGGTCGCTG
TCGATGGCCTGGCACTGAATTTTTATGAGGGCCAGATCACCTCCTTCCTGGGCCACAATG
GAGCGGGGAAGACGACCACCATGTCAATCCTGACCGGGTTGTTCCCCCCGACCTCGGGCA
CCGCCTACATCCTGGGAAAAGACATTCGCTCTGAGATGAGCACCATCCGGCAGAACCTGG
GGGTCTGTCCCCAGCATAACGTGCTGTTTGACATGCTGACTGTCGAAGAACACATCTGGT
TCTATGCCCGCTTGAAAGGGCTCTCTGAGAAGCACGTGAAGGCGGAGATGGAGCAGATGG
CCCTGGATGTTGGTTTGCCATCAAGCAAGCTGAAAAGCAAAACAAGCCAGCTGTCAGGTG
GAATGCAGAGAAAGCTATCTGTGGCCTTGGCCTTTGTCGGGGATCTAAGGTTGTCATTC
TGGATGAACCCACAGCTGGTGTGGACCCTTACTCCCGCAGGGAATATGGGAGCTGCTGC
TGAAATACCGACAAGGCCGCACCATTATTCTCTCTACACACCACATGGATGAAGCGGACG
TCCTGGGGGACAGGATTGCCATCATCTCCCATGGGAAGCTGTGCTGTGTGGGCTCCTCCC
TGTTTCTGAAGAACCAGCTGGGAACAGGCTACTACCTGACCTTGGTCAAGAAAGATGTGG
AATCCTCCCTCAGTTCCTGCAGAAACAGTAGTAGCACTGTGTCATACCTGAAAAACGAGG
ACAGTGTTTCTCAGAGCAGTTCTGATGCTGGCCTGGGCAGCGACCATGAGAGTGACACGC
TGACCATCGATGTCTCTGCTATCTCCAACCTCATCAGGAAGCATGTGTCTGAAGCCCGGC
TGGTGGAAGACATAGGGCATGAGCTGACCTATGTGCTGCCATATGAAGCTGCTAAGGAGG
GAGCCTTTGTGGAACTCTTTCATGAGATTGATGACCGGCTCTCAGACCTGGGCATTTCTA
GTTATGGCATCTCAGAGACGACCCTGGAAGAAATATTCCTCAAGGTGGCCGAAGAGAGTG
GGGTGGATGCTGAGACCTCAGATGGTACCTTGCCAGCAAGACGAAACAGGCGCGCCTTCG
GGGACAAGCAGAGCTGTCTTCGCCCGTTCACTGAAGATGATGCTGCTGATCCAAATGATT
```

Fig. 9C

```
CTGACATAGACCCAGAATCCAGAGAGACAGACTTGCTCAGTGGGATGGATGGCAAAGGGT
CCTACCAGGTGAAAGGCTGGAAACTTACACAGCAACAGTTTGTGGCCCTTTTGTGGAAGA
GACTGCTAATTGCCAGACGGAGTCGGAAAGGATTTTTTGCTCAGATTGTCTTGCCAGCTG
TGTTTGTCTGCATTGCCCTTGTGTTCAGCCTGATCGTGCCACCCTTTGGCAAGTACCCCA
GCCTGGAACTTCAGCCCTGGATGTACAACGAACAGTACACATTTGTCAGCAATGATGCTC
CTGAGGACACGGGAACCCTGGAACTCTTAAACGCCCTCACCAAAGACCCTGGCTTCGGGA
CCCGCTGTATGGAAGGAAACCCAATCCCAGACACGCCCTGCCAGGCAGGGAGGAAGAGT
GGACCACTGCCCCAGTTCCCCAGACCATCATGGACCTCTTCCAGAATGGGAACTGGACAA
TGCAGAACCCTTCACCTGCATGCCAGTGTAGCAGCGACAAAATCAAGAAGATGCTGCCTG
TGTGTCCCCAGGGGCAGGGGGCTGCCTCCTCCACAAAGAAAACAAAACACTGCAGATA
TCCTTCAGGACCTGACAGGAAGAAACATTTCGGATTATCTGGTGAAGACGTATGTGCAGA
TCATAGCCAAAAGCTTAAAGAACAAGATCTGGGTGAATGAGTTTAGGTATGGCGGCTTTT
CCCTGGGTGTCAGTAATACTCAAGCACTTCCTCCGAGTCAAGAAGTTAATGATGCCATCA
AACAAATGAAGAAACACCTAAAGCTGGCCAAGGACAGTTCTGCAGATCGATTTCTCAACA
GCTTGGGAAGATTTATGACAGGACTGGACACCAGAAATAATGTCAAGGTGTGGTTCAATA
ACAAGGGCTGGCATGCAATCAGCTCTTTCCTGAATGTCATCAACAATGCCATTCTCCGGG
CCAACCTGCAAAAGGGAGAGAACCCTAGCCATTATGGAATTACTGCTTTCAATCATCCCC
TGAATCTCACCAAGCAGCAGCTCTCAGAGGTGGCTCTGATGACCACATCAGTGGATGTCC
TTGTGTCCATCTGTGTCATCTTTGCAATGTCCTTCGTCCCAGCCAGCTTTGTCGTATTCC
TGATCCAGGAGCGGGTCAGCAAAGCAAAACACCTGCAGTTCATCAGTGGAGTGAAGCCTG
TCATCTACTGGCTCTCTAATTTTGTCTGGGATATGTGCAATTACGTTGTCCCTGCCACAC
TGGTCATTATCATCTTCATCTGCTTCCAGCAGAAGTCCTATGTGTCCTCCACCAATCTGC
CTGTGCTAGCCCTTCTACTTTTGCTGTATGGTGGTCAATCACACCTCTCATGTACCCAG
CCTCCTTTGTGTTCAAGATCCCCAGCACAGCCTATGTGGTGCTCACCAGCGTGAACCTCT
TCATTGGCATTAATGGCAGCGTGGCCACCTTTGTGCTGGAGCTGTTCACCGACAATAAGC
TGAATAATATCAATGATATCCTGAAGTCCGTGTTCTTGATCTTCCCACATTTTTGCCTGG
GACGAGGGCTCATCGACATGGTGAAAAACCAGGCAATGGCTGATGCCCTGGAAAGGTTTG
GGGAGAATCGCTTTGTGTCACCATTATCTTGGGACTTGGTGGGACGAAACCTCTTCGCCA
TGGCCGTGGAAGGGGTGGTGTTCTTCCTCATTACTGTTCTGATCCAGTACAGATTCTTCA
TCAGGCCCAGACCTGTAAATGCAAAGCTATCTCCTCTGAATGATGAAGATGAAGATGTGA
GGCGGGAAAGACAGAGAATTCTTGATGGTGGAGGCCAGAATGACATCTTAGAAATCAAGG
AGTTGACGAAGATATATAGAAGGAAGCGGAAGCCTGCTGTTGACAGGATTTCCGTGGCA
TTCCTCCTGGTGAGTGCTTTGGGCTCCTGGGAGTTAATGGGCTGGAAAATCATCAACTT
TCAAGATGTTAACAGGAGATACCACTGTTACCAGACGAGATGCTTTCCTTAACAAAAATA
```

Fig. 9D

```
GTATCTTATCAAACATCCATGAAGTACATCAGAACATGGGCTACTGCCCTCAGTTTGATG
CCATCACAGAGCTGTTGACTGGGAGAGAACACGTGGAGTTCTTTGCCCTTTTGAGAGGAG
TCCCAGAGAAAGAAGTTGGCAAGGTTGGTGAGTGGGCGATTCGGAAACTGGCCTCGTGA
AGTATGGAGAAAAATATGCTGGTAACTATAGTGGAGGCAACAAACGCAAGCTCTCTACAG
CCATGGCTTTGATCGGCGGGCCTCCTGTGGTGTTTCTGGATGAACCCACCACAGGCATGG
ATCCCAAAGCCCGGCGGTTCTTGTGGAATTGTGCCCTAAGTGTTGTCAAGGAGGGAGAT
CAGTAGTGCTTACATCTCATAGTATGGAAGAATGTGAAGCTCTTTGCACTAGGATGGCAA
TCATGGTCAATGGAAGGTTCAGGTGCCTTGGCAGTGTCCAGCATCTAAAAAATAGGTTTG
GAGATGGTTATACAATAGTTGTACGAATAGCAGGGTCCAACCCGGACCTGAAGCCTGTCC
AGGATTTCTTTGGACTTGCATTTCCTGGAAGTGTTCTAAAAGAGAAACACCGGAACATGC
TACAATACCAGCTTCCATCTTCATTATCTTCTCTGGCCAGGATATTCAGCATCCTCTCCC
AGAGCAAAAAGCGACTCCACATAGAAGACTACTCTGTTTCTCAGACAACACTTGACCAAG
TATTTGTGAACTTTGCCAAGGACCAAAGTGATGATGACCACTTAAAAGACCTCTCATTAC
ACAAAAACCAGACAGTAGTGGACGTTGCAGTTCTCACATCTTTTCTACAGGATGAGAAAG
TGAAAGAAAGCTATGTATGAAGAATCCTGTTCATACGGGGTGGCTGAAAGTAAAGAGGAA
CTAGACTTTCCTTTGCACCATGTGAAGTGTTGTGGAGAAAAGAGCCAGAAGTTGATGTGG
GAAGAAGTAAACTGGATACTGTACTGATACTATTCAATGCAATGCAATTCAATGCAATGA
AAACAAAATTCCATTACAGGGGCAGTGCCTTTGTAGCCTATGTCTTGTATGGCTCTCAAG
TGAAAGACTTGAATTTAGTTTTTTACCTATACCTATGTGAAACTCTATTATGGAACCCAA
TGGACATATGGGTTTGAACTCACACTTTTTTTTTTTTTTTGTTCCTGTGTATTCTCATT
GGGGTTGCAACAATAATTCATCAAGTAATCATGGCCAGCGATTATTGATCAAAATCAAAA
GGTAATGCACATCCTCATTCACTAAGCCATGCCATGCCCAGGAGACTGGTTTCCCGGTGA
CACATCCATTGCTGGCAATGAGTGTGCCAGAGTTATTAGTGCCAAGTTTTTCAGAAAGTT
TGAAGCACCATGGTGTGTCATGCTCACTTTTGTGAAAGCTGCTCTGCTCAGAGTCTATCA
ACATTGAATATCAGTTGACAGAATGGTGCCATGCGTGGCTAACATCCTGCTTTGATTCCC
TCTGATAAGCTGTTCTGGTGGCAGTAACATGCAACAAAAATGTGGGTGTCTCCAGGCACG
GGAAACTTGGTTCCATTGTTATATTGTCCTATGCTTCGAGCCATGGGTCTACACGGTCAT
CCTTATGAGACTCTTAAATATACTTAGATCCTGGTAAGAGGCAAAGAATCAACAGCCAAA
CTGCTGGGCTGCAACTGCTGAAGCCAGGCATGGGATTAAAGAGATTGTGCGTTCAAAC
CTAGGGAAGCCTGTGCCCATTTGTCCTGACTGTCTGCTAACATGGTACACTGCATCTCAA
GATGTTTATCTGACACAAGTGTATTATTTCTGGCTTTTTGAATTAATCTAGAAAATGAAA
```

Fig. 9E

| | Exon Forward Primer | (bp) | SEQ ID No. | Reverse Primer | SEQ ID No. | | intron(kb) | intron (kb) |
|---|---|---|---|---|---|---|---|---|
| exon 1 | GGCTGGATTAGCAGTCCTCA | 140 | 70 | ATCCCCAACTCAAAACCACA | 119 | intron 1 | >6.413 | >6.4 |
| exon 2 | GGATTTCCCAGATCCCAGTG | 94 | 71 | AAGTCCAATTTAGCCCACGTT | 120 | intron 2 | >4.241 | >4.2 |
| exon 3 | GACAGACTTGGCATGAAGCA | 142 | 72 | CCAGCCATTCAAAATTCTCC | 121 | intron 3 | >1.248(1.6) | 1.6 |
| exon 4 | GCACTTGGCAGTCACTTCTG | 119 | 73 | GGGTGCAGGTCAATTCCAAT | 122 | intron 4 | >1.512 | >1.5 |
| exon 5 | CGTTTCTCCACTGTCCCATT | 122 | 74 | CCCCTTCACCACCATTACAA | 123 | intron 5 | >1.796(3) | 3 |
| exon 6 | ACTTCAAGGACCCAGCTTCC | 177 | 75 | TGTCCAAGGAAAAGCTCAC | 124 | intron 6 | >2.726(10) | 10 |
| exon 7 | TCGGTTTCTTGTTGTTAAACTCA | 93 | 76 | AGGACCTCTTGCCAGACTCA | 125 | intron 7 | 4.975 | 5 |
| exon 8 | TCCAAGGCTTTGAGATGAC | 241 | 77 | AGGAGATGACACAGGCCAAG | 126 | intron 8 | >2.311(.5) | 2.5 |
| exon 9 | GGCTCCAAAGCCCTTGTAA | 140 | 78 | CGCACACCTCTGAAGCTACC | 127 | intron 9 | 0.332 | 0.3 |
| exon 10 | GCTGCTGTGATGGGGTATCT | 117 | 79 | ACCTCACTCACACCTGGGAA | 128 | intron 10 | 4.208 | 4.2 |
| exon 11 | TTTGTAAATTTGTAGTGCTTCCTCA | 198 | 80 | GCCTCCTGCCTGAACCTTAT | 129 | intron 11 | 0.747 | 0.7 |
| exon 12 | TAGTCAGCCCTTGGTAAGGCTA | 206 | 81 | CAAAATCATGACACCAAGTTGAG | 130 | intron 12 | 0.523 | 0.5 |
| exon 13 | AAAGGGCTTGGTCTCCTCTA | 177 | 82 | CATGCACATGCACACACATA | 131 | intron 13 | 1.787 | 1.8 |
| exon 14 | GATGTGGTGCTCCCTCTAGC | 223 | 83 | CCTTAGCCGTGTTGAGCTA | 132 | intron 14 | 1.747 | 1.7 |
| exon 15 | CAAGTGAGTGCTTGGGATTG | 222 | 84 | TGCTTTATTCAGGGACTCCA | 133 | intron 15 | 1.059 | 1.1 |
| exon 16 | GCAAATTCAAATTTCTCCAGG | 205 | 85 | CCCATGCACTGCAGAGATTC | 134 | intron 16 | 1.105 | 1.1 |
| exon 17 | TCAAGGAGGAAATGGACCTG | 114 | 86 | AAGGCAGGAGACATCGCTT | 135 | intron 17 | 1.789 | 1.8 |
| exon 18 | CTGAAAGTTCAAGCGCAGTG | 172 | 87 | GGGATCAGCAGCATGGTTCCTA | 136 | intron 18 | 0.99 | 1 |
| exon 19 | TGCAGACTGAATGGAGCATC | 132 | 88 | GCTTAAGTCCCACTCCTCCC | 137 | intron 19 | 1.307 | 1.3 |
| exon 20 | GCCAGGGGACACTGTATTCT | 143 | 89 | ATTTTCCTCCGCATGTGTGT | 138 | intron 20 | 0.204 | 0.2 |
| exon 21 | AGTTCCTCTGCCTTCACTCA | 138 | 90 | TCACAGAAGCCTAGCCATGA | 139 | intron 21 | 0.706 | 0.7 |
| exon 22 | CCAGTGCTTACCCCTGCTAA | 221 | 91 | AACAGAGCAGGAGATGGTG | 140 | intron 22 | >0.866(1.7) | 1.7 |
| exon 23 | CACACAACAGAGCTTCTTGGA | 73 | 92 | TCTGCACCTCTCCTCCTCTG | 141 | intron 23 | 0.986 | 1 |
| exon 24 | ACCTGGAACAGGTGGTGT | 203 | 93 | ACGTGGGGCCAACATTAATCA | 142 | intron 24 | 1.668 | 1.7 |
| exon 25 | GGGCTAACATGCCACTCAGTA | 49 | 94 | CTTCCCCATCTGCAACAAAC | 143 | intron 25 | 0.196 | 0.2 |

Figure 10A

| | | | | | |
|---|---|---|---|---|---|
| exon 26 | 114 | GTTTGTTGCAGATGGGAAG | 95 | GCTAAAGGCCATCAAAGAA | 144 | intron 26 | 1.396 | 1.4 |
| exon 27 | 149 | CACCAGAAGAGGAGCATGG | 96 | TCAAGTGCATCTGGGCATAA | 145 | intron 27 | 1.649 | 1.6 |
| exon 28 | 125 | CTGGACTCGTAGGGATTTGC | 97 | TCTGAAGTCCATTCCCTTGG | 146 | intron 28 | >0.728(1.4) | 1.4 |
| exon 29 | 99 | GCCTGTCACAGAGAAATGCTT | 98 | CAATGTGGCATGCAGTTGAT | 147 | intron 29 | >2.589(3) | 3 |
| exon 30 | 190 | TTACGGAATGATCCTGTGCTC | 99 | GAAGCTACCAGCCCATCCT | 148 | intron 30 | 1.521 | 1.5 |
| exon 31 | 95 | AGTCAGGTTTCCGGTCACAC | 100 | CATTTCCCCACTGTTTCAG | 149 | intron 31 | >0.944(\) | >0.9 |
| exon 32 | 33 | CCGTTCCTTATATCCTCAGGTG | 101 | CCAAGGCTTTCTTCAATCCA | 150 | intron 32 | >1.062(/6.5) | >1.0 |
| exon 33 | 106 | CCTTGTACACTCGCACTGA | 102 | GATCCGTTTAACCTGCCAAC | 151 | intron 33 | 1.475 | 1.5 |
| exon 34 | 75 | TGTTGTCACAGGTTCCAGA | 103 | ATGCCCCTGCCAACTTTAC | 152 | intron 34 | 0.522 | 0.5 |
| exon 35 | 170 | TGAGGTTTATGGGCATGGTT | 104 | CTCTGCAGCTGTTCCCCTAC | 153 | intron 35 | 1.228 | 1.2 |
| exon 36 | 178 | ATGTTTTTCCTTGGCTGTGC | 105 | TATCAATCCATGGCCCTGAC | 154 | intron 36 | >1.898(2) | 2 |
| exon 37 | 116 | ATCTGCCCTTTCTTGTCTGA | 106 | AGAGTCCCTGCCCTCCTTCT | 155 | intron 37 | 0.112 | 0.1 |
| exon 38 | 145 | AGGGAGCTGCACAGTGGATA | 107 | AAGGCAGTCAGCAGTGTCAA | 156 | intron 38 | 1.545 | 1.5 |
| exon 39 | 124 | TCACTCCATATTTCAGAACTTGA | 108 | GGGAACATCCTGTGCTTAG | 157 | intron 39 | 1.087 | 1.1 |
| exon 40 | 130 | TGTTTATTGAGATCGGTGAA | 109 | CCATTGGTGAGTGTTTCCCT | 158 | intron 40 | 0.265 | 0.3 |
| exon 41 | 121 | CGTTAGGACTGAATCTTTGTCCTG | 110 | AGTGCTGCAAACTGCTGGGTT | 159 | intron 41 | >0.622(0.9) | 0.9 |
| exon 42 | 63 | AGTCCTGCCTTCCACAGTTG | 111 | ATTGCTCCATCCTGGCATAA | 160 | intron 42 | 0.909 | 0.9 |
| exon 43 | 107 | GGTAGTTACGTGTTAGGGGCA | 112 | TCATGGATGATTTTATGTGCTTC | 161 | intron 43 | 2.355 | 2.4 |
| exon 44 | 142 | CAGGAACATTAGGCCAGATTG | 113 | GCGTGTGGAAAAGCCATAAG | 162 | intron 44 | 0.372 | 0.4 |
| exon 45 | 135 | CATGTATGTAGGACAGCATGA | 114 | GCCAATCATACAACAGCCCT | 163 | intron 45 | >1.059(1.3) | 1.3 |
| exon 46 | 104 | CTGTTTCAAAGATGCTTCTGC | 115 | TGATCGCATATTCTACTTGGAAA | 164 | intron 46 | 0.483 | 0.5 |
| exon 47 | 93 | CCTAGGAAGCTGGAATGCTG | 116 | TCCCTTTATTTTAGAGGACCA | 165 | intron 47 | 0.659 | 0.7 |
| exon 48 | 244 | GGGTTCCAGGGTTCAGTAT | 117 | GATCAGGAATTCAAGCACCAA | 166 | intron 48 | 0.941 | 0.9 |
| exon 49 | 295 | CTTGACCTAATTTCAACATCTGG | 118 | TGGGTTCCATAATAGAGTTTCACA | 167 | | >1.075 | |

Figure 10B

ERRORS IN PUBLIC SEQUENCE (differences between samples and Genbank entry AJ012376.1):

| Exon/Intron | Nucleotides | Amino Acid Change | | Sequence difference/context | SEQ ID NO: |
|---|---|---|---|---|---|
| 2 | T150C A152G | no change | Public sequence: Correct sequence: | TGTCAGCTGTTACTGGAAGTGG TGTCAGCTGCTGCTGGAAGTGG | 168 169 |
| 7 | C839T | no change | Public sequence: Correct sequence: | AGGAGCTGGCCGAAGCCACAA AGGAGCTGGCTGAAGCCACAA | 170 171 |
| 33 | C4738T | T1495I | Public sequence: Correct sequence: | AATGATGCCACCAAACAAATG AATGATGCCATCAAACAAATG | 172 173 |
| 35 | C5017T | P1588L | Public sequence: Correct sequence: | GAGGTGGCTCCGATGACCACA GAGGTGGCTCTGATGACCACA | 174 175 |
| 43 | G5995A | R1914K | Public sequence: Correct sequence: | TTCCTTAACAGAAATAGTATC TTCCTTAACAAAAATAGTATC | 176 177 |
| 48 | C6577T | P2108L | Public sequence: Correct sequence: | GGAAGTGTTCCAAAGAGAAA GGAAGTGTTCTAAAAGAGAAA | 178 179 |
| 49 | G6899A | not applicable | Public sequence: Correct sequence: | AGTAAAGAGGACTAGACTTT AGTAAAGAGGAACTAGACTTT | 180 181 |

Mutations:

| Exon/Intron | Nucleotides | Amino Acid Change | | Sequence difference/context | SEQ ID NO: |
|---|---|---|---|---|---|
| 13 | A1864G | Q597R | More common: Less common: | GCCTACTTGCAGGATGTGGTG GCCTACTTGCGGGATGTGGTG | 182 183 |
| 14 | delta CTT 2151-3 | deltaL093 | More common: Less common: | CCTCATTCCTCTCTGTGAGCG CCTCATTCCT/CTTGTGAGCG | 184 185 |
| 15 | G2385A | V771M | More common: Less common: | GCAGGACTACGTGGGCTTCAC GCAGGACTACATGGGCTTCAC | 186 187 |
| 18 | C2799T | R909Stop | More common: Less common: | AAAAGTCTACCGAGATGGGAT AAAAGTCTACTGAGATGGGAT | 188 189 |
| 18 | C2860T | T929I | More common: Less common: | GGCCAGATCACCTCCTTCCTG GGCCAGATCATCTCCTTCCTG | 190 191 |
| 22 | T3346C | M1091T | More common: Less common: | ACACACCACATGGATGAAGCG ACACACCACACGGATGAAGCG | 192 193 |

Figure 11A

| Intron 24 | (+1) G to C splice donor site | Altered transcript lenght | More common: | CCTGAAGAAGTAAGTAAGT | 194 |
|---|---|---|---|---|---|
| | | | Less common: | CCTGAAGAAGAACTAAGTAAGT | 195 |
| 30 | T4503C | C1477R | More common: | GCTGCCTGTGTGTCCCCAGG | 196 |
| | | | Less common: | GCTCCCTGTGCGTCCCCAGG | 197 |
| 35 | GG 4958-57 to C | Frameshift at aa 1628 | More common: | TAGCCATTATGAATTACTGCT | 198 |
| | | | Less common: | TAGCCATTATCAATTACTGCT | 199 |
| 41 | delta AAGATG 5752-7 | delta(E,D)1893-1894 | More common: | GATGAAGATGAAGATGTGAGGCGGGA | 200 |
| | | | Less common: | GATGAAGATG/TGAGGCGGGA | 201 |
| 48 | C6504T | R2144Stop | More common: | AATAGTTGTACGAATAGCAGG | 202 |
| | | | Less common: | AATAGTTGTATGAATAGCAGG | 203 |
| Promoter Variants: Location | Position Relative to Xenon cDNA | Position Realitive to SEQ ID NO: 14 Containing Exon 1 | | | SEQ ID NO: |
| 1 | G57C | 8216 | More common: | ACACGCTGGGGTGCTGGCTG | 204 |
| | | | Less common: | ACACGCTGGGGGTGCTGGCTG | 205 |
| 5 | (-)4 ins, G | 8158 | More common: | GACCAGCCACGGCGTCCCTG | 206 |
| | | | Less common: | GACCAGCCACGGGCGTCCCTG | 207 |
| 5 | A (-)380 G | 7780 | More common: | CATTTCTTAGAAAAGAGAGGT | 208 |
| | | | Less common: | CATTTCTTAGAGAAGAGAGGT | 209 |
| 5 | A (-)479 C | 7681 | More common: | GAAAATTAGTATGTAAGAAG | 210 |
| | | | Less common: | GAAAATTAGTCTGTAAGAAG | 211 |
| 5 | A (-)738 G | 7422 | More common: | CCTCCGCCTGCCAGGTTCAGCGATT | 212 |
| | | | Less common: | CCTCCGCCTGCCGGGTTCAGCGATT | 213 |
| 5 | A (-)1045 G | 7115 | More common: | TATGTGCTGACCATGGGAGCTTGTT | 214 |
| | | | Less common: | TATGTGCTGACCGTGGGAGCTTGTT | 215 |
| 5 | A (-)1113 G | 7047 | More common: | GTGACACCCAACGGAGTAGGG | 216 |
| | | | Less common: | GTGACACCGAGCGGAGTAGGG | 217 |
| 5 | (-)1181 ins, CCCT | 6979 | More common: | AGTATCCCCT/TGTTCACGAGAA | 218 |
| | | | Less common: | AGTATCCCCTCCCTTGTTCACGAGAA | 219 |

Figure 11B

| Polymorphisms: | | | | | |
|---|---|---|---|---|---|
| Exon/Intron | Nucleotides | Amino Acid Change | | Sequence differences/context | SEQ ID NO: |
| 5 | G548A | no change | More common: Less common: | CTGGGTTCCTGTATCACAACC CTGGGTTCCTATATCACAACC | 220 221 |
| 6 | G730A | R219K | More common: Less common: | GGCCTACCAAGGGAGAAACTG GGCCTACCAAAGGAGAAACTG | 222 223 |
| Intron 7 | G(+)2383 T | Not applicable | Allele 1: Allele 2: | TTTAAAGGGGTGATTAGGA TTTAAAGGGGTTGATTAGGA | 224 225 |
| Intron 7 | G(+)3035 T | Not applicable | Allele 1: Allele 2: | GAAGAATTGTTTTTTGATT GAAGAATTTTTTTTTGATT | 226 227 |
| 8 | C1010T | no change | More common: Less common: | GCGGGCATCCGAGGAGGGG GCGGGCATCCTAGGGGAGGGG | 228 229 |
| 8 | G1022A | no change | More common: Less common: | AGGGAGGGGGCTGAAGATCA AGGGAGGGGACTGAAGATCA | 230 231 |
| Intron 9 | (-)42 ins. G | Not applicable | More common: Less common: | AGAGCCAAACGCTCATTGT AGAGCCAAAGGCTCATTGT | 232 233 |
| Intron 13 | T(+)24 A | Not applicable | More common: Less common: | AAGCCACTGTTTTAACCAGT AAGCCACTGTATTTAACCAGT | 234 235 |
| 15 | A2394C | T774P | More common: Less common: | CGTGGGCTTCACACTCAAGAT CGTGGGCTTCCCACTCAAGAT | 236 237 |
| 15 | G2402C | K776N | More common: Less common: | TCACACTCAAGATCTTCGCTG TCACACTCAACATCTTCGCTG | 238 239 |
| Intron 14 | C(+)16 T | Not applicable | Allele 1: Allele 2: | GCAGCCTCACCCGCTCTTCCC GCAGCCTCACTCGCTCTTCCC | 240 241 |
| 17 | A2723G | I883M | Allele 1: Allele 2: | AGAAGAGAATATCAGAAATCT AGAAGAGAATGTCAGAAATCT | 242 243 |
| Intron 17 | C(+)2000 G | Not applicable | Allele 1: Allele 2: | GCGCAGTGCCCTGCGTCCTTA GCGCAGTGCGCTGCGTCCTTA | 244 245 |

Figure 11C

| | | | | SEQ ID NO: |
|---|---|---|---|---|
| 21 | T3233G | no change | More common: GATCTAAGGTTGCATTCTGG<br>Less common: GATCTAAGGTGGTCATTCTGG | 246<br>247 |
| Intron 21 | G(+)118 T | Not applicable | Allele 1: CTCTTCTGTTAGGACAGAAGAGA<br>Allele 2: CTCTTCTGTTATCAGAAGAGA | 248<br>249 |
| Intron 21 | A(+)1563 G | Not applicable | Allele 1: CATTCTAGGGATCATAGCCAT<br>Allele 2: CATTCTAGGGGTCATAGCCAT | 250<br>251 |
| Intron 24 | G(+)321 T | Not applicable | Allele 1: AAGTACAGTGGGAGGAACAGCG<br>Allele 2: AAGTACAGTGTGAGGAACAGCG | 252<br>253 |
| Intron 29 | A(-)1624 G | Not applicable | Allele 1: AATTCCTAAAAATAGAAATGCA<br>Allele 2: AATTCCTAAAAAGTAGAAATGCA | 254<br>255 |
| Intron 31 | T(+)30 C | Not applicable | More common: GGCCCCTGCCTTATTATTACT<br>Less common: GGCCCCTCGCCTATTATTATTACT | 256<br>257 |
| Intron 33 | A(+)732 G | Not applicable | Allele 1: TGAGAGAATTACTTGAACCCGG<br>Allele 2: TGAGAGAATTGCTTGAACCCGG | 258<br>259 |
| Intron 33 | C(+)1898 T | Not applicable | Allele 1: TTTGCTGAAACAATCACTGCA<br>Allele 2: TTTGCTCAAATAATCACTGAC | 260<br>261 |
| Intron 34 | C(+)234 T | Not applicable | Allele 1: AACCTCAGTTCCCTCATCTGTG<br>Allele 2: AACCTCAGTTCCTCATCAGTG | 262<br>263 |
| 34 | G4834A | R158TK | More common: CTGGACACCGAGAAATAATGTC<br>Less common: CTGGACACCGAAATCCGTC | 264<br>265 |
| 37 | C_5266G | S1731C | More common: TCCTATGTGTCCTCCACCAAT<br>Less common: TCCTATGTGCGCTCCACCAT | 266<br>267 |
| Intron 43 | T(+)118 C | Not applicable | More common: AAGAGTGGCTTGTATTTGC<br>Less common: AAGAGTGGCCTGTATTTGC | 268<br>269 |
| Intron 43 | C(+)1665 G | Not applicable | Allele 1: AACTGATTTGATTGGTATAGCTG<br>Allele 2: AACTGATTGTGGTATAGCTG | 270<br>271 |
| 48 | C6521T | no change | More common: CAGGGCTTCCAACCCGGACCTGA<br>Less common: CAGGGCTTCCAATCCGGACCTGA | 272<br>273 |
| Intron 10 | (+)14 ins T | Not applicable | More common: GCGTCAGGGATGGGACAG<br>Less common: GCGTCAGGGATTGGGACAG | 284<br>285 |
| Exon 16 | G2547A | V825I | More common: CCACTTCGGTCTCCATG<br>Less common: CCACTTCGGATCTCCATG | 286<br>287 |
| Polymorphism in an ABC1 BAC contig:<br>This polymorphism is within approximately 200Kb of the ABC1 gene | | | | |
| | A or G | Not applicable | Allele 1: TTGGAGGCTAAGCAGGAGAA<br>Allele 2: TTGGAGGCTCAGGCAGGAGAA | 274<br>275 |

Figure 11D

Genomic contig containing ABC1 exon 1:
Underline = putitive promotor element

```
acctcttatagaatgatagaattcctctggaatgattggataacttcatttcatccttgacttttaccttggaggattt
cttacccctttggcttctcaaatttgactattaaaatgttgcctttaaaaataggaacacagtttcagggggggagtac
cagcccatgacccttctgcaaggccccctaactcaaggtagtttccctggaactgtggtttatggaatgtttcaggagt
gtgaggaggtataatttaaggctgtcctagcaaggatacccttaaggatagagggcccagtagcatctggaggccagaa
aagttaaactgaggcagtcagattagcttcaggctcaattaagctgatgggtcagcctgggagaaattgcaggatgact
ctcaatatcccctcccaccccacagcagccacgatctgtctgtctttaatcatgggtgcagtgaacctgttctttcca
ggtgtcttggccttcagtaaccttgttaggcttgtccctgaacgtggctaccgatccaaagacacatgatcagagaggc
aattagagaacagacctttccaaagcaagcatgttctgttgggcttagaagtttcatgtcctaatattataggaccct
gtgcatctctctggagatgaggcacatgagtcatatctgtgattcttgcttttgtgtcaacatctcatgaataggcaat
cagagcttggcaccaatgtatttcagttcatatctgatgtagttaaatccacctcctgctttgtagtttactggcaa
gctgttttgatataagacatctagaacactgtaaatatataacattttatttgtctattatacctcaattacgaaaa
agacatctagaagcaacctcatcaagagagatactgaggccgggcatggtagctcacacttgcaatcccattactttgg
gaggctgaggcaggtagatcacttgaggtcaagagtttgaaaccagcctggccaacatgttgaaaccctgtctctatta
aaaatacaaaaaagttagctgggcttggtggtgggcacctgtaatcccagctactccggaggctgaggcaggagaatca
cttgaacctgggaggcagaggttgcagtgagctgagatcacaccactgcactccaacctgggcaccagagtgagattac
atctaaaaaataaaataaagtaataaaaaagagagatattgatagctgttgttggaaatttcaacttccatctcacttc
tggtaacttttggaagtttgttgaacaaagtggaatacacgcacatacacacacacacatactctcttgtttgtttaa
ggtttaatgaaatagctgtcatataatcactgtttttgaaagaggagaattagttgctatctgtacatttgggtatgt
gaactatttggatagaactctgagaaatgcattcagaacaacaaacaaaatcataggagaaatagctaagtgggaaggg
gcatataagagttgttgaaaaagttatttcttgagaaaccagctctaatgctaggcaagtcacttgctttgggggaggc
ctcagcttctctgtctataagattgcagcaggggtgtagtgggaatgagtcttcaacattccaagagatttatctact
aatacgacagtcaaatggagcatgactttgtggaagcctctcctcttccacccagaggggccaatttctctgtcccagt
gagatgttgacacttgtatgatccctgcttggagacttccctcttctggaacctgccctggctcaggcatgagggctga
ctgtcacccttcgataggagcccagcactaaagctcatgtgttggcagtgttcttgcgggaaggaaaaagaccagccag
cccatttgttactgcacaagcaaacagcttctggtagctgtacagatacatgcactttctttcctcactgtgtttccat
agacagatttagtgctgtagaagagtagagggcagtcacgggaaggagttcctgtttttcttttggctatgccaaatgg
ggaaaaatcctcctatcttgtctttttagtgtcatcctctctccccttttcttcttctttataattctcatctctcatc
tctcctggaaatgtgcatgtcaagttcaaaagggcacaatgtttggtgaggaagaggtgggagaacacgtgccaggtg
ctaactagggtcatcatttcccccttcacagccagcttcctgtgaatgtgtgtgtgtgtgtgtgtgtgtgtgtgtgt
gtgtgtgtgtgtgtatttctttgccagcatcactgaatctgtctgctgtctggtattccaggttttggtttagggaaa
agtaaaagtaatttataatcccagctgtcatttaagccaccccttgtgggtagcatatggtccactctctcagttca
ttgtcctaaagatgcttcatcagaaaggaataacttccacccccgttactctctgtccccttactctgcttttatttttct
tcgtcaatcctaccaccaccacccactgtttgaacaacccactattatttgtctgtttcccatccctggtagaatagga
gccccatgaatgaaggaactttgcttctgttgttcaccactgaatctctaaggtatggaacacacctggcatgtgatag
gcactcgataaatatttgttgtggctcatgggcaccttgcagagttaaggctgcagttgtttgtggaatttataagtgg
taatgaatatttatctactattcctcttccaaggcgatcacacaataatcaggctttacactatccagttcttaggtct
tccaagttatgacttgtgaggtatgttaattatgataatagaaggcagtttatttggttcagatttattgatgtgtaat
ttaccacagtaagacttcccctttacaaaagtatgatgagttttgacaaatggatacacatgtgtatctaccactgcca
tgctcctttcagtctgtcgtcccctccacccatgaccactggtcaccactgcagtgatttctgtccccttcatttcac
cttttccagaatgtcatataaatggaatcatgcagtatgtagttttttgtgtctggcttatttttcttagcattaggct
tttgggattcatccaggttgtcgcatgtaacagtagcttattccttttatggctgagtaagtgtcccagttttattta
tatatttatttatgaggaggtgtctcactctgtcacccaggctggagtgcggtagcgcgatctcagctcactgcaacct
ccgcctcccaggttcaagcaattctcctgcctcctgagtagctgggattacaggcacccaccgccacgcccaactaatt
tttatatttttagtagagatggggtttcaccatgttggccaggctgatctcaaactcttgacctcaggtgatccgccca
cctctggctcccaaagtgctaggattacaggcatgagccactgtgcccagccccagtttatttattcaccagttgatg
gtcttttcgacaactaattgtttccagttttttggctattctgtataaggcttctataaatattcacaaatacctaggat
gggatgactgggtcatataatagtactgtataaccttagcagaaactgtcaaactattttccaaagtggctcttccatt
ttacaattccacagtgtattgagtcccagtgtctccatacacatgctagcactttttaatatttaatttagtgggtatgt
aatgatatctcattgtggttttaatttgcatttctctgcagctaatgatgagtgtttctgcttatttgggaaggtttta
atttagcagtctgttgtattctgtagatattaataacttcaaaatatcagtggcatttgcagttaaaatttccttaaaa
aattggccaaaggtttccagcagtcacttctgccatgcccaaactgtatgaaacaaggctgaggtgtggagattgtcac
attttggcaaggagtgatccacttgggtgactgatgagacccagagagcgtacgcctcgggcttgagggtgaggacggg
cgggaagtcgactgcatggccctgctggccttgggaggctgcccagtccttagctaaagctggcagttatgggaaacag
```

Figure 12A-(1)

```
acttagattctattacgttttcaggatgtcccaggagtcacctgggaagctcagcagtcctttgtgactttcaagcat
atggtagaagctgctgaacacagagctccctctttggggataatttgcccaaatcatttaatcaggcttgagaaatgag
ttaccacaggtccaggagtgctgccaccccttgaattctgacacccctatttctcctatccgtctcttaattaattaagca
gacatccccaagtgcttacgacaagccaggaccccttttgcatactaaggaaaacagggatgaaggaaacagaaatggtc
tctgctctgactcagaaggtagaaatcctctttcccagccaagtcttcctagggagcacgtaggaagggctctgaaccc
acgtgtcagttgcaggggaggatatcaggaaaggacattgaagaagtggagacctaagtttgagacctaggcattagcc
aggctagcagtgcttgaaaaagtgtcttaggacaagagaactcaccagtgaagtcccagtggtaggagagcgtgcagca
tattctgagcctgtatacacatctccagggcattgcttagcaggtggggagtggcaagagagtaggctggagtcacaga
agggaggccaggtagaccttggtgagcactggactctatgttcaggtgctgaggagctggcaaaaggttttaagtcggg
gagaggcatgttcagatatttggtctagctgagtaactttgggtgctctgtgacaaatggttgggagaccagtgaggtg
gcagttgcggtcatctaggagcaggatcagagtggcctattgactgggatgactgtgaagtgggatcctttccagccag
taactggaaatgtgtatgagggcagaagtgagtgtactgcatttgaaacattgagaaatctagtacatagtactgtctc
ttttatatcttttttttttttttttttgattttggtttgtttgttcactaacttggaaaactgatgtggaaatgtccct
ttggcttcagttacctgagcagaagggggccgggcattgccaaactctcctcttaggacagaattgctcccagtattgat
cattgtgttctgagttgggggagcaaattgtgcaggaggccaggtcagtgccaaggtgggtgggaggaattggagcagg
aagcttgcctaagtgtgcccagcaaagccacggtagaactttctactgtggctctatgctacttcttagcaaccttctc
catgtgcttcctggagagtccttggagtcagaaccttttcttgaaacccagacactttacttccaagaaaatgctgtc
caagaaaactcatccttcccttcttctcatgaacgttgtgtagaggtgtgtcttctcttcctttgagcttttccactca
gggtttaggggaggtgatattctatatttgggtttggctctgggtactgcaacactaggctattaagatttcatcctta
ctgctttgccctcctatctttccagaaaccccacaatggatttgctagaaataatggaacgtcctgtttggacaggata
taaccatttctcagctagaggatattgttggaatgaagaaagataaatggggagaagggaactcacattgctttggcac
ttaaattaagccatgtactgtgttgggaaattatttatattatctcgttgaatccacagtagaacacagttgaacacca
tacaaggtaagtattgtcatccttattttaccatgaggaaattgatgcttagagagcataaagccttggccagggggcac
atagttgggaagccggggctaattcatgcctgggctctttctgatagttttcctttttaattgtcccotcctcattgt
tacctgggggatttcaagagattcatgtagcttctaaatcaacgaactgattcctggagagcagcttctgtatgagaaa
aatctagctaattattatttcagtgtctctggaatgcaagctctgtcctgagccacttagaaaacaatttgggatgac
aagcatgtgtctcacaatgctgctctggttgccagtgctgtgctgccagttgtcatctttgaacaaactgatgcagtgc
tggtttaactcttcctcttttttggagtaagaaacttggaggcctgtgtccttctagaagtttgctgagcaaatggtaa
ggaaaagaaataggtcctaaggcttgactatttcagagaatttcttgatttattggactgtcaatgaatgaattggaat
acatagtggtaggctgtcttttcttctcagacactgcaatttcctccaatctcttgacttttctagaagtttttaatcca
agtccttgttgggtggtagataaaagggtattgttctactagagactgaccttggcatggagatctcatttggactcac
agatttctagtctagcgcttggttttgtatccatacctcgctactgcattcttagttccttctgctccttgttcctcat
gcccagtgtcccaccctacccttgcccctactcctctagaggccacagtgattcactgagccatttcataagcacagct
aggagagttcatggctaccaagtgccagcagggccgaattttcacctgtgtgtcctcccttccattttttcatcttctgc
cccctccccagctttaactttaatataactacttgggactattccagcattaaataagggtaactgctggatgggtggc
tgggatacacagaatgtagtatcccttgttcacgagaagaccttcttgccctagcatggcaaacagtcctccaaggagg
cacctgtgacacccaacggagtagggggggcggtgtgttcaggtgcaggtggaacaaggccagaagtgtgcatatgtgct
gaccatgggagcttgttttgtcggtttcacagttgatgccctgagcctgccatagcagacttgtttctccatgggatgct
gtttttcttccagagacacagcgctagggttgtcctcattacctgagagccaggtgtcggtagcatttttcttggtgttt
actcacactcatctaaggcacgttgtggttttccagattaggaaactgctttattgatggtgctttttttttttttttttt
tgagacagagtctcgctctgtcgccatgctggagtgtagtggcacaatcttggctcactgcacctccgcctgccaggtt
cagcgattctcctgcctcagcctcccaagtagctgggactacaggtgcctgccaccatgcccagctaatttttgtattt
ttagtagagacggggtttcaccgtattggctaggatggtctcgatttcttgacctcgtgatccgcctgcctcggcctcc
caaagtgctgggattataggcttgagccaccacgcctggccgatggtgcttttatcatttgaaggactcagttgtata
acccactgaaaattagtatgtaaggaagttcagggaatagtataagtcactccaggcttgaggcaaaatttacaaatgc
tgctgactttgtatgtaaggggaggcatttcttagaaaagagaggtaggtctctgggattccagtatgccatttccat
cctcagtgttttggccacctgagagaggtctatttcagaaatgcattcttcattcccagatgataacatctatagaa
ctaaaatgattaggaccataacacgtagctcctagcctgctgtcggaacacctcccgagtccctctttgtgggtgaacc
cagaggctgggagctggtgactcatgatccattgagaagcagtcatgatgcagagctgtgtgttggaggtctcagctga
gagggctggattagcagtcctcattggtgtatggctttgcagcaataactgatggctgttttccctcctgctttatctt
tcagttaatgaccagccacggcGTCCCTGCTGTGAGCTCTGGCCGCTGCCTTCCAGGGCTCCCGAGCCACACGCTGGGG
GTGCTGGCTGAGGGAACATGGCTTGTTGGCCTCAGCTGAGGTTGCTGCTGTGGAAGAACCTCACTTTCAGAAGAAGACA
AACAgtaagcttgggtttttcagcagcggggggttctctcattttttctttgtggttttgagttggggattggaggagg
```

Figure 12A-(2)

```
gagggagggaaggaagctgtgttggttttcacacagggattgatggaatctggctcttatggacacagaactgtgtggt
ccggatatggcatgtggcttatcatagagggcagatttgcagccaggtagaaatagtagctttggtttgtgctactgcc
caggcatgagttctgatccctaggacctggctccgaatcgccctgagcacccacttttttccttttgctgcagccctg
ggaccacctggctctccaaaagcccctaatgggcccctgtatttctggaagctgtgggtgaagtgagttagtggcccca
ctcttagagatcaatactgggtatcttggtgtcaatctggattctttccttcaggcctggaggaatataataactgaga
cttgttttatttctgcagagggttctaagccattcacttcccagatgggccaataatgctttgagtaatctggagatca
tctttaatgcgcaggtgaatggaactcttccacagagggatgtgagggctgtagagcagagtgaactccctgaaactca
gacgtcagctctttgtctctctatctctgaacacccttccttagagatcccatctctaggatgcatttctctgtagtta
gtttctaagtctcttgttcctgttctgcctttattttttttcctggattctaagccagtatccccacttggctgtctt
aatgtagcttaacatgtctgtaatcaaaatgatcatctttctgagattcaaagggctataagggactttggagagaatt
tcattcagttttcctcaaactagaataatgcttgcactgtctgtaaaagaacaaaagtgtcaaagcatcctttgttca
ctaaatttccttttttattatagtgttacttaaatattaggaagttaaaagtaggtataaacttcttataggctgttat
tatacaactatatgacccatacatatttacaaattaagtgcagccaaaattgcaaaatcaataccattcaaattaatac
cttaaatgtggtgaggcagctgttgttcaactgaaaccaaattataagttgcatggcagtaaatgctatcatgctgatc
attttgagtttggccagtctatattatcatgtgctaatgattgaattctccacccatttttctacttgtatgaccttaa
tttgatggcacctgttccatcctcatgagtttgctacaattatactggtgccaacacaatcataaacacaaatataaac
ttgggctttgaaatcttgtgccagaacttggctttaaagtaagcatttaaaaaatccatatgtgtttattagactttgt
ttagatgactgttgaaatgaaaacaaagtgtttaaaatcctcttagagaacttaaatataatccctcagcaatatgtat
acagatcttcctttgagaaaaactgattgtgttcagcctctcatgttacaaatggggaacctgaattctgaggtctcta
gtgagagaacagggactggaatctgtggatcctatctgttttaataataattgtaaagtataatagataatattatatt
aaaaagagagnnnnnnacacttagaatgagcttccatgtgtgaggcactaactgattaggcattattaactagatttat
tccttttaaggccccgcgatgtactgttatttccacatgttgtagctggggaacgtgctactcagagaggttaagtaac
ttgtctgaggtccacaccactaacaaggagcacaggtagggttcaaatccagataatctgactttggagctggcactct
aactcaatgtgcctaatcgcttttcagtggtgtcattattttgcctattctccatctgagaatattgaagtttctgact
ccttccttgcctttctccctgcctcccgtggttatccccaggtcttggtgttccagtcctctatgtccgtccttactct
tattcctttgctacagtgtgatccagggctcctgcccttcttatcctggtagagggggcccacttgctgggaaattgtc
tccgccatggtttatccatgttgtgtgtccattagtgagtagtgggaagaatcatatcatgttggcaatgaaagggggg
ctatggctctggggtagtctagtctgaactcttattt
```

Figure 12A-(3)

SEQ ID NO: 15
Genomic contig containing ABC1 exon 2:

```
ctttttttttttttttttttttttttttttttgaggtgaagtctcactctgttgcccaggctggagtgcaatggagcgatc
ttggctcaccccaacctctgtctcctgggttcaaacagttctcctgcctcagcctcccgagtagctgggattacaggctc
ccgccaccatgcccagctatttttttgtattttcagtagagatggggtttcacccttttgaccaggctggtcttgaactc
ctgacctcatgatcaacccacctcagcctcccaaagtgctgggattacaggtgtgagccaccacgcccggcctcataagt
attttctaaatttatttacagtcatgccatttaaaaggaaagttgtattcctgtctttgttaatatttataagtgatttt
attcagctacaagcttggaatggcatataatttgtattctgcttttttcacttaatattacatggctaatgatttctgt
gtttcataaacattattctgatgatggcatgatatattgttgagtacatgtaccataattgaatcatttccctattgcta
tgcaattaagttgtttccaatattttgcaattataatgtttcaatgaatgaataactttatgcatatagcttttgatat
cttaagttcagtttcctaggatgaatttccaggaatagtatttcgtgttcattatcttttaaaccagctcatttactcacc
gttaacattgctttcccaaagggctcaactgatttatatttcgtgttcattatcttttaaaccagctcatttactcacc
aaacattttaaagccattatcatgtggtaggcttagtaagaagaaagtgaccctaagggagaagcttatatataaatag
ggtccctggtgtaccaagtgctgatacagacacaaagtacctggggaaattgagatgagggagtcctggctcagctggga
gaaaagttcattttcatagagtcatggttttgttctttggcagaaagaaaattgctttcttccccacccccaccccage
tttattgaggtataattgacaaataaaaattgtatatctttaagatatgcaatgtgatatatatgtatatctcaacttaa
aaaataagctacagaataaaaaggtgtttgctattaaaaaaaaagaaaaaggctgaatgtcattcccaagcttggaaattt
gagtatgttgcctctttgggattatttacagaaatattagcaagaccagccccatctttggtcttgagtactccactgtc
agcatgctttcttccagagagggatccatttgcctttatttttcattctgttgtgccgtctatgcaaactattcttgata
gttttatggtaacagtgttttttgttccatgagataaatttatacatgctcattgtggaaaatttagaaaagacaggaa
agtattaaaaacatcmcyttttttttttttttttttttttttttttamgcagacagagtcttgctctgtcgcccaggcc
ggagtgcagtggcgtgatctcagctcacagcaacctccgcttcccaggtttaagtgattctcctgcctcagcctcccaag
tagctgggagtacaggcatgcaccaccacgcccggctaattttgtattttagtagagatggggtttcaccatgttggcc
aggctggtctcaaactcctgacctcaggtgatccgcctgccttggcctcgcaaagttctgggattataggcaggagccac
tgcgccagccacacctacgttcttatcatcctagtacatccactgtcattatcttgctgtatttccttctgcccagtctc
actctgatcatgcagtggcgtgatcatgcagtgatctcggctcactgcaacctaggccttctgggttcgagtgattctcc
tgccttagcctcctgggttcaagtgattctcttgccttggcctccaagtagctgggattacaggcatacacccccatgc
ccatctaatttttgtattttagtagacacagcgtttcactataaaatttgtattttagtagagatggggtttcaccatg
ttggccaggctggtctccaactcctgacctcaggtgatccgcctgccttggcctcacaaagtgattacaggcatgagcca
ctgcatccatcgccaaaaagatttttaaaagagtttaatgtagaaccatatcaaaggtctttggaaataaaaaacagtt
ttttaaaaaatatcagaaataaaacaacaaataaataaataaataccccaaaacaatctgaagcacgagcacctag
cagaaaggttcaattatgatctattcatagagtggaatatcaagtagacattacaggacatgttttaagattatattta
tgtcatgggaaatgctctcccagtatgatgttaaatgaaaaaacagaatacaaaagtatatatgctgcatagtctcaata
ttgtagagaaaaatattatttatgtatgcatgaaaaaagacaaaagatgttaacagagatccattgttacttcagttta
ctagggattgtctctgggaggtaggattaaggtgatttatatttacctttttaaactttttctgtatttttttattttcaa
attttccataaaaatataaggacttgaagatcaagaaaaaatttctgctttggctcagtgcagtcgtcacgcctgtaatc
ccagcagtttgggagccctaggggagaggatcacttgaacccaagagtttgacgttccagtgagctatgatctccggatc
gtaccgcctggacgatggagcaagaccctgtctcaaaaaaaaaatctttgctttttttttttgtttgttttgagacgg
agtctctctctgttgcccagctggagtacagtggcacatgcacccaccactatgcccagctacttttttgtattttcagta
ttctcttgcctcagcctcccaagtacctgggattccatgcacccaccactatgcccagctacttttttgtattttcagta
gagacagggtttcaccatgttggccaggctggtctcgaattcctgacctcagctgatccaccggccttggcctcccaaag
tgctgggattacaggcatgagccactgtgcccagcccaatctttgcttttttaaaaaagaagacaaaagggatttt
ataccagtattatcttggctgtgtgactctgaagccacagttgtaagttataattactctgaaacacaaggccctgtgac
tcttttgggctctttggtgtttatcttgattacaacgttggaatatagaaatgaaaggaatgggagaggtgatagacttc
aggcagtgtaactagttgtctgaacactactggctcaattatattgtgtctagtgatttccatcttgtccgtctgctaat
ttatcgcctggtaactcactgaggcagggttttcctttggagaaacctcattgttttaaccagtgtatcatgcttgttta
gaagttcaatgatctttttaactcatcggagaagatgatgaccagacctggacagatggggaaggactttgcactctctc
tttacagtcctgagtgcacacaggtcaatatggaactatgtgtgaatttcattgtctttgagagccctcttctctgccc
catagggagcagctttgtgtgcaattagaggagcaagggttgtgtgtatttagcacagcaggttggcctggtcctctcct
ctcaacatagtcaccacatacctggcactatgctaaggctgggaatgcagacagatgggtgcctgctttcagagtgctca
atgtgctgaggaagccagcaacagaaacagatgatttcaggagctccaggaaaatgctacaggaggagtgtgcctgggtt
```

Figure 12B - (1)

actggagtagcacaggaggagggcttctagctcaggctgagatttagtaaaggaaattatgccacgatgaatcctgaag
aatgaatagaagtgaaccagataaagcacgataggaagcatcttcccttacctaagggaagacacagaggtatatggaat
ggtatgttaaaaggttgggactccaaacagttctgttaaagcttagagagtggtgggagagactggagaagttgattaat
tagtaaatgaagttgtctgtggatttcccagatcccagtggcattggatatccatattattttaaatttacagtgttct
atcttatttcccactcagTGTCAGCTGCTGCTGGAAGTGGCCTGGCCTCTATTTATCTTCCTGATCCTGATCTCTGTTCG
GCTGAGCTACCCACCCTATGAACAACATGAATgtaagtaactgtggatgttgcctgagactcaccaatggcagggaaaat
ccaggcaattaacgtgggctaaattggacttttccaaagatgctgtctttgggaaacatcacacatgctttggatcagaa
aacctaggcttctaatttgttgataaggcatgaactcaggagactgttttcagtcctagtgaatggtgataattgtaatt
ataacagtagacaacatctcttttacacattttaaatcatgaaaatagaataaccttactgataatttagaaagtggtg
attaaaagcacatttaagataatgccttaacacctagtcttttccatatgcatgatgtcttaatcacacattgcaaatca
tggaacacagaatttt

Figure 12B - (2)

SEQ ID NO 16
Genomic contig containing ABC1 exon 3:
atcttacaatcacagtctttctcttagggctgggctcagtgggtggattgacactgcagaaatggccagatctaaaggat
caacatttacgtagctgggaaatgtagctgggacttcagtttcactgccctagtgattttcctaccactaagcagctca
gtccatacccctacgagacccacaagcttatgagatactgttcttccaggaaagcagtggggccagggccacctttaat
tgtgtttcttggcctggtccatctttctcacaatatatagcaacagttatttacttgctgattttctaatgcacatcac
acatagtcatattaaacacacacacacacacacacacacaccccctcaagaaacatttctgagacgtgatttcc
tgatttcatcaaaaagaaaagagcgggccaggcacagtgggaagtcaaggtgggtggatcacttgaggtcaggagtttg
aaaccagcctggccaacacggtggaacctcgtctctactaaaaatacaaaaattagccaggcgtggtggcgcacacctgt
aatcccagctactggggaggctgaggcaggagaattgcttcaacctgcgaggctgaggttgcagtgagccgagattgcgc
cattgcactccagcctgggcaacagagtgagactctgtctcaaaaaaaaaaaaaaaaaaagcataaactgaaattta
tatgcaatttatatgcctgtgagataattctgttttctcttttggaaccccaaagagatttttttgattgatgagcaaat
acattttagattttatttaagcattatgccaagcaccactgaagtataagtttcaagggcaaactcagttttttcatcta
ctagacgaatgatttctggaatgattacaagcaggcaagatggtgtagtggaaatagcaaatgtcttcggcatcagaca
agttgggggtttgtttgtatcctgcctctgcccttcaccgaggttgtgatcttgggcagattgttgagttttaacctagat
tcctctgactccagatcataaattttcagaaaagttctgaaattcttgtatatactgatggtaaatgagacttttcctta
catctatgcacttctttgtttgtttgttttgagatggtcttgctctgttgcccagactggagtgcagtagtgcaatctcc
gctcactacaatgtctgcctcccaggttccagtgagcctcctgcctcagcctcccaaatagctgagactacaggcatgtg
ccaccacgtccggctaatttttgtattttagtagagacaggggttttgccatgttgaccacactggtctcgaactcctgg
cctcaggtgattcgcccgcctcagcctcccaaagtgctgggattacaggcatgagccaccatgcccggccatatccatgc
acttcttgcaaccttaccttcttttctcatcaccctccagggacctagttggaagagcagagttaaaagttaaggtgaaa
cttggagaggtgtcttgtccctaggaacaaaggactggtttgaaattctctgtaaatcttcccagttcaaaccagagtt
atcaaggtcttaaaaacttccctgggtcctgagagcccattatattatttacttgtcttcctgtacacccactgcctagt
cctgatcctacttttgtttgcaataggatggggcacaacgtacaaggaagggcctttgccacccctgctaagggataac
ctgaaataccttcaccatcactgccctgtgctgcttttcacctatgccagtctgtctacagtgccagtgtctcctggcat
tgaaaggggagaatctttggtcctttgagtatttggttgggttacataaatctccctgaatgaagagcagctgacttag
gcaagggccttgtttggttttccttgaactattaacaggaagatagggagattaactgtgtaaatgttcaataggccag
agtccctgcagagggtggccacagtgatcagatcttatcacatccttgctttgggtgttgcctctctggttggagtatgg
atagaaaagaaagaaagacccctatattgaaatgcaaagtgcagcaagtcctgactttggattaacttctcagcccatttg
catgaaaataaaaagatgaataaaacaaggttcccactttggagggaggtggtagctgtgagatggaaggagtgttcctg
ctgggcaacagcagagtaagtgctggggtagattcactcccacagtgcctggaaaatcctcataggctcatttgttgagt
ctttgtcctacaccaggcactctgcaaaaacgctttgcctgcaaggtctcatgcgatgctcaccacagctctgtgaagtt
aattgtactttatcaccatttacagatgagaaaactgagggtatggggtcaatgacttggctaaagtcactgcttagc
aagctgcagggactggatgtgaattccaattggtttgactccaaagcctgtgaagctacttgttcttcaccacctagagc
tgtggttcttgataactgtgaactcttttggggtcacaaatagccctgagaatatgatagaagcaggagctctggcctt
ctgtccatacctgaacaggtccttgggttaagagccctcgtccagggcctattaatcttgatcctcataagcagcatcc
atgtattacggccgcaaaccaaactgtgccagaccgaatcctaggaccaagcccaaatatgtccatcatccttttggta
agaagctcattgtaagaaagaaagaggagagcaagaggatgacctagtgcatggggcctcattgttttaattagtgacaa
aacaacaataacaacaaaaccccgaagcttcacagatgacatcagacccaagcctgtgtgttttcaggtgccct
tgaggagctttgtagctggcagaggaggtgaaactgacaaatgtttggcagatggaggagagtaccagaggggtttgaga
tgagctaaattccaatctaaccgcagtgttgaggaagaggcttggattgggaccatggagatgggggttctactcccagt
cacgccagctgactttgcgagtgttctttgtcagtcactttatcttattttatttattttttatttttttgaaatggagtt
tcgctcttgtcgcccaggctggagtgaaatggcgcgatcttggctcactgcaacctccccctcctgagttcaagcgattc
tcctgcctcagcctccagagtacctgggattacaggcgcctgccaccaagcccatcgattttgtatgcttagtagaga

Figure 12C - (1)

```
cagggtttcgccatgttggccagggtggtcttgaactcctgacctcaggtgatccgcccaccttggcctcccaaagtgct
gggattacaggcgcgagccactgtgcccagcccacttcatcttaccgtagttacctccttagagtatgaaaaaataggct
tagggcatccccaagtcccctctatgtctgagagctgaggctggctgtcaaagaggaactaaggatgccagggactttct
gcttaggacccctctcatcacttctccaacgctggtatcatgaacccattctacagatgatgtccactagattaagaat
ggcatgtgaggccaagtttccacctgagagtcagttttattcagaagagacaggtctctgggatgtggggaatgggacgg
acagacttggcatgaagcattgtataaatggagcctcaaaatcgcttcagggaattaatgtttctccctgtgtttttcta
ctcctcgatttcaacagGCCATTTTCCAAATAAAGCCATGCCCTCTGCAGGAACACTTCCTTGGGTTCAGGGGATTATCT
GTAATGCCAACAACCCCTGTTTCCGTTACCCGACTCCTGGGGAGGCTCCCGGAGTTGTTGGAAACTTTAACAAATCCATg
taagtatcagatcaggttttctttccaaacttgtcagttaatccttttccttcctttcttgtcctctggagaattttgaa
tggctggatttaagtgaagttgttttttgtaaatgcttgtgtgatagagtctgcagaatgagggaagggagaattttggag
aatttggggtatttggggtatccatcacctcgagtatttatcatttctgtatgttgtgaacatttcaagtcctgtctgct
agctattttggaatatactatatgttgttaatgatatcatgcagcagacgtgcatctgaatgggctggctctaggagcta
gagggtaggggctggcacaaagatgcatgctggaagggtccttgcccataagaagcttacagccaaggctaggggagttc
tgtcttctctgcatcaggtcacctctctcacctctgtcactgcccatcagactacaatgtctgcaggtctttctcccct
gagtgtgagctccctgagcaaagcaggatgctgccccttcccttgtattccttgctccttgcttcagtgcctgtacata
agtatgggcataataagtgtcccccaaatgagacattgaggattcttcaaatgcacaggaccgtgatgtgagttaggacg
gagtaaggacgatgggatgtggctcatgacaatcctgaggaagctgcagctgcggcacgcagggccacactgtcatgttc
atggaccctagactggctttgtagcctccatgggccccttccatacac
```

Figure 12C - (2)

SEQ ID NO 17
Genomic contig containing ABC1 exon 4:

tcatgactgccattggtataaagatgaatataatccagaccagattcatgattattcatacattttagtgtattaactt
ttaattctgcttttaaaataaattaaaacattctaatatgcccttaagagtatcccagcccaggccactgagcctactgt
ggttcatggataagtttgcccctgggggcatgtgtgtgcatgcatgtgtgtgcacatgcatgatgagccgggccttgaag
ggtggtaagatttgggtgtgtagaccaatggagaaaggcatttggggcagtgatgatgggtgggggagggaacatggtga
tgaatggagctgggtgtggggagccatgggagtgggttagggccagcctgtggaggacctgggagccaggctgagttcta
tgcacttggcagtcacttctgtaaagcagcagaggcagttggcctagctaaagcctttcgccttttcttgcaccctttac
agTGTGGCTCGCCTGTTCTCAGATGCTCGGAGGCTTCTTTTATACAGCCAGAAAGACACCAGCATGAAGGACATGCGCAA
AGTTCTGAGAACATTACAGCAGATCAAGAAATCCAGCTCAAgtaagtaaaaaccttctctgcatccgtttataattggaa
attgacctgcaccagggaaagagagtagcccaggtgtctggggcttgttcccattagatcttccccaagggggtttttctc
cttggtggctggcctgtggggcccctctccaggaggcattggtgaagaaactaggggagctggttgccacagacagtgat
gtactaatcttctctgggaagacagaagaaaagtccccagggaagaatactacagacttggccttagggacagctagggg
tgcagattgctgccaactgcattttttctgaagttggccatatggttgcagtgaatggatttatagacagagtatttctg
tgcatataagagcaattacagttgtaagttgatatggataagtgaaagttaagcacttctttctaaaaagagaatgcaat
tcattttcccctaatcatttcaattagtctgatgggcatttgaacttgttgtctttaaaaagtgaaatctttacctctga
tctggtaagtatccaggcaatttcttgtgtgccacccaggaggtatctggggagtgggcattttctgactgaggcattgg
ctgccatagcatcagagcagccttccaggcagtggcctggcaaggggacagaggctggtgggagcagctggctgagtgca
gccagtaatggcatgt

Figure 12D

SEQ ID NO 18
Genomic contig containing ABC1 exon 5:

agctctccaggtgattctgatgcatacttaagtttgagaaccattgcttgttttgcattaaacaggagattagtctctgc
agcttgtgggaataaagctttaaatctctccaattttagctctgtgaaaaggcagtggggagacaggaatgaacggacta
gtgccacaaagctcaggtggggtgggtgagatcatttagaagagaaagaccgggcatggtggctcacgcctgtactgtca
gcactttgggaggccaaggcaggttggatcacaaggtcaggagtttgagaccagcctgcctatcatggtgaaaccctgtc
tgtactaaagataaaaaaaaaaaatttgccagtcatggtgatgcatacctgtaatcccagctactcgggaggctgaggc
aggagaatctcttgaacccgggaggcgggggttgcagtgagctgagattccaccattgcactccaacctaggtgacaggg
tgagactccgtctcaaaataaaaaaaaaaaaagaaaaggaaaggctgtgtgtgtgtgtatgtgtgtgtgtgtgtgtgtgt
gtgtgtgtaacagcaccatcacactgtttgagttgaggagcacatgctgagtgtggctcaacatgttaccagaaagcaat
attttcatgcctctcctgatatggcgatgctcccctatctcattcctgtgtgtgtttagccaggcaactgttgatcatca
atattatgataacgtttctccactgtcccattgtgcccactttttttttttttttgagttacttactaaataaaaataaa
acactatttctcaatagACTTGAAGCTTCAAGATTTCCTGGTGGACAATGAAACCTTCTCTGGGTTCCTGTATCACAACC
TCTCTCTCCCAAAGTCTACTGTGGACAAGATGCTGAGGGCTGATGTCATTCTCCACAAGgtaagctgatgcctccagctt
cctcagtagggctgatggcaattacgttgtgcagctactggaaagaaatgaataaacccttgtccttgtaatggtggtga
aggggagggaggtagtttgaatacaacttcacttaatttacttccctattcaggcaggaattgccaaaccatccaggag
tggaatatgcaacctggcgtcatgggccagctggttaaaataaaattgatttctggcttatcacttggcatttgtgatga
tttcctcctacaagggatacattttaagttgagttaaacttaaaaaatattcacagttctgaggcaataaccgtggttaa
gggttattgatctggaggagctctgtctaaaaaattgaggacaggagactttagacaagggtgtatttggagacttttaa
gaattttataaaataagggctggacgcagtggcactgagttgagaactgttgcttgctttgcattaaataggagatcagt
ccctgcagcttgtgggaataaggctttaaatctctccaattttagctctgtgagatggcactggggaaacagaaatgaac
ggactagtgtcacaaagctcaggtgggatggacgagatcacttcaaaggtctgtaatcccacgtctataatcccagcact
ttgggaggccaaggcgggaaaatcacttgaggtcaggagttcgagaccatcctggccaacaatgcaaagcctgtctctac
taaaaatatgaaaattagctcagcgtggtggcatgctcctgtagtcccagctactcgtgaggctgagacaggagaatcgt
ttgaacctgggaggcggaggttgcagtgagccaatatcacgccattgcactccagcctggctgacagagtgagactccat
ctcaaaaaaaaaaaaaaaaaaagaatttttataaaatcaggaaataatattagtgtttatgttgaatttttaactttagaat
catagaaaacttcctctggcatcattattagacagctcttgtgcagtgggtagcaccagacccagcttgcatggttattg
attttcagagacactttttgagcttattctctggcagaaaggggaactgcttcctcccctatctcgtgtctgcatacta
gcttgtctttacaagaagcagaagtagtggaaatgtttattcttgaaaataagcttttttgcttcacatgatctagaattt
ttaaaattagaaaaatgtgcttactgcg

Figure 12E

SEQ ID NO 19
Genomic contig containing ABC1 exon 6:

agtaaaatggagaattccaaattctgaaattgttagaacatagttctgtgtcttagttaaatatcgacacttacagataa
atagcataaatgctttctccccatatttcagcccagtcctacttaaagacaacataaattgcaaaatagtgaggatgttg
ttcatctaataaaagtggttccaggaattcagactctggattcctgtttgccaaatcatgtgtcccactcttaagaaaac
gagttggactntggatttttctttgcaagagggacaagagtgtgggagatactgagttaatgcaacttgcaggttttaag
tgtcctgtcattgtgccttgtgctttgatacattctgagtttcagtaaagagacctgatgcattggactgttgcaatgga
acctgttttaagatcttcaaagctgtattgatatgaagttctccaaaagacttcaaggacccagcttccaatcttcataa
tcctcttgtgcttgtctctctttgcatgaaatgcttccagGTATTTTTGCAAGGCTACCAGTTACATTTGACAAGTCTGT
GCAATGGATCAAAATCAGAAGAGATGATTCAACTTGGTGACCAAGAAGTTTCTGAGCTTTGTGGCCTACCAAGGGAGAAA
CTGGCTGCAGCAGAGCGAGTACTTCGTTCCAACATGGACATCCTGAAGCCAATCCTGgtgagtagacttgctcactggag
aaacttcaagcactaatgctttcggaatgtgaggcttttccttggacagcatgactttgttttgtagaaaagtacggctg
gctgggagtttgtgatataatttagttcagtggtattctaagtgttcttagtgttctttcagactttgggccatctccc
aaagggtgaatgggaagaataagctgggtgtggctgagtttaagccaaaagttttttgtgcttgtttcaatcagagaaga
cctgcttttcatgtttttactattataatactaagcaagagctcatttgaaaacagagttcttcatatttaaaaaaaaa
aagtcttgaaaccattgatgggaagatggatatctatttatgtttaaaaacccatcataaagatgacattgtgggctgtc
acagttggaaggccctggaattagatgagaccacactatttagcttacttagtaataacattg

Figure 12F

SEQ ID NO 20
Genomic contig containing ABC1 exon 8:

```
ccgtttggcaaatgctcagtaaaagaaaaggggttagaaggggagaaaggcatttatcccaagccttcaggaatcaggat
gaggatgtcttcaccttgtggtggggagtaattatacaattagagacagcacattggagtgtggctgatatgctgtgtga
tgatagctctagctctctgcctagcagaggaaggacatttcaatagaagaaaaagtttaagaccttgccgagaaacagag
aaaggatgtttgtcttttttaagaagttgaaaaccctgtttgcagacaaaagccctccagttttggcagtaaactttcatg
caagggaagaaaaaggcaggggatgacattgttgacaattgtgaggaattaccatgtgccaggcactgtgcgagggggctt
tgtacatatcctctagttttagtgcttataaaaactctgtgatatgtgcacagcatttttaaactttgctgcatagtcgag
aaaatggaaggatggggaatttgagtcatttgcccagggttctatagctaccccaggttcccatgactggagaattgggg
cacagggtggcgggggagagtgagtgacaagaatcctaacaatcttatttccattgagtccttataaaagaagtggatta
actaccacgttttttaagttttttcttaaatttaggttatgtggatctggcgtttcttgttttgtcctgggtttgttttgtt
tttgctatgctgtcttgaacatctgtcatcttgtaggcctaacggtaaacacaaaaacactttacctcctatagctttca
attaagatctctcagtttgtgtttgtaatagttttccaggcaagttctccctaggttcggcttctagtgtgttaacctttt
agttataaagtgaacccaaagagagaaagtagaaacaaaacacctcacctgtttttgctcatgaattactctctatggaa
ggaacaatcatgaacacctctgcgtatcacagaggcctatctgagtctgacgtttaagggagaccgcgtaggtccctttg
aggactgtgaatgtgggagtcctgggactctggtgaagaacccgttccagaagagatgaatgagctggacaagttctttc
atagaaccctttaggcaggttttcttagaaatgcacattgaggattatgcttggatattgtgatgatcagaatgatactca
atcccttctgcatttggaattctctttgaaagaaaacatcccaggcagctatttctcagagatagtgagtcccagccact
tctagacatttttcttgtgtagtctacattataatttcacagcagtctctgatatgacaaatgtcaaaatagcccaaccttt
ctctaaacttcagagatgtctgatatgatattgaataaaaacaatgctcatagaaacatcaagaaaggtggattttccctg
gatactttttttcctgcttgacaaataacagtgaagaaactgatctcacgtcttttttctctttggaagcctgaacactcag
aacccaacttgaggctcctcagctatagcaattctgacttcacagtctgtaaattattgttcttttttttcttagctta
tgctttctgccctaattttatcttttccctgttctaatgaattattgtcctatatctgctgtgcagttaggtgacatataa
cagcaattaaatatatgaattggtacatataaagatttgactaaaactcgatgtaaaaataagtgttctacattcaattt
ccagtgttagaaacagtgctgacttgaacagagtgacagaattccatctttccctattttttgacagctttaaactttata
ttttcttcctttcttgtgagccgtcattaacttgtttctcaaagccattcccgtattacccatcttgcagacgcagacag
atttgggaatttgcggtcagagttgtattggacacatccccccagcccacatgagatccttttaatctattgcatattaa
ctagttttaagtacaatattcctacttcattttaaaaccattaatcaaagaatgagtttgaaaatgaacaaaatgcaaact
tacagttagaaataattgtagtgtctttagttttggttaggagtcggttttcttgtttgttaaactcaagattgtgaacag
ttttaattcacttgttttatttccaatagagatttcaggtttacatttgaattcagaaacaaagttttctttctcattaca
gAGAACACTAAACTCTACATCTCCCTTCCCGAGCAAGGAGCTGGCCGAAGCCACAAAAACATTGCTGCATAGTCTTGGGA
CTCTGGCCCAGGAGgtaagttgtgtctttccagtaccaggaagcggatcatccactgtatcagtattttcattcctgagt
ctggcaagaggtccttttgagttgaatatcacatgggatgtaatatcaattttcaaagtataagtgatgtaaacaataat
gttttgatttccttatttttagaaatgaagaaacctaaaactcatagatgtctcagagctaattggttagtggctaacagc
tggatatctagtttagaaccttctccattttttcttttgccctaggtaatcatacatttgtaaagaggagaattatct
ctgccactgcccatgcactgcttttgtctgaccagcaatttctccatattgcttcttcagtagcaaggccaatcattta
ccaacacacatgcttgctaactaacaggaataacgtggtacccctaattcagccctttcccttgaaagcatctggcttct
gaggttcaactatgggaatatggtctcttaatgaacattaagttgagtttgccttttaggtccacatgttgacaaatgta
tcagagtaatctctgtcctaggatcagagggcctgtaggcacttgcaaaagcagttagctctgactcccagccagtgcac
actccacctttctgactcccagccttgtctcaaattaggcttggaagcgaggaactgtctggtgtccccagcataggaa
gctgagccaggggcagtgctcacaaacaatacagactttaacgtgtaggatattggaaaataataatttgtggggaaat
tgtctcagacttggtccaccctatttttagctgcttctctaatccgtttttctttttttggtgcttgtatctaacctac
ccattttttggtgcttgcatcatttttcaaatatcaaaaacgaactttatgttttctaacaatgaaagtattgcatgtt
cattgtggaaaatgctgaagacttggaaaatacaaaaatgctgagatcaaacactattgatacgttagtgtatttcttcc
tgtcctgttctactttctttctttgaattctgctcacgtgtttctgactgatgaggtctgacttttgggttccttttcca
gaggagaagccttctttcagcttgccatttgttaccctggttatgaaggctggtaacctttttactaggtagagaagct
```

Figure 12G - (1)

```
ggaccaactgggggttcttccaggggggagaatgagaaagagaaactgttttgcaagtccgtagctatttctctagggccct
gttagctgacattgacatgccttgcattgctctgcagatccctcgcagccctctgtcccttgttcatttctggccttag
agaaagcaaagcagggtctgtaacaggggggaggctgcctctaaactcagggtttggttacagctgttttcacttacatcac
tggccctggttttttttttttttctggcattaaaaaaaaaaaattggaagcaggtgatgttcccattgctgatgtggtgga
aactctccaagtgaacaatatacgttttcttggcagctgtttcttgtgccctgcttgctcctggtccaggacaagcaag
gaccatctgcctctttcaatagaacacctccagatcccttttgatcaaaagttactcattgtctgacttgctatttctgtg
agataaatgggagaagatcaataaatgcacttgtttgtccagtcagcgtgtggaaagttgataattttgaccaaagcaca
accctgaaaggaaaagaaaaagggagtgaatgtcttctgagaagctgcctaggttcagacagtgtcacccatttccctgt
atgctccacatgacaaacctgagtgggtctcatcatgtccattttgcagatggcaccaaggctcagaaaggttaggcaac
ttttccagtcacccaatgagttaattgacaaaactgggattcaaacccagaactgttggattccaaagcctgtgttgttg
cctgcttcgtgaaaaactccagtagcgactggaatagaaaggagaaccttccaagaaagaaaatacgcactagcagaacc
tggaaattgggaggaaatgaggacttgaggaataagatgaatgaaagctgacctgagtttcacacctgggtgatgggaag
ggaggacagggaggcagcatctcagatgtccacccagcaccgaccagctgcctggcattgctaggtgttgaggactcagc
agtgaacacgctaacttctctgctttcttggggcacgtatagggtgagagacagaaacaaacaggtcagtgtacaatgcc
acaggagggatatatgcagtgaagaaaaagcagggtaaggggcatagagcatgagaaggtgcttttttttaaagggktga
ttaggaaagctctctctaaggtgacagttggacctgaaggagatgatagcatgtctgtggtgagggaaggaaactccgaa
caggaagaatggcagatacaaagacattgatgctagagcatgcctaaggaatgtgtttaaggaccagggaaagtgagcaa
gtggtggggggaggagaggagctcagagcaggaggaggtgagtgccatacaggcctggcaagactttggattcctgctgg
gtgagatgagaatccagcggagggcttgagggaggggacatgatgtgatctagagtttagactgtttacactctggttgt
tgggttgagaagagactgggatgggggaaagggaggacaaaggacattgtgctggattgagaaagcagtaagtcagtttc
attcattcactcaaccgatgatgttcaaataccaccatcatccgtgggctaaaggatgaagagccatccctccctgagag
tcaggaagcacttcccagataaagtttggagtgtgagctgaggtgtaggagaaagagtaagagtttaccccctgaaacggg
tgctgggaagagtcaatagtttggaataactcaataatttatggtgcttctttagaaagatttgctggctttatgtggga
agaaatttktttttttgattggggagtggtgggttggtggtgaggctgcctgtgaaagagaagtgagtgttttgactca
ctgttatttaaaaatctctagggctgttccaataagcaacaaaaggcaaaatggcctggttctctgtcccctttctgtct
gtatgcctcgtacaggttatgaaaagaaaaagttggggaaaagctgtccacctcacctaattgtgttcttgtggagtgtgc
tagatgccccctctctggagaaaaaaaaatccttgtggcctctgacccacctctggagagcctagttcccttctggaggca
gaaggcaaagcttaggacctagagagtgctggaccacgccactcacaggaaccagcaggctgtgaggttgaaagctaggc
atatggagctttccaggctgggtgcagggcctcgtggcccttcccctccctctgtgctctatagctcagtcttcccagg
cggtgtgaacacgcagtgacatttccaggaatacagggatttattaatgatttcttgtgaaatgtttggaaatacaaagt
actctataaatatttcataatagcattgggggctgagaactccacaaagtgccggaatacatttgcatgtaagacagaacg
ctgcctgggtcattgatgcctgttgagtggcagtcacagacactgcctagggtttctgactcacgctgttgggactgttc
tatgcagggcaccctcttgtgtggcataggatttgtgcctcaccacacactgttgtagctttgctgtcttgatgatgagt
agagggcagtgtccaggccatggtataagcatctactgccccccaggggttaccaaaaccaagccaagttgtgtctcagcg
agctccgtgaagcatggagaagttgagtactcagagacatgacgtgactttcaaaggctgtaagctgacgagggacata
gctagggtcagacttgagttttttctttttcttttcttttttttttaagactgagtcttgcttttgtcgccca
ggctggattgcagtggtgcttggctcactgcaacctctgcctcccgggttcaagcaattctcctgcctcagcctccccag
tagctgggattacaggcacctgccaccatgcctggccaacatttttgtatttttttagtagagatggggtttcaccatgt
tggccaggctggtcttgaactcctgacctcaggtgatccacccgcctcgacctcccaaagtactgggattacaggtgtga
gccactgcacccggcccagactcgagttttcatcttaatgcttttcattgcctgacactttactgagaccaagatagg
gaacttcacatacagtaccttttctcccaaggcggaagagggctgttcaatttctacactagagttcggggagttttaga
aatgagtcagttatcgaggatgagagcagttcctgataggctcaaccacaatgagatgtagctgttcagagaaagcattc
ttttatctataaactggaagataatcccggtgaaacgaagcccagccccagggggcttcactaactccaggctgtgcttct
caaactttagtgagcataggaatcacctgggcatcttgtgaagctgtagatttgaattctgcaggtcggcagaggggtct
```

Figure 12G - (2)

```
cagaatccgcatttccaacaatgtctccagtaatgctgatgctgctcgtccctggaccacagattgggtagccaggttct
ggcaagctcatcccaaggctttgagatgacatcagacaaaatatgttctgggacatggcttttgagaggtcaagaaaata
agatgtttctttctcttctcatccccaacccttgcactgccttttctcccttcccctacccttctttctgtccccatcc
ctgacgccagCTGTTCAGCATGAGAAGCTGGAGTGACATGCGACAGGAGGTGATGTTTCTGACCAATGTGAACAGCTCCA
GCTCCTCCACCCAAATCTACCAGGCTGTGTCTCGTATTGTCTGCGGGCATCCCGAGGGAGGGGGCTGAAGATCAAGTCT
CTCAACTGGTATGAGGACAACAACTACAAAGCCCTCTTTGGAGGCAATGGCACTGAGGAAGATGCTGAAACCTTCTATGA
CAACTCTACAAgtgagtgtccatgcagaccccagccctgtccccaaccccatccctcccttagttctggccttggcctgt
gtcatctcctccctctgtagcagcgttagatgtctacatgcccatttgcccaccagactgagctcttcctagaggagaga
ggcttctcttgaatagctacctgtccccagttctctgaatgcagcctggcacatctcaggtgcacagtagtgtttatcaa
tggaatgaatgattgacagccaaccttctggttttctggggatgtggaagggtggcttccagggtgatcaagaatgaga
taatggcagaaggacaaatcctgcaagatctcacttatatatggaatatatgtaaggtagaaagtgtcagtttcacatga
tgaataagttcctgggatcttgatgtacatcgtgatgactatagttagtaacactgtatagtatacttgaaatttgctaa
gagagtagatccgaagtgttcacactacacaaaaaaggcaactatgaggtgatggatttattaacagcttgattgtggtg
atcctttttacaaagtatacatatattaaaacatcacattgtataccttaaatatatacaattttttatttgtcagttgtaa
ctcaaaaaagctagaaaagcatttttaaaaggatgatgtactggtcttaatattaccattgagataagctttataataa
cataaaaagaaataacagtaatgataatagcaacaacaacaacaaagaactaacatttaagtagaatttcttgtgca
ctgtgcattctgtttaagttatctcatttttaccctcatgataacctgcagggaagattctttaaccccacatttcatagg
ctcagagaggttaagtgccttggttagagccacatcagagttaatccacaagagccaggattcaagcccaaatctgcctg
gatctgtgctctctaagataactgttagtggtggcgtgtgtgttctcacactcagacatttgatctgcccttttgtttccc
attcttagctgcaaggcagtgttaaagaaccctgtgtctccatatccactccccacacttaagcactttgtgggcccgt
gtgccgtatgcctcgtggcagcagggatccaatgtcacagttttaggcagtggcatccttttccttgaaaacttgatgca
ggggaacctttctccatttccaaccacaggtgtgtctttcagacactgagtgaggcaggttttgtactttattgtaacac
aagaaccttttcttctctggagtaaagcactccagacattcgcaagttgctttacaagccttaaaaggatggtattgtag
gcaactttaattaaatcccatctcctcctctcccccagcttgcaagttgacccaaggaagccttcatttccatgacagac
ttaattgtgagggcatcctca
```

Figure 12G - (3)

SEQ ID NO 21
Genomic contig containing ABC1 exon 9 through 22:

actgtgttagcaaggatggtctcgatctcctgacctcgtgatccgcctgtatcggcctcccaaagtgctgggattacagg
cgtgaaccactgcgccctgttgagaattttttttttttttttgggagaaagagtttcgctcttgttgcccgggctagag
tgcagtgacacaatctcggctcactgcaacctctgcctcctggttcaagcaattctcctgcctcagcctcatgcgtcac
cacgcccagctaattttgtattttagtagagacagggtttctccatgttggtcaggctggtctcgaactcccaacctca
ggtggttcgccgccttggcctcccaaagtgctgggattgcaggcatgagccactgcgcccagccccaaatttggtttt
tgcttgaaaactgaggtctgaattcagccttctggttgcccctcaagagtcagtttaaatgttggtcatgttagttgtca
gtgaaaacaatggtgaggctggcatgagagtgtgaatctggatgggagggcttgtgcttcatgaaaacattttttccagat
cagctcagtcgtgagttatccgtcattgacgttataataagctctgattattatcaagcatcattctttatagatatct
cagtttaatctgagataatcttctccacatctctccacatagatgttatgaattttactttacagaggagccaactgag
gctcagataagttacttattatatgactagtagtggtagagctggggtttcaactaagaactctctggctccaaagccct
tgtaagtttctatcagtatatgaccatgcatatgagcatttgtctctcctcttcttcatagCTCCTTACTGCAATGATTT
GATGAAGAATTTGGAGTCTAGTCCTCTTTCCCGCATTATCTGGAAAGCTCTGAAGCCGCTGCTCGTTGGGAAGATCCTGT
ATACACCTGACACTCCAGCCACAAGGCAGGTCATGGCTGAGgtaagctgcccccagcccaagactccctccccagaatct
ccccagaactgggggcaaaaaactcaaggtagcttcagaggtgtgcgctaagtatactcacggctcttctggaattccca
gagtgaaaacctcaagtctgatgcagaccagagctgggccagctcccccagtcgtgggtatagaatcatagttacaagcag
gcatttcttggggatggggaggactggcacaggggctgctgtgatggggtatcttttcagggaggagccaaacgctcattg
tctgtgcttctcctccttttctgcggtccctggctccccacctgactccagGTGAACAAGACCTTCCAGGAACTGGCTG
TGTTCCATGATCTGGAAGGCATGTGGGAGGAACTCAGCCCCAAGATCTGGACCTTCATGGAGAACAGCCAAGAAATGGAC
CTTGTCCGGgtgagtgtccctcccattattaccatgtgcctgcttgatactggagaggtgagtttctggtcactttccca
ggtgtgagtgaggtgagaattctttcagtttatctagctgggggaatgtagtgagcatagctaaagtcacagggcaccac
ctctccagaagtacaggccatggtgcagagataacgctgtgcatatcagcatccatgccactcacggtcaaatagcagtt
ttctgcaaaacttagtgagggctggtgtttggaagtggagttgagtaattgcagtaccctattttccttttgctgcagc
ctctcagccagccacagcatctccctgtgtcttggtaggttttggaaagaagtgtgggagcaaaagcatgatgttacatg
tagactggcctgagatactcattctcagggcactgtgtgaatgatgagctgctgttactgtgtggaggggaaatgcactt
agtgcttcagagccacttgaaagggataagtgctctagagacaattgggttcaaatgtggagcaggctgagcaagaacag
aatgtctcctttgcctgagcctgagtgctgttaatcacatcttcctgccttgggctgagttagagaatcattagactatt
tcctgtttccatggtgagggaggcctcttccttttgtctctgctccccttaagaagcaggtgaggattttgccaggttttc
ttgttttgaaccttattgactttaagggcggctgggttttagagactgtacctacctaggggggaacacttccgaagttta
ggactattccctgatccgctgggaggcaggttactgaggaagtcccttttaaaaacaaaggagtttatactgagaaaagca
taaacagtgatttgtatggattcacactgactaatatagctcatgccattaaagtggggtctcttctctaaaggagggtt
atatgatctagcccgtagacctaagtgtggtttcagacctgttcttcctggtcctctccttggaatccatatttctact
agttggacttttctgtttgtctggctctcagaggattataggaggccctgtgaagtgactcagtgaattttgatttgtg
ggcaagtagatggttcccagtctgaaattgactttgccttaggtgcttcaattcttcataagctcccagttcttaaagg
acaagatccttgtaaacatggcaatggcattcattaggaatctagctgggaaaatccagtgtgtatgcttggaaatgagg
gatctggggctggagagaaaggcatgggcatgccttggagggacttgtgtgtcaagctgaggacctttactttaagctct
aggggaccaggcaaggggagatgtagatacgttactctgatggggtggatgaattgaagaaggatgaggcaagaatgaag
gcagagaccagggaggaggctctccaagtggccaaggcataaagcaagaaatgaggcctggtgactgcttagtggcagag
cagtgaaagagagggaggcatcaaagtgagtctcgatttctagctgggtgggtggtagcgatgtccagtaggccagtggc
tactgaggtctgcagtggaggagggtggttgggctggagacagatgatgagggagtcatcagcctgtgggtggaagaaaa
gggaacctcttccaactgttttctttgcttcttccctctctttctcttttttttttttttggacagagtcttgctctgt
cacccaggctgaaatgcagtggcatgatcttggctcaccacagcctccgcctcctgggttcaagcaattctcctgtctca
gcctccagagtagctgggattacaggcacatatcactgtgcccggctaattttgtattttcagtggagatgggatttca
ccatgttggtcgggctggaatgaactcctgacctcaagtgatccacctgcctcagcctcccaaagtgtgggattacagg
catgagccaccgcgcccggcctttcttccctctcttaaagagtgtttatttaattccacaaacatgagcttgtcaccccc
tgtagcctggcatctcctacacgaggtgatggctgaggcttctgcttctgctggggtagctctgatctttctgctttctc

Figure 12H - (1)

```
tggcactgtctacccatgttgcctcaccccacaggtcccagggcacctctctcgggcaagtcttggaaccctctgacact
gatttgctctcttttctgagctgcttttagccacccatcctcgggacctgttttctctctgcctccacccctgcgggcag
tcttaggtctcctgcccctcacgagcaccccagagaggccacgtgctcagtgatctcagtgggcgcatctttctagtctt
gctattcttttggccatgttgttcagaaaccatactgggcagggccgacttcaccctaaaggctgcgtctcttcactct
gcttttgtttgttccaaataaagtggcttcagaattgctaaccctagcctctgtgaacttgtgaggtacaattttgtgtc
tgttatgttaacaaaaatacatacataccttcctggtgatggtataaattgctattctctattggaaagcaatttggaat
gaaaatttaaagaaccatttaaaatatgctatcctgcgtacctccattccacccaccccagggatgtagcctactgaa
ataattttaaagaagtcaccatatgagagaaatgttattgctatattgttattgtgagaaattggaaatagactaaatg
ttcagcactataggaataattaatgaaattacatatactctatacaatcattatgctgccattgaaataataaatacaaa
ggcgcaaggggggaaaagcttataatgttagtgaaactaagactgattttttataaagcagcagttttcagacccttgg
agactccaattcggtagaaccagagcttcatcttctctgtcgaagctgtgacaggagttgcaaatgcctctccttttgc
tgagtttgcagctgctgttttccggcagcacatctgtgcaggcctctgcctcggcccctctggatctgctgattgagca
gcggattgatctgtccttctctttcgtgttgacccatgtgaggaaccaactggcaagggaacaagaaatggaaataggcc
tcctttgcatcatgacctgtacatcctgcaattggaaaagattgtactttagttggtttaaccagcagcattattttct
aaactaagcagtaagaaggaattaggtttatgtgggatcaacagactgggtctcaaaagaggaaggtgatagaacacag
tgggagggggaggtgcactagaaacagagggcctatgctttcattctggctttgctacttaatagctgtgtgacccaat
cttagagacttaacctctctgaacttccatttctcatgtataaaatgggaaatattaaaggatactcactgggctggtg
gcttgtgcctgtaatcccagcacttggggaggttgaggtgggaggatcacttgagcccaggtgttcaagaccagcccagg
caacatggcaagactctgtctctatgaaaaaattaaaaattagccaggtgtggtggtgtgcacctgtagtcttagctact
tggtaggctgagatggaggatcacttgggcttggaggtcaaggctgcggtgagctgtgattccatcactgcactccag
cccgggcggcagagcgagacactgaatccaaacgacaacaacaacaaaaggcaaaaaataaaagtgccctctttatgga
gttgtgtaaggtgaagcatatacactattcaacatagtaactatataaggaagtattgttgttgttactgtagttaata
ccattaagtgagatgtttcgtatagtggaaagcacatggactctgaattcagactggtctgactttgagtctcagctcca
catctagtaatactatgaccaagccctggttaaaatcatgttttttttttcttcagcctcagtcttctcacatataaaata
gggacactgtcatttacctcagttttctgtgaggataaaacaacgacagtgtatatgcaagtatttttgtaaattttgtag
tgctcctcaagatttagttggtgttactacttgtactttctcactggaatggcagATGCTGTTGGACAGCAGGGACAAT
GACCACTTTTGGGAACAGCAGTTGGATGGCTTAGATTGGACAGCCCAAGACATCGTGGCGTTTTTGGCCAAGCACCCAGA
GGATGTCCAGTCCAGTAATGGTTCTGTGTACACCTGGAGAGAAGCTTTCAACGAGACTAACCAGGCAATCCGGACCATAT
CTCGCTTCATGGAGgtgaatctgttgctgggatcatttagaaaagacttaacggcttctttctctgagacgttacaataa
ggttcaggcaggaggcaagtttagaaataatgtatagtctcatttacaaaactatccctcaagcctaacacaggatttga
taacaaaaggcacttaataaatgttagttgagtggttgaatgagtaaataaactctagctttagtaaattaactctagct
tattctatataggctcaagagaatatttctacccatttttcttctaggttttcctatctcagtgactaatggtagcaaagc
attcccttaaaaaggcattatttgtgaaacttayctaaaatcgaattcgggtccaattaaatttttgaaattttatatta
aaaattatattagtagggatgggtaagaggtgttttggtctggttggttggttagttgctatgactcagaattgctaaga
aaacagaaaagtaagataagatcattgttttaacctcttttcctccacaaaatcaataaataacatatccctaaattact
cttagaatttctcttaaattgcagtgaaaaaccaaaatccttcattcttggttgaaggttggaaaactacgttagagagg
attagagagagaggatgagcaatcgtgtagtcagcccttgcctcctagtgtaggatttgtctcagccactgcttgttgtc
ctggctgccaacgttctcatgaaggctgttcttctatcagTGTGTCAACCTGAACAAGCTAGAACCCATAGCAACAGAAG
TCTGGCTCATCAACAAGTCCATGGAGCTGCTGGATGAGAGGAAGTTCTGGGCTGGTATTGTGTTCACTGGAATTACTCCM
RGCAGCATTGAGCTGCCCCATCATGTCAAGTACAAGATCCGAATGGACATTGACAATGTGGAGAGGACAAATAAAATCAA
GGATGGtaagtggaatcccatcacaccagcctggtcttggggaggtccagagcacctattatattaggacaagaggtac
tttatttaactaaaaatttggtagaaatttcaacaacaacaaaaaaactcaacttggtgtcatgattttggtgaaattg
gtacatgacttgctggaaggttttcataggtcataaaataacagtatcttttgatttagcatttctactcaagggaatt
aattccaggaattttggtggcaggcacctgtaatcccagctactcgggaggctgaggcaggagaattgcttgaacccagg
aggcagaggttgcagtgagctaagatcgcatcattgcactcccgcctgggcaataagagtgaaactccatctcaaaaaaa
```

Figure 12H - (2)

```
aaaaaagatacaaaaatagaaaaaggggcttggtaagggtagtagggttttgggcaatttttttttttttttttttttt
attgtatggttctaaaggaatggttgattacctgtggtttggttttagGTACTGGGACCCTGGTCCTCGAGCTGACCCCT
TTGAGGACATGCGGTACGTCTGGGGGGGCTTCGCCTACTTGCAGGATGTGGTGGAGCAGGCAATCATCAGGGTGCTGACG
GGCACCGAGAAGAAAACTGGTGTCTATATGCAACAGATGCCCTATCCCTGTTACGTTGATGACATgtaagttacctgcaa
gccactgtttttaaccagtttatactgtgccagatgggggtgtatatatgtgtgtgcatgtgcatgcatgtgtaatgat
ctggaaataagatgccagatgtaagttgtcaacagttgcagccacatgacagacatagatatatgtgcacacactagtaa
acctctttccttctcatccatggttgccacttttatctttttattttattttttttttgagatggagtctcgctctga
cgcccaggctggagtgcagtggctcgatctcggctcactgcaacctttgcctcccgggttcaagctattctcctgcctca
gcctccacagtagctgggactacaggctcatgctgccacgcccggctgacttttgtattttagtagagacgaggtttca
ccatgttacccaggctagacttcaactcctgagctcaggcaatccaccctccttggcctcccaaagtgctgggattacag
gtgtgagccactgcacccagcccaccacttttaatttttacactctaccctttggtcaaaatttgctcaatctgcaagc
ttaaaatgtgtcatgacaaacacatgcaagcacatactcacacatagatgcagaaacagcgtctaaacttataaaagcac
agtttatgtaaatgtgtgcacttcttctccctaggtggtaaaccacatttcaaaacaacccaaataaaactgaacaaagc
ttcttcctcttagacttttagaaaatctttcagtgctgagtcactaagctgccaagttctcattgtgggaactatgcct
ttggatgtaatgatttcttctaagacaatgggcggaggtgtagttattgcagacatctgaaatatgtaatgtttcttcca
gattctggaaattctcttattctctgtggttggtggtggtgggatgtgtgtgtgtgtgtgtgtgtgtgtgtgtgtgtgt
gtgtgtagggatcaggatgcgggaggagctgggttctgcttgtattggttctctgttttgcattgaatagtgtgtttcct
tgtatggctatctatagcttttcaaggtcaccagaaattatcctgttttcaccttctaaacaattagctggaattttc
aaaggaagacttttacaaagacccctaagctaaggtttactctagaaaggatgtcttaagacagggcacaggagttcaga
ggcattaagagctggtgcctgttgtcatgtagtgagtatgtgcctacatggtaaagctttgacgtgaacctcaagttcag
ggtccaaaatctgtgtgccttttttactttgcacatctgcattttctattctagcttggaatctgaaacattgacaagagc
tgcctgaaatgtatgtctgtggtgtgattagagttacgataagcaagtcaatagtgagatgaccttggagatgttgaact
tttgtgagagaatgagttgtttttttgttttggttttagtactttaacataatctacctttagtttaagtatcgctcac
agttacctagttactgaagcaagcccccaaagaaatttggtttggcaacactttgttagcctcgttttctctctacatt
gcattgctcgtgaagcattggatcatacgtacatttcagagtctagagggcctgtccttctgtgcccagatgtggtgct
ccctctagcatgcaggctcagaggccttggcccatcaccctggctcacgtgtgtctttctttctccccttgtccttcctt
ggggcctccagCTTTCTGCGGGTGATGAGCCGGTCAATGCCCCTCTTCATGACGCTGGCCTGGATTTACTCAGTGGCTGT
GATCATCAAGGGCATCGTGTATGAGAAGGAGGCACGGCTGAAAGAGACCATGCGGATCATGGGCCTGGACAACAGCATCC
TCTGGTTTAGCTGGTTCATTAGTAGCCTCATTCCTCTTCTTGTGAGCGCTGGCCTGCTAGTGGTCATCCTGAAGgtaagg
cagcctcactcgctcttccctgccaggaaactccgaaatagctcaacacgggctaagggaggagaagaagaaaaaaaatc
caagcctctggtagagaaggggtcatacctgtcatttcctgcaatttcatccatttatagttggggaaagtgaggcccag
agaggggcagtgacttgcccaaggtcaacccagccgggtagcagctaagtaggatgagagtgcagggttcatgctttcca
gataaccacatgctcaactgtgccatgctgtctcattggtagtggttcatggcagcatctgaaagctatttattttctta
gatatattgggtggcgattcttcctaagtttctaagaacaataatcagaaggatatatattgttgcaggttagactgtct
ggaagcagaggctgaaatagagtttgatgtatgggtatttatgagggctcaataccatggaagagatatggaagatgca
ggattgggcagagggaggagttgaactgtgatatagggccaaccccgtggggcactctagagaatatgcagcttgttgga
gttgttcttcatcgagctgaaacatccagccctttgtgctcccccaaggcctccctcctgacaccacctacctcagccct
ctcaatcaatcactggatgtgggctgccctgggaaggtcgtgcccagggcctacatggctctctgctgctgtgacaaac
ccagagttgctgatgcctgaggccgtctactgacagctgggcaacaaggcttccctgaatggggactctgggcagtgcag
ttttgtgtctgaaccatacattaatatatttatatccgaattttctttctctgcaagcatttcatataaagacacatcag
gtaaaaataaatgttttgaagcaaaaggagtacaaagagataagaactaactaatttaatactagttaccatctgttac
aaatagttcctactgattgccaaggactgtttaaacacatcacatgggcttcttcttctatcctcactaacccttttaac
agacaaggaaatgaggctcaggaaggtcaaggactttattgaggttccacagtaggatacagttcttgctaaaagcaacc
cctccctcatgctctgttatctaactgcaagggggaaggtcagtggcagaggtagtggtcccatggttggtgcataagagc
tgctctgagacaactgcatgctggtgggtcctgcagacatgtacccatcagccggagataggctcaaaatatccacaaga
```

Figure 12H - (3)

```
gtttggatgattgtgggaatgcagaatccatggtgatcaagagggaaagtcaagttgcctggccatttccttggctttt
agacagaaaagttacgtgggatattatctcccacagctcttctgtggtgccaccagtcatagtccttatataaggagaaa
ccagttgaaattacctattgaagaaacaaagagcaaactcgcccactgaaatgcgtagaaagccctggactctgttgtat
tcataactctgccattattttctgcgtagttttgggtaagtcacttatcttctttaggatggtaatgatcagttgcctc
atcagaaagatgaacagcattacgcctctgcattgtctctaacatgagtaggaataaaccctgtctttttctgtagatc
atacaagtgagtgcttgggattgttgaggcagcacatttgatgtgtctcttccttcccagTTAGGAAACCTGCTGCCCTA
CAGTGATCCCAGCGTGGTGTTTGTCTTCCTGTCCGTGTTTGCTGTGGTGACAATCCTGCAGTGCTTCCTGATTAGCACAC
TCTTCTCCAGAGCCAACCTGGCAGCAGCCTGTGGGGCATCATCTACTTCACGCTGTACCTGCCCTACGTCCTGTGTGTG
GCATGGCAGGACTACGTGGGCTTCACACTCAAGATCTTCGCTgtgagtacctctggcctttcttcagtggctgtaggcat
ttgaccttcctttggagtccctgaataaaagcagcaagttgagaacagaagatgattgtcttttccaatgggacatgaac
cttagctctagattctaagctctttaagggtaagggcaagcattgtgtttattaaattgtttacctttagtcttctcag
tgaatcctggttgaattgaattgaatggaattttccgagagccagactgcatcttgaactgggctggggataaatggca
ttgaggaatggcttcaggcaacagatgccatctctgccctttatctcccagctctgttggctatgttaagctcatgacaa
accaaggccacaaatagaactgaaaactcttgatgtcagagatgacctctcttgtcttccttgtgtccagtatggtgttt
tgcttgagtaatgttttctgaactaagcacaactgaggagcaggtgcctcatcccacaaattcctgacttggacacttcc
ttccctcgtacagagcaggggatatcttggagagtgtgtgagcccctacaagtgcaagttgtcagatgtccccaggtca
cttatcaggaaagctaagagtgactcataggatgctcctgttgcctcagtctgggcttcataggcatcagcagccccaaa
caggcacctctgatcctgagccatccttggctgagcagggagcctcagaagactgtgggtatgcgcatgtgtgtggggga
acaggattgctgagccttggggcatctttggaaacataaagttttaaaagttttatgcttcactgtatatgcatttctga
aatgtttgtatataatgagtggttacaaatggaatcattttatatgttacttggtagcccaccactccctaaagggactc
tataggtaaatactacttctgcaccttatgattgatccattttgcaaattcaaatttctccaggtataatttacactaga
agagatagaaaaatgagactgaccaggaaatggataggtgactttgcctgtttctcacagAGCCTGCTGTCTCCTGTGGC
TTTTGGGTTTGGCTGTGAGTACTTTGCCCTTTTTGAGGAGCAGGGCATTGGAGTGCAGTGGGACAACCTGTTTGAGAGTC
CTGTGGAGGAAGATGGCTTCAATCTCACCACTTCGGTCTCCATGATGCTGTTTGACACCTTCCTCTATGGGGTGATGACC
TGGTACATTGAGGCTGTCTTTCCAGgtacactgctttgggcatctgtttggaaaatatgacttctagctgatgtcctttc
tttgtgctagaatctctgcagtgcatgggcttccctgggaagtggtttgggctatagatctatagtaaacagatagtcca
aggacaggcagctgatgctgaaagtacaattgtcactacttgtacagcacttgtttcttgaaaactgtgtgccaggcagc
atgcaaaatgtttttatacacattgcttcatttaattctcacaaggctactctgaagtagttactataataaccagcaatt
ttcaaatgagagaactgtgactcaaagacgttaagtaaccagctttggtcacacaactgttaaatgttggtacgtggagg
tgaatccacttcggttacactgggtcaataagcccaggcgaatcctcccaatgctcacccaattctgtatttctgtgtcc
tcagaggggtacaactaggagaggttctgtttcctgagtacaggttgttaataattaaatatactagctctaaggcctg
cctgtgatttaattagcattcaataaaaattcatgttgaattttctttagtacttctttcttaatataatacatcttct
tgaccaagtccaagaggaacctgcgttggacagttttcatatgagatcaaattctgagagagcaagatttaacccttttt
ggttcaccttctgatcctccctaaggaggtatacatgaaatatttattactcctgcctgaacttctttcattgaatatg
caattttgcagcatgcagattctggatttaaattctgagtcttaacttactggctgagggaccttggataggctccttat
ccctcagtttcctcatctctaaaatggggatggcacctgcccgtgggttgttggaaggacttacagaggtgcagaatgt
acgttgtacatagcaggtttcagcaaatgttagctccctcttttcccacatccattcaaatctgttccttctccaaagga
tgtgtcaaggaggaaatggacctggctgggaaaccctcagaatactgggatgatgctgagcttggctcatacctgtgctt
tgctttcagGCCAGTACGGAATTCCCAGGCCCTGGTATTTTCCTTGCACCAAGTCCTACTGGTTTGGCGAGGAAAGTGAT
GAGAAGAGCCACCCTGGTTCCAACCAGAAGAGAATGTCAGAAAgtaagtgctgttgacctcctgctctttctttaaccta
gtgctgctgcctctgctaactgttgggggcaagcgatgtctcctgcctttctaaaagactgtgaaaccactccaggggca
gagaaatcacatgcagtgtcccctttccaaatcctcccatgccatttatgtccaatgctgttgacctattgggagttcacg
gtctcgatccctgagggacatttttctttgttgtcttggcttctagaagagtatcttttacttgccccctcccaaacacac
atttcatggtctcctaacaagctagaagaaagaggtaaagacaagcgtgattgtggaaccatagcctcgctgcctgcctg
tgacatggtgacctgtgtatcagcctgtgtgggctgagaccaagtggctaccacagagctcagcctatgcttcataatgt
```

Figure 12H - (4)

```
aatcattacccagatccctaatcctctcttggctcttaactgcagacagagatgtccacagctcatcaaaggctctgctt
ctggggttctttgtgcttagagtggcttcctaaatatttaataggtccctttctgccagtctcttctgtgcccatcccct
gattgcccttggtaaaagtatgatgccccttagtgtagcacgcttgcctgctgttcctaatcatcttctcctacctcctc
tttacacctagctcctgtttcagtcacctagaaatgctcacagtcgctggaatatgtcatgttcttccacacctccatgc
ctttgtaggtactgtttgctctcacaggagaactttctctctaacttgcctatcttctcaactcctcctttctctccaag
atctagttccggatccctcccctgagcatccctccttggttctcaggtagtcagtcactctctgccctgaacttccatg
gcacgtgaaagaaaatcttttatttttaaaacaattacagactcacaagaagtaatacaaattacatgaggggttccct
taaacctttcatccagtttccccaatggtagcagcatgtgtaactgtagaatagtatcaaaaccatgaaattgacatagg
tacaattcacaaaccttcttcagatttcactagctttatgtgcgctcatttgtgtgtgtgtgcgtatttagttctatg
caattttatcatgtgtgaattcatgtaattactagctcagtcaagctgcagaaatatctcattgtcacaaagctccttca
tgctaccccttaatggccacagccacctccttcttcctcagttcctgacacctgtcaaccactaatgcgttcctcgttt
ttacagtttattatttctagaatgttacataaatggaaccatacagtaggtatccttttgatactggctttttttttttt
tttcactcagcagtattcccttagatctatccaagttgtgtgtgtcaacagttcattcctcttcactgctgagtagtgtt
ccctgggaggggtgtatcacagttccatggcattttagatgtatttttaaacagctttcagcatcctctattttaatt
gttcatcaagtccttttccccaatagactctgaatgctcctttatcatcgtattcccatcaccaacatcagtacccaaat
aggccctaaataaacatttatagcctcctgcctgcctgagaaaccagggtggacatggagagaaggcacttctgaaagtt
caagcgcagtgcctgtgtccttacactccactcctcagtgctttctgtgggttcatttctgtcttctctcctgtcacag
TCTGCATGGAGGAGGAACCCACCCACTTGAAGCTGGGCGTGTCCATTCAGAACCTGGTAAAAGTCTACCGAGATGGGATG
AAGGTGGCTGTCGATGGCCTGGCACTGAATTTTTATGAGGGCCAGATCACCTCCTTCCTGGGCCACAATGGAGCGGGGAA
GACGACCACCATGtaagaagagggtgtggttcccgcagaatcagccacaggagggttctgcagtagagttagaaatttat
accttaggaaaccatgctgatccctgggccaagggaaggagcacatgaggagttgccgaatgtgaacatgttatctaatc
atgagtgtctttccacgtgctagtttgctagatgttatttcttcagcctaaaacaagctggggcctcagatgaccttttcc
catgtagttcacagaattctgcagtggtcttggaacctgcagccacgaaaagatagattacatatgttggagggagttgg
taattcccaggaactctgtctctaagcagatgtgagaagcacctgtgagacgcaatcaagctgggcagctggcttgattg
ccttccctgcgacctcaaggaccttacagtgggtagtatcaggaggggtcagggctgtaaagcaccagcgttagcctca
gtggcttccagcacgattcctcaaccattctaaccattccaaagggtatatctttgggggggtgacattcttttcctgttt
tcttttaatctttttttaaaacatagaattaatatattatgagcttttcagaagatttttaaaaggcagtcagaaatcc
tactacctaacacaaaaattgttttttatctttgaataatatgttcttgtttgtccattttccatgcatgcgatgttaggc
atacaaaatacatttttttaaagaatactttcattgcaaattggaaacttcgtttaaaaaatgctcatactaaaattggca
tttctaacccataggcccacttgtagttatttaccgaagcaaaaggacagctttgctttgtgtgggtctggtagggttca
ttagaaaggaatgggggcggtggggagggttggtgttctgttctctctgcagactgaatggagcatctagagttaagggta
ggtcaaccctgacttctgtacttctaaatttttgtcctcagGTCAATCCTGACCGGGTTGTTCCCCCCGACCTCGGGCAC
CGCCTACATCCTGGGAAAAGACATTCGCTCTGAGATGAGCACCATCCGGCAGAACCTGGGGGTCTGTCCCCAGCATAACG
TGCTGTTTGACATGtgagtaccagcagcacgttaagaataggccttttctggatgtgtgtgtgtcatgccatcatgggag
gagtgggacttaagcatttt actttgctgtgtttttgttttttctttttttctttttttatttttttgagatggagtctcg
ctctgtagccaggctggactgtagtggcgcgatctcggctcactgcaaccttggcctcccaggttcaagcgattctcctg
cctcagcctcccgagtagctgggactctaggcacacaccaccatgcccagctaattttgtgttttagtagagacgggg
tttcaccatgttggccaggatggtctcaatgtcttgacctcgtgatccgcccacctcggtctcccaaagtgctgggaaca
caggcatgagccactgtgtctggccacatttactttctttgaatatggcaggctcacctccgtgaacaccttgagacct
agttgttctttgatttaggagaagtggaggtgaatggttgagctgtagaggtgacatcagcccagccagtggatgggg
gcttgggaaacattgcttcccattattgtcatgctggagggccctttagcccatcctctcccccgccaccctccttatt
gaggcctggagcagacttcccagacctggtagtgcttcagggccctggtatgatggacctatatttgctgcttaagacat
ttgctcccactcaggttgtcccatcagccataaggcccccagggagcccgtgtgatggagcagagagagacctgagctct
gcaatcttgggcaaggcttttcccttatgtttcttcttatctaaagtgaacagctggggctcatgtgctccctcctcatc
taaagtgaacacatggggctcatgtgcagggtcctcccgcttcagagcctgaggtcccctgaggctcaggaaggctgc
```

Figure 12H - (5)

```
tccaggtgagtgccgagctgacttcttggtggacgtgctgtggggacagcccattaaagaccacatcttggggccctgaa
attgaaagttgtaactgcctggtgcatggtggccaggcctgctggaaacaggttggaagcgatctgtcacctttcacttt
gatttcctgagcagctcatgtggttgctcactgttgttctaccttgaatcttgaagattattttcagaaattgataaag
ttattttaaaaagcacggggagagaaaaatatgcccattctcatctgttctgggccaggggacactgtattctggggtat
ccagtagggcccagagctgacctgcctccctgtccccagGCTGACTGTCGAAGAACACATCTGGTTCTATGCCCGCTTGA
AAGGGCTCTCTGAGAAGCACGTGAAGGCGGAGATGGAGCAGATGGCCCTGGATGTTGGTTTGCCATCAAGCAAGCTGAAA
AGCAAAACAAGCCAGCTGTCAGgtgcggcccagagctaccttccctatccctctccctcctcctccggctacacacatg
cggaggaaaatcagcactgccccagggtcccaggctgggtgcggttggtaacagaaacttgtccctggctgtgccctag
gtcctctgccttcactcactgtctggggctggtcctggagtttgtcttgctctgtttttttgtagGTGGAATGCAGAGAA
AGCTATCTGTGCCCTTGGCCTTTGTCGGGGATCTAAGGTTGTCATTCTGGATGAACCCACAGCTGGTGTGGACCCTTAC
TCCCGCAGGGGAATATGGGAGCTGCTGCTGAAATACCGACAAGgtgcctgatgtgtatttattctgagtaaatggactga
gagagagcgggggcttttgagaagtgtggctgtatctcatggctaggcttctgtgaagccatgggatactcttctgtta
kcacagaagagataaagggcattgagactgagattcctgagaggagatgctgtgtctttattcatcttttgtccccaac
atggtgcactaaatttatggttagttgaaagggtggatgcttaaatgaatggaagcggagaggggcaggaagacgattgg
gctctctggttagagatctgatgtggtacagtatgaggagcacaggcaggcttggagccaactctggcttggccctgaga
cattgggaaagtcacaacttgcctcaccttctttgccgataataatagtggtgcgttacctcatagaggattaaattaaa
tgagaatgcacacaaaccacctagcacaatgcctggcatatagcaagttcccaaataaaatgcgtactgttcttacctct
gtgaggatgtggtacctatatatacaaagctttgccattctaggggtcatagccatacagggtgaaaggtggcttccagg
tctcttccagtgcttacccctgctaatatctctctagtccctgtcactgtgacaaatcagaactgagaggcctcacctgt
cccacatccttgtgtttgtgcctggcagGCCGCACCATTATTCTCTCTACACACCACATGGATGAAGCGGACGTCCTGGG
GGACAGGATTGCCATCATCTCCCATGGGAAGCTGTGCTGTGTGGGCTCCTCCCTGTTTCTGAAGAACCAGCTGGGAACAG
GCTACTACCTGACCTTGGTCAAGAAAGATGTGGAATCCTCCCTCAGTTCCTGCAGAAACAGTAGTAGCACTGTGTCATAC
CTGAAAAAGgtgagctgcagtcttggagctgggctggtgttgggtctgggcagccaggacttgctggctgtgaatgattt
ctccatctccaccccttttgccatgttgaaaccaccatctccctgctctgttgcccctttgaaatcatatcatacttaag
gcatggaaagctaaggggccctctgctcccattgtgctagttctgttgaatcccgttttccttttcctatgaggcacana
gagtgatggagaaggtccttagaggacattattatgtcaaagaaaagagacttgtcaagaggtaagagccttggctacaa
atgacctggtcgttcctgctcattacttttcaatctcattgaccttaactttaaactataaaacagccaatatttatta
ggcactgatttcatgccagagacactctgggcattgaaagaaagtaatgataatagttaattttatatagcgttgttacc
atttcaacctttttttttttttaacctctatcatctcaattaaag
```

Figure 12H - (6)

SEQ ID NO: 22
Genomic contig containing ABC1 exon 23 to 28:

gtgaacacacattaaagcatgagaagcatgaactagacatgtagccaggtaaaggccttgctgagatggttggcaaaggc
ctcattgcagcattcattggcaggccacagttcttttggcagctctgcttcctgacctttcaccctcaggaagcgaggct
gttcacacggcacacacatgccagacagggtcctctgaagccacggctgccagtgcatgtgtcccagggaaagcttttc
ctttagttctcacacaacagagcttcttggaagccctcccggcgaaggtgctggtggctctgccttgctccgtccctga
cccgttctcacctccttctttgccatcagGAGGACAGTGTTTCTCAGACCAGTTCTGATGCTGGCCTGGGCAGCGACCAT
GAGAGTGACACGCTGACCATCGgtaaggactctggggtttcttattcaggtggtgcctgagcttcccccagctgggcaga
gtggaggcagaggaggagaggtgcagaggctggtggcgctgactcaaggtttgctgctgggctggggctgggtggctgcg
ggggtgggagcagcttggtggcgggttggcctaatgcttgctggggtgcctggggctcggtttgggagctagcagggcag
tgtcccagagagctgagatgattggggtttggggaatcccttaggggagtggacactgaataccagggatgaggagctga
gggccaagccaggagggtgggatttgagcttagtacataagaagagtgagagcccaggagatgaggaacagccttccaga
ttttcttgggtagcgtgtgtaggaggccagtgtcaccagtagcatatgtggaacagaagtcttgacccttgctatctct
gcctagtcctaatggctggcttttcccaggaaggcttctgcttccatggactgttagattaaccctttatttaggtaaat
gagggaacctactttataagcataggaaagggtgaagaatcttttaagattcctttactcaagttttctttgaagaatc
ccagagcttaggcaatagacaccagactttgagcctcagttatccattcacccatccacccacccacccacccatccttc
catcctcccatcctcccattcacccatccacccatccagctgtccaccattctacactgagtacctataatgtgcctgg
ctttggtgatacaaaggtgaataagacatagtcctttcctttgccccaacctcagaccagagatgaacatgtggaatg
acctaaacacctggaacaggtgtggtgtatgagcggcaggcctctgatgagagggtgggggatggccagccctcactcg
aagcccctctgagttgattgagccatctttgcattctggtcctgcagATGTCTCTGCTATCTCCAACCTCATCAGGAAGC
ATGTGTCTGAAGCCCGGCTGGTGGAAGACATAGGGCATGAGCTGACCTATGTGCTGCCATATGAAGCTGCTAAGGAGGGA
GCCTTTGTGGAACTCTTTCATGAGATTGATGACCGGCTCTCAGACCTGGGCATTTCTAGTTATGGCATCTCAGAGACGAC
CCTGGAAGAAgtaagttaagtggctgactgtcggaatatatagcaaggccaaatgtcctaaggccagaccagtagcctgc
attgggagcaggattatcatggagttagtcattgagttttaggtcatcgacatctgattaatgttggccccagtgagcc
atttaagatggtagtgggagatagcaggaaagaagtgttttcctctgtaccacagtacatgcctgagatttgtgtgttga
aaccagtggtacctaacacatttacatcccaaccttaaactcctatgcacttatttaccctttaatgagcctcttacttt
aagtacagtgkgaggaacagcggcatcaggatcacttgggaacttgttagaaattcagcaacttgggcccagctcagacc
tactgaatcagaatcaggagcaattctctggtgtgactgtgtcacagccaggtatcaactggattctcatacataggaaa
tgacaaacgtttatggatggatagtctacttgtgccaggtgctgagatttgttttttgttttttgatttttttttaatca
ctgtgacctcatttaattctcaaaaaaagatgaaaaaatgaacactcaggaatgctgacatgagattcagaatcaggggt
ttgggcttcaaagtccatcctctctctttatccatgtaatgcctccccttagagatacaacatcacagaccttgaaggctg
aaggggatataaaagctgtctggccaagtggtctccaagcttgacagtgcagcagaatcacctggggatattattaaaaa
taaacatactaaggtttggcttcagggcctgtgaatcagaatttctggaggtgaggccttgaagtctgtatttctattgc
atactttggacacagtggtctatagactagagtttggaaatgattgcgctcattcagattctcttctgatgtttgaattg
ctgccatcatatttctagtgctctatttcctcctgctcattctgtcttggataacttatcatagtactagcctactcaaa
gatttagagccacagtcctgaaagaagccacttgactcattccctgtaggttcagaataaatttcttctgcgcagtgtct
gtcatagcttttttaaattttttttttattttgatgagactggagttttgctcttattgcccaagctggagtgcagtgg
tgcgatttggctcactgcaacctccacctcccaggttcaagcgattctcctgcctcagcctcccaagtagctgagatta
caagcatgtgctaccacgcccagctaattttgtatttttagtagagatgggtttttatccatgttggtcaggctggtctcg
agctccagacctcaggtgatctgcccgcctcggcctcccaaagtgctgggattataggcctgagccacagcgctcagcca
taactttaatttgaaaatgattgtctagcttgatagctctcaccactgaggaaatgttctctggcaaaaacggcttctct
cccaggtaactctgagaaagtgttattaagaaatgtggcttctactttctctgtcttacggggctaacatgccactcagt
aatataataatcgtggcagtggtgactactctcgtaatgttggtgcttataatgttctcatctctctcatttttccagATA
TTCCTCAAGGTGGCCGAAGAGAGTGGGGTGGATGCTGAGACCCTCAGgtaactgccttgagggagaatggcacacttaaga
tagtgccttctgctggctttctcagtgcacgagtattgttcctttcccttgaattgttctattgcattctcatttgtag
agtgtaggtttgttgcagatggggaaggtttgttttgttgtaaataaaataaagtatgggattcttttccttgtgccttca

Figure 12 I - (1)

```
gATGGTACCTTGCCAGCAAGACGAAACAGGCGGGCCTTCGGGACAAGCAGAGCTGTCTTCGCCCGTTCACTGAAGATGA
TGCTGCTGATCCAAATGATTCTGACATAGACCCAGgtctgttagggcaagatcaaacagtgtcctactgtttgaatgtga
aattctctctcatgctctcacctgttttctttggatggcctttagccaaggtgatagatccctacagagtccaaagagaa
gtgaggaaatggtaaaagccacttgttctttgcagcatcgtgcatgtgatcaaacctgaaagagcctatccatatcactt
cctttaaagacataaagatggtgcctcaatcctctgaacccatgtatttattatctttctgcggggtcctagtttcttg
tatacattaggtgtttaattgttgaacaaatattcattcgagtagatgagtgatttgaaagagtcagaaaggggaattt
gctgttagagttaattgtaccctaagacttagatatttgaggctgggcatggtggctcatgccagtaatcccagcgcttt
gagaggctgaggtgggtagatcacctgaggtcaggagtttgagaccagtctgaccaacaaggtgaaacccgtctctact
aaatacaaaaaattagccgagtgtggtggcacatgcctgtcatcccagctacttgggaggctgaggcaggagaatcgctt
gaacccaggaggcagaggttgcagtcagccacggttgcgccattgcactccagactgggcaacaagagtgaaaactccat
ctcaaaaaagaaaaaaaagaattagatattttggatgagtgtgtctttgtgtgtttaactgagatggagaggagagcta
agacatcaaacaaatattgttaagatgtaaaagcacatcagttaggtatcattagtttaggacaaggatttctagaaaat
ttttaggaacagaaaactttccagttctctcacccctgctcaaagagtgtatggctcttacattatatataactgcctga
cttcatacagtatcagtacttagatcatttgaaatgtgtccacgttttaccaaaatataatagggtgagaagctgagatg
ctaattgccattgtgtattctcaaatatgtcaagctacgtacatggcctgtttcatagagtagtctataagaaattgatg
acttgattcatccgaatggctggctgtaacacctggttacgcatgaacacctcttttcagttgtctcaagacaccttct
tttctgtacttatcagacaaggactgaaaggcagagactgctactgttagacattttgagtcaagcttttccttggacat
agctttgtcatgaaagccctttacttctgagaaacttctagcttcagacacatgccttcaagatagttgttgaagacacc
agaagaaggagcatggcaatgccgaaaacacctaagataataggtgaccttcagtgttggcttcttgcagAATCCAGAGA
GACAGACTTGCTCAGTGGGATGGATGGCAAAGGGTCCTACCAGGTGAAAGGCTGGAAACTTACACAGCAACAGTTTGTGG
CCCTTTTGTGGAAGAGACTGCTAATTGCCAGACGGAGTCGGAAAGGATTTTTTGCTCAGgtgagacgtgctgttttcgcc
agagactctggcttcatgggtgggctgcaggctctgtgaccagtgaaggcaggatagcatcctggtcaagatatggatgc
cggagccagatttatctgtatttcaatcccagttctattccttgccagttgtgtatccgctggcaagttacttctctatg
cctcaatctcctcatctgtaaaatggggataataatattacctgcaatacagggttgttacgaaaataaaaatgaatagg
tgcttagaatgggggcctgacattagtaagtgcttagttttgtgtgtgtatatgttattttatttggaggagaacataa
aaaggacaaagtgtagaaaaactggttgggtgtattcagctgtcataacatgagagttgttatgcccagatgcacttgac
atgtgaatttattagaaacatgattttttctctgagttgatgtttaactcaaactgatagaaaagataggtcagaatatag
ttggccaacagagaagacttgttagactattgtctgcatgtcagtgtttgcatgctaacttgcttagttagaaaggttaa
attttttcactctataaaatcaagaaatatagagaaaaggtctgcagagagtctttcatttgatgatgtggatattgtta
agagcgggagtttggagcatacagagctcaagttgaatcctgactttgctacttattggctatatgaccttgggcaagct
gcttagtctctctgatcctcagttaccctttgtttgttgatgatgaccattgataacacaaccataaataatgacaacata
gagatagttctcattatagtagttgttatacagaattattcactcaatgttaattttctgcattgaaatcccagaacatt
agaattgggggcattatttgaatcttttaaggttataaggaatacatttctcagcaataaatggaaggagttttgggttaa
cttataaagtatacccaagtcatttttttttcagagaagatatggtagaaagtcttaggaggttgaagaaggaattggata
tttattctttctgagactatcatgggagataatgactatggttgtccatgattggagccgttgctgtagagttggtttta
ttatagtgtaggatttgaatgggccatgtgttctcagacctcagaataaaaagagaaaactgaggccagtggggagcgtg
acttcacatgggtacacttgtgctagagacagaaccaggattcaggacttctggctcctggtcctgggttcatggcccaa
tgtagtctttctcagtcttcaggaggaggaagggcaggacccagtgttctgagtcaccctgaatgtgagcactatttact
tcgtgaacttcttggcttagtgcctctgccaggtggccataacctctggccttgtgttgccagagaaaaggtttagtttt
caggctccattgcttcccagctgccaagaatgccttggtgcagcacagtcataggccctgcattcctcattgccgtgctg
gttggtcggggaggtgggctggactcgtagggatttgccccttggccttgtttctaacacttgccgtttcctgctgtccc
cctgccccctccactgcctgggtaaagATTGTCTTGCCAGCTGTGTTTGTCTGCATTGCCCTTGTGTTCAGCCTGATCGT
GCCACCCTTTGGCAAGTACCCCAGCCTGGAACTTCAGCCCTGGATGTACAACGAACAGTACACATTTGTCAGgtatgttt
gtcttctacatcccaggaggggtaagattcgagcagaccaaagatgtttacgagggccaagggaatggacttcagaatt
acacggtggaat
```

Figure 12 I - (2)

SEQ ID NO: 23
Genomic contig containing ABC1 exon 29:

gggaagcatttaaaaaaaaaaaagtatatatatatatatatatatatatgtaatgtgaattggcctcttttctctaa
gcccacatttcttcttacatagttcaggttttacttttattttttcctttccggctgctgaccctgtattgcccgtagttg
tggaacatagcatgtgtttgtgacctgtgcctgttattttgtgctttctagttgtgcatgcaaagagtacaaagttttc
ttgccctttcttggaaaatcctgcttgtctgtgccaaagggataattgtgaaagcacttttgaaatacttaatgagttga
tttcttcaaattaaaaaaaatatataaatgtatatgtgtatgtacatgtgtgtacacatacacacctttatacatacag
cccatttaaaacaagctccactttggagtgctctacgtcaccctgatgccgaatacagggccagagtctgagatccttct
gggtggtttctgtgttttgttcatttctgttttaagagcctgtcacagagaaatgcttcctaaaatgtttaatttataaa
aacatttttatctctcgattactggttttaatgaattactaagctggctgcctctcatgtacccacagCAATGATGCTCC
TGAGGACACGGGAACCCTGGAACTCTTAAACGCCCTCACCAAAGACCCTGGCTTCGGGACCCGCTGTATGGAAGGAAACC
CAATCCCgtgagtgccactttagccataagcagggcttcttgtgcttgttgcctggtttgatttctaatatgctgcattt
atcaactgcatgccacattgtgaccgccagcatttgccctttgaattattattatgttttatttacaaaaagcgaaggta
gtaaccgaactaaattatctaggaacaaacgtttggagagtcttctaacaccgyscaaagcacgtcattacagacatttg
tttactgatttagaaccttaatatttaatttaaatacgcactttacacttactgatgaaatgcttttcctttctttctct
cccagcccctgtacttaagtgcttcaataggctctcattatatatgattttttaggttttgcttatcagcttcttcgcttt
tataatctgaaaagatggcatatgaatttttataaaaagggacactttcttcttctcaaattgtatattttattgtact
ttccttcaaaaccccctttttaaaaagtaagcagtggataaataaattcagtgaagcatccatatgacccttaagtgagtg
taggggaagggaggtcaccagatcactgtgagtgaagatggtggagaggtgaggatcttatgaggccgtgctcaaggctg
gtagaggtgggttagtgtttccaggtttaggcagaatctcagctgaggtcatgaaacaacagtgatctctgaaaaattat
ggcaaggtgggaaggtgctggagaattggagaggggggcaaacttgactttcaagtttcaatgggaagataggtgactctg
cacaccacagaacagtgagcatgataacctgtttatacaaggttctagagcagatttctaaatggatagctactgtgtgc
ttgtttgttcttaattagtattggatagttactaaatacttgttagtacttagtacataatgggtggtaaatcctagcag
ctaatattggttcccaaataaccagatgacaaggatagagaaggacacagacacggcctatctggatttcatggtgccttt
tgattttccacatgaaggttgtgtagggaagatagaagcatgagatgagatgataatatagttatctggattcatcactg
gccagctgaaccatatgaactcatggattgatgctagcttaggaaggctctgtaggagccagaactgggctgagagccag
cccatagagacaaaagaggcccggccctgacatcagagggttcaaacatgatgtctgagccccacctacagtctgccgga
ggtggttggaaggaagagcctttatccttacaattcttactgaaattcaaattttttaggttttgcaaaaaaatggtggac
ctgaaggaaatttgacaggagcatgtctcagctgtatttaaatttgtctcagccaatccccttttgaatgttcagagtgt
aagcttcaggagggcagcgcgtcttagtgtgacttttctggtcagttcaggtgctttaaggagacaattagagatcaatc
tggaaaacttcatttgaatttttaatacataagaaaacaataagaaatagttaaaaatatatatttatataatatatata
tgtgtgtgtgtgtgtgtgtgtgtgtgtgtatatatatatatattttatttatttattttttttgagatggagtctcg
ctctgttgcccaggctggagtgcagtggctcaatcttggctcactgccacctctgcctcccaggttcaagtgattctcct
acctcagcctcctgagtagctgggattacaagcatgtgccaccacactggctaa

Figure 12J

SEQ ID NO: 24
Genomic contig containing ABC1 exon 30 and 31:

tcttgccagtctctactcattttcagcacatcgagcataagatccagactctttcccaggcctctctcatctggctcct
ctcctcctcctttatcattactcttcttcgtagcttatcctactccagccatgctgtcttcctattattcctaaaaarta
gaaatgcatttcttcctagggcctttgtacctgcacttgccatcgcttttgctcagaatgttctttttgccaagcttttg
cccagcttgttctccatcattgttatgtttggctgaaatgtcttctcttagtaggttcattctccccagtcactgtctt
tttatttgctttattttgggccatctaaggttatcttattagtgtatttgttgttcgtctcctccatgggcatacacct
ccatgaaggcaggtattttcaccttaggccctcgaatatactggacagcatctggcacgtagtagatgctcaacgaatgt
ttgttgtgtgagcaaatggttggttgattggattgaactgagttcagtatgtaaatatttagggcctctttgcattctat
tttacttatgtataaaatgatacataatgatgatataaatgatgtcacagtgtacaaggctgttgtgggatcaagcaatc
aaatgagatcatgcttgtcttttccaaatggtgagggaatagatgcatgtttgtggttgttacggaatgatcctgtgctc
ctgaggcaacagaaaggccaggccatctctggtaatcctactcttgctgtcttcccttgcagAGACACGCCCTGCCAGG
CAGGGGAGGAAGAGTGGACCACTGCCCCAGTTCCCCAGACCATCATGGACCTCTTCCAGAATGGGAACTGGACAATGCAG
AACCCTTCACCTGCATGCCAGTGTAGCAGCGACAAAATCAAGAAGATGCTGCCTGTGTGTCCCCAGGGGCAGGGGGGCT
GCCTCCTCCACAAgtgagtcactttcagggggtgattgggcagaaggggtgcaggatgggctggtagcttccgcttggaa
gcaggaatgagtgagatatcatgttgggagggtctgtttcagtcttttttgttttttgttttttttttctgaggcggagtc
ttgctctgtcgcccaggctggagtgctgtggcatgatcttgcctcactgcaacctccacctcccaggttcaagcgattct
cctgcctcagcctcctgagtagctgggattacaggcacgcaccaccatgtctggctaattttgtgttttagtagagat
agggtttcgccgtgttggctaggctggtctggaattcctgacctcaggtgatccaccgcctcggcctcccaaagtgctg
ggattacaggcgtgagccactacgcccagccctgtttcagtctttaactcgcttcttgtcataagaaaaagcatgtgagt
tttgaggggagaaggtttggaccacactgtgcccatgcctgtcccacagcagtaaagtcacaggacagactgtggcaggc
ctggcttccaatcttggctctgcaacaaatgagctggtagcctttgacaggcctgggcctgtttcttcacctctgaatta
gggaggctggaccagaaaactcctgtggatcttgtcaactctggtattcttagagactctgtttgggaaggagtcctgag
ccattttttttttcttgagaatttcaggaagaggagtgcttatgatagctctctgctgcttttatcagcaaccaaattgc
aggatgaggacaagcaattctaaatgagtacaggaactaaaagaaggcttggttaccactcttgaaaataatagctagtc
caggtgcggggtggctcacacctgtaatctcagtattttgggatgccgaggtggactgatcacctaaggtcaggagttcg
aaaccagcttggccaatgtggcgaaaccctgtctctactaaaaattcaaaaattagccaggcatggtggcacatgcctgt
aatcccagttacttgggaggctgaagcaggagaattgcttgaacctgggaggtggaggtcgcagggagccaaaattgcgc
cactgtactccagcctgagcaacacagcaaaactccatatcaaaaaataaaatgaataaaataacagctaatctagtcat
cagtataactccagtgaacagaagatttattaggcatagtgaatgatggtgcttcctaaaaatctcttgactacaaagaa
tctcatttcaatgtttattgtttagatgttcagaataaattcttgggaaagaccttggcttggtgtaagtgaattaccag
tgccgagggcagggtgaaccaagtctcagtgctggttgactgagggcagtgtctgggacctgtagtcaggtttccggtca
cactgtggacatggtcactgttgtccttgatttgttttctgtttcaattcttgtctataaagacccgtatgcttggtttt
catgtgatgacagAGAAAACAAAACACTGCAGATATCCTTCAGGACCTGACAGGAAGAAACATTTCGGATTATCTGGTGA
AGACGTATGTGCAGATCATAGCCAAAAGgtgacttttactaaacttggcccctgccttattattactaattagaggaat
taaagacctacaaataacagactgaaacagtgggggaaatgccagattatggcctgattctgtctattggaagtttagga
tattatcccaaactagaaaagatgacgagagggactgtgaacattcagttgtcagcttcaaggctgaggcagcctggtct
agaatgaaaatagaaatggattcaacgtcaaattttgccac

Figure 12K

SEQ ID NO: 25
Genomic contig containing ABC1 exon 32:_ gcatgctggagtgatagtgaccatgagtttctaagaaagaagcataatttctccatatgtcatccacaattgaaatatta
ttgttaattgaaaaagcttctaggccaggcacggtggctcatgcctgtaatcccagcactttaggagccaaggcgggtgg
atcacttgaggtcaggagtttgagaccagcctggccaacatggggaaaccctgtctctactaaaaatacaaaataagctg
ggcgtggtggtgcgtgcctgtaatcccagctacttgggaggctgaggcaggagaactgcttgaatctgggaggcggaggt
tgcagtgagctgagttcatgccattgcattccagcctgggcaacaagagcgaaaccatctcccaaaagaaaaaaaaaaga
aagaaaaagcttctagtttggttacatcttggtctataaggtggtttgtaaattggtttaacccaaggcctggttctcat
ataagtaatagggtatttatgatggagagaaggctggaagaggcctgaacacaggcttcttttctctagcacaaccctac
aaggccagctgattctagggttatttctgtccgttccttatatcctcaggtggatatttactccttttgcatcattagga
ataggctcagtgctttctttgaactgattttttgtttctttgtctctgcagCTTAAAGAACAAGATCTGGGTGAATGAGT
TTAGgtaagttgctgtctttctggcacgtttagctcaggggaggatggtgttgtaggtgtgcttggattgaagaaagcc
ttggggattgtttgtcactcacacacttgtgggtgccatctcactgtgagga

Figure 12L

SEQ ID NO: 26
Genomic contig containing ABC1 exon 33 to 36:

gctttatagagtttctgcctagagcatcatggctcagtgcccagcagcccctccagaggcctctgaatatttgatatact
gatttccttgaggagaatcagaaatctcctgcaggtgtctagggatttcaagtaagtagtgttgtgaggggaatacctac
ttgtactttccccccaaaccagattcccgaggcttcttaaggactcaaggacaatttctaggcatttagcacgggactaa
aaaggtcttagaggaaataagaagcgccaaaaccatctctttgcactgtatttcaacccatttgtccttctgggttttga
aggaacaggtggggactggggacagaagagttcttgaagccagtttgtccatcatggaaaatgagataggtgatgtggcta
cgtcagggggcccgaaggctccttgttactgatttccgtcttttctctctgccttttccccaagggccaggacccctgga
tctctgggcagagcagacgcaggcccctataatagccctcatgctagaaaggagccggagcctgtgtataaggccagcgc
agcctactctggacagtgcagggttcccactctcccaactccccatctgcttgcctccagacccacattcacacacgagc
cactgggttggaggagcatctgtgagatgaaacaccattctttcctcaatgtctcagctatctaactgtgtgtgtaatca
ggccaggtcctccctgctgggcagaaaccatgggagttaagagattgccaacatttattagaggaagctgacgtgtaact
tctgaggcaaaatttagccctcctttgaacaggaatttgactcagtgaaccttgtacacactcgcactgagtctgctgct
gatgatactgtgcaccccactgtctgggttttaatgtcaggctgttcttttagGTATGGCGGCTTTTCCCTGGGTGTCAG
TAATACTCAAGCACTTCCTCCGAGTCAAGAAGTTAATGATGCCATCAAACAAATGAAGAAACACCTAAAGCTGGCCAAGg
taaaatatctatcgtaagatgtatcagaaaaatgggcatgtagctgctgggatataggagtagttggcaggttaaacgga
tcacctggcagctcattgttctgaatatgttggcatacagagccgtctttggcatttagcgatttgagccagacaaaact
gaattacttagttgtacgtttaaaagtgtaggtcaaaaacaaatccagaggccaggagctgtggctcatgcctgtaatcc
tagcactttgggaggctgaagcgggtggatcacttgaggtcaggagttcgagaccagcctggcctacatgacaaaacccc
gtatctactaaaaatacaaaaaaattagctgggcttggtggcacacacctgtaatcccagctacttgggaggctgaggca
ggagaattgcttgaaccctgtaggaagaggttgtagtgagccaagatcgcaccgttgcactccagcctgggcaacaagag
caaaactccatctcaaaaaacaaattaaatccagagatttaaaagctctcagaggctgggcgcggtggcttacacctgtt
atcccagcatttgggatgccgaggcgggcaaagcacaaggtcaggagtttgagaccagcctggccaacatagtgaaacc
ctgtctctgctaaaaacatagaaaaattagccgggcatggtggcgtgcgcctgtaatcccagctactcgggaggctgagg
tgagagaattrcttgaacccggggaggcggaggttgcagtgagcccagattgcaccactgcactccagcctgggcgacaga
gcaagactccatctcaaaaaaagctctcagaacaaccaggtttacaaatttggtcagttggtaaataaactgggtttcaa
acatactttgctgaaayaatcactgactaaataggaaatgaatctttttttttttttttttaagctggcaagctggtctg
taggacctgataagtactcacttcatttctctgtgtctcaggtttcccattttaggtgagaattaaggggctctgataa
aacagaccctaggattgtggacagcagtgatagtcctagagtccacaagtctgcttttgagtgatgggcccatgtatctg
gcacatctgcaggcagagcgtggttctggctcttcagatgatgccggtggagcactttgaggagtcctcaccccaccgtg
ataaccagacattaaaatcttggggctttgcatcccaggatttctctgtgattccttctagacttgtggcatcatggcag
catcactgctgtagatttctagtcacttggttctcaggagccgtttatttaatggcttcacatttaatttcagtgaacaa
ggtagtggcattgctcttcacagggccgtcctgttgtccacaggttccagattgactgttgccccttatctatgtgaaca
gtcacaactgaggcaggtttctgttgtttacagGACAGTTCTGCAGATCGATTTCTCAACAGCTTGGGAAGATTTATGAC
AGGACTGGACACCAGAAATAATGTCAAGgtaaaccgctgtctttgttctagtagcttttttgatgaacaataatcctatg
tttcctggagtactttcaactcatggtaaagttggcaggggcattcacaacagaaaagagcaaactattaactttaccag
tgaggcagtacggtgtagtgtagtgattcagagaatttgctttgccaccagacataccaggtaaccttgactaagttact
taacctatctaaacctcagttycctcatctgtgaaatggagacagtaatcatagctatttccaaactgttgtgagaattc
aatgagttaaaggtataaggtcctcaccacagcgcctgcccacatagtcagtgatcactatgtcctgaacactgtaatta
cttcgccatattctctgatcatagtgttttgccttggtatgtgactagaatttctttctgaggtttatgggcatggttgg
tgggtatgcacctgcctgcaggagcccggtttgggggcattaccttgtacctggtatgttttctttcagGTGTCGTTCAA
TAACAAGGGCTGGCATGCAATCAGCTCTTTCCTGAATGTCATCAACAATGCCATTCTCCGGCCAACCTGCAAAAGCGAG
AGAACCCTAGCCATTATGGAATTACTGCTTTCAATCATCCCCTGAATCTCACCAAGCAGCAGCTCTCAGAGGTGGCTCTg
taagtgtggctgtgtctgtatagatggagtgggcaagggagagggttatggagaagggagaaaatgtgaatctcatt
gtaggggaacagctgcagagaccgttatattatgataaatctggattgatccaggctctgggcagaagtgataagtttac
gaattggctggttgggcttcttgaactgcagaagagaaaatgacactgatatgtaaaaatcgtaacatttagtgaattca

Figure 12M – (1)

```
tataaagtgagttcaaaaattgttaattaaattataatttaattataagtgtttaatcagtttgatttgtttaaaaacca
ctgttttaaatttggtggaatatgttttttattagcttgtatctttaattcctaaattaagctgtgtgtgtgtgtgtgt
gtgtgtgtgtgtgtgtgtgtgtgtgtgtgtgaagtttaaagccaggatgagctagtttaaagtatgcagcctttggagtc
atacagatctgggtttgaatctggtctctaaactttatagatgtatgatattaaatgaggcagttcatgtaaattgccaa
gcccagcactcagcacagagttgatatttcacacacattagatacctttcctgtatgtggagcatggcagttcctgtttc
tgctttactcctacaggatactaatataggacactaggatctttataccaagacccatgtaatgggcttatgagaccat
tcttcttataaaaatctgacagaattttttgtatgtgttagatcaataggctgcatactgttattttcaagttgatttaca
gccagaaatattaatttatttgagtagttacagagtaatatttctgctctcatttagttttcaagccccactagtcctt
gtgtgtgaaaatttacaacttactgctcttacaaggtcatgaacagtggaccaaagtgaatgccattaaccactctgact
tccttcattagttttattgtgacagtggactcttttgacctcagtaataccagtttggcatttacattgtcatatttta
gacttaaaaatgatcatcttaaccctgaataaaatgtgtctggtgaacagatgttttccttggctgtgcctcagatatc
tctgtgtgtgtgtacgtgtgtgtttgtctgtgtgtccatgtcctcactgattgagccctaactgcatcaaagacccctca
gattttcacacgcttttctctctccagGATGACCACATCAGTGGATGTCCTTGTGTCCATCTGTGTCATCTTTGCAATGTC
CTTCGTCCCAGCCAGCTTTGTCGTATTCCTGATCCAGGAGCGGGTCAGCAAAGCAAAACACCTGCAGTTCATCAGTGGAG
TGAAGCCTGTCATCTACTGGCTCTCTAATTTTGTCTGGGATATGgtaaggacacaggcctgctgtatctttctgatgtct
gtcagggccatggattgatatggataagaaagaaagagctctggctatcatcaggaaatgttccagctactctaaagatg
tatgaaaagaaatagccagaggcaggtgatcactttcatgacaccaaacacagcattgggtaccagagttcatgtcaca
ccagagggaaaattctgtacacaatgatgaaaattaataccactaccacttaagttcctatgtgacaactttcccaagaa
tcagagagatacaagtcaaaactccaagtcaatgcctctaacttctctgatgggttttaacctccagagtcagaatgttc
tttgccttactaggaaagccatctgtcatttagaaaactctgtacatttatcagcagcttatccatccattgcaaatat
tgttttttgtgccasccacaatatattgcttctatttggaccaatatgggggatttgaaggaattctgaagttctaattat
atttcaactctactttacaatatctccctgaaatatatctccctgtaacttctattaattataagctacacagagcaaat
ctaattcttctcccaccgaacaagtccctggatatttaaaaataactctcatactctcatttaacctgagtattacccag
ataagatgatatatgagaatacaccttgtaacctccgaagcactgtacaaatgtgagcaatgatggtggagatgatgatg
agatctttgctgtttataccaagcccctttagactgtgtcactcttctgatccggttgtccttgtatggccatgctgtata
ttgtgaatgtcccgttttcaaaagcaaagccaagaattaaccttgtgttcaggctgtggtctgaatggttatgggtccag
agggagttgatctttagctcacacttctattactgcagcacaaagattttgcatttggaaggagcaccgtcttactggc
aacttagtggtaaaccaaaacctccatttcacacaaatgattgtgaaattcgggtctccttcattctatacaaattcatt
tgatttttttgaaactaaactttatatttatccatattaaattacatgggttttattttttgttttatcttgattcagtaa
ttactcctttcagtaaacacagactgagtgctgtgtgtctgacttatgccaggcataggtgattcagagatgaaaggtca
agtccctgaacccatctcttgtcttcctgggtattatctgtccctccctgctttagagctcctgaaatttgctagaagca
tgtcttcatctaagttgttgataaacacatcaagtaggattggactgaggcagagccctgtagtctgaagctgcagttct
tctagcggctgacaagccccactatcacttccctgctggtgctttgctctgccagctgtgaattctcataattgtcctat
cgtcaagtctttatttctgcattttactgcttgatacactgtcaggacagactttaaaattattctcagtgcgatgaaac
aattctgacattcatgttatgagcagttacctcataaatagattacatg
```

Figure 12M – (2)

SEQ ID NO: 27
Genomic contig containing ABC1 exon 37 to 41:

aaattactctgactgggaatccatcgttcagtaagtttactgagtgtgacaccttggcttgactgttggaaagacagaaa
gggcatgtagtttataaaatcagccaaggggaaaatgcttgtcaaaatgtattgtcgggtattttgattaatagtttatg
tggcttcattaattcagagttactctccaatatgtttatctgccctttcttgtctgataatggtgaaaacttgtgtgatg
cattgtatatttgatttaggggtgaactggatgtctttgttttcacttttagTGCAATTACGTTGTCCCTGCCACACTGG
TCATTATCATCTTCATCTGCTTCCAGCAGAAGTCCTATGTGTCCTCCACCAATCTGCCTGTGCTAGCCCTTCTACTTTTG
CTGTATGGgtaagtcacctctgagtgagggagctgcacagtggataaggcatttggtgcccagtgtcagaaggagggcag
ggactctcagtagacacttatctttttgtgtctcaacagGTGGTCAATCACACCTCTCATGTACCCAGCCTCCTTTGTGT
TCAAGATCCCCAGCACAGCCTATGTGGTGCTCACCAGCGTGAACCTCTTCATTGGCATTAATGGCAGCGTGGCCACCTTT
GTGCTGGAGCTGTTCACCGACAATgtgagtcatgcagagagaacactcctgctgggatgagcatctctgggagccagagg
acagtgtttaattgtgatcttattccacttgtcagtggtattgacactgctgactgccttgtcctgtcttcagagtctgt
cttccctgagaaggcaaagcaccttctttcttgctgtgccttacatttgctggtcaagcctttcagtttcttttgaca
gtttttttttacttcttttctttttcaatgttgctcttaccaagagtagctcctctgccttccactttacacatgagagct
gggcgacgcattcagtcctaaggcttttaccatcacctctcttggtgttttattgtcatctctaagatcaatgccttta
gccttgatcataaccttgaactctaatctcaaattctcacttgcctagtggattgctccatttagatagtatatagatac
cccaacctggatatgtcctagttttctttccccttggaacttaatgcttttcttgccatccctgtcacactcagtggcac
taccatccactcggttgcccaagctggctcttagagttatcctagatgcttgctttgctgttgcagatttcccacattca
actggttatgttgtcagttcttccaggtatggacctctaaaataaggcttcctctccattccggttgtcattgccttgt
ccaaacacagcacacaaggccttttacagttgcacaactcttcctgtccatacccaccacacccttttcccagctgtaagc
ttcagatgagttgcctccaaccaccatgctcctgtaggcctggcttgaaatgcccttcttctgtcacagggtctggtagt
atatcccttgcccttcaagatttagctaaaatgtgaagcttccttacctgctgggaggtgttctctcttttctctgtgc
tctcagagtccttagtccatgcctccagtacaacgtacatccacttacatggtaatttcctgtttacatactttcctac
tcggagtggagtctgtttcttaataattttgcctctcccatgccctagcacagtgcatccagcgtatagccccttattca
gttggtagatatttggccactgttgccttgtgggatcataagttctgatgtatttgagaagaatttctaaaattctgaca
aaatcctgaaactcaaatattgacccagacatgagcaattgttttcaaatgctaagggatttttaatggatttgcttt
aattaaatctagcctgtttctaagctttattcattatttctccatactcagagcatttctccagattttctaaagaatag
aatttttattgctacatatcatcagctatgcctgctgctatttaattggtatctgaattaaaaggtctggtttgtccctag
agaatcaaatttttttcttcactcccatatttcagaacttgatacatttttaggataaaccatgaatgacacccgtttctt
ctccctcaccctcccttccctcccatttttttttttttttttttttttagAAGCTGAATAATATCAATGATATCCTGAAGTC
CGTGTTCTTGATCTTCCCACATTTTTGCCTGGGACGAGCGCTCATCGACATGGTGAAAAACCAGGCAATGGCTGATGCCC
TGGAAAGGTTTGgtgagtgaagcagtggctgtaggatgctttaatggagatggcactctgcataggccttggtaccctga
actttgttttggaaagaagcaggtgactaagcacaggatgttcccccaccccccatgcccagtgacagggctcatgccaac
acagctggttgtggcatggggttttgtgacacaaccatttgtctgtgtctctgatagcattgagaaaagtgaaagggcagt
tttgaaggtaaggaaaatagtgttatttgcttggatccactggctcatgccactgtctgggttggttagaagcactggaa
aagtcaaaccataactttgagaattaggtgatcagggaatcagaaggaaagatgcaaactttggctcttttaggcgaatc
atgtgcctgcagatgaggtcatttattatctttacacagtctataaaattataatgtattacatcttttctacctttta
gaatggttaaaaatatttctccggtagccatatgattattattcatccattagataatatagtcaaatgggccatgttat
ttactgttcatagaagaggggctttttgcaacttgggctacaaaggagatatgtaaggaatttaaggaatggttacatgg
aactagatttaattgaatctagtggtttaattgattcactaggatatatgctactgaaaggggaatctgcttaaagtgct
ttctgatatttattattactaaaacttagaatttattaaaaatactgactgtgaaaattacttgggtcgtttgccttttt
aaaaggattttttggcatgtctcattaaaaaagaaatactagatatcttcagtgaagttacaaatcgaatacacattggc
tctgaaattctgattgatactgggtcataaaaagttttcccaaatcagacttggaaagtgatcactctcttgttactctt
ttttccttgtcatgggtgatagccatttgtgtttattggaagatcggtgaattttaaggaacataggcccaaatttgagg
aagggccatggttttttgatccctccattctgaccggatctctgcattgtgtctactagCGGAGAATCGCTTTGTGTCACC
ATTATCTTGGGACTTGGTGGGACGAAACCTCTTCGCCATGGCCGTGGAACGGGTGGTGTTCTTCCTCATTACTGTTCTGA

Figure 12N – (1)

```
TCCAGTACAGATTCTTCATCAGGCCCAGgtgagcttttcttagaacccgtggagcacctggttgagggtcacagaggag
gcgcacagggaaacactcaccaatgggggttgcattgaactgaactcaaaatatgtgataaaactgattttcctgatgtg
ggcatcccgcagcccctccctgcccatcctggagactgtggcaagtaggttttataatactacgttagagactgaatct
ttgtcctgaaaaatagtttgaaaggttcattttcttgttttttccccaagACCTGTAAATGCAAAGCTATCTCCTCTG
AATGATGAAGATGAAGATGTGAGGCGGGAAAGACAGAGAATTCTTGATGGTGGAGGCCAGAATGACATCTTAGAAATCAA
GGAGTTGACGAAGgtgagagagtacaggttacaatagctcatcttcagttttttttcagctttatgtgctgtaacccagca
gtttgctgacttgcttaataaaagggcatgtgttcccaaaatgtacatctataccaaggttctgtcaattttattttaaa
aacaccatggagacttcttaaagaattcttactgagaattcttttgtgatatgaattcccattctcgaatactttggttt
tatatgcttacatttatgtgttagttattaaaacatactaatattgtatatctagtcaaactgagtagagagataatggt
gatt
```

Figure 12N – (2)

SEQ ID NO: 28
Genomic contig containing ABC1 exon 42 to 45:

ttttaaaatacctgcaatacatatatatgttgaatagatgaaaaattatgtagatgataatgaatgatacggttctaaaa
agacaggttaaaaagtaagttcactttttattttgagcttcagaatcattcagaagccagtcgccacaaacgcagaccaag
gctcttggcacatcaaatatgcctatggcttagggttattgacaagtcttatgttgcagtgtatgtggtttatagtcctg
ccttccacagttgcttgggagagctgtgagtcactgaggcttatgaatgtttacattttgtttgttgcagATATATAGAA
GGAAGCGGAAGCCTGCTGTTGACAGGATTTGCGTGGGCATTCCTCCTGGTGAGgtaaagacactttgtctatattgcgtt
tgtccctattagttcagactatctctacccaatcaagcaacgatgctcgttaagaggtaaaagtggattttaaaggcttc
tgtatttatgccaggatggagcaattagtcatcgagaagagagggaccctgtatgtcaagagaatgatttcagagaatcc
aatacaatttaagaaaaagcatggggctgggcgcagtgattcactcctgtaatcccagcactttgggaggccgaggtggg
cggactcacgaggtcaggagattgagaccatcctggccaacatggtgaaaccccatctctactataaatacaaaaattag
ctgggcatagtagtgcattcctgtagtcccagctactcgggaggctgaggcaggagaattgcttgaacctaggaggggga
ggttgcccagattgcgctgctgcactccagcctggtgacagagtgagactcatgtcaacaacaaaaacagaaaaagcacg
cacatctaaaacatgcttttgtgatccatttgggatggtgatgacattcaaatagttttttaaaaatagattttctcctt
tctggtttccgtttgtgttctttatgccttttgccagagtaggtggtgcaatttggctagctggctttcattactgtt
tttcacacattaactttggcctcaacttgacaactcaaataatatttataaatacagccacacttaaaatggtcccatta
tgaaatacatatttaaatatctatacgatgtgttaaaaccaagaaaatatttgattcttctctgatatttaagaattgaa
ggtttgaggtagttacgtgttaggggcatttatattcatgtttttagagtttgcttatacaacttaatctttccttttca
gTGCTTTGGGCTCCTGGGAGTTAATGGGGCTGGAAAATCATCAACTTTCAAGATGTTAACAGGAGATACCACTGTTACCA
GAGGAGATGCTTTCCTTAACAAAAATAGgtgagaaaagaagtggcttgtattttgctgcaaagactttgttttttaattta
tttaaagaaataggttgttatttttgattacagtggtatttttagagttcataaaaatgttgaaatatagtaaagggtaa
agaagcacataaaatcatccatgatttcaatatctagagataatcacaatttacatttcctttcagtctcattctcttct
tttaacagctttattcaggtataatttacatacaatataatttgcttgttttttaagagtataatttagtgattttggt
aaattgagagttttgcaaccatcaccacaatccagttttagaacttttccatcacccacatctgtcttatatacacata
taaatgtgccatacaattgagatcatactgtatgtagaatttaaaattagttttttattgttaatgagtgtattatgaata
tttcccagtggggttacatttcctaagatgtggaattttacattgctacataaaatcccctatgtacatgtacctataat
ttatttaataaattccttataaatgttggacacattagtttccatttttcactatgtaaatatgtccctgtatacatctt
ttattatttcctcaggaacaattcctacaaagtaaattgccctctctaaagagcatacaaattgactgagccaccgttag
gccatttctgagactgcacaggtcacaaagcaatctgatctttgggaatacagctacattttataggcttcttagataa
tgttactctaagtactttaaatatgtggggcttctctgggcttttttttttttgagacggagtttcactcttactgccca
ggctggagagcaatggcgcgaccttggctcactgcaacctccgcctcccaggttcaagcgattctcctgcctcagcctcc
tgagtagctgagattacaggtgcccgccacaatgcctgcctaattttttttgtatttcagtagagatgggtttcaccat
gttggccagactggtctcgagctcctgacctcaggtgatccacctgcctcagcctcccaaagttctgggattacaggcat
gagccactgcgcccggcttctctggacttattatgtggagagatagtacaaggcagtggctttcagagttttttgaccat
gaccgttgtgggaaatacatttatatctcaacctagtatgtacacacagacatgtagacacatgtataacctaaagttt
cataaagcagtacctactgttactaattgtagtgcactctgctatttcttattctacctatactgcgtcattaaaaaag
tgctggtcatgacccactaaatttatttcccaaaccactaatgaacaatgactcacaatttgaacacactggacagggggg
atagccaataaaattgaaaagagcaaggaaattaatgtattcatgatctcctctcctgtctcttacatttttgcagtagc
aatgtaaaggaatcctaagagaacagacattctgggaatagcaggcctagcgctgcacaactgctttcctaggcttgctc
ctagtaccaagctcctgacgcatatagcagtggcagtaataaccagcccatagtaaggtttgtcacagggactggttgta
agaactgatttgrttggtatagctgtgagggcctggcacggtgtccacgtgtgcctcaatcctaattctgaaaaaggctg
accctggggggtgctaattagatacacagagaggaatgaatgctgccagaaggccaagttcatggcaatgccgctgtggct
gaggtgcagtcatcagtctggaacgtgaacactgaacttctctcacatgtgattcttcacttgactggcttcatagaacc
ccaaagccaccccaccaccacataaattgtgtctctaggttctgtgttgctcacactcaaaatttctgggccttctcatt
tggtgcatgtgaatggtgcatatgagtgaagtctaggatggggccttagcgttaaagccctggggtagtgtgactgagat
tgttggtaaagaatgtgcagtggttggcatgacctcagaaattctgaaatgggactgcacctgcagactgaagtgttcag

```
agagccagggaggtgcaaggactggggagggtagaggcaggaaccctgcctgccaggaagagctagcatcctgggggcag
aaaggctgtgctttcaagtagcagcagatgtattggtatctttgtaatggagaagcatactttacaggaacattaggcca
gattgtctaaccagagtatctctacctgcttaaaatctaagtagtttcttgtcctttgcagTATCTTATCAAACATCCA
TGAAGTACATCAGAACATGGGCTACTGCCCTCAGTTTGATGCCATCACAGAGCTGTTGACTGGGAGAGAACACGTGGAGT
TCTTTGCCCTTTTGAGAGGAGTCCCAGAGAAAGAAGTTGGCAAGgtactgtgggcacctgaaagccagcctgtctcctt
ggcatcctgacaatatatacctatggctttccacacgcattgacttcaggctgttttcctcatgaatgcagcagcac
aaaatgctggttctttgtatctgctttcagggtggaaacctgtaacggtggtggggcagggctgggtgggcagagaggga
gtgctgctcccaccacacgagtccttctccctgctttggctcctcaccagttgtcaggttatgattatagaatctagtc
ctactcagtgaaagaactttcatacatgtatgtgtaggacagcatgataaaattcccaagccagaccaaagtcaaggtgc
tttttatcactgtagGTTGGTGAGTGGGCGATTCGGAAACTGGGCCTCGTGAAGTATGGAGAAAAATATGCTGGTAACTA
TAGTGGAGGCAACAAACGCAAGCTCTCTACAGCCATGGCTTTGATCGGCGGGCCTCCTGTGGTGTTTCTGgtgagtataa
ctgtggatggaaaactgttgttctggcctgagtggaaaacatgactgttcaaaagtcctatatgtccagggctgttgtat
gattggcttgtcttccccagggacagcagagcaaccttggaaaagcagagggaagcttctcccttggcacacactgggg
tggctgtaccatgcctgcagatgctcccaaatagaggcactccaagcactttgtttcttagcgtgattgaggctggatat
gtgatttgatctttctctggaacattctttctaatcatctttgtgttcattccctgaaaatgaagagtgtggacacagct
ttaaaatccccaaggtagcaactaggtcatagttccttacacacggatagatgaaaaacagatcagactgggaagtggcc
cttgaccttttttcttctgtagataagagcattgatgttattacgggaagaagcctttgaggcttttatgtattccacct
cggtctggaatttgtttctgtaaggctaacagttgcaatatactagggtaatctgagtgagctggaattaaaaaaaaaa
ggaatttcaccccaatcttatactgacttcaatagaggtttcagacaaaaagttgttttgtat
```

Figure 12O – (2)

SEQ ID NO: 29
Genomic contig containing ABC1 exon 46 to 49:

ngccnngttnaaaangaaaatttnnnnnaaattnaannttanngggngnnntttccccagaaaaaacnaaaangatttccn
cccnggggggnccccccnantcnaaaaggccccncttntttgnggngagggaaagnttttttttggaatttttaatttttgg
tcccccaaaacctattattgagaatttaattacataaaaaagtactcagaatatttgagtttcctgcatcaataagacat
ttataataatgaccttgtttacaaatgaatttgaaagttactctaattctttgattcatcaagaaataactagaatggca
agttaaaatttaagctgtttcaaagatgcttctgcatttaaaaacaaatttatctttgatttttttccccccagcaaat
aagacttattttattctaattacagGATGAACCCACCACAGGCATGGATCCCAAAGCCCGGCGGTTCTTGTGGAATTGTG
CCCTAAGTGTTGTCAAGGAGGGGAGATCAGTAGTGCTTACATCTCATAGgtccgtagtaaagtcttgggttcctcactgt
gggatgttttaactttccaagtagaatatgcgatcattttgtaaaaattagaaaatacagaaaagcaaagagtaaaacaa
ttattacctgaaattatatatgcatattcttacaaaaatgcaagcccagtataaatactgctcttttttcacttaatatat
tgtaaacattattccaagtcagtgcatttaggtgtcatttcttatagctggatagtattccattaggatatactcttatt
taactattcccccttttgtagacatttggattatttccaacttgttcacaattgtaaacaccactacactgaacagcatc
atccctatatccacatgtacttgtaacagaatacaattccctaggaagctggaatgctggaagtcatggtgatgttctca
tggttacagagaatctctctaaaactaaaacctctttctgttttaccgcagTATGAAGAATGTGAAGCTCTTTGCACTA
GGATGGCAATCATGGTCAATGGAAGGTTCAGGTGCCTTGGCAGTGTCCAGCATCTAAAAAATAGgtaataaagataattt
ctttgggatagtgcctagtgagaaggcttgatatttattcttttgtgagtatataaatggtgcctctaaaataaagggaa
ataaaactgagcaaaacagtatagtggaaagaatgagggctttgaagtccgaactgcattcaaattctgtctttaccatt
tactggttctgtgactcttgggcaagttacttaactactgtaagagttagtttccctggaagatctacctcctagctttg
tgctatagatgaaatgaaaaaatttacatgtgccagtactggtgagagcgcaagctttggagtcaaacacaaatgggtt
tgcatcctggccctaccaattatgagctctgagccatgggcaagtgactaactccctgggcctcagtttctctgtaacat
ctgtcagacttcatgggtccaggtgaggattaaaggagatcatgtatttacagcacatggcatggtgcttcacataaaat
aagtatttagtaaatgataactggttccttctctcagaaacttatttctgggcctgccaggggccgccctttttcatggc
acaagttgggttcccagggttcagtattcttttaaatagtttctggagatcctcatttgggtattttttcctgctttc
agGTTTGGAGATGGTTATACAATAGTTGTACGAATAGCAGGGTCCAACCCGGACCTGAAGCCTGTCCAGGATTTCTTTGG
ACTTGCATTTCCTGGAAGTGTTCYAAAAGAGAAACACCGGAACATGCTACAATACCAGCTTCCATCTTCATTATCTTCTC
TGGCCAGGATATTCAGCATCCTCTCCCAGAGCAAAAAGCGACTCCACATAGAAGACTACTCTGTTTCTCAGACAACACTT
GACCAAgtaagctttgagtgtcaaaacagatttacttctcagggtgtggattcctgccccgacactcccgcccataggtc
caagagcagtttgtatcttgaattggtgcttgaattcctgatctactattcctagctatgcttttactaaacctctctg
aacctgaaaagggagatgatgcctatgtactctataggattattgtgagaatttactgtaataataaccataaaaactac
catttagtgagcacctaccatgggccaggcatttttacttggtgcctaatcctatttaaattagataaaaaagtaccaaat
aggtcctgacacttaagaagtactcagtaaatatttcttccctcttcccttttaatcaagaccgtatgtgccaaagtaaa
tggatgactgagcagttggtgatgtaggggtgggggggcgatatagaaagtcagttttggccgggcgtggtggctcatgc
ctgtaatcccagcactttgggaggctgaggagcaggcagatcatgaggtcaggagatccagataatcctggccaacaggg
tgaaaccccgtctctactaaaaatacaaaaattagctgggcatggtggtgcgcacttgtagtcccagctacttgcgaggc
tgaggcaggagaattgctcgaacccaggaggtggaggttacagtgagccaaggtctcgccactgcactccagcctgggga
cagagcaagacccatttcaagggggaaaaaaagtctatttttaagttgttattgcttttttcaagtattcttccctcc
ttcacacacagttttctagttaatccatttatgtaattctgtatgctcctacttgacctaatttcaacatctggaaaaat
agaactagaataaagaatgagcaagttgagtggtatttataaaggtccatcttaatcttttaacagGTATTTGTGAACTT
TGCCAAGGACCAAAGTGATGATGACCACTTAAAAGACCTCTCATTACACAAAAACCAGACAGTAGTGGACGTTGCAGTTC
TCACATCTTTTCTACAGGATGAGAAAGTGAAAGAAAGCTATGTATGAAGAATCCTGTTCATACGGGGTGGCTGAAAGTAA
AGAGGAACTAGACTTTCCTTTGCACCATGTGAAGTGTTGTGGAGAAAAGAGCCAGAAGTTGATGTGGGAAGAAGTAAACT
GGATACTGTACTGATACTATTCAATGCAATGCAATTCAATGcaatgaaaacaaaattccattacaggggcagtgcctttg
tagcctatgtcttgtatggctctcaagtgaaagacttgaatttagttttttacctatacctatgtgaaactctattatgg
aacccaatggacatatgggtttgaactcacacttttttttttttttttgttcctgtgtattctcattggggttgcaacaa
taattcatcaagtaatcatggccagcgattattgatcaaaatcaaaaggtaatgcacatcctcattcactaagccatgcc

Figure 12P – (1)

```
atgcccaggagactggtttcccggtgacacatccattgctggcaatgagtgtgccagagttattagtgccaagtttttca
gaaagtttgaagcaccatggtgtgtcatgctcacttttgtgaaagctgctctgctcagagtctatcaacattgaatatca
gttgacagaatggtgccatgcgtggctaacatcctgctttgattccctctgataagctgttctggtggcagtaacatgca
acaaaaatgtgggtgtctccaggcacgggaaacttggttccattgttatattgtcctatgcttcgagccatgggtctaca
gggtcatccttatgagactcttaaatatacttagatcctggtaagaggcaaagaatcaacagccaaactgctggggctgc
aactgctgaagccagggcatgggattaaagagattgtgcgttcaaacctagggaagcctgtgcccatttgtcctgactgt
ctgctaacatggtacactgcatctcaagatgtttatctgacacaagtgtattatttctggcttttttgaattaatctagaa
aatgaaaagatggagttgtattttgacaaaaatgtttgtacttttttaatgttatttggaattttaagttctatcagtgac
ttctgaatccttagaatggcctctttgtagaaccctgtggtatagaggagtatggccactgcccactattttattttct
tatgtaagtttgcatatcagtcatgactagtgcctagaaagcaatgtgatggtcaggatctcatgacattatatttgagt
ttctttcagatcatttaggatactcttaatctcacttcatcaatcaaatattttttgagtgtatgctgtagctgaaagag
tatgtacgtacgtataagactagagagatattaagtctcagtacacttcctgtgccatgttattcagctcactggtttac
aaatataggttgtcttgtggttgtaggagcccactgtaacaatactgggcagcctttttttttttttttttaattgcaac
aatgcaaaagccaagaaagtttaagggtcacaagtctaaacaatgaattcttcaacagggaaaacagctagcttgaaaac
ttgctgaaaaacacaacttgtgtttatggcatttagtaccttcaaataattggctttgcagatattggatacccattaa
atctgacagtctcaaattttcatctcttcaatcactagtcaagaaaaaatataaaaacaacaaatacttccatatggag
cattttcagagttttctaacccagtcttatttttctagtcagtaaacatttgtaaaaatactgtttcactaatacttac
tgttaactgtcttgagagaaaagaaaaatatgagagaactattgtttggggaagttcaagtgatctttcaatatcattac
taacttcttccactttttccagaatttgaatattaacgctaaaggtgtaagacttcagatttcaaattaatctttctata
tttttaaatttacagaatattatataacccactgctgaaaaagaaacaaatgattgttttagaagttaaaggtcaatat
tgattttaaaatattaag
```

Figure 12P – (2)

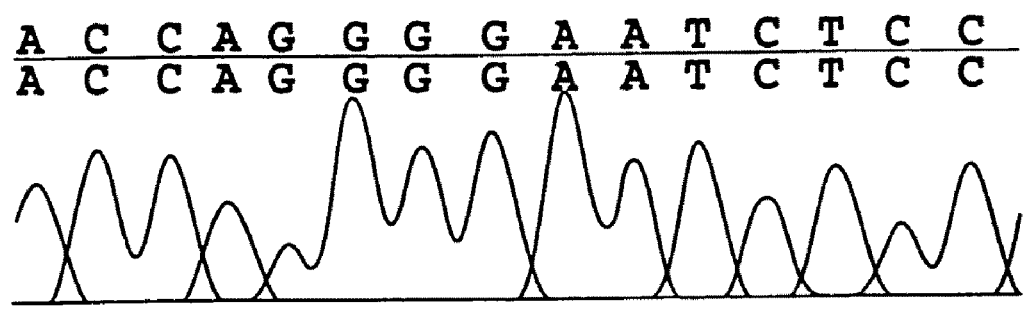
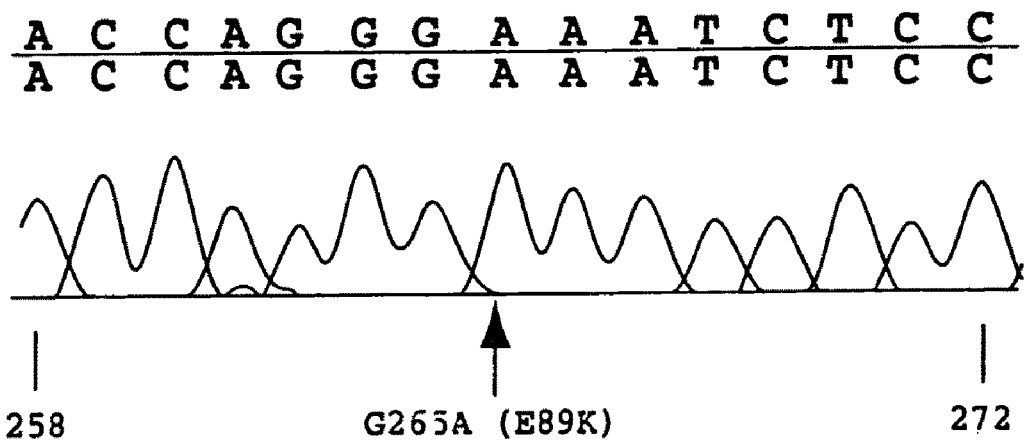
Fig. 14

| No. | Name | Location in SEQ ID No. 14 | Sequence | Sequence Length | Strand |
|---|---|---|---|---|---|
| 1 | PPRE | 58-69 | AGGTAAAAGTCA | 12 | Complement |
| 2 | PPRE | 1997-2009 | AGAGTAGAGGGCA | 13 | Lead |
| 3 | PPRE | 2150-2161 | ATGTCAAGTTCA | 12 | Lead |
| 4 | PPRE | 2156-2169 | AGTTCAAAAGGGCA | 14 | Lead |
| 5 | PPRE | 4126-1139 | AGGCCAGCAGGCC | 13 | Complement |
| 6 | PPRE | 5075-5087 | AGGCAGAAGTGA | 13 | Lead |
| 7 | PPRE | 6604-6615 | ATGCCAAGTCA | 12 | Complement |
| 8 | PPRE | 6731-6743 | GGGGCAAGGTA | 13 | Complement |
| 9 | PPRE | 7220-7233 | AGGTAATGAGACA | 14 | Complement |
| 10 | PPRE | 7554-7568 | GGATCACGAGGTCA | 15 | Complement |
| 1 | SRE | 159-166 | CAGCCCAT | 8 | Lead |
| 2 | SRE | 1133-1140 | CAGCTCAC | 8 | Complement |
| 3 | SRE | 1145-1152 | CACACCAC | 8 | Lead |
| 4 | SRE | 1809-1816 | CAGCCCTC | 8 | Complement |
| 5 | SRE | 1894-1901 | CAGCCCAT | 8 | Lead |
| 6 | SRE | 2563-2570 | CAACCCAC | 8 | Lead |
| 7 | SRE | 3303-3310 | CAGCTCAC | 8 | Lead |
| 8 | SRE | 3470-3477 | CCGCCCAC | 8 | Lead |
| 9 | SRE | 4784-4791 | CTCCCCAC | 8 | Complement |
| 10 | SRE | 4802-4809 | CAGCCTAC | 8 | Complement |
| 11 | SRE | 4970-4977 | CACCTCAC | 8 | Complement |
| 12 | SRE | 6487-6494 | CAGCCTAC | 8 | Complement |
| 13 | SRE | 6565-6572 | CACCCAAC | 8 | Complement |
| 14 | SRE | 6727-6734 | CACCCTCA | 8 | Complement |
| 15 | SRE | 7041-7048 | CACCCAAC | 8 | Lead |
| 16 | SRE | 8059-8066 | CAGCCCTC | 8 | Complement |
| 1 | ROR(retinoic acid receptor related) | 166-172 | AGGGTCA | 7 | Complement |
| 2 | ROR(retinoic acid receptor related) | 166-173 | AAGGGTCA | 8 | Complement |
| 3 | ROR(retinoic acid receptor related) | 263-370 | ATGGGTCA | 8 | Lead |
| 4 | ROR(retinoic acid receptor related) | 264-370 | TGGGTCA | 7 | Lead |
| 5 | ROR(retinoic acid receptor related) | 2218-2225 | TAGGGTCA | 8 | Lead |
| 6 | ROR(retinoic acid receptor related) | 2219-2225 | AGGGTCA | 7 | Lead |
| 7 | ROR(retinoic acid receptor related) | 3643-2649 | TGGGTCA | 7 | Lead |
| 8 | ROR(retinoic acid receptor related) | 6604-6610 | AAGGTCA | 7 | Complement |
| 1 | SREBP-1 or "E box" | 473-479 | ACACCTG | 7 | Complement |
| 2 | SREBP-1 or "E box" | 536-541 | ACACATG | 7 | Lead |
| 3 | SREBP-1 or "E box" | 537-543 | TCATGTG | 7 | Complement |
| 4 | SREBP-1 or "E box" | 655-661 | TCATGTG | 7 | Lead |
| 5 | SREBP-1 or "E box" | 925-931 | ACACTTG | 7 | Lead |
| 6 | SREBP-1 or "E box" | 967-973 | TCACTTG | 7 | Lead |
| 7 | SREBP-1 or "E box" | 968-974 | ACAGTG | 7 | Complement |
| 8 | SREBP-1 or "E box" | 1053-1069 | ACAGTG | 7 | Complement |
| 9 | SREBP-1 or "E box" | 1104-1110 | TCACTTG | 7 | Lead |
| 10 | SREBP-1 or "E box" | 1105-1111 | TCAAGTG | 7 | Complement |
| 11 | SREBP-1 or "E box" | 1561-1567 | TCACTTG | 7 | Lead |

SEQUENCE LISTING

<160> NUMBER OF SEQ ID NOS: 287

<210> SEQ ID NO 1
<211> LENGTH: 2261
<212> TYPE: PRT
<213> ORGANISM: Homo sapiens

<400> SEQUENCE: 1

```
Met Ala Cys Trp Pro Gln Leu Arg Leu Leu Trp Lys Asn Leu Thr
 1               5                  10                  15

Phe Arg Arg Arg Gln Thr Cys Gln Leu Leu Leu Glu Val Ala Trp Pro
                20                  25                  30

Leu Phe Ile Phe Leu Ile Leu Ile Ser Val Arg Leu Ser Tyr Pro Pro
            35                  40                  45

Tyr Glu Gln His Glu Cys His Phe Pro Asn Lys Ala Met Pro Ser Ala
        50                  55                  60

Gly Thr Leu Pro Trp Val Gln Gly Ile Ile Cys Asn Ala Asn Asn Pro
65                  70                  75                  80

Cys Phe Arg Tyr Pro Thr Pro Gly Glu Ala Pro Gly Val Val Gly Asn
                85                  90                  95

Phe Asn Lys Ser Ile Val Ala Arg Leu Phe Ser Asp Ala Arg Arg Leu
            100                 105                 110

Leu Leu Tyr Ser Gln Lys Asp Thr Ser Met Lys Asp Met Arg Lys Val
            115                 120                 125

Leu Arg Thr Leu Gln Gln Ile Lys Lys Ser Ser Ser Asn Leu Lys Leu
            130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
            180                 185                 190

Ser Leu Cys Asn Gly Ser Lys Ser Glu Glu Met Ile Gln Leu Gly Asp
            195                 200                 205

Gln Glu Val Ser Glu Leu Cys Gly Leu Pro Arg Glu Lys Leu Ala Ala
        210                 215                 220

Ala Glu Arg Val Leu Arg Ser Asn Met Asp Ile Leu Lys Pro Ile Leu
```

```
                225                 230                 235                 240
Arg Thr Leu Asn Ser Thr Ser Pro Phe Pro Ser Lys Glu Leu Ala Glu
                245                 250                 255

Ala Thr Lys Thr Leu Leu His Ser Leu Gly Thr Leu Ala Gln Glu Leu
        260                 265                 270

Phe Ser Met Arg Ser Trp Ser Asp Met Arg Gln Glu Val Met Phe Leu
        275                 280                 285

Thr Asn Val Asn Ser Ser Ser Ser Thr Gln Ile Tyr Gln Ala Val
    290                 295                 300

Ser Arg Ile Val Cys Gly His Pro Glu Gly Gly Leu Lys Ile Lys
305                 310                 315                 320

Ser Leu Asn Trp Tyr Glu Asp Asn Tyr Lys Ala Leu Phe Gly Gly
                325                 330                 335

Asn Gly Thr Glu Glu Asp Ala Glu Thr Phe Tyr Asp Asn Ser Thr Thr
            340                 345                 350

Pro Tyr Cys Asn Asp Leu Met Lys Asn Leu Glu Ser Ser Pro Leu Ser
        355                 360                 365

Arg Ile Ile Trp Lys Ala Leu Lys Pro Leu Leu Val Gly Lys Ile Leu
    370                 375                 380

Tyr Thr Pro Asp Thr Pro Ala Thr Arg Gln Val Met Ala Glu Val Asn
385                 390                 395                 400

Lys Thr Phe Gln Glu Leu Ala Val Phe His Asp Leu Glu Gly Met Trp
                405                 410                 415

Glu Glu Leu Ser Pro Lys Ile Trp Thr Phe Met Glu Asn Ser Gln Glu
            420                 425                 430

Met Asp Leu Val Arg Met Leu Leu Asp Ser Arg Asp Asn Asp His Phe
        435                 440                 445

Trp Glu Gln Gln Leu Asp Gly Leu Asp Trp Thr Ala Gln Asp Ile Val
    450                 455                 460

Ala Phe Leu Ala Lys His Pro Glu Asp Val Gln Ser Ser Asn Gly Ser
465                 470                 475                 480

Val Tyr Thr Trp Arg Glu Ala Phe Asn Glu Thr Asn Gln Ala Ile Arg
                485                 490                 495

Thr Ile Ser Arg Phe Met Glu Cys Val Asn Leu Asn Lys Leu Glu Pro
            500                 505                 510

Ile Ala Thr Glu Val Trp Leu Ile Asn Lys Ser Met Glu Leu Leu Asp
        515                 520                 525

Glu Arg Lys Phe Trp Ala Gly Ile Val Phe Thr Gly Ile Thr Pro Gly
    530                 535                 540

Ser Ile Glu Leu Pro His His Val Lys Tyr Lys Ile Arg Met Asp Ile
545                 550                 555                 560

Asp Asn Val Glu Arg Thr Asn Lys Ile Lys Asp Gly Tyr Trp Asp Pro
                565                 570                 575

Gly Pro Arg Ala Asp Pro Phe Glu Asp Met Arg Tyr Val Trp Gly Gly
            580                 585                 590

Phe Ala Tyr Leu Gln Asp Val Val Glu Gln Ala Ile Ile Arg Val Leu
        595                 600                 605

Thr Gly Thr Glu Lys Lys Thr Gly Val Tyr Met Gln Gln Met Pro Tyr
    610                 615                 620

Pro Cys Tyr Val Asp Asp Ile Phe Leu Arg Val Met Ser Arg Ser Met
625                 630                 635                 640

Pro Leu Phe Met Thr Leu Ala Trp Ile Tyr Ser Val Ala Val Ile Ile
                645                 650                 655
```

-continued

```
Lys Gly Ile Val Tyr Glu Lys Glu Ala Arg Leu Lys Glu Thr Met Arg
            660                 665                 670

Ile Met Gly Leu Asp Asn Ser Ile Leu Trp Phe Ser Trp Phe Ile Ser
        675                 680                 685

Ser Leu Ile Pro Leu Leu Val Ser Ala Gly Leu Leu Val Val Ile Leu
    690                 695                 700

Lys Leu Gly Asn Leu Leu Pro Tyr Ser Asp Pro Ser Val Val Phe Val
705                 710                 715                 720

Phe Leu Ser Val Phe Ala Val Val Thr Ile Leu Gln Cys Phe Leu Ile
                725                 730                 735

Ser Thr Leu Phe Ser Arg Ala Asn Leu Ala Ala Ala Cys Gly Gly Ile
            740                 745                 750

Ile Tyr Phe Thr Leu Tyr Leu Pro Tyr Val Leu Cys Val Ala Trp Gln
        755                 760                 765

Asp Tyr Val Gly Phe Thr Leu Lys Ile Phe Ala Ser Leu Leu Ser Pro
    770                 775                 780

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
                805                 810                 815

Asp Gly Phe Asn Leu Thr Thr Ser Val Ser Met Met Leu Phe Asp Thr
            820                 825                 830

Phe Leu Tyr Gly Val Met Thr Trp Tyr Ile Glu Ala Val Phe Pro Gly
        835                 840                 845

Gln Tyr Gly Ile Pro Arg Pro Trp Tyr Phe Pro Cys Thr Lys Ser Tyr
    850                 855                 860

Trp Phe Gly Glu Glu Ser Asp Glu Lys Ser His Pro Gly Ser Asn Gln
865                 870                 875                 880

Lys Arg Ile Ser Glu Ile Cys Met Glu Glu Pro Thr His Leu Lys
                885                 890                 895

Leu Gly Val Ser Ile Gln Asn Leu Val Lys Val Tyr Arg Asp Gly Met
            900                 905                 910

Lys Val Ala Val Asp Gly Leu Ala Leu Asn Phe Tyr Glu Gly Gln Ile
        915                 920                 925

Thr Ser Phe Leu Gly His Asn Gly Ala Gly Lys Thr Thr Thr Met Ser
    930                 935                 940

Ile Leu Thr Gly Leu Phe Pro Pro Thr Ser Gly Thr Ala Tyr Ile Leu
945                 950                 955                 960

Gly Lys Asp Ile Arg Ser Glu Met Ser Thr Ile Arg Gln Asn Leu Gly
                965                 970                 975

Val Cys Pro Gln His Asn Val Leu Phe Asp Met Leu Thr Val Glu Glu
            980                 985                 990

His Ile Trp Phe Tyr Ala Arg Leu Lys Gly Leu Ser Glu Lys His Val
        995                 1000                1005

Lys Ala Glu Met Glu Gln Met Ala Leu Asp Val Gly Leu Pro Ser Ser
    1010                1015                1020

Lys Leu Lys Ser Lys Thr Ser Gln Leu Ser Gly Gly Met Gln Arg Lys
1025                1030                1035                1040

Leu Ser Val Ala Leu Ala Phe Val Gly Gly Ser Lys Val Val Ile Leu
                1045                1050                1055

Asp Glu Pro Thr Ala Gly Val Asp Pro Tyr Ser Arg Arg Gly Ile Trp
            1060                1065                1070

Glu Leu Leu Leu Lys Tyr Arg Gln Gly Arg Thr Ile Ile Leu Ser Thr
        1075                1080                1085
```

```
His His Met Asp Glu Ala Asp Val Leu Gly Asp Arg Ile Ala Ile Ile
    1090                1095                1100

Ser His Gly Lys Leu Cys Cys Val Gly Ser Ser Leu Phe Leu Lys Asn
1105                1110                1115                1120

Gln Leu Gly Thr Gly Tyr Tyr Leu Thr Leu Val Lys Lys Asp Val Glu
                1125                1130                1135

Ser Ser Leu Ser Ser Cys Arg Asn Ser Ser Thr Val Ser Tyr Leu
                1140                1145                1150

Lys Lys Glu Asp Ser Val Ser Gln Ser Ser Asp Ala Gly Leu Gly
                1155                1160                1165

Ser Asp His Glu Ser Asp Thr Leu Thr Ile Asp Val Ser Ala Ile Ser
    1170                1175                1180

Asn Leu Ile Arg Lys His Val Ser Glu Ala Arg Leu Val Glu Asp Ile
1185                1190                1195                1200

Gly His Glu Leu Thr Tyr Val Leu Pro Tyr Glu Ala Ala Lys Glu Gly
                1205                1210                1215

Ala Phe Val Glu Leu Phe His Glu Ile Asp Asp Arg Leu Ser Asp Leu
                1220                1225                1230

Gly Ile Ser Ser Tyr Gly Ile Ser Glu Thr Thr Leu Glu Glu Ile Phe
                1235                1240                1245

Leu Lys Val Ala Glu Glu Ser Gly Val Asp Ala Glu Thr Ser Asp Gly
                1250                1255                1260

Thr Leu Pro Ala Arg Arg Asn Arg Arg Ala Phe Gly Asp Lys Gln Ser
1265                1270                1275                1280

Cys Leu Arg Pro Phe Thr Glu Asp Ala Ala Asp Pro Asn Asp Ser
                1285                1290                1295

Asp Ile Asp Pro Glu Ser Arg Glu Thr Asp Leu Leu Ser Gly Met Asp
                1300                1305                1310

Gly Lys Gly Ser Tyr Gln Val Lys Gly Trp Lys Leu Thr Gln Gln Gln
                1315                1320                1325

Phe Val Ala Leu Leu Trp Lys Arg Leu Leu Ile Ala Arg Arg Ser Arg
    1330                1335                1340

Lys Gly Phe Phe Ala Gln Ile Val Leu Pro Ala Val Phe Val Cys Ile
1345                1350                1355                1360

Ala Leu Val Phe Ser Leu Ile Val Pro Pro Phe Gly Lys Tyr Pro Ser
                1365                1370                1375

Leu Glu Leu Gln Pro Trp Met Tyr Asn Glu Gln Tyr Thr Phe Val Ser
                1380                1385                1390

Asn Asp Ala Pro Glu Asp Thr Gly Thr Leu Glu Leu Leu Asn Ala Leu
                1395                1400                1405

Thr Lys Asp Pro Gly Phe Gly Thr Arg Cys Met Glu Gly Asn Pro Ile
    1410                1415                1420

Pro Asp Thr Pro Cys Gln Ala Gly Glu Glu Trp Thr Thr Ala Pro
1425                1430                1435                1440

Val Pro Gln Thr Ile Met Asp Leu Phe Gln Asn Gly Asn Trp Thr Met
                1445                1450                1455

Gln Asn Pro Ser Pro Ala Cys Gln Cys Ser Ser Asp Lys Ile Lys Lys
                1460                1465                1470

Met Leu Pro Val Cys Pro Pro Gly Ala Gly Gly Leu Pro Pro Pro Gln
                1475                1480                1485

Arg Lys Gln Asn Thr Ala Asp Ile Leu Gln Asp Leu Thr Gly Arg Asn
    1490                1495                1500

Ile Ser Asp Tyr Leu Val Lys Thr Tyr Val Gln Ile Ile Ala Lys Ser
```

-continued

```
              1505                1510                1515                1520
Leu Lys Asn Lys Ile Trp Val Asn Glu Phe Arg Tyr Gly Gly Phe Ser
                  1525                1530                1535
Leu Gly Val Ser Asn Thr Gln Ala Leu Pro Pro Ser Gln Glu Val Asn
                  1540                1545                1550
Asp Ala Ile Lys Gln Met Lys Lys His Leu Lys Leu Ala Lys Asp Ser
                  1555                1560                1565
Ser Ala Asp Arg Phe Leu Asn Ser Leu Gly Arg Phe Met Thr Gly Leu
                  1570                1575                1580
Asp Thr Arg Asn Asn Val Lys Val Trp Phe Asn Asn Lys Gly Trp His
1585                1590                1595                1600
Ala Ile Ser Ser Phe Leu Asn Val Ile Asn Asn Ala Ile Leu Arg Ala
                  1605                1610                1615
Asn Leu Gln Lys Gly Glu Asn Pro Ser His Tyr Gly Ile Thr Ala Phe
                  1620                1625                1630
Asn His Pro Leu Asn Leu Thr Lys Gln Gln Leu Ser Glu Val Ala Leu
                  1635                1640                1645
Met Thr Thr Ser Val Asp Val Leu Val Ser Ile Cys Val Ile Phe Ala
                  1650                1655                1660
Met Ser Phe Val Pro Ala Ser Phe Val Val Phe Leu Ile Gln Glu Arg
1665                1670                1675                1680
Val Ser Lys Ala Lys His Leu Gln Phe Ile Ser Gly Val Lys Pro Val
                  1685                1690                1695
Ile Tyr Trp Leu Ser Asn Phe Val Trp Asp Met Cys Asn Tyr Val Val
                  1700                1705                1710
Pro Ala Thr Leu Val Ile Ile Ile Phe Ile Cys Phe Gln Gln Lys Ser
                  1715                1720                1725
Tyr Val Ser Ser Thr Asn Leu Pro Val Leu Ala Leu Leu Leu Leu Leu
                  1730                1735                1740
Tyr Gly Trp Ser Ile Thr Pro Leu Met Tyr Pro Ala Ser Phe Val Phe
1745                1750                1755                1760
Lys Ile Pro Ser Thr Ala Tyr Val Val Leu Thr Ser Val Asn Leu Phe
                  1765                1770                1775
Ile Gly Ile Asn Gly Ser Val Ala Thr Phe Val Leu Glu Leu Phe Thr
                  1780                1785                1790
Asp Asn Lys Leu Asn Asn Ile Asn Asp Ile Leu Lys Ser Val Phe Leu
                  1795                1800                1805
Ile Phe Pro His Phe Cys Leu Gly Arg Gly Leu Ile Asp Met Val Lys
                  1810                1815                1820
Asn Gln Ala Met Ala Asp Ala Leu Glu Arg Phe Gly Glu Asn Arg Phe
1825                1830                1835                1840
Val Ser Pro Leu Ser Trp Asp Leu Val Gly Arg Asn Leu Phe Ala Met
                  1845                1850                1855
Ala Val Glu Gly Val Val Phe Phe Leu Ile Thr Val Leu Ile Gln Tyr
                  1860                1865                1870
Arg Phe Phe Ile Arg Pro Arg Pro Val Asn Ala Lys Leu Ser Pro Leu
                  1875                1880                1885
Asn Asp Glu Asp Glu Asp Val Arg Arg Glu Arg Gln Arg Ile Leu Asp
                  1890                1895                1900
Gly Gly Gly Gln Asn Asp Ile Leu Glu Ile Lys Glu Leu Thr Lys Ile
1905                1910                1915                1920
Tyr Arg Arg Lys Arg Lys Pro Ala Val Asp Arg Ile Cys Val Gly Ile
                  1925                1930                1935
```

-continued

```
Pro Pro Gly Glu Cys Phe Gly Leu Leu Gly Val Asn Gly Ala Gly Lys
        1940                1945                1950

Ser Ser Thr Phe Lys Met Leu Thr Gly Asp Thr Val Thr Arg Gly
    1955                1960                1965

Asp Ala Phe Leu Asn Lys Asn Ser Ile Leu Ser Asn Ile His Glu Val
    1970                1975                1980

His Gln Asn Met Gly Tyr Cys Pro Gln Phe Asp Ala Ile Thr Glu Leu
1985                1990                1995                2000

Leu Thr Gly Arg Glu His Val Glu Phe Phe Ala Leu Leu Arg Gly Val
            2005                2010                2015

Pro Glu Lys Glu Val Gly Lys Val Gly Glu Trp Ala Ile Arg Lys Leu
        2020                2025                2030

Gly Leu Val Lys Tyr Gly Glu Lys Tyr Ala Gly Asn Tyr Ser Gly Gly
        2035                2040                2045

Asn Lys Arg Lys Leu Ser Thr Ala Met Ala Leu Ile Gly Gly Pro Pro
    2050                2055                2060

Val Val Phe Leu Asp Glu Pro Thr Thr Gly Met Asp Pro Lys Ala Arg
2065                2070                2075                2080

Arg Phe Leu Trp Asn Cys Ala Leu Ser Val Val Lys Glu Gly Arg Ser
        2085                2090                2095

Val Val Leu Thr Ser His Ser Met Glu Glu Cys Glu Ala Leu Cys Thr
            2100                2105                2110

Arg Met Ala Ile Met Val Asn Gly Arg Phe Arg Cys Leu Gly Ser Val
        2115                2120                2125

Gln His Leu Lys Asn Arg Phe Gly Asp Gly Tyr Thr Ile Val Val Arg
    2130                2135                2140

Ile Ala Gly Ser Asn Pro Asp Leu Lys Pro Val Gln Asp Phe Phe Gly
2145                2150                2155                2160

Leu Ala Phe Pro Gly Ser Val Leu Lys Glu Lys His Arg Asn Met Leu
            2165                2170                2175

Gln Tyr Gln Leu Pro Ser Ser Leu Ser Ser Leu Ala Arg Ile Phe Ser
        2180                2185                2190

Ile Leu Ser Gln Ser Lys Lys Arg Leu His Ile Glu Asp Tyr Ser Val
        2195                2200                2205

Ser Gln Thr Thr Leu Asp Gln Val Phe Val Asn Phe Ala Lys Asp Gln
    2210                2215                2220

Ser Asp Asp Asp His Leu Lys Asp Leu Ser Leu His Lys Asn Gln Thr
2225                2230                2235                2240

Val Val Asp Val Ala Val Leu Thr Ser Phe Leu Gln Asp Glu Lys Val
            2245                2250                2255

Lys Glu Ser Tyr Val
        2260

<210> SEQ ID NO 2
<211> LENGTH: 7860
<212> TYPE: DNA
<213> ORGANISM: Homo sapiens

<400> SEQUENCE: 2
gtccctgctg tgagctctgg ccgctgcctt ccagggctcc cgagccacac gctggggtg        60 ctggctgagg aacatggct tgttggcctc agctgaggtt gctgctgtgg aagaacctca      120
ctttcagaag aagacaaaca tgtcagctgt tactggaagt ggcctggcct ctatttatct      180
tcctgatcct gatctctgtt cggctgagct acccacccta tgaacaacat gaatgccatt      240
ttccaaataa agccatgccc tctgcaggaa cacttccttg ggttcagggg attatctgta      300
```

```
atgccaacaa cccctgtttc cgttacccga ctcctgggga ggctcccgga gttgttggaa    360
actttaacaa atccattgtg gctcgcctgt tctcagatgc tcggaggctt cttttataca    420
gccagaaaga caccagcatg aaggacatgc gcaaagttct gagaacatta cagcagatca    480
agaaatccag ctcaaacttg aagcttcaag atttcctggt ggacaatgaa accttctctg    540
ggttcctgta tcacaacctc tctctcccaa agtctactgt ggacaagatg ctgagggctg    600
atgtcattct ccacaaggta ttttttgcaag gctaccagtt acatttgaca agtctgtgca    660
atggatcaaa atcagaagag atgattcaac ttggtgacca agaagtttct gagctttgtg    720
gcctaccaag ggagaaactg gctgcagcag agcgagtact tcgttccaac atggacatcc    780
tgaagccaat cctgagaaca ctaaactcta catctccctt cccgagcaag agctggctg    840 aagccacaaa aacattgctg catagtcttg ggactctggc ccaggagctg ttcagcatga    900
gaagctggag tgacatgcga caggaggtga tgtttctgac caatgtgaac agctccagct    960
cctccaccca aatctaccag gctgtgtctc gtattgtctg cgggcatccc gagggagggg    1020
ggctgaagat caagtctctc aactggtatg aggacaacaa ctacaaagcc ctctttggag    1080
gcaatggcac tgaggaagat gctgaaacct tctatgacaa ctctacaact ccttactgca    1140
atgatttgat gaagaatttg gagtctagtc ctctttcccg cattatctgg aaagctctga    1200
agccgctgct cgttgggaag atcctgtata cacctgacac tccagccaca aggcaggtca    1260
tggctgaggt gaacaagacc ttccaggaac tggctgtgtt ccatgatctg gaaggcatgt    1320
gggaggaact cagccccaag atctggacct tcatggagaa cagccaagaa atggaccttg    1380
tccggatgct gttggacagc agggacaatg accactttg ggaacagcag ttggatggct    1440
tagattggac agcccaagac atcgtggcgt ttttggccaa gcacccagag gatgtccagt    1500
ccagtaatgg ttctgtgtac acctggagag aagctttcaa cgagactaac caggcaatcc    1560
ggaccatatc tcgcttcatg gagtgtgtca acctgaacaa gctagaaccc atagcaacag    1620
aagtctggct catcaacaag tccatggagc tgctggatga gaggaagttc tgggctggta    1680
ttgtgttcac tggaattact ccaggcagca ttgagctgcc ccatcatgtc aagtacaaga    1740
tccgaatgga cattgacaat gtggagagga caaataaaat caaggatggg tactgggacc    1800
ctggtcctcg agctgacccc tttgaggaca tgcggtacgt ctgggggggc ttcgcctact    1860
tgcaggatgt ggtggagcag gcaatcatca gggtgctgac gggcaccgag aagaaaactg    1920
gtgtctatat gcaacagatg ccctatccct gttacgttga tgacatcttt ctgcgggtga    1980
tgagccggtc aatgcccctc ttcatgacgc tggcctggat ttactcagtg ctgtgatca    2040 tcaagggcat cgtgtatgag aaggaggcac ggctgaaaga gaccatgcgg atcatgggcc    2100
tggacaacag catcctctgg tttagctggt tcattagtag cctcattcct cttcttgtga    2160
gcgctggcct gctagtggtc atcctgaagt taggaaacct gctgccctac agtgatccca    2220
gcgtggtgtt tgtcttcctg tccgtgtttg ctgtggtgac aatcctgcag tgcttcctga    2280
ttagcacact cttctccaga gccaacctgg cagcagcctg tggggcatc atctacttca    2340 cgctgtacct gccctacgtc ctgtgtgtgg catggcagga ctacgtgggc ttcacactca    2400
agatcttcgc tagcctgctg tctcctgtgg cttttgggtt tggctgtgag tactttgccc    2460
tttttgagga gcagggcatt ggagtgcagt gggacaacct gtttgagagt cctgtggagg    2520
aagatggctt caatctcacc acttcggtct ccatgatgct gtttgacacc ttcctctatg    2580
gggtgatgac ctggtacatt gaggctgtct ttccaggcca gtacgaatt cccaggcccc    2640 ggtattttcc ttgcaccaag tcctactggt ttggcgagga aagtgatgag aagagccacc    2700
```

```
ctggttccaa ccagaagaga atatcagaaa tctgcatgga ggaggaaccc acccacttga   2760
agctgggcgt gtccattcag aacctggtaa aagtctaccg agatgggatg aaggtggctg   2820
tcgatggcct ggcactgaat ttttatgagg gccagatcac ctccttcctg gccacaatg    2880 gagcggggaa gacgaccacc atgtcaatcc tgaccgggtt gttccccccg acctcgggca   2940
ccgcctacat cctgggaaaa gacattcgct ctgagatgag caccatccgg cagaacctgg   3000
gggtctgtcc ccagcataac gtgctgtttg acatgctgac tgtcgaagaa cacatctggt   3060
tctatgcccg cttgaaaggg ctctctgaga agcacgtgaa ggcggagatg gagcagatgg   3120
ccctggatgt tggtttgcca tcaagcaagc tgaaaagcaa acaagccag ctgtcaggtg     3180 gaatgcagag aaagctatct gtggccttgg cctttgtcgg gggatctaag gttgtcattc   3240
tggatgaacc cacagctggt gtggacccctt actcccgcag gggaatatgg gagctgctgc  3300
tgaaataccg acaaggccgc accattattc tctctacaca ccacatggat gaagcggacg   3360
tcctggggga caggattgcc atcatctccc atgggaagct gtgctgtgtg ggctcctccc   3420
tgtttctgaa gaaccagctg gaacaggct actacctgac cttggtcaag aaagatgtgg    3480
aatcctccct cagttcctgc agaaacagta gtagcactgt gtcatacctg aaaaaggagg   3540
acagtgtttc tcagagcagt tctgatgctg gcctgggcag cgaccatgag agtgacacgc   3600
tgaccatcga tgtctctgct atctccaacc tcatcaggaa gcatgtgtct gaagcccggc   3660
tggtggaaga catagggcat gagctgacct atgtgctgcc atatgaagct gctaaggagg   3720
gagcctttgt ggaactcttt catgagattg atgaccggct ctcagacctg gcatttctca   3780
gttatggcat ctcagagacg accctggaag aaatattcct caaggtggcc aagagagtg    3840 gggtggatgc tgagacctca gatggtacct tgccagcaag acgaaacagg cgggccttcg   3900
gggacaagca gagctgtctt cgcccgttca ctgaagatga tgctgctgat ccaaatgatt   3960
ctgacataga cccagaatcc agagagacag acttgctcag tgggatggat ggcaaagggt   4020
cctaccaggt gaaaggctgg aaacttacac agcaacagtt tgtggcccctt ttgtggaaga   4080 gactgctaat tgccagacgg agtcggaaag gattttttgc tcagattgtc ttgccagctg   4140
tgtttgtctg cattgcccctt gtgttcagcc tgatcgtgcc acccttttggc aagtacccca   4200 gcctggaact tcagccctgg atgtacaacg aacagtacac atttgtcagc aatgatgctc   4260
ctgaggacac gggaaccctg gaactcttaa acgccctcac caaagaccct ggcttcggga   4320
cccgctgtat ggaaggaaac ccaatcccag acacgccctg ccaggcaggg gaggaagagt   4380
ggaccactgc cccagttccc cagaccatca tggacctctt ccagaatggg aactggacaa   4440
tgcagaaccc ttcacctgca tgccagtgta gcagcgacaa aatcaagaag atgctgcctg   4500
tgtgtccccc aggggcaggg gggctgcctc ctccacaaag aaaacaaaac actgcagata   4560
tccttcagga cctgacagga agaaacattt cggattatct ggtgaagacg tatgtgcaga   4620
tcatagccaa aagcttaaag aacaagatct gggtgaatga gtttaggtat ggcggctttt   4680
ccctgggtgt cagtaatact caagcacttc ctcccgagtca agaagttaat gatgccatca   4740
aacaaatgaa gaaacaccta aagctggcca aggacagttc tgcagatcga tttctcaaca   4800
gcttgggaag atttatgaca ggactggaca ccagaaataa tgtcaaggtg tggttcaata   4860
acaagggctg gcatgcaatc agctctttcc tgaatgtcat caacaatgcc attctccggg   4920
ccaacctgca aaaggagag aaccctagcc attatggaat tactgctttc aatcatccccc   4980 tgaatctcac caagcagcag ctctcagagg tggctctgat gaccacatca gtggatgtcc   5040
ttgtgtccat ctgtgtcatc tttgcaatgt ccttcgtccc agccagcttt gtcgtattcc   5100
```

```
tgatccagga gcgggtcagc aaagcaaaac acctgcagtt catcagtgga gtgaagcctg    5160
tcatctactg gctctctaat tttgtctggg atatgtgcaa ttacgttgtc cctgccacac    5220
tggtcattat catcttcatc tgcttccagc agaagtccta tgtgtcctcc accaatctgc    5280
ctgtgctagc ccttctactt tgctgtatg ggtggtcaat cacacctctc atgtacccag    5340
cctcctttgt gttcaagatc cccagcacag cctatgtggt gctcaccagc gtgaacctct    5400
tcattggcat taatggcagc gtggccacct tgtgctgga gctgttcacc gacaataagc    5460
tgaataatat caatgatatc ctgaagtccg tgttcttgat cttcccacat ttttgcctgg    5520
gacgagggct catcgacatg gtgaaaaacc aggcaatggc tgatgccctg aaaggtttg    5580 gggagaatcg ctttgtgtca ccattatctt gggacttggt gggacgaaac ctcttcgcca    5640
tggccgtgga aggggtggtg ttcttcctca ttactgttct gatccagtac agattcttca    5700
tcaggcccag acctgtaaat gcaaagctat ctcctctgaa tgatgaagat gaagatgtga    5760
ggcgggaaag acagagaatt cttgatggtg gaggccagaa tgcatctta gaaatcaagg    5820 agttgacgaa gatatataga aggaagcgga agcctgctgt tgacaggatt tgcgtgggca    5880
ttcctcctgg tgagtgcttt gggctcctgg gagttaatgg ggctgaaaaa tcatcaactt    5940
tcaagatgtt aacaggagat accactgtta ccagaggaga tgctttcctt aacaaaaata    6000
gtatcttatc aaacatccat gaagtacatc agaacatggg ctactgccct cagtttgatg    6060
ccatcacaga gctgttgact gggagagaac acgtggagtt ctttgcccct ttgagaggag    6120
tcccagagaa agaagttggc aaggttggtg agtgggcgat tcggaaactg gcctcgtga    6180 agtatggaga aaaatatgct ggtaactata gtggaggcaa caaacgcaag ctctctacag    6240
ccatggcttt gatcggcggg cctcctgtgg tgtttctgga tgaacccacc acaggcatgg    6300
atcccaaagc ccggcggttc ttgtggaatt gtgccctaag tgttgtcaag gaggggagat    6360
cagtagtgct tacatctcat agtatggaag aatgtgaagc tctttgcact aggatggcaa    6420
tcatggtcaa tggaaggttc aggtgccttg gcagtgtcca gcatctaaaa aataggtttg    6480
gagatggtta taacagtt gtacgaatag cagggtccaa cccggacctg aagcctgtcc    6540
aggatttctt tggacttgca tttcctggaa gtgttctaaa agagaaacac cggaacatgc    6600
tacaatacca gcttccatct tcattatctt ctctggccag gatattcagc atcctctccc    6660
agagcaaaaa gcgactccac atagaagact actctgtttc tcagacaaca cttgaccaag    6720
tatttgtgaa ctttgccaag gaccaaagtg atgatgacca cttaaaagac ctctcattac    6780
acaaaaacca gacagtagtg gacgttgcag ttctcacatc ttttctacag gatgagaaag    6840
tgaaagaaag ctatgtatga agaatcctgt tcatacgggg tggctgaaag taaagaggaa    6900
ctagactttc ctttgcacca tgtgaagtgt tgtggagaaa agagccagaa gttgatgtgg    6960
gaagaagtaa actggatact gtactgatac tattcaatgc aatgcaattc aatgcaatga    7020
aaacaaaatt ccattacagg ggcagtgcct ttgtagccta tgtcttgtat ggctctcaag    7080
tgaaagactt gaatttagtt ttttaccttat acctatgtga aactctatta tggaacccaa    7140
tggacatatg ggtttgaact cacacttttt tttttttttt tgttcctgtg tattctcatt    7200
ggggttgcaa caataattca tcaagtaatc atggccagcg attattgatc aaaatcaaaa    7260
ggtaatgcac atcctcattc actaagccat gccatgccca ggagactggt ttcccggtga    7320
cacatccatt gctggcaatg agtgtgccag agttattagt gccaagtttt tcagaaagtt    7380
tgaagcacca tggtgtgtca tgctcacttt tgtgaaagct gctctgctca gagtctatca    7440
acattgaata tcagttgaca gaatggtgcc atgcgtggct aacatcctgc tttgattccc    7500
```

-continued

```
tctgataagc tgttctggtg gcagtaacat gcaacaaaaa tgtgggtgtc tccaggcacg    7560
ggaaacttgg ttccattgtt atattgtcct atgcttcgag ccatgggtct acagggtcat    7620
ccttatgaga ctcttaaata tacttagatc ctggtaagag gcaaagaatc aacagccaaa    7680
ctgctggggc tgcaactgct gaagccaggg catgggatta agagattgt gcgttcaaac     7740 ctagggaagc ctgtgcccat ttgtcctgac tgtctgctaa catggtacac tgcatctcaa    7800
gatgtttatc tgacacaagt gtattatttc tggcttttg aattaatcta gaaaatgaaa     7860
```

<210> SEQ ID NO 3
<211> LENGTH: 22
<212> TYPE: DNA
<213> ORGANISM: Homo sapiens

<400> SEQUENCE: 3
gcagagggca tggctttatt tg                                              22

<210> SEQ ID NO 4
<211> LENGTH: 24
<212> TYPE: DNA
<213> ORGANISM: Homo sapiens

<400> SEQUENCE: 4
ctgccaggca ggggaggaag agtg                                            24

<210> SEQ ID NO 5
<211> LENGTH: 23
<212> TYPE: DNA
<213> ORGANISM: Homo sapiens

<400> SEQUENCE: 5
gaaagtgact cacttgtgga gga                                             23

<210> SEQ ID NO 6
<211> LENGTH: 20
<212> TYPE: DNA
<213> ORGANISM: Homo sapiens

<400> SEQUENCE: 6
aaagggcctt ggtaagggta                                                 20

<210> SEQ ID NO 7
<211> LENGTH: 20
<212> TYPE: DNA
<213> ORGANISM: Homo sapiens

<400> SEQUENCE: 7
catgcacatg cacacacata                                                 20

<210> SEQ ID NO 8
<211> LENGTH: 27
<212> TYPE: DNA
<213> ORGANISM: Homo sapiens

<400> SEQUENCE: 8
ctttctgcgg gtgatgagcc ggtcaat                                         27

<210> SEQ ID NO 9
<211> LENGTH: 20
<212> TYPE: DNA
<213> ORGANISM: Homo sapiens

<400> SEQUENCE: 9

```
ccttagcccg tgttgagcta                                                 20

<210> SEQ ID NO 10
<211> LENGTH: 26
<212> TYPE: DNA
<213> ORGANISM: Homo sapiens

<400> SEQUENCE: 10
cctgtaaatg caaagctatc tcctct                                          26

<210> SEQ ID NO 11
<211> LENGTH: 26
<212> TYPE: DNA
<213> ORGANISM: Homo sapiens

<400> SEQUENCE: 11
cgtcaactcc ttgatttcta agatgt                                          26

<210> SEQ ID NO 12
<211> LENGTH: 20
<212> TYPE: DNA
<213> ORGANISM: Homo sapiens

<400> SEQUENCE: 12
gggttcccag ggttcagtat                                                 20

<210> SEQ ID NO 13
<211> LENGTH: 21
<212> TYPE: DNA
<213> ORGANISM: Homo sapiens

<400> SEQUENCE: 13
gatcaggaat tcaagcacca a                                               21

<210> SEQ ID NO 14
<211> LENGTH: 10545
<212> TYPE: DNA
<213> ORGANISM: Homo sapiens
<220> FEATURE:
<221> NAME/KEY: misc_feature
<222> LOCATION: (1)...(10545)
<223> OTHER INFORMATION: n = a, t, c, or g

<400> SEQUENCE: 14 acctctttata gaatgataga attcctctgg aatgattgga taacttcatt tcatccttga    60
cttttacctt ggaggatttc ttaccccttt tggcttctca aatttgacta ttaaaatgtt   120
gcctttaaaa ataggaacac agtttcaggg gggagtacca gcccatgacc cttctgcaag   180 gcccctaac tcaaggtagt ttccctggaa ctgtggttta tggaatgttt caggagtgtg    240
aggaggtata atttaaggct gtcctagcaa ggatacccttt aaggatagag ggccagtag   300 catctggagg ccagaaaagt taaactgagg cagtcagatt agcttcaggc tcaattaagc   360
tgatgggtca gcctgggaga aattgcagga tgactctcaa tatcccctcc caccccaca    420 gcagccacga tctgtctgtc tttaatcatg ggtgcagtga acctgttctt tccaggtgtc   480
ttggccttca gtaaccttgt taggcttgtc cctgaacgtg gctaccgatc caaagacaca   540
tgatcagaga ggcaattaga gaacagacct ttccaaagc aagcatgttc tgttgggctt    600
agaagtttca tgtcctaata ttataggacc ctgtgcatct ctctggagat gaggcacatg   660
agtcatatct gtgattcttg cttttgtgtc aacatctcat gaataggcaa tcagagcttt   720
ggcaccaatg tattttcagt tcatatctga tgtagttaaa tccacctcct gctttgtagt   780
```

```
ttactggcaa gctgtttttg atataagaca tctagaacac tgtaaatata taacattttt    840
atttgtctat tatacctcaa ttacgaaaaa gacatctaga agcaacctca tcaagagaga    900
tactgaggcc gggcatggta gctcacactt gcaatcccat tactttggga ggctgaggca    960
ggtagatcac ttgaggtcaa gagtttgaaa ccagcctggc caacatgttg aaaccctgtc   1020
tctattaaaa atacaaaaaa gttagctggg cttggtggtg gcacctgta atcccagcta    1080 ctccggaggc tgaggcagga gaatcacttg aacctgggag gcagaggttg cagtgagctg   1140
agatcacacc actgcactcc aacctgggca ccagagtgag attacatcta aaaaataaaa   1200
taaagtaata aaaagagag atattgatag ctgttgttgg aaatttcaac ttccatctca    1260
cttctggtaa cttttttggaa gtttgttgaa caaagtggaa tacacgcaca tacacacaca   1320
cacatactct cttgtttgtt taaggtttaa tgaaatagct gtcatataat cactgttttt   1380
gaaagaggag aattagttgc tatctgtaca ttttgggtat gtgaactatt tggatagaac   1440
tctgagaaat gcattcagaa caacaaacaa aatcatagga gaaatagcta agtgggaagg   1500
ggcatataag agttgttgaa aaagttattt cttgagaaac cagctctaat gctaggcaag   1560
tcacttgctt tgggggaggc ctcagcttct ctgtctataa gattgcagca ggggtgtagt   1620
gggaatgagt cttcaacatt ccaagagatt ttatctacta atacgacagt caaatggagc   1680
atgactttgt ggaagcctct cctcttccac ccagaggggc caatttctct gtcccagtga   1740
gatgttgaca cttgtatgat ccctgcttgg agacttccct cttctggaac ctgccctggc   1800
tcaggcatga gggctgactg tcacccttcg ataggagccc agcactaaag ctcatgtgtt   1860
ggcagtgttc ttgcgggaag gaaaaagacc agccagccca tttgttactg cacaagcaaa   1920
cagcttctgg tagctgtaca gatacatgca ctttctttcc tcactgtgtt tccatagaca   1980
gatttagtgc tgtagaagag tagagggcag tcacgggaag gagttcctgt ttttcttttg   2040
gctatgccaa atggggaaaa atcctcctat cttgtctttt tagtgtcatc ctctctcccc   2100
ttttcttctt ctttataatt ctcatctctc atctctcctg gaaatgtgca tgtcaagttc   2160
aaaagggcac aatgttttgg tgaggaagag gtgggagaac acgtgccagg tgctaactag   2220
ggtcatcatt tcccccttca cagccagctt cctgtgaatg tgtgtgtgtg tgtgtgtgtg   2280
tgtgtgtgtg tgtgtgtgtg tgtgtatttc ttttgccagc atcactgaat ctgtctgctg   2340
tctggtattc caggttttgg tttagggaaa agtaaaagta atttataat cccagctgtc    2400 atttaagcca cccctttgtg ggtagcatat ggtccactct ctcagttcat tgtcctaaag   2460
atgcttcatc agaaaggaat aacttccacc ccgttactct ctgtcccctt actctgcttt   2520 attttcttc gtcaatccta ccaccaccac ccactgtttg aacaacccac tattatttgt    2580
ctgtttccca tccctggtag aataggagcc ccatgaatga aggaactttg cttctgttgt   2640
tcaccactga atctctaagg tatggaacac acctggcatg tgataggcac tcgataaata   2700
tttgttgtgg ctcatgggca ccttgcagag ttaaggctgc agttgtttgt ggaatttata   2760
agtggtaatg aatatttatc tactattcct cttccaaggc gatcacacaa taatcaggct   2820
ttacactatc cagttcttag gtcttccaag ttatgacttg tgaggtatgt taattatgat   2880
aatagaaggc agtttatttg gttcagattt attgatgtgt aatttaccac agtaagactt   2940
cccctttaca aaagtatgat gagttttgac aaatggatac acatgtgtat ctaccactgc   3000
catgctcctt tcagtctgt cgtcccctcc acccatgacc actggtcacc actgcagtga    3060
tttctgtccc cttcatttca cctttttccag aatgtcatat aaatgaatc atgcagtatg   3120 tagttttttg tgtctggctt attttttctta gcattaggct tttgggattc atccaggttg   3180
```

```
tcgcatgtaa cagtagctta ttccttttta tggctgagta agtgtcccag ttttatttat   3240
atatttattt atgaggaggt gtctcactct gtcacccagg ctggagtgcg gtagcgcgat   3300
ctcagctcac tgcaacctcc gcctcccagg ttcaagcaat tctcctgcct cctgagtagc   3360
tgggattaca ggcacccacc gccacgccca actaattttt atattttag tagagatggg    3420 gtttcaccat gttggccagg ctgatctcaa actcttgacc tcaggtgatc cgcccacctc   3480
tggctcccaa agtgctagga ttacaggcat gagccactgt gcccagcccc agttttattt   3540
attcaccagt tgatggtctt ttcgacaact aattgtttcc agttttggc tattctgtat    3600 aaggcttcta taaatattca caaataccta ggatgggatg actgggtcat ataatagtac   3660
tgtataacct tagcagaaac tgtcaaacta ttttccaaag tggctcttcc atttacaat    3720 tccacagtgt attgagtccc agtgtctcca tacacatgct agcacttta atatttaatt    3780 tagtgggtat gtaatgatat ctcattgtgg ttttaatttg catttctctg cagctaatga   3840
tgagtgtttc tgcttatttg ggaaggtttt aatttagcag tctgttgtat tctgtagata   3900
ttaataactt caaatatca gtggcatttg cagttaaaat ttccttaaaa aattggccaa    3960
aggtttccag cagtcacttc tgccatgccc aaactgtatg aaacaaggct gaggtgtgga   4020
gattgtcaca ttttggcaag gagtgatcca cttgggtgac tgatgagacc cagagagcgt   4080
acgcctcggg cttgagggtg aggacgggcg ggaagtcgac tgcatggccc tgctggcctt   4140
gggaggctgc ccagtcctta gctaaagctg gcagttatgg gaaacagact tagattctat   4200 tacgttttc aggatgtccc aggagtcacc tgggaagctc agcagtcctt tgtgactttc    4260
aagcatatgg tagaagctgc tgaacacaga gctccctctt tggggataat ttgcccaaat   4320
catttaatca ggcttgagaa atgagttacc acaggtccag gagtgctgcc acccttgaat   4380
tctgacaccc tatttctcct atccgtctct taattaatta agcagacatc cccaagtgct   4440
tacgacaagc caggacccctt ttgcatacta aggaaaacag ggatgaagga aacagaaatg  4500
gtctctgctc tgactcagaa ggtagaaatc ctctttccca gccaagtctt cctagggagc   4560
acgtaggaag ggctctgaac ccacgtgtca gttgcagggg aggatatcag gaaaggacat   4620
tgaagaagtg gagacctaag tttgagacct aggcattagc caggctagca gtgcttgaaa   4680
aagtgtctta ggacaagaga actcaccagt gaagtcccag tggtaggaga gcgtgcagca   4740
tattctgagc ctgtatacac atctccaggg cattgcttag caggtgggga gtggcaagag   4800
agtaggctgg agtcacagaa gggaggccag gtagaccttg gtgagcactg gactctatgt   4860
tcaggtgctg aggagctggc aaaaggtttt aagtcgggga gaggcatgtt cagatatttg   4920
gtctagctga gtaactttgg gtgctctgtg acaaatggtt gggagaccag tgaggtggca   4980
gttgcggtca tctaggagca ggatcagagt ggcctattga ctgggatgac tgtgaagtgg   5040 gatccttttcc agccagtaac tggaaatgtg tatgagggca gaagtgagtg tactgcattt   5100
gaaacattga gaaatctagt acatagtact gtctctttta tatcttttt tttttttttt    5160 ttgattttgg tttgtttgtt cactaacttg gaaaactgat gtggaaatgt ccctttggct   5220
tcagttacct gagcagaagg ggccgggcat tgccaaactc tcctcttagg acagaattgc   5280
tcccagtatt gatcattgtg ttctgagttg ggggagcaaa ttgtgcagga ggccaggtca   5340
gtgccaaggt gggtgggagg aattggagca ggaagcttgc ctaagtgtgc ccagcaaagc   5400
cacggtagaa ctttctactg tggctctatg ctacttctta gcaaccttct ccatgtgctt   5460 cctgagagt ccttggagtc agaaccttttt tcttgaaacc cagacacttt acttccaaga   5520
aaatgctgtc caagaaaact catccttccc ttcttctcat gaacgttgtg tagaggtgtg   5580
```

```
tcttctcttc ctttgagctt ttccactcag ggtttagggg aggtgatatt ctatatttgg    5640
gtttggctct gggtactgca acactaggct attaagattt catccttact gctttgcccc    5700
tcctatcttt ccagaaaccc acaatggatt tgctagaaat aatggaacgt cctgtttgga    5760
caggatataa ccatttctca gctagaggat attgttggaa tgaagaaaga taaatgggga    5820
gaagggaact cacattgctt tggcacttaa attaagccat gtactgtgtt gggaaattat    5880
ttatattatc tcgttgaatc cacagtagaa cacagttgaa caccatacaa ggtaagtatt    5940
gtcatcctta ttttaccatg aggaaattga tgcttagaga gcataaagcc ttggccaggg    6000
gcacatagtt gggaagccgg ggctaattca tgcctgggct ctttctgata gttttccttt    6060
tttaattgtc ccctcctcat tgttaccttg gggatttcaa gagattcatg tagcttctaa    6120
atcaacgaac tgattcctgg agagcagctt ctgtatgaga aaaatctagc taattattta    6180
tttcagtgtc tctggaatgc aagctctgtc ctgagccact tagaaaacaa tttgggatga    6240
caagcatgtg tctcacaatg ctgctctggt tgccagtgct gtgctgccag ttgtcatctt    6300
tgaacaaact gatgcagtgc tggtttaact cttcctcttt ttggagtaag aaactttgga    6360
ggcctgtgtc cttctagaag tttgctgagc aaatggtaag gaaaagaaat aggtcctaag    6420
gcttgactat ttcagagaat ttcttgattt attggactgt caatgaatga attggaatac    6480
atagtggtag gctgtctttt cttctcagac actgcaattt cctccaatct cttgactttt    6540
ctagaagttt taatccaagt ccttgttggg tggtagataa aagggtattg ttctactaga    6600
gactgacctt ggcatggaga tctcatttgg actcacagat ttctagtcta gcgcttggtt    6660
ttgtatccat acctcgctac tgcattctta gttccttctg ctccttgttc ctcatgccca    6720
gtgtcccacc ctacccttgc ccctactcct ctagaggcca cagtgattca ctgagccatt    6780
tcataagcac agctaggaga gttcatggct accaagtgcc agcagggccg aattttcacc    6840
tgtgtgtcct cccttccatt tttcatcttc tgccccctcc ccagctttaa ctttaatata    6900
actacttggg actattccag cattaaataa gggtaactgc tggatgggtg gctgggatac    6960
acagaatgta gtatcccttg ttcacgagaa gaccttcttg ccctagcatg gcaaacagtc    7020
ctccaaggag gcacctgtga cacccaacgg agtagggggg cggtgtgttc aggtgcaggt    7080
ggaacaaggc cagaagtgtg catatgtgct gaccatggga gcttgtttgt cggtttcaca    7140
gttgatgccc tgagcctgcc atagcagact tgttctcca tgggatgctg ttttctttcc    7200
agagacacag cgctagggtt gtcctcatta cctgagagcc aggtgtcggt agcatttttct    7260 tggtgtttac tcacactcat ctaaggcacg ttgtggtttt ccagattagg aaactgcttt    7320
attgatggtg cttttttttt tttttttga gacagagtct cgctctgtcg ccatgctgga    7380
gtgtagtggc acaatcttgg ctcactgcac ctccgcctgc caggttcagc gattctcctg    7440
cctcagcctc ccaagtagct gggactacag gtgcctgcca ccatgcccag ctaattttg    7500 tattttagt agagacgggg tttcaccgta ttggctagga tggtctcgat tcttgacct    7560 cgtgatccgc ctgcctcggc ctcccaaagt gctgggatta taggcttgag ccaccacgcc    7620
tggccgatgg tgcttttat catttgaagg actcagttgt ataacccact gaaaattagt    7680
atgtaaggaa gttcagggaa tagtataagt cactccaggc ttgaggcaaa atttacaaat    7740
gctgctgact ttgtatgtaa ggggaggcat tttcttagaa aagagaggta ggtctctggg    7800
attccagtat gccatttcca tcctcagtgt ttttggccac ctgagagagg tctatttca    7860 gaaatgcatt cttcattccc agatgataac atctataga ctaaaatgat taggaccata    7920
acacgtagct cctagcctgc tgtcggaaca cctcccgagt ccctctttgt gggtgaaccc    7980
```

```
agaggctggg agctggtgac tcatgatcca ttgagaagca gtcatgatgc agagctgtgt    8040
gttggaggtc tcagctgaga gggctggatt agcagtcctc attggtgtat ggctttgcag    8100
caataactga tggctgtttc ccctcctgct ttatctttca gttaatgacc agccacggcg    8160
tccctgctgt gagctctggc cgctgccttc cagggctccc gagccacacg ctggggggtgc   8220 tggctgaggg aacatggctt gttggcctca gctgaggttg ctgctgtgga agaacctcac    8280
tttcagaaga agacaaacag taagcttggg ttttttcagca gcggggggtt ctctcatttt   8340
ttctttgtgg ttttgagttg gggattggag gagggaggga gggaaggaag ctgtgttggt    8400
tttcacacag ggattgatgg aatctggctc ttatggacac agaactgtgt ggtccggata    8460
tggcatgtgg cttatcatag agggcagatt tgcagccagg tagaaatagt agctttggtt    8520
tgtgctactg cccaggcatg agttctgatc cctaggacct ggctccgaat cgcccctgag    8580 cacccccactt tttccttttg ctgcagccct gggaccacct ggctctccaa aagcccctaa   8640
tgggcccctg tatttctgga agctgtgggt gaagtgagtt agtggcccca ctcttagaga    8700
tcaatactgg gtatcttggt gtcaatctgg attctttcct tcaggcctgg aggaatataa    8760
taactgagac ttgttttatt tctgcagagg gttctaagcc attcacttcc cagatgggcc    8820
aataatgctt tgagtaatct ggagatcatc tttaatgcgc aggtgaatgg aactcttcca    8880
cagagggatg tgagggctgt agagcagagt gaactccctg aaactcagac gtcagctctt    8940
tgtctctcta tctctgaaca cccttcctta gagatcccat ctctaggatg catttctctg    9000
tagttagttt ctaagtctct tgttcctgtt ctgcctttat tttttttttcc tggattctaa   9060 gccagtatcc ccacttggct gtcttaatgt agcttaacat gtctgtaatc aaaatgatca    9120
tctttctgag attcaaaggg ctataaggga cttttggagag aatttcattc agttttcctc   9180
aaactagaat aatgcttgca ctgtctgtaa aagaacaaaa gtgtcaaagc atcctttttgt   9240 tcactaaatt tcctttttta ttatagtgtt acttaaatat taggaagtta aaagtaggta    9300
taaacttctt ataggctgtt attatacaac tatatgaccc atacatattt acaaattaag    9360
tgcagccaaa attgcaaaat caataccatt caaattaata ccttaaatgt ggtgaggcag    9420
ctgttgttca actgaaacca aattataagt tgcatggcag taaatgctat catgctgatc    9480
attttgagtt tggccagtct atattatcat gtgctaatga ttgaattctc cacccatttt    9540
tctacttgta tgaccttaat ttgatggcac ctgttccatc ctcatgagtt tgctacaatt    9600
atactggtgc caacacaatc ataaacacaa atataaactt gggctttgaa atcttgtgcc    9660
agaacttggc tttaaagtaa gcatttaaaa aatccatatg tgtttattag actttgttta    9720
gatgactgtt gaaatgaaaa caaagtgttt aaaatcctct tagagaactt aaatataatc    9780
cctcagcaat atgtatacag atcttccttt gagaaaaact gattgtgttc agcctctcat    9840
gttacaaatg gggaacctga attctgaggt ctctagtgag agaacaggga ctggaatctg    9900
tggatcctat ctgtttttaat aataattgta aagtataata gataatatta tattaaaaag    9960
agagnnnnnn acacttagaa tgagcttcca tgtgtgaggc actaactgat taggcattat    10020
taactagatt tattcctttt aaggccccgc gatgtactgt tatttccaca tgttgtagct    10080
ggggaacgtg ctactcagag aggttaagta acttgtctga ggtccacacc actaacaagg    10140
agcacaggta gggttcaaat ccagataatc tgactttgga gctggcactc taactcaatg    10200
tgcctaatcg cttttcagtg gtgtcattat tttgcctatt ctccatctga gaatattgaa    10260
gtttctgact cctttccttgc cttttctccct gcctcccgtg ttatccccca ggtcttggtg   10320
ttccagtcct ctatgtccgt ccttactctt attcctttgc tacagtgtga tccagggctc    10380
```

```
ctgcccttct tatcctggta gagggggccc acttgctggg aaattgtctc cgccatggtt     10440
tatccatgtt gtgtgtccat tagtgagtag tgggaagaat catatcatgt tggcaatgaa     10500 agggggggcta tggctctggg gtagtctagt ctgaactctt atttt                    10545

<210> SEQ ID NO 15
<211> LENGTH: 4736
<212> TYPE: DNA
<213> ORGANISM: Homo sapiens

<400> SEQUENCE: 15 ctttttttt tttttttttt tttttttttt tgaggtgaag tctcactctg ttgcccaggc       60
tggagtgcaa tggagcgatc ttggctcacc ccaacctctg tctcctgggt tcaaacagtt     120
ctcctgcctc agcctcccga gtagctggga ttacaggctc cgccaccat gcccagctat      180 ttttttgtat tttcagtaga gatggggttt caccctttg accaggctgg tcttgaactc      240
ctgacctcat gatcaaccca cctcagcctc ccaaagtgct gggattacag gtgtgagcca     300
ccacgcccgg cctcataagt attttctaaa tttatttaca gtcatgccat ttaaaaggaa     360
agttgtattc ctgtctttgt taatatttat aagtgatttt attcagctac aagcttggaa     420
tggcatataa ttttgtattc tgcttttttc acttaatatt acatggctaa tgatttctgt     480
gtttcataaa cattattctg atgatggcat gatatattgt tgagtacatg taccataatt     540
gaatcatttc cctattgcta tgcaattaag ttgtttccaa tattttgcaa ttataatgtt     600
tcaatgaatg aataaactta tgcatatagc ttttgatat cttaagttca gtttcctagg     660
atgaatttcc aggaatagta attgggcaaa tgggataaac atgactcttg aatacgtatt     720
gttaacattg ctttcccaaa gggctcaact gatttatatt tccgtgttca ttatctttta     780
aaccagctca tttactcacc aaacattttt aaagccatta tcatgtggta ggcttagtaa     840
gaagaaagtg accctaaggg agaagcttat atataaatag ggtccctggt gtaccaagtg     900
ctgatacaga cacaaagtac ctggggaaat tgagatgagg gagtcctggc tcagctggga     960
gaaaagttca ttttcataga gtcatggttt tgttctttgg cagaaagaaa attgctttct    1020
tccccacccc caccccccagc tttattgagg tataattgac aaataaaaat tgtatatctt    1080
taagatatgc aatgtgatat atatgtatat ctcaacttaa aaaataagct acagaataaa    1140
aaggtgtttg ctattaaaaa aaaagaaaag gctgaatgtc attcccaagc ttggaaattt    1200
gagtatgttg cctctttggg attatttaca gaaatattag caagaccagc ccatctttg    1260 gtcttgagta ctccactgtc agcatgcttt cttccagaga gggatccatt tgcctttatt    1320
tttcattctg ttgtgccgtc tatgcaaact attcttgata gttttatggt aacagtgttt    1380
ttttgttcca tgagataaat ttatacatgc tcattgtgga aaatttagaa aagacaggaa    1440
agtattaaaa acatcmcytt tttttttttt tttttttttt ttttttttamg cagacagagt    1500 cttgctctgt cgcccaggcc ggagtgcagt ggcgtgatct cagctcacag caacctccgc    1560
ttcccaggtt taagtgattc tcctgcctca gcctcccaag tagctgggag tacaggcatg    1620
caccaccacg cccggctaat tttgtatttt tagtagagat ggggtttcac catgttggcc    1680
aggctggtct caaactcctg acctcaggtg atccgcctgc cttggcctcg caaagttctg    1740
ggattatagg caggagccac tgcgccagcc acacctacgt tcttatcatc ctagtacatc    1800
cactgtcatt atcttgctgt atttccttct gcccagtctc actctgatca tgcagtggcg    1860
tgatcatgca gtgatctcgg ctcactgcaa cctaggcctt ctgggttcga gtgattctcc    1920
tgccttagcc tcctgggttc aagtgattct cttgccttgg cctcccaagt agctgggatt    1980
```

```
acaggcatac accccatgc catctaatt tttgtatttt tagtagacac agcgtttcac    2040
taaaattttg tattttagt agagatgggg tttcaccatg ttggccaggc tggtctccaa    2100
ctcctgacct caggtgatcc gcctgccttg gcctcacaaa gtgattacag gcatgagcca    2160
ctgcatccat cgccaaaaag attttttaaa agagtttaat gtagaaccat atcaaaggtc    2220
tttggaaata aaaacagtt ttttaaaaat atcagaaata aacaacaaa taaataaata    2280 aataaaaaca cccaaaacaa tctgaagcac gagcacctag cagaaaggtt caattatgat    2340
ctattcatag agtggaatat caagtagaca ttacaggaca tgttttaaga ttatatttta    2400
tgtcatggga aatgctctcc cagtatgatg ttaaatgaaa aaacagaata caaaagtata    2460
tatgctgcat agtctcaata ttgtagaaa aaaatattat ttatgtatgc atgaaaaaag    2520
acaaaagatg ttaacagaga tccattgtta cttcagttta ctaggattg tctctgggag    2580 gtaggattaa ggtgatttat atttaccttt ttaaactttt ctgtatttt ttattttcaa    2640 attttccata aaaatataag gacttgaaga tcaagaaaaa atttctgctt tggctcagtg    2700
cagtcgtcac gcctgtaatc ccagcagttt gggagccta ggggagagga tcacttgaac    2760
ccaagagttt gacgttccag tgagctatga tctccggatc gtaccgcctg gacgatggag    2820
caagaccctg tctcaaaaaa aaaaatcttt gctttttttt tttgtttgtt tttgagacgg    2880
agtctctctc tgttgcccca gctggagtac agtggcacaa tctcagctca ccgcaacctc    2940
tgcctcctgg gttcaagcga ttctcttgcc tcagcctccc aagtacctgg gattccatgc    3000
acccaccact atgcccagct actttttgt attttcagta gagacagggt ttcaccatgt    3060
tggccaggct ggtctcgaat tcctgacctc agctgatcca ccggccttgg cctcccaaag    3120
tgctgggatt acaggcatga gccactgtgc ccagcccaat ctttttgcttt ttttaaaaaa    3180 agaagacaaa aagggattt ataccagtat tatcttggct gtgtgactct gaagccacag    3240
ttgtaagtta taattactct gaaacacaag gccctgtgac tcttttgggc tctttggtgt    3300
ttatcttgat tacaacgttg gaatatagaa atgaaaggaa tgggagaggt gatagacttc    3360
aggcagtgta actagttgtc tgaacactac tggctcaatt atattgtgtc tagtgatttc    3420
catcttgtcc gtctgctaat ttatcgcctg gtaactcact gaggcagggt tttcctttgg    3480
agaaacctca ttgttttaac cagtgtatca tgccttgttta gaagttcaat gatctttta    3540 actcatcgga gaagatgatg accagacctg gacagatggg gaaggacttt gcactctctc    3600
tttacagtcc tgagtgcaca caggtcaata tggaactatg tgtgaatttt cattgtcttt    3660
gagagccctc ttctctgccc catagggagc agctttgtgt gcaattagag gagcaagggt    3720
tgtgtgtatt tagcacagca ggttggcctg gtcctctcct ctcaacatag tcaccacata    3780
cctggcacta tgctaaggct gggaatgcag acagatgggg gcctgctttc agagtgctca    3840
atgtgctgag gaagccagca acagaaacag atgatttcag gagctccagg aaaatgctac    3900
aggaggagtg tgcctgggtt actggagtag cacaggagga gggcttctag ctcaggctga    3960
gattttagta aaggaaatta tgccacgatg aatcctgaag aatgaataga agtgaaccag    4020
ataaagcacg ataggaagca tcttccctta cctaaggaa gacacagagg tatatggaat    4080
ggtatgttaa aaggttggga ctccaaacag ttctgttaaa gcttagagag tggtgggaga    4140
gactggagaa gttgattaat tagtaaatga agttgtctgt ggatttccca gatcccagtg    4200
gcattggata tccatattat ttttaaattt acagtgttct atcttatttc ccactcagtg    4260
tcagctgctg ctggaagtgg cctggcctct atttatcttc ctgatcctga tctctgttcg    4320
gctgagctac ccacccatg aacaacatga atgtaagtaa ctgtggatgt tgcctgagac    4380
```

| | |
|---|---:|
| tcaccaatgg cagggaaaat ccaggcaatt aacgtgggct aaattggact tttccaaaga | 4440 |
| tgctgtctttt gggaaacatc acacatgctt tggatcagaa aacctaggct tctaatttgt | 4500 |
| tgataaggca tgaactcagg agactgtttt cagtcctagt gaatggtgat aattgtaatt | 4560 |
| ataacagtag acaacatctc ttttacacat tttaaatcat gaaaatagaa taaccttact | 4620 |
| gataattta gaaagtggtg attaaaagca catttaagat aatgccttaa cacctagtct | 4680 |
| tttccatatg catgatgtct taatcacaca ttgcaaatca tggaacacag aatttt | 4736 |

<210> SEQ ID NO 16
<211> LENGTH: 4768
<212> TYPE: DNA
<213> ORGANISM: Homo sapiens

<400> SEQUENCE: 16

| | |
|---|---:|
| atcttacaat cacagtcttt ctcttagggc tgggctcagt gggtggattg acactgcaga | 60 |
| aatggccaga tctaaaggat caacatttac gtagctggga aatgtagctg ggacttcagt | 120 |
| ttcactgccc tagtgatttt tcctaccact aagcagctca gtccataccc ctacgagacc | 180 |
| cacaagctta tgagatactg ttcttccagg aaagcagtgg ggccagggcc acctttaat | 240 |
| tgtgtttctt ggcctggtcc catctttctc acaatatata gcaacagtta tttacttgct | 300 |
| gattttctaa tgcacatcac acatagtcat attaaacaca cacacacaca cacacacaca | 360 |
| cacacacccc tcaagaaaca tttctgaga cgtgatttcc tgatttcatc aaaaaagaaa | 420 |
| agagcgggcc aggcacagtg ggaagtcaag gtgggtggat cacttgaggt caggagtttg | 480 |
| aaaccagcct ggccaacacg gtggaacctc gtctctacta aaaatacaaa aattagccag | 540 |
| gcgtggtggc gcacacctgt aatcccagct actggggagg ctgaggcagg agaattgctt | 600 |
| caacctgcga ggctgaggtt gcagtgagcc gagattgcgc cattgcactc cagcctgggc | 660 |
| aacagagtga gactctgtct caaaaaaaaa aaaaaaaaaa aaagcataaa ctgaaattta | 720 |
| tatgcaattt atatgcctgt gagataattc tgttttctct tttggaaccc caaagagatt | 780 |
| ttttgattg atgagcaaat acattttaga ttttattaaa gcattatgcc aagcaccact | 840 |
| gaagtataag tttcaagggc aaactcagtt ttttcatcta ctagacgaat gattttctgg | 900 |
| aatgattaca agcaggcaag atggtgtagt ggaaatagca aatgtcttcg gcatcagaca | 960 |
| agttgggggtt tgtttgtatc ctgcctctgc ccttcaccga ggttgtgatc ttgggcagat | 1020 |
| tgttgagttt taacctagat tcctctgact ccagatcata aattttcaga aaagttctga | 1080 |
| aattcttgta tatactgatg gtaaatgaga ctttccttta catctatgca cttctttgtt | 1140 |
| tgtttgtttt gagatggtct tgctctgttg cccagactgg agtgcagtag tgcaatctcc | 1200 |
| gctcactaca atgtctgcct cccaggttcc agtgagcctc ctgcctcagc ctcccaaata | 1260 |
| gctgagacta caggcatgtg ccaccacgtc cggctaattt ttgtattttt agtagagaca | 1320 |
| gggttttgcc atgttgacca cactggtctc gaactcctgg cctcaggtga ttcgcccgcc | 1380 |
| tcagcctccc aaagtgctgg gattacaggc atgagccacc atgcccggcc atatccatgc | 1440 |
| acttcttgca accttacctt cttttctcat cacccctccag ggacctagtt ggaagagcag | 1500 |
| agttaaaagt taaggtgaaa cttggagagg tgtcttgtcc ctaggaacaa aggactggtt | 1560 |
| tgaaattctc tgtaaatctt ccccagttca aaccagagtt atcaaggtct taaaaacttc | 1620 |
| cctgggtcct gagagcccat tatattattt acttgtcttc ctgtacaccc actgcctagt | 1680 |
| cctgatccta cttttgtttg caaataggat ggggcacaac gtacaaggaa gggcctttgc | 1740 |
| caccctgct aagggataac ctgaaatacc ttcaccatca ctgccctgtg ctgctttca | 1800 |

```
cctatgccag tctgtctaca gtgccagtgt ctcctggcat tgaaagggga gaatcttttg    1860
gtcctttgag tatttggttg ggttacataa atctccctga atgaagagca gctgacttag    1920
gcaaggggcc ttgtttggtt ttccttgaac tattaacagg aagatgggga gattaactgt    1980
gtaaatgttc aataggccag agtccctgca gagggtggcc acagtgatca gatcttatca    2040
catccttgct ttgggtgttg cctctctggt tggagtatgg atagaaaaga aagaaagacc    2100
ctatattgaa atgcaaagtg cagcaagtcc tgactttgga ttaacttctc agcccatttg    2160
catgaaaata aaaagatgaa taaaacaagg ttcccacttt ggaggaggt ggtagctgtg     2220
agatggaagg agtgttcctg ctgggcaaca gcagagtaag tgctggggta gattcactcc    2280
cacagtgcct ggaaaatcct cataggctca tttgttgagt cttgtccta caccaggcac     2340
tctgcaaaaa cgctttgcct gcaaggtctc atgcgatgct caccacagct ctgtgaagtt    2400
aattgtactt ttatcaccat tttacagatg agaaaactga gggtatgggg tcaatgactt    2460
ggctaaagtc actgcttagc aagctgcagg gactggatgt gaattccaat tggtttgact    2520
ccaaagcctg tgaagctact tgttcttcac cacctagagc tgtggttctt gataactgtg    2580
aactcttttg gggtcacaaa tagccctgag aatatgatag aagcaggagc tctggccttt    2640
ctgtccatac ctgaacaggt ccttgggtta agagcccctc gtccagggcc tattaatctt    2700
gatcctcata agcagcatcc atgtattacg gccgcaaacc aaactgtgcc agaccgaatc    2760
ctaggaccaa gcccaaatat gtcccatcat ccttttggta agaagctcat tgtaagaaag    2820
aaagaggaga gcaagaggat gacctagtgc atggggcctc attgttttaa ttagtgacaa    2880
aacaacaata ataacaacaa aacccccgaa gcttcacaga tgacatcaga ccccaagcct    2940
gtgtgttttt caggtgccct tgaggagctt tgtagctggc agaggaggtg aaactgacaa    3000
atgtttggca gatggaggag agtaccagag gggtttgaga tgagctaaat tccaatctaa    3060
ccgcagtgtt gaggaagagg cttgattgg accatggag atggggttc tactcccagt       3120
cacgccagct gactttgcga gtgttctttg tcagtcactt tatcttattt tatttatttt    3180
tatttttttg aaatggagtt tcgctcttgt cgcccaggct ggagtgaaat ggcgcgatct    3240
tggctcactg caacctcccc ctcctgagtt caagcgattc tcctgcctca gcctccagag    3300
tacctgggat tacaggcgcc tgccaccaag cccatcgaat ttttgtatgc ttagtagaga    3360
cagggtttcg ccatgttggc cagggtggtc ttgaactcct gacctcaggt gatccgccca    3420
ccttggcctc ccaaagtgct gggattacag gcgcgagcca ctgtgcccag cccacttcat    3480
cttaccgtag ttacctcctt agagtatgaa aaaataggct tagggcatcc ccaagtcccc    3540
tctatgtctg agagctgagg ctggctgtca agaggaact aaggatgcca gggactttct    3600
gcttaggacc cctctcatca cttctccaac gctggtatca tgaaccccat tctacagatg    3660
atgtccacta gattaagaat ggcatgtgag gccaagtttc cacctgagag tcagttttat    3720
tcagaagaga caggtctctg ggatgtgggg aatgggacgg acagacttgg catgaagcat    3780
tgtataaatg gagcctcaaa atcgcttcag ggaattaatg tttctccctg tgttttcta    3840
ctcctcgatt tcaacaggcc attttccaaa taaagccatg ccctctgcag gaacacttcc    3900
ttgggttcag gggattatct gtaatgccaa caaccctgt ttccgttacc cgactcctgg     3960
ggaggctccc ggagttgttg gaaactttaa caaatccatg taagtatcag atcaggtttt    4020
cttttccaaac ttgtcagtta atccttttcc ttcctttctt gtcctctgga gaattttgaa   4080
tggctggatt taagtgaagt tgttttttgta aatgcttgtg tgatagagtc tgcagaatga   4140
gggaagggag aattttggag aatttggggt atttggggta tccatcacct cgagtattta   4200
```

```
tcatttctgt atgttgtgaa catttcaagt cctgtctgct agctattttg gaatatacta      4260
tatgttgtta atgatatcat gcagcagacg tgcatctgaa tgggctggct ctaggagcta      4320
gagggtaggg gctggcacaa agatgcatgc tggaagggtc cttgcccata agaagcttac      4380
agccaaggct aggggagttc tgtcttctct gcatcaggtc acctctctca cctctgtcac      4440
tgccccatca gactacaatg tctgcaggtc tttctcccct gagtgtgagc tccctgagca      4500
aagcaggatg ctgccccttc cctttgtatt ccttgctcct tgcttcagtg cctgtacata      4560
agtatgggca taataagtgt cccccaaatg agacattgag gattcttcaa atgcacagga      4620
ccgtgatgtg agttaggacg gagtaaggac gatgggatgt ggctcatgac aatcctgagg      4680
aagctgcagc tgcggcacgc agggccacac tgtcatgttc atggaccta gactggcttt      4740 gtagcctcca tgggccccctt ccatacac                                        4768
```

<210> SEQ ID NO 17
<211> LENGTH: 1295
<212> TYPE: DNA
<213> ORGANISM: Homo sapiens

<400> SEQUENCE: 17

```
tcatgactgc cattggtata aagatgaata taatccagac cagattcatg attattcata        60 cattttagt gtattaactt ttaattctgc ttttaaaata aattaaaaca ttctaatatg       120
cccttaagag tatcccagcc caggccactg agcctactgt ggttcatgga taagtttgcc       180
cctgggggca tgtgtgtgca tgcatgtgtg tgcacatgca tgatgagccg ggccttgaag       240
ggtggtaaga tttgggtgtg tagaccaatg gagaaaggca tttggggcag tgatgatggg       300
tgggggaggg aacatggtga tgaatggagc tgggtgtggg gagccatggg agtgggttag       360
ggccagcctg tggaggacct gggagccagg ctgagttcta tgcacttggc agtcacttct       420
gtaaagcagc agaggcagtt ggcctagcta aagcctttcg ccttttcttg caccctttac       480
agtgtggctc gcctgttctc agatgctcgg aggcttcttt tatacagcca gaaagacacc       540
agcatgaagg acatgcgcaa agttctgaga acattcagc agatcaagaa atccagctca       600
agtaagtaaa aaccttctct gcatccgttt ataattggaa attgacctgc accagggaaa       660
agagtagccc aggtgtctgg ggcttgttcc cattagatct tccccaaggg gttttctcc       720 ttggtggctg gcctgtgggg cccctctcca ggaggcattg gtgaagaaac tagggagct       780 ggttgccaca gacagtgatg tactaatctt ctctgggaag acagaagaaa agtccccagg       840
gaagaatact acagacttgg ccttagggac agctaggggt gcagattgct gccaactgca       900
ttttttctga agttggccat atggttgcag tgaatggatt tatagacaga gtatttctgt       960
gcatataaga gcaattacag ttgtaagttg atatggataa gtgaaagtta agcacttctt      1020
tctaaaaaga gaatgcaatt cattttccc taatcatttc aattagtctg atgggcatt       1080 gaacttgttg tctttaaaaa gtgaaatctt tacctctgat ctggtaagta ccaggcaat      1140 ttcttgtgtg ccacccagga ggtatctggg gagtgggcat tttctgactg aggcattggc      1200
tgccatagca tcagagcagc cttccaggca gtggcctggc aaggggacag aggctggtgg      1260
gagcagctgg ctgagtgcag ccagtaatgg catgt                                1295
```

<210> SEQ ID NO 18
<211> LENGTH: 2188
<212> TYPE: DNA
<213> ORGANISM: Homo sapiens

<400> SEQUENCE: 18

```
agctctccag gtgattctga tgcatactta agtttgagaa ccattgcttg ttttgcatta      60
aacaggagat tagtctctgc agcttgtggg aataaagctt taaatctctc caattttagc     120
tctgtgaaaa ggcagtgggg agacaggaat gaacggacta gtgccacaaa gctcaggtgg     180
ggtgggtgag atcatttaga agagaaagac cgggcatggt ggctcacgcc tgtactgtca     240
gcactttggg aggccaaggc aggttggatc acaaggtcag gagtttgaga ccagcctgcc     300
tatcatggtg aaaccctgtc tgtactaaag ataaaaaaaa aaaaatttgc cagtcatggt     360
gatgcatacc tgtaatccca gctactcggg aggctgaggc aggagaatct cttgaacccg     420
ggaggcgggg gttgcagtga gctgagattc caccattgca ctccaaccta ggtgacaggg     480
tgagactccg tctcaaaata aaaaaaaaa agaaaagga aaggctgtgt gtgtgtgtat       540
gtgtgtgtgt gtgtgtgtgt gtgtgtgtaa cagcaccatc acactgtttg agttgaggag     600
cacatgctga gtgtggctca acatgttacc agaaagcaat attttcatgc ctctcctgat     660
atggcgatgc tcccctatct cattcctgtg tgtgtttagc caggcaactg ttgatcatca     720
atattatgat aacgtttctc cactgtccca ttgtgcccac tttttttttt tttttgagtt     780
acttactaaa taaaaataaa acactatttc tcaatagact tgaagcttca agatttcctg     840
gtggacaatg aaaccttctc tgggttcctg tatcacaacc tctctctccc aaagtctact     900
gtggacaaga tgctgagggc tgatgtcatt ctccacaagg taagctgatg cctccagctt     960
cctcagtagg gctgatggca attacgttgt gcagctactg gaaagaaatg aataaaccct    1020
tgtccttgta atggtggtga agggaggga ggtagtttga atacaacttc acttaatttt     1080
acttccctat tcaggcagga attgccaaac catccaggag tggaatatgc aacctggcgt    1140
catgggccag ctggttaaaa taaaattgat ttctggctta tcacttggca tttgtgatga    1200
tttcctccta caagggatac attttaagtt gagttaaact taaaaaatat tcacagttct    1260
gaggcaataa ccgtggttaa gggttattga tctggaggag ctctgtctaa aaaattgagg    1320
acaggagact ttagacaagg gtgtatttgg agactttaa gaattttata aataagggc      1380 tggacgcagt ggcactgagt tgagaactgt tgcttgcttt gcattaaata ggagatcagt    1440
ccctgcagct tgtgggaata aggctttaaa tctctccaat tttagctctg tgagatggca    1500
ctggggaaac agaaatgaac ggactagtgt cacaaagctc aggtgggatg gacgagatca    1560
cttcaaaggt ctgtaatccc acgtctataa tcccagcact ttgggaggcc aaggcgggaa    1620
aatcacttga ggtcaggagt tcgagaccat cctggccaac aatgcaaagc ctgtctctac    1680
taaaaatatg aaaattagct cagcgtggtg gcatgctcct gtagtcccag ctactcgtga    1740
ggctgagaca ggagaatcgt ttgaacctgg gaggcggagg ttgcagtgag ccaatatcac    1800
gccattgcac tccagcctgg ctgacagagt gagactccat ctcaaaaaaa aaaaaaaaa     1860 aagaattta taaatcagg aataatatt agtgtttatg ttgaatttta actttagaat       1920
catagaaaac ttcctctggc atcattatta gacagctctt gtgcagtggg tagcaccaga    1980
cccagcttgc atggttattg attttcaga gacactttt gagcttattc tctggcagaa      2040 agggggaactg cttcctcccc tatctcgtgt ctgcatacta gcttgtcttt acaagaagca    2100
gaagtagtgg aaatgtttat tcttgaaaat aagcttttg cttcacatga tctagaattt     2160
ttaaaattag aaaaatgtgc ttactgcg                                       2188

<210> SEQ ID NO 19
<211> LENGTH: 1183
<212> TYPE: DNA
<213> ORGANISM: Homo sapiens
```

<220> FEATURE:
<221> NAME/KEY: misc_feature
<222> LOCATION: (1)...(1183)
<223> OTHER INFORMATION: n = a, t, c, or g

<400> SEQUENCE: 19

| | | | | | |
|---|---|---|---|---|---|
| agtaaaatgg | agaattccaa | attctgaaat | tgttagaaca | tagttctgtg | tcttagttaa | 60 |
| atatcgacac | ttacagataa | atagcataaa | tgctttctcc | ccatatttca | gcccagtcct | 120 |
| acttaaagac | aacataaatt | gcaaaatagt | gaggatgttg | ttcatctaat | aaaagtggtt | 180 |
| ccaggaattc | agactctgga | ttcctgtttg | ccaaatcatg | tgtcccactc | ttaagaaaac | 240 |
| gagttggact | ntggattttt | ctttgcaaga | gggacaagag | tgtgggagat | actgagttaa | 300 |
| tgcaacttgc | aggttttaag | tgtcctgtca | ttgtgccttg | tgctttgata | cattctgagt | 360 |
| ttcagtaaag | agacctgatg | cattggactg | ttgcaatgga | acctgtttta | agatcttcaa | 420 |
| agctgtattg | atatgaagtt | ctccaaaaga | cttcaaggac | ccagcttcca | atcttcataa | 480 |
| tcctcttgtg | cttgtctctc | tttgcatgaa | atgcttccag | gtattttgc | aaggctacca | 540 |
| gttacatttg | acaagtctgt | gcaatggatc | aaaatcagaa | gagatgattc | aacttggtga | 600 |
| ccaagaagtt | tctgagcttt | gtggcctacc | aagggagaaa | ctggctgcag | cagagcgagt | 660 |
| acttcgttcc | aacatggaca | tcctgaagcc | aatcctggtg | agtagacttg | ctcactggag | 720 |
| aaacttcaag | cactaatgct | ttcggaatgt | gaggcttttc | cttggacagc | atgactttgt | 780 |
| tttgtagaaa | agtacggctg | gctgggagtt | tgtgatataa | tttagttcag | tggtattcta | 840 |
| agtgttctta | gtgttctttc | agacttttgg | gccatctccc | aaagggtgaa | tgggaagaat | 900 |
| aagctgggtg | tggctgagtt | taagccaaaa | gttttttgtg | cttgtttcaa | tcagagaaga | 960 |
| cctgcttttt | catgttttta | ctattataat | actaagcaag | agctcatttg | aaaacagagt | 1020 |
| tcttcatatt | taaaaaaaaa | aagtcttgaa | accattgatg | ggaagatgga | tatctattta | 1080 |
| tgtttaaaaa | cccatcataa | agatgacatt | gtgggctgtc | acagttggaa | ggccctggaa | 1140 |
| ttagatgaga | ccacactatt | tagcttactt | agtaataaca | ttg | | 1183 |

<210> SEQ ID NO 20
<211> LENGTH: 8981
<212> TYPE: DNA
<213> ORGANISM: Homo sapiens

<400> SEQUENCE: 20

| | | | | | |
|---|---|---|---|---|---|
| ccgtttggca | aatgctcagt | aaaagaaaag | ggttagaagg | ggagaaaggc | attttatccc | 60 |
| aagccttcag | gaatcaggat | gaggatgtct | tcaccttgtg | gtggggagta | attatacaat | 120 |
| tagagacagc | acattggagt | gtggctgata | tgctgtgtga | tgatagctct | agctctctgc | 180 |
| ctagcagagg | aaggacattt | caatagaaga | aaaagtttaa | gaccttgccg | agaaacagag | 240 |
| aaaggatgtt | tgtcttttta | agaagttgaa | aaccctgttt | gcagacaaaa | gccctccagt | 300 |
| tttggcagta | aactttcatg | caaggaagaa | aaaaggcagg | ggatgacatt | gttgacaatt | 360 |
| gtgaggaatt | accatgtgcc | aggcactgtg | cgagggcctt | tgtacatatc | ctctagtttt | 420 |
| agtgcttata | aaaactctgt | gatatgtgca | cagcatttta | aactttgctg | catagtcgag | 480 |
| aaaatgaaag | gatggggaat | ttgagtcatt | tgcccagggt | tctatagcta | ccccaggttc | 540 |
| ccatgactgg | agaattgggg | cacagggtgg | cgggggagag | tgagtgacaa | gaatcctaac | 600 |
| aatcttattt | ccattgagtc | cttataaaag | aagtggatta | actaccacgt | ttttaagttt | 660 |
| ttcttaaatt | taggttatgt | ggatctggcg | tttcttgttt | tgtcctgggt | ttgttttgtt | 720 |
| tttgctatgc | tgtcttgaac | atctgtcatc | ttgtaggcct | aacggtaaac | acaaaaacac | 780 |

```
tttacctcct atagctttca attaagatct ctcagtttgt gtttgtaata gttttccagg    840
caagttctcc ctaggttcgg cttctagtgt gttaacctttt agttataaag tgaacccaaa    900
gagagaaagt agaaacaaaa cacctcacct gtttttgctc atgaattact ctctatggaa    960
ggaacaatca tgaacacctc tgcgtatcac agaggcctat ctgagtctga cgtttaaggg   1020
agaccgcgta ggtccctttg aggactgtga atgtgggagt cctgggactc tggtgaagaa   1080
cccgttccag aagagatgaa tgagctggac aagttctttc atagaacctt taggcaggtt   1140
ttcttagaaa tgcacattga ggattatgct tggatattgt gatgatcaga atgatactca   1200
atcccttctg catttggaat tctctttgaa agaaaacatc ccaggcagct atttctcaga   1260
gatagtgagt cccagccact tctagacatt ttcttgtgta gtctacatta taatttcaca   1320
gcagtctctg atatgacaaa tgtcaaaata gcccaacctt ctctaaactt cagagatgtc   1380
tgatatgata ttgaataaaa caatgctcat agaaacatca agaaaggtgg attttccctg   1440 gatactttt tcctgcttga caaataacag tgaagaaact gatctcacgt ctttttctct   1500
ttggaagcct gaacactcag aacccaactt gaggctcctc agctatagca attctgactt   1560
cacagtctgt aaattattgt tcttttttttt ctttagctta tgcttctgc cctaattttat   1620 cttttccctg ttctaatgaa ttattgtcct atatctgctg tgcagttagg tgacatataa   1680
cagcaattaa atatatgaat tggtacatat aaagatttga ctaaaactcg atgtaaaaat   1740
aagtgttcta cattcaattt ccagtgttag aaacagtgct gacttgaaca gagtgacaga   1800
attccatctt tccctatttt tgacagcttt aaactttata ttttcttcct ttcttgtgag   1860
ccgtcattaa cttgtttctc aaagccattc ccgtattacc catcttgcag acgcagacag   1920
atttgggaat ttgcggtcag agttgtattg gacacatccc cccagcccac atgagatcct   1980
tttaatctat tgcatattaa ctagttttaa gtacaatatt cctacttcat ttaaaaccat   2040
taatcaaaga atgagtttga aaatgaacaa aatgcaaact tacagttaga ataattgta   2100 gtgtctttag ttttggttag gagtcggttt cttgtttgtt aaactcaaga ttgtgaacag   2160
ttttaattca cttgtttatt tccaatagag atttcaggtt tacatttgaa ttcagaaaca   2220
aagttttctt tctcattaca gagaacacta aactctacat ctcccttccc gagcaaggag   2280
ctggccgaag ccacaaaaac attgctgcat agtcttggga ctctggccca ggaggtaagt   2340
tgtgtctttc cagtaccagg aagcggatca tccactgtat cagtattttc attcctgagt   2400
ctggcaagag gtccttttga gttgaatatc acatgggatg taatatcaat tttcaaagta   2460
taagtgatgt aaacaataat gttttgattt ccttatttta gaaatgaaga aacctaaaac   2520
tcatagatgt ctcagagcta attggttagt ggctaacagc tggatatcta gtttagaacc   2580
ttctccattt tttcttttg ccccctaggta atcatacatt tgtaaagagg agaattatct   2640
ctgccactgc ccatgcactg cttttgtctg accagcaatt tctccatatt gcttcttcag   2700
tagcaaggcc aatcatttta ccaacacaca tgcttgctaa ctaacaggaa taacgtggta   2760
cccctaattc agccctttcc cttgaaagca tctggcttct gaggttcaac tatgggaata   2820
tggtctctta atgaacatta agttgagttt gccttttagg tccacatgtt gacaaatgta   2880
tcagagtaat ctctgtccta ggatcagagg gcctgtaggc acttgcaaaa gcagttagct   2940
ctgactccca gccagtgcac actccacctt tctgactccc agccttgtct caaattaggc   3000
ttggaagcga ggaactgtct ggtgtccccc agcataggaa gctgagccag ggggcagtgc   3060
tcacaaacaa tacagacttt aacgtgtagg atattggaaa ataataattt gtggggaaat   3120
tgtctcagac ttggtccacc cttattttta gctgcttctc taatccgttt tctttttttt   3180
```

```
ggtgcttgta tctaacctac ccattttttg gtgcttgcat catttttttca aatatcaaaa    3240
acgaacttta tgttttctaa caatgaaagt attgcatgtt cattgtggaa aatgctgaag    3300
acttggaaaa tacaaaaatg ctgagatcaa acactattga tacgttagtg tatttcttcc    3360
tgtcctgttc tactttcttt ctttgaattc tgctcacgtg tttctgactg atgaggtctg    3420
acttttgggt tccttttcca gaggagaagc cttcttcag cttgccattt gttaccctgg     3480
ttatgaaggc tggtaacctt ttttactagg tagagaagct ggaccaactg gggttcttcc    3540
agggggagaa tgagaaagag aaactgtttt gcaagtccgt agctattcct ctagggccct    3600
gttagctgac attgacatgc cttgcattgc tctgcagatc ccctcgcagc cctctgtccc    3660
ttgttcattt ctggccttag agaaagcaaa gcagggtctg taacagggga ggctgcctct    3720
aaactcaggg tttggttaca gctgttttca cttacatcac tggccctggt ttttttttt     3780
tttctggcat taaaaaaaaa aattggaagc aggtgatgtt cccattgctg atgtggtgga    3840
aactctccaa gtgaacaata tacgttttc ttggcagctg tttcttgtgc cctgcttgct     3900
cctggtccag acaagcaag gaccatctgc ctctttcaat agaacacctc cagatccctt     3960
tgatcaaaag ttactcattg tctgacttgc tatttctgtg agataaatgg gagaagatca    4020
ataaatgcac ttgtttgtcc agtcagcgtg tggaaagttg ataatttga ccaaagcaca     4080
accctgaaag gaaagaaaaa agggagtgaa tgtcttctga gaagctgcct aggttcagac    4140
agtgtcaccc atttccctgt atgctccaca tgacaaacct gagtgggtct catcatgtcc    4200
attttgcaga tggcaccaag gctcagaaag gttaggcaac ttttccagtc acccaatgag    4260
ttaattgaca aaactgggat tcaaacccag aactgttgga ttccaaagcc tgtgttgttg    4320
cctgcttcgt gaaaaactcc agtagcgact ggaatagaaa ggagaacctt ccaagaaaga    4380
aaatacgcac tagcagaacc tggaaattgg gaggaaatga ggacttgagg aataagatga    4440
atgaaagctg acctgagttt cacatctggg tgatgggaag ggaggacagg gaggcagcat    4500
ctcagatgtc cacccagcac cgaccagctg cctggcattg ctaggtgttg aggactcagc    4560
agtgaacacg ctaacttctc tgctttcttg gggcacgtat agggtgagag acagaaacaa    4620
acaggtcagt gtacaatgcc acaggaggga tatatgcagt gaagaaaaag cagggtaagg    4680
ggcatagagc atgagaaggt gcttttttta aaggggktga ttaggaaagc tctctctaag    4740
gtgacagttg gacctgaagg agatgatagc atgtctgtgg tgagggaagg aaactccgaa    4800
caggaagaat ggcagataca aagacattga tgcctagagca tgcctaagga atgtgtttaa    4860
ggaccaggga aagtgagcaa gtggtgggg gaggagagga gctcagagca ggaggaggtg    4920
agtgccatac aggcctggca agactttgga ttcctgctgg gtgagatgag aatccagcgg    4980
agggcttgag ggaggggaca tgatgtgatc tagagtttag actgtttaca ctctggttgt    5040
tgggttgaga agagactggg atggggaaa gggaggacaa aggacattgt gctggattga    5100
gaaagcagta agtcagtttc attcattcac tcaaccgatg atgttcaaat accaccatca    5160
tccgtgggct aaaggatgaa gagccatccc tccctgagag tcaggaagca cttcccagat    5220
aaagtttgga gtgtgagctg aggtgtagga gaaagagtaa gagtttaccc ctgaaacggg    5280
tgctgggaag agtcaatagt ttggaataac tcaataattt atggtgcttc tttagaaaga    5340
tttgctggct ttatgtggga agaaatttkt ttttttgatt ggggagtggt gggttggtgg    5400
tgaggctgcc tgtggaaaga gaagtgagtg ttttgactca ctgttatta aaaatctcta    5460
gggctgttcc aataagcaac aaaaggcaaa atggcctggt tctctgtccc ctttctgtct    5520
gtatgcctcg tacaggttat gaaaagaaaa agttgggaaa agctgtccac ctcacctaat    5580
```

```
tgtgttcttg tggagtgtgc tagatgcccc ctctctggag aaaaaaaatc cttgtggcct    5640
ctgacccacc tctggagagc ctagttccct tctggaggca gaaggcaaag cttaggacct    5700
agagagtgct ggaccacgcc actcacagga accagcaggc tgtgaggttg aaagctaggc    5760
atatggagct ttccaggctg ggtgcagggc ctcgtggccc ttcccctccc ctctgtgctc    5820
tatagctcag tcttcccagg cggtgtgaac acgcagtgac atttccagga atacagggat    5880
ttattaatga tttcttgtga aatgtttgga aatacaaagt actctataaa tatttcataa    5940
tagcattggg gctgagaact ccacaaagtg ccggaataca tttgcatgta agacagaacg    6000
ctgcctgggt cattgatgcc tgttgagtgg cagtcacaga cactgcctag ggtttctgac    6060
tcacgctgtt gggactgttc tatgcagggc accctcttgt gtggcatagg atttgtgcct    6120
caccacacac tgttgtagct ttgctgtctt gatgatgagt agagggcagt gtccaggcca    6180
tggtataagc atctactgcc ccccagggtt accaaaacca agccaagttg tgtctcagcg    6240
agctccgtga agcatggaga agttgagtac tcagagacat gacgtgactt ttcaaaggct    6300
gtaagctgac gagggacata gctagggttc agacttgagt ttttctttt cttttctttt    6360
ttcttttttt tttaagactg agtcttgctt ttgtcgccca ggctggattg cagtggtgct    6420
tggctcactg caacctctgc ctcccgggtt caagcaattc tcctgcctca gcctccccag    6480
tagctgggat tacaggcacc tgccaccatg cctggccaac attttttgtat ttttttagta    6540
gagatggggt ttcaccatgt tggccaggct ggtcttgaac tcctgacctc aggtgatcca    6600
cccgcctcga cctcccaaag tactgggatt acaggtgtga gccactgcac ccggcccaga    6660
ctcgagtttt tcatcttaat gctttttcat tgcctgacac tttactgaga ccaagatagg    6720
gaacttcaca tacagtacct tttctcccaa ggcggaagag ggctgttcaa tttctacact    6780
agagttcggg gagttttaga aatgagtcag ttatcgagga tgagagcagt tcctgatagg    6840
ctcaaccaca atgagatgta gctgttcaga gaaagcattc ttttatctat aaactggaag    6900
ataatcccgg tgaaacgaag cccagcccca ggggcttcac taactccagg ctgtgcttct    6960
caaactttag tgagcatagg aatcacctgg gcatcttgtg aagctgtaga tttgaattct    7020
gcaggtcggc agaggggtct cagaatccgc atttccaaca atgtctccag taatgctgat    7080
gctgctcgtc cctggaccac agattgggta gccaggttct ggcaagctca tcccaaggct    7140
ttgagatgac atcagacaaa atatgttctg ggacatggct tttgagaggt caagaaaata    7200
agatgttcct ttctcttctc atccccaacc cttgcactgc ccttttctcc cttccctac    7260
cctcctttct gtccccatcc ctgacgccag ctgttcagca tgagaagctg gagtgacatg    7320
cgacaggagg tgatgtttct gaccaatgtg aacagctcca gctcctccac ccaaatctac    7380
caggctgtgt ctcgtattgt ctgcgggcat cccgagggag ggggctgaa gatcaagtct    7440
ctcaactggt atgaggacaa caactacaaa gccctctttg gaggcaatgg cactgaggaa    7500
gatgctgaaa ccttctatga caactctaca agtgagtgtc catgcagacc ccagccctgt    7560
ccccaacccc atccctccct tagttctggc cttggcctgt gtcatctcct ccctctgtag    7620
cagcgttaga tgtctacatg cccatttgcc caccagactg agctcttcct agaggagaga    7680
ggcttctctt gaatagctac ctgtccccag ttctctgaat gcagcctggc acatctcagg    7740
tgcacagtag tgtttatcaa tggaatgaat gattgacagc caaccttctg gttttctggg    7800
ggatgtggaa gggtggcttc cagggtgatc aagaatgaga taatggcaga aggacaaatc    7860
ctgcaagatc tcacttatat atggaatata tgtaaggtag aaagtgtcag tttcacatga    7920
tgaataagtt cctgggatct tgatgtacat cgtgatgact atagttagta acactgtata    7980
```

| | | |
|---|---|---|
| gtatacttga aatttgctaa gagagtagat ccgaagtgtt cacactacac aaaaaaggca | 8040 |
| actatgaggt gatggattta ttaacagctt gattgtggtg atccttttac aaagtataca | 8100 |
| tatattaaaa catcacattg tataccttaa atatatacaa tttttatttg tcagttgtaa | 8160 |
| ctcaaaaaag ctagaaaagc attttttaaaa aggatgatgt actggtctta atattaccat | 8220 |
| tgagataagc tttataataa cataaaaaga aataacagta atgataatag caacaacaac | 8280 |
| aacaacaaag aactaacatt taagtagaat ttcttgtgca ctgtgcattc tgtttaagtt | 8340 |
| atctcatttt accctcatga taacctgcag ggaagattct ttaacccccac atttcatagg | 8400 |
| ctcagagagg ttaagtgcct tggttagagc cacatcagag ttaatccaca agagccagga | 8460 |
| ttcaagccca aatctgcctg gatctgtgct ctctaagata actgttagtg gtggcgtgtg | 8520 |
| tgttctcaca ctcagacatt tgatctgccc tttgtttccc attcttagct gcaaggcagt | 8580 |
| gttaaagaac cctgtgtctc catatccact ccccacactt aagcacttttt gtgggcccgt | 8640 |
| gtgccgtatg cctcgtggca gcagggatcc aatgtcacag ttttaggcag tggcatcctt | 8700 |
| ttccttgaaa acttgatgca ggggaacctt tctccatttc caaccacagg tgtgtctttc | 8760 |
| agacactgag tgaggcaggt tttgtacttt attgtaaac aagaaccttt tcttctctgg | 8820 |
| agtaaagcac tccagacatt cgcaagttgc tttacaagcc taaaaggat ggtattgtag | 8880 |
| gcaactttaa ttaaatccca tctcctcctc tccccccagct tgcaagttga cccaaggaag | 8940 |
| ccttcatttc catgacagac ttaattgtga gggcatcctc a | 8981 |

<210> SEQ ID NO 21
<211> LENGTH: 20284
<212> TYPE: DNA
<213> ORGANISM: Homo sapiens
<220> FEATURE:
<221> NAME/KEY: misc_feature
<222> LOCATION: (1)...(20284)
<223> OTHER INFORMATION: n = a, t, c, or g

<400> SEQUENCE: 21

| | | |
|---|---|---|
| actgtgttag caaggatggt ctcgatctcc tgacctcgtg atccgcctgt atcggcctcc | 60 |
| caaagtgctg ggattacagg cgtgaaccac tgcgccctgt tgagaatttt ttttttttttt | 120 |
| tttgggagaa agagtttcgc tcttgttgcc cgggctagag tgcagtgaca caatctcggc | 180 |
| tcactgcaac ctctgcctcc tgggttcaag caattctcct gcctcagcct catgcgtcac | 240 |
| cacgcccagc taattttgta ttttagtag agacagggtt tctccatgtt ggtcaggctg | 300 |
| gtctcgaact cccaacctca ggtggttcgc ccgccttggc ctcccaaagt gctgggattg | 360 |
| caggcatgag ccactgcgcc cagccccaaa ttttggtttt tgcttgaaaa ctgaggtctg | 420 |
| aattcagcct tctggttgcc cctcaagagt cagtttaaat gttggtcatg ttagttgtca | 480 |
| gtgaaaacaa tggtgaggct ggcatgagag tgtgaatctg gatgggaggg cttgtgcttc | 540 |
| atgaaaacat ttttccagat cagctcagtc gtgagttatc cgtcattgac gttataataa | 600 |
| gctctgatta tttatcaagc atcattcttt atagatatct cagtttaatc tgagataatc | 660 |
| ttctccacat ctctccacat agatgttatg aattttactt ttacagagga gccaactgag | 720 |
| gctcagataa gttacttatt atatgactag tagtggtaga gctggggttt caactaagaa | 780 |
| ctctctggct ccaaagccct tgtaagtttc tatcagtata tgaccatgca tatgagcatt | 840 |
| tgtctctcct cttcttcata gctccttact gcaatgattt gatgaagaat ttggagtcta | 900 |
| gtcctctttc ccgcattatc tggaaagctc tgaagccgct gctcgttggg aagatcctgt | 960 |
| atacacctga cactccagcc acaaggcagg tcatggctga ggtaagctgc ccccagccca | 1020 |

```
agactccctc cccagaatct ccccagaact gggggcaaaa aactcaaggt agcttcagag    1080
gtgtgcgcta agtatactca cggctcttct ggaattccca gagtgaaaac ctcaagtctg    1140
atgcagacca gagctgggcc agctccccag tcgtgggtat agaatcatag ttacaagcag    1200
gcatttcttg gggatgggga ggactggcac agggctgctg tgatggggta tcttttcagg    1260
gaggagccaa acgctcattg tctgtgcttc cctccttttt tctgcggtcc ctggctcccc    1320
acctgactcc aggtgaacaa gaccttccag gaactggctg tgttccatga tctggaaggc    1380
atgtgggagg aactcagccc caagatctgg accttcatgg agaacagcca agaaatggac    1440
cttgtccggg tgagtgtccc tcccattatt accatgtgcc tgcttgatac tggagaggtg    1500
agtttctggt cactttccca ggtgtgagtg aggtgagaat ctttcagtt tatctagctg     1560 ggggaatgta gtgagcatag ctaaagtcac agggcaccac ctctccagaa gtacaggcca    1620
tggtgcagag ataacgctgt gcatatcagc atccatgcca ctcacggtca aatagcagtt    1680
ttctgcaaaa cttagtgagg ctggtgtttt ggaagtggag ttgagtaatt gcagtaccct    1740
attttccttt ttgctgcagc ctctcagcca gccacagcat ctccctgtgt cttggtaggt    1800
tttgaaaaga agtgtgggag caaaagcatg atgttacatg tagactggcc tgagatactc    1860
attctcaggg cactgtgtga atgatgagct gctgttactg tgtggagggg aaatgcactt    1920
agtgcttcag agccacttga aagggataag tgctctagag acaattgggt tcaaatgtgg    1980
agcaggctga gcaagaacag aatgtctcct ttgcctgagc ctgagtgctg ttaatcacat    2040
cttcctgcct tgggctgagt tagagaatca ttagactatt tcctgtttcc atggtgaggg    2100
aggcctcttc cttttgtctc tgctcccctt aagaagcagg tgaggatttt gccaggtttc    2160 ttgtttgaa ccttattgac tttaagggcg gctgggtttt agagactgta cctacctagg     2220
gggaacactt ccgaagttta ggactattcc ctgatccgct gggaggcagg ttactgagga    2280 agtccccttta aaacaaagg agtttatact gagaaaagca taaacagtga tttgtatgga    2340
ttcacactga ctaatatagc tcatgccatt aaagtggggt ctcttctcta aaggagggtt    2400
atatgatcta gccccgtaga cctaagtgtg gtttcagacc tgttcttcct ggtcctctcc    2460
ttggaatcca tatttctact agttggactt ttttctgttg tctggctctc agaggattat    2520
aggaggccct gtgaagtgac tcagtgaatt ttgatttgtg ggcaagtaga tggttcccta    2580
gtctgaaatt gactttgcct taggtgcttc aattcttcat aagctcccag ttcttaaagg    2640
acaagatcct tgtaaacatg gcaatggcat tcattaggaa tctagctggg aaaatccagt    2700
gtgtatgctt ggaaatgagg gatctggggc tggagagaaa ggcatgggca tgccttggag    2760
ggacttgtgt gtcaagctga ggaccttac tttaagctct aggggaccag gcaaggggag     2820
atgtagatac gttactctga tggggtggat gaattgaaga aggatgaggc aagaatgaag    2880
gcagagacca gggaggaggc tctccaagtg gccaaggcat aaagcaagaa atgaggcctg    2940
gtgactgctt agtggcagag cagtgaaaga gagggaggca tcaaagtgag tctcgatttc    3000
tagctgggtg ggtggtagcg atgtccagta ggccagtggc tactgaggtc tgcagtggag    3060
gagggtggtt gggctggaga cagatgatga gggagtcatc agcctgtggg tggaagaaaa    3120
gggaacctct tccaactgtt ttcttttgctt cttccctctc tttctctttt tttttttttt    3180
tggacagagt cttgctctgt cacccaggct gaaatgcagt ggcatgatct tggctcacca    3240
cagcctccgc ctcctgggtt caagcaattc tcctgtctca gcctccagag tagctgggat    3300
tacaggcaca tatcactgtg cccggctaat ttttgtattt tcagtggaga tgggatttca    3360
ccatgttggt cgggctggaa tgaactcctg acctcaagtg atccacctgc ctcagcctcc    3420
```

```
caaagtgttg ggattacagg catgagccac cgcgcccggc ctttcttccc tctcttaaag   3480
agtgtttatt taattccaca acatgagct tgtcaccccc tgtagcctgg catctcctac   3540
acgaggtgat ggctgaggct tctgcttctg ctggggtagc tctgatcttt ctgctttctc   3600
tggcactgtc tacccatgtt gcctcacccc acaggtccca gggcacctct ctcgggcaag   3660
tcttggaacc ctctgacact gatttgctct cttttctgag ctgcttttag ccacccatcc   3720
tcgggacctg ttttctctct gcctccaccc ctgcgggcag tcttaggtct cctgcccctc   3780
acgagcaccc cagagaggcc acgtgctcag tgatctcagt gggcgcatct ttctagtctt   3840
gctattcttt ttggccatgt tgttcagaaa ccatactggg cagggccgac ttcaccctaa   3900
aggctgcgtc tcttcactct gcttttgttt gttccaaata aagtggcttc agaattgcta   3960
accctagcct ctgtgaactt gtgaggtaca attttgtgtc tgttatgtta acaaaaatac   4020
atacatacct tcctggtgat ggtataaatt gctattctct attggaaagc aatttggaat   4080
gaaaatttaa agaaccattt taaaatatgc tatcctgcgt acctccattc cacccacccc   4140
cagggatgta gcctactgaa ataattttaa agaagtcacc atatgagaga aaatgttatt   4200
gctatattgt tattgtgaga aattggaaat agactaaatg ttcagcacta taggaataat   4260
taatgaaatt acatatactc tatacaatca ttatgctgcc attgaaataa taaatacaaa   4320
ggcgcaaggg gggaaaagct tataatgtta gtgaaactaa gactgatttt tttataaagc   4380
agcagttttc agacccttgg agactccaat tcggtagaac cagagcttca tcttctctgt   4440
cgaagctgtg acaggagttg caaatgcctc tccttttgc tgagtttgca gctgctgttt   4500
ttccggcagc acatctgtgc aggcctctgc ctcggcccct ctggatctgc tgattgagca   4560
gcggattgat ctgtccttct ctttcgtgtt gacccatgtg aggaaccaac tgcaagggga   4620
acaagaaatg gaaataggcc tcctttgcat catgacctgt acatcctgca attggaaaag   4680
attgtacttt agttggttta accagcagca ttatttttct aaactaagca gtaagaagga   4740
attaggtttt atgtgggatc aacagactgg gtctcaaaag aggaaggtga tagaacacag   4800 tgggagggg gaggtgcact agaaacagag ggcctatgct ttcattctgg ctttgctact   4860
taatagctgt gtgacccaat cttagagact taacctctct gaacttccat tttctcatgt   4920
ataaaatggg aaatattaaa ggatactcac tgggctggtg gcttgtgcct gtaatcccag   4980
cacttgggga ggttgaggtg ggaggatcac ttgagcccag gtgttcaaga ccagcccagg   5040
caacatggca agactctgtc tctatgaaaa aattaaaaat tagccaggtg tggtggtgtg   5100
cacctgtagt cttagctact tggtaggctg agatgggagg atcacttggg cttgggaggt   5160
caaggctgcg gtgagctgtg attccatcac tgcactccag cccgggcggc agagcgagac   5220
actgaatcca aacgacaaca acaacaaaag gcaaaaaaat aaaagtgccc tctttatgga   5280
gttgtgtaag gtgaagcata tacactattc aacatagtaa ctatataaag gaagtattgt   5340
tgttgttact gtagttaata ccattaagtg agatgtttcg tatagtggaa agcacatgga   5400
ctctgaattc agactggtct gactttgagt ctcagctcca catctagtaa tactatgacc   5460
aagccctggt taaaatcatg tttttttttc ttcagcctca gtcttctcac atataaaata   5520
gggacactgt catttacctc agttttctgt gaggataaaa caacgacagt gtatatgcaa   5580
gtattttgta aattttgtag tgctcctcaa gatttagttg gtgtttacta cttgtacttt   5640
ctcactggaa tggcagatgc tgttggacag cagggacaat gaccacttt gggaacagca   5700 gttggatggc ttagattgga cagcccaaga catcgtggcg tttttggcca agcacccaga   5760
ggatgtccag tccagtaatg gttctgtgta cacctggaga gaagctttca acgagactaa   5820
```

```
ccaggcaatc cggaccatat ctcgcttcat ggaggtgaat ctgttgctgg gatcatttag    5880
aaaagactta acggcttctt tctctgagac gttacaataa ggttcaggca ggaggcaagt    5940
ttagaaataa tgtatagtct catttacaaa actatccctc aagcctaaca caggatttga    6000
taacaaaagg cacttaataa atgttagttg agtggttgaa tgagtaaata aactctagct    6060
ttagtaaatt aactctagct tattctatat aggctcaaga gaatatttct acccattttc    6120
ttctaggttt tcctatctca gtgactaatg gtagcaaagc attcccttaa aaaggcatta    6180
tttgtgaaac ttayctaaaa tcgaattcgg gtccaattaa attttgaaa ttttatatta     6240 aaaattatat tagtagggat gggtaagagg tgttttggtc tggttggttg gttagttgct    6300
atgactcaga attgctaaga aaacagaaaa gtaagataag atcattgttt taacctcttt    6360
tcctccacaa aatcaataaa taacatatcc ctaaattact cttagaattt tcttaaatt     6420 gcagtgaaaa accaaaatcc ttcattcttg gttgaaggtt ggaaaactac gttagagagg    6480
attagagaga gaggatgagc aatcgtgtag tcagcccttg cctcctagtg taggatttgt    6540
ctcagccact gcttgttgtc ctggctgcca acgttctcat gaaggctgtt cttctatcag    6600
tgtgtcaacc tgaacaagct agaacccata gcaacgaaag tctggctcat caacaagtcc    6660
atggagctgc tggatgagag gaagttctgg gctggtattg tgttcactgg aattactccm    6720
rgcagcattg agctgcccca tcatgtcaag tacaagatcc gaatggacat tgacaatgtg    6780
gagaggacaa ataaaatcaa ggatgggtaa gtggaatccc atcacaccag cctggtcttg    6840
gggaggtcca gagcacctat tatattagga caagaggtac tttattttaa ctaaaaattt    6900
ggtagaaatt tcaacaacaa caaaaaaact caacttggtg tcatgatttt ggtgaaattg    6960
gtacatgact tgctggaagg ttttttcatag gtcataaaat aacagtatct tttgatttag    7020
catttctact caagggaatt aattccagga attttggtgg caggcacctg taatcccagc    7080
tactcgggag gctgaggcag gagaattgct tgaacccagg aggcagaggt tgcagtgagc    7140
taagatcgca tcattgcact cccgcctggg caataagagt gaaactccat ctcaaaaaaa    7200
aaaaagatac aaaaatagaa aaggggcctt ggtaagggta gtagggtttt gggcaatttt    7260
tttttttttt tttttttta ttgtatggtt ctaaaggaat ggttgattac ctgtggtttg    7320
gttttaggta ctgggaccct ggtcctcgag ctgaccccctt tgaggacatg cggtacgtct    7380
gggggggctt cgcctacttg caggatgtgg tggagcaggc aatcatcagg gtgctgacgg    7440
gcaccgagaa gaaaactggt gtctatatgc aacagatgcc ctatccctgt tacgttgatg    7500
acatgtaagt tacctgcaag ccactgtttt taaccagttt atactgtgcc agatgggggt    7560
gtatatatgt gtgtgcatgt gcatgcatgt gtgaatgatc tggaaataag atgccagatg    7620
taagttgtca acagttgcag ccacatgaca gacatagata tatgtgcaca cactagtaaa    7680
cctctttcct tctcatccat ggttgccact tttatctttt tatttttatt tttttttttg    7740
agatggagtc tcgctctgac gcccaggctg gagtgcagtg gctcgatctc ggctcactgc    7800
aacctttgcc tcccgggttc aagctattct cctgcctcag cctccacagt agctgggact    7860
acaggctcat gctgccacgc ccggctgact tttttgtattt tagtagagac gaggtttcac    7920
catgttaccc aggctagact tcaactcctg agtcaggca atccaccctc cttggcctcc    7980
caaagtgctg ggattacagg tgtgagccac tgcacccagc ccaccacttt aattttttac    8040
actctaccct tttggtcaaa atttgctcaa tctgcaagct taaatgtgt catgacaaac    8100 acatgcaagc acatactcac acatagatgc agaaacagcg tctaaactta taaaagcaca    8160
gtttatgtaa atgtgtgcac ttcttctccc taggtggtaa accacatttc aaaacaaccc    8220
```

```
aaataaaact gaacaaagct tcttcctctt agactttta gaaaatcttt cagtgctgag    8280
tcactaagct gccaagttct cattgtggga actatgcctt tggatgtaat gatttcttct    8340
aagacaatgg gcggaggtgt agttattgca gacatctgaa atatgtaatg tttcttccag    8400
attctggaaa ttctcttatt ctctgtggtt ggtggtggtg gtgggatgtg tgtgtgtgtg    8460
tgtgtgtgtg tgtgtgtgtg tgtgtaggga tcaggatgcg ggaggagctg ggttctgctt    8520
gtattggttc tctgttttgc attgaatagt gtgtttcctt gtatggctat ctatagcttt    8580
tcaaggtcac cagaaattat cctgtttttc accttctaaa caattagctg gaattttca    8640 aaggaagact tttacaaaga cccctaagct aaggtttact ctagaaagga tgtcttaaga    8700
cagggcacag gagttcagag gcattaagag ctggtgcctg ttgtcatgta gtgagtatgt    8760
gcctacatgg taaagctttg acgtgaacct caagttcagg gtccaaaatc tgtgtgcctt    8820
tttactttgc acatctgcat tttctattct agcttggaat ctgaaacatt gacaagagct    8880
gcctgaaatg tatgtctgtg gtgtgattag agttacgata agcaagtcaa tagtgagatg    8940
accttggaga tgttgaactt ttgtgagaga atgagttgtt ttttgtttt ggttttagt    9000 actttaacat aatctacctt tagtttaagt atcgctcaca gttacctagt tactgaagca    9060 agccccaaa gaaatttggt ttggcaacac tttgttagcc tcgtttttct ctctacattg    9120
cattgctcgt gaagcattgg atcatacgta catttcagag tctagagggc ctgtccttct    9180
gtggcccaga tgtggtgctc cctctagcat gcaggctcag aggccttggc ccatcaccct    9240
ggctcacgtg tgtctttctt tctccccttg tccttccttg gggcctccag ctttctgcgg    9300
gtgatgagcc ggtcaatgcc cctcttcatg acgctggcct ggatttactc agtggctgtg    9360
atcatcaagg gcatcgtgta tgagaaggag gcacggctga aagagaccat gcggatcatg    9420
ggcctggaca acagcatcct ctggtttagc tggttcatta gtagcctcat tcctcttctt    9480
gtgagcgctg gcctgctagt ggtcatcctg aaggtaaggc agcctcactc gctcttccct    9540
gccaggaaac tccgaaatag ctcaacacgg gctaagggag gagaagaaga aaaaaaatcc    9600
aagcctctgg tagagaaggg gtcatacctg tcatttcctg caatttcatc catttatagt    9660
tggggaaagt gaggcccaga gaggggcagt gacttgccca aggtcaaccc agccgggtag    9720
cagctaagta ggatgagagt gcagggttca tgctttccag ataaccacat gctcaactgt    9780
gccatgctgt ctcattggta gtggttcatg gcagcatctg aaagctattt attttcttag    9840
atatattggg tggcgattct tcctaagttt ctaagaacaa taatcagaag gatatatatt    9900
gttgcaggtt agactgtctg gaagcagagg ctgaaataga gtttgatgta tgggtattta    9960
tgagggctca ataccatgg aagagatatg gaagatgcag gattgggcag agggaggagt    10020
tgaactgtga tatagggcca accccgtggg gcactctaga gaatatgcag cttgttggag    10080
ttgttcttca tcgagctgaa acatccagcc ctttgtgctc ccccaaggcc tccctcctga    10140
caccacctac ctcagccctc tcaatcaatc actggatgtg ggctgccctg ggaaggtcgt    10200
gccccagggc ctacatggct ctctgctgct gtgacaaacc cagagttgct gatgcctgag    10260
gccgtctact gacagctggg caacaaggct tccctgaatg gggactctgg gcagtgcagt    10320
tttgtgtctg aaccatacat taatatattt atatccgaat tttctttctc tgcaagcatt    10380
tcatataaag acacatcagg taaaaataaa tgttttgaa gcaaaggag tacaagagaa    10440 taagaactaa ctaatttaat actagttacc atctgttaca aatagttcct actgattgcc    10500
aaggactgtt taaacacatc acatgggctt cttcttctat cctcactaac ccttttaaca    10560
gacaaggaaa tgaggctcag gaaggtcaag gactttattg aggttccaca gtaggataca    10620
```

```
gttcttgcta aaagcaaccc ctccctcatg ctctgttatc taactgcaag gggaaggtca   10680
gtggcagagg tagtggtccc atggttggtg cataagagct gctctgagac aactgcatgc   10740
tggtgggtcc tgcagacatg tacccatcag ccggagatag gctcaaaata tccacaagag   10800
tttggatgat tgtgggaatg cagaatccat ggtgatcaag agggaaagtc aagttgcctg   10860
gccattttcc ttggcttttä dacagaaaag ttacgtggga tattatctcc cacagctctt   10920
ctgtggtgcc accagtcata gtccttatat aaggagaaac cagttgaaat tacctattga   10980
agaaacaaag agcaaactcg cccactgaaa tgcgtagaaa gccctggact ctgttgtatt   11040
cataactctg ccattatttt tctgcgtagt tttgggtaag tcacttatct tctttaggat   11100
ggtaatgatc agttgcctca tcagaaagat gaacagcatt acgcctctgc attgtctcta   11160
acatgagtag gaataaaccc tgtcttttt  ctgtagatca tacaagtgag tgcttgggat   11220
tgttgaggca gcacatttga tgtgtctctt ccttcccagt taggaaacct gctgccctac   11280
agtgatccca gcgtggtgtt tgtcttcctg tccgtgtttg ctgtggtgac aatcctgcag   11340
tgcttcctga ttagcacact cttctccaga gccaacctgg cagcagcctg tggggcatc    11400 atctacttca cgctgtacct gccctacgtc ctgtgtgtgg catggcagga ctacgtgggc   11460
ttcacactca agatcttcgc tgtgagtacc tctggccttt cttcagtggc tgtaggcatt   11520
tgaccttcct ttggagtccc tgaataaaag cagcaagttg agaacagaag atgattgtct   11580
tttccaatgg gacatgaacc ttagctctag attctaagct cttaagggt aagggcaagc    11640 attgtgtttt attaaattgt ttacctttag tcttctcagt gaatcctggt tgaattgaat   11700
tgaatggaat ttttccgaga gccagactgc atcttgaact gggctgggga taaatggcat   11760
tgaggaatgg cttcaggcaa cagatgccat ctctgccctt tatctcccag ctctgttggc   11820
tatgttaagc tcatgacaaa ccaaggccac aaatagaact gaaaactctt gatgtcagag   11880
atgacctctc ttgtcttcct tgtgtccagt atggtgtttt gcttgagtaa tgttttctga   11940
actaagcaca actgaggagc aggtgcctca tcccacaaat tcctgacttg acacttcct    12000 tccctcgtac agagcagggg gatatcttgg agagtgtgtg agcccctaca agtgcaagtt   12060
gtcagatgtc cccaggtcac ttatcaggaa agctaagagt gactcatagg atgctcctgt   12120
tgcctcagtc tgggcttcat aggcatcagc agccccaaac aggcacctct gatcctgagc   12180
catccttggc tgagcaggga gcctcagaag actgtgggta tgcgcatgtg tgtgggggaa   12240
caggattgct gagccttggg gcatctttgg aaacataaag ttttaaaagt tttatgcttc   12300
actgtatatg catttctgaa atgtttgtat ataatgagtg gttacaaatg gaatcatttt   12360
atatgttact tggtagccca ccactcccta aagggactct ataggtaaat actacttctg   12420
caccttatga ttgatccatt ttgcaaattc aaatttctcc aggtataatt tacactagaa   12480
gagatagaaa aatgagactg accaggaaat ggataggtga cttgcctgt ttctcacaga    12540 gcctgctgtc tcctgtggct tttgggtttg gctgtgagta cttgcccttt tttgaggagc   12600
agggcattgg agtgcagtgg gacaacctgt tgagagtcc tgtggaggaa gatggcttca   12660
atctcaccac ttcggtctcc atgatgctgt ttgacacctt cctctatggg gtgatgacct   12720
ggtacattga ggctgtcttt ccaggtacac tgctttgggc atctgtttgg aaaatatgac   12780
ttctagctga tgtcctttct ttgtgctaga atctctgcag tgcatgggct tccctgggaa   12840
gtggtttggg ctatagatct atagtaaaca gatagtccaa ggacaggcag ctgatgctga   12900
aagtacaatt gtcactactt gtacagcact tgtttcttga aaactgtgtg ccaggcagca   12960
tgcaaaatgt tttatacaca ttgcttcatt taattctcac aaggctactc tgaagtagtt   13020
```

```
actataataa ccagcaattt tcaaatgaga gaactgtgac tcaaagacgt taagtaacca   13080
gctttggtca cacaactgtt aaatgttggt acgtggaggt gaatccactt cggttacact   13140
gggtcaataa gcccaggcga atcctcccaa tgctcaccca attctgtatt tctgtgtcct   13200 cagaggggt acaactagga gaggttctgt ttcctgagta caggttgtta ataattaaat    13260
atactagctc taaggcctgc ctgtgattta attagcattc aataaaaatt catgttgaat   13320
ttttctttag tacttctttc ttaatataat acatcttctt gaccaagtcc aagaggaacc   13380
tgcgttggac agttttcata tgagatcaaa ttctgagaga gcaagattta acccttttg    13440 gttcaccttc tgatcctccc ctaaggaggt atacatgaaa tatttattac tcctgcctga   13500
acttctttca ttgaatatgc aattttgcag catgcagatt ctggatttaa attctgagtc   13560
ttaacttact ggctgaggga ccttggatag gctccttatc cctcagtttc ctcatctcta   13620
aaatggggat ggcacctgcc ccgtgggttg ttggaaggac ttacagaggt gcagaatgta   13680
cgttgtacat agcaggtttc agcaaatgtt agctccctct ttccccacat ccattcaaat   13740
ctgttccttc tccaaaggat gtgtcaagga ggaaatggac ctggctggga accctcaga   13800 atactgggat gatgctgagc ttggctcata cctgtgcttt gctttcaggc cagtacggaa   13860
ttcccaggcc ctggtatttt ccttgcacca agtcctactg gtttggcgag gaaagtgatg   13920
agaagagcca ccctggttcc aaccagaaga gaatgtcaga aagtaagtgc tgttgacctc   13980
ctgctctttc tttaacctag tgctgctgcc tctgctaact gttgggggca agcgatgtct   14040
cctgcctttc taaagactg tgaaaccact ccaggggcag agaaatcaca tgcagtgtcc    14100
ctttccaaat cctcccatgc catttatgtc caatgctgtt gacctattgg gagttcacgg   14160
tctcgatccc tgagggacat tttctttgtt gtcttggctt ctagaagagt atcttttact   14220 tgcccctcc caaacacaca tttcatggtc tcctaacaag ctagaagaaa gaggtaaaga   14280
caagcgtgat tgtggaacca tagcctcgct gcctgcctgt gacatggtga cctgtgtatc   14340
agcctgtgtg ggctgagacc aagtggctac cacagagctc agcctatgct tcataatgta   14400
atcattaccc agatccctaa tcctctcttg gctcttaact gcagacagag atgtccacag   14460
ctcatcaaag gctctgcttc tgggttcttt gtgcttagag tggcttccta aatatttaat   14520
aggtcccttt tctgccagtc tcttctgtgc ccatcccctg attgcccttg gtaaaagtat   14580
gatgcccctt agtgtagcac gcttgcctgc tgttcctaat catcttctcc tacctcctct   14640
ttacacctag ctcctgtttc agtcacctag aaatgtcac agtcgctgga atatgtcatg   14700
ttcttccaca cctccatgcc tttgtaggta ctgtttgctc tcacaggaga actttctctc   14760
taacttgcct atcttctcaa ctcctccttt ctctccaaga tctagttccg gatcccctcc   14820
cctgagcatc cctccttggt tctcaggtag tcagtcactc tctgccctga acttccatgg   14880
cacgtgaaag aaaatctttt tattttaaaa caattacaga ctcacaagaa gtaatacaaa   14940
ttacatgagg gggttcccctt aaaccttttca tccagtttcc ccaatggtag cagcatgtgt   15000
aactgtagaa tagtatcaaa accatgaaat tgacataggt acaattcaca aaccttcttc   15060
agatttcact agctttatgt gcgctcattt gtgtgtgtgt gtgcgtattt agttctatgc   15120
aattttatca tgtgtgaatt catgtaatta ctagctcagt caagctgcag aaatatctca   15180
ttgtcacaaa gctccttcat gctacccctt aatggccaca gccacctccc ttcttcctca   15240
gttcctgaca cctgtcaacc actaatgcgt tcctcgtttt tacagtttta ttatttctag   15300
aatgttacat aaatgggaacc atacagtagg tatccttttg atactggctt ttttttttt    15360 ttcactcagc agtattccct tagatctatc caagttgtgt gtgtcaacag ttcattcctc   15420
```

```
ttcactgctg agtagtgttc cctgggaggg gtgtatcaca gttccatggc attttagat    15480
gtattttta  aacagctttc agcatcctct attttaattg ttcatcaagt cctttttccc   15540
aatagactct gaatgctcct ttatcatcgt attcccatca ccaacatcag tacccaaata   15600
ggccctaaat aaacatttat agcctcctgc ctgcctgaga accagggtg  gacatggaga   15660
gaaggcactt ctgaaagttc aagcgcagtg csctgtgtcc ttacactcca ctcctcagtg   15720
ctttctgtgg gttcatttct gtcttctctc ctgtcacagt ctgcatggag gaggaaccca   15780
cccacttgaa gctgggcgtg tccattcaga acctggtaaa agtctaccga gatgggatga   15840
aggtggctgt cgatggcctg gcactgaatt tttatgaggg ccagatcacc tccttcctgg   15900
gccacaatgg agcggggaag acgaccacca tgtaagaaga gggtgtggtt cccgcagaat   15960
cagccacagg agggttctgc agtagagtta gaaatttata ccttaggaaa ccatgctgat   16020
ccctgggcca agggaaggag cacatgagga gttgccgaat gtgaacatgt tatctaatca   16080
tgagtgtctt tccacgtgct agtttgctag atgttatttc ttcagcctaa acaagctgg    16140
ggcctcagat gacctttccc atgtagttca cagaattctg cagtggtctt ggaacctgca   16200
gccacgaaaa gatagattac atatgttgga gggagttggt aattcccagg aactctgtct   16260
ctaagcagat gtgagaagca cctgtgagac gcaatcaagc tgggcagctg cttgattgc    16320
cttccctgcg acctcaagga ccttacagtg ggtagtatca ggaggggtca ggggctgtaa   16380
agcaccagcg ttagcctcag tggcttccag cacgattcct caaccattct aaccattcca   16440
aagggtatat ctttgggggg tgacattctt ttcctgtttt cttttttaatc tttttttaaa   16500
acatagaatt aatatattat gagcttttca gaagattttt aaaaggcagt cagaaatcct   16560
actacctaac acaaaaattg ttttatcttt tgaataatat gttcttgttt gtccattttc   16620
catgcatgcg atgttaggca tacaaaatac attttttaaa gaatactttc attgcaaatt   16680
ggaaacttcg tttaaaaaat gctcatacta aaattggcat ttctaaccca taggcccact   16740
tgtagttatt taccgaagca aaaggacagc tttgctttgt gtgggtctgg tagggttcat   16800
tagaaaggaa tggggcggt  gggagggttg gtgttctgtt ctctctgcag actgaatgga   16860
gcatctagag ttaagggtag gtcaaccctg acttctgtac ttctaaattt ttgtcctcag   16920
gtcaatcctg accgggttgt tcccccgac  ctcgggcacc gcctacatcc tgggaaagaa   16980
cattcgctct gagatgagca ccatccggca gaacctgggg gtctgtcccc agcataacgt   17040
gctgtttgac atgtgagtac cagcagcacg ttaagaatag gccttttctg gatgtgtgtg   17100
tgtcatgcca tcatgggagg agtgggactt aagcatttta ctttgctgtg tttttgtttt   17160
ttcttttttt ctttttttatt ttttgagat  ggagtctcgc tctgtagcca ggctggactg   17220
tagtggcgcg atctcggctc actgcaacct tggcctccca ggttcaagcg attctcctgc   17280
ctcagcctcc cgagtagctg ggactctagg cacacaccac catgcccagc taatttttgt   17340
gttttagta  gagacggggt ttcaccatgt tggccaggat ggtctcaatg tcttgacctc   17400
gtgatccgcc cacctcggtc tcccaaagtg ctgggaacac aggcatgagc cactgtgtct   17460
ggccacattt tactttcttt gaatatgcaa ggctcacctc cgtgaacacc ttgagaccta   17520
gttgttcttt gatttagga  gaagtgggag gtgaatggtt gagctgtaga ggtgacatca   17580
gcccagccag tggatggggg cttgggaaac attgcttccc attattgtca tgctggaggg   17640
cccttagcc  catcctctcc ccccgccacc ctccttattg aggcctggag cagacttccc   17700
agacctggta gtgcttcagg gccctggtat gatggaccta tatttgctgc ttaagacatt   17760
tgctcccact caggttgtcc catcagccat aaggccccca gggagcccgt gtgatggagc   17820
```

```
agagagagac ctgagctctg caatcttggg caaggctttt cccttatgtt tcttcttatc   17880
taaagtgaac agctggggct catgtgctcc ctcctcatct aaagtgaaca catgggctc    17940 atgtgcaggg tcctcccgc tttcagagcc tgaggtcccc tgaggctcag gaaggctgct   18000
ccaggtgagt gccgagctga cttcttggtg gacgtgctgt ggggacagcc cattaaagac  18060
cacatcttgg ggccctgaaa ttgaaagttg taactgcctg gtgcatggtg gccaggcctg  18120
ctggaaacag gttggaagcg atctgtcacc tttcactttg atttcctgag cagctcatgt  18180
ggttgctcac tgttgttcta ccttgaatct tgaagattat ttttcagaaa ttgataaagt  18240
tattttaaaa agcacgggga gagaaaaata tgcccattct catctgttct gggccagggg  18300
acactgtatt ctggggtatc cagtagggcc cagagctgac ctgcctccct gtccccaggc  18360
tgactgtcga agaacacatc tggttctatg cccgcttgaa agggctctct gagaagcacg  18420
tgaaggcgga gatggagcag atggccctgg atgttggttt gccatcaagc aagctgaaaa  18480
gcaaaacaag ccagctgtca ggtgcggccc agagctacct tccctatccc tctcccctcc  18540
tcctccggct acacacatgc ggaggaaaat cagcactgcc ccagggtccc aggctgggtg  18600
cggttggtaa cagaaacttg tccctggctg tgccccctagg tcctctgcct tcactcactg  18660 tctgggggctg gtcctggagt ttgtcttgct ctgttttttt gtaggtggaa tgcagagaaa  18720
gctatctgtg gccttggcct ttgtcggggg atctaaggtt gtcattctgg atgaacccac  18780
agctggtgtg gacccttact cccgcagggg aatatgggag ctgctgctga aataccgaca  18840
aggtgcctga tgtgtattta ttctgagtaa atggactgag agagagcggg gggcttttga  18900
gaagtgtggc tgtatctcat ggctaggctt ctgtgaagcc atgggatact cttctgttak  18960
cacagaagag ataaagggca ttgagactga gattcctgag aggagatgct gtgtctttat  19020
tcatcttttt gtccccaaca tggtgcacta aatttatggt tagttgaaag ggtggatgct  19080
taaatgaatg gaagcggaga ggggcaggaa gacgattggg ctctctggtt agagatctga  19140
tgtggtacag tatgaggagc acaggcaggc ttggagccaa ctctggcttg gccctgagac  19200
attgggaaag tcacaacttg cctcaccttc tttgccgata ataatagtgg tgcgttacct  19260
catagaggat taaattaaat gagaatgcac acaaaccacc tagcacaatg cctggcatat  19320
agcaagttcc caaataaaat gcgtactgtt cttacctctg tgaggatgtg gtacctatat  19380
atacaaagct ttgccattct aggggtcata gccatacagg gtgaaaggtg gcttccaggt  19440
ctcttccagt gcttacccct gctaatatct ctctagtccc tgtcactgtg acaaatcaga  19500
actgagaggc ctcacctgtc ccacatcctt gtgtttgtgc ctggcaggcc gcaccattat  19560
tctctctaca caccacatgg atgaagcgga cgtcctgggg gacaggattg ccatcatctc  19620
ccatgggaag ctgtgctgtg tgggctcctc cctgtttctg aagaaccagc tgggaacagg  19680
ctactacctg accttggtca agaaagatgt ggaatcctcc ctcagttcct gcagaaacag  19740
tagtagcact gtgtcatacc tgaaaaaggt gagctgcagt cttggagctg ggctggtgtt  19800
gggtctgggc agccaggact tgctggctgt gaatgatttc tccatctcca ccccttttgc  19860
catgttgaaa ccaccatctc cctgctctgt tgccccttg aaatcatatc atacttaagg   19920
catgaaaagc taaggggccc tctgctccca ttgtgctagt tctgttgaat cccgttttcc  19980
ttttcctatg aggcacanag agtgatggag aaggtcctta gaggacatta ttatgtcaaa  20040
gaaaagagac ttgtcaagag gtaagagcct tggctacaaa tgacctggtc gttcctgctc  20100 attactttc aatctcattg accttaactt ttaaactata aaacagccaa tatttattag    20160
gcactgattt catgccagag acactctggg cattgaaaga aagtaatgat aatagttaat  20220
```

```
tttatatagc gttgttacca tttcaacctt tttttttttt taacctctat catctcaatt    20280
aaag                                                                 20284

<210> SEQ ID NO 22
<211> LENGTH: 7052
<212> TYPE: DNA
<213> ORGANISM: Homo sapiens

<400> SEQUENCE: 22
gtgaacacac attaaagcat gagaagcatg aactagacat gtagccaggt aaaggccttg      60
ctgagatggt tggcaaaggc ctcattgcag cattcattgg caggccacag ttcttttggc     120
agctctgctt cctgaccttt caccctcagg aagcgaggct gttcacacgg cacacacatg     180
ccagacaggg tcctctgaag ccacggctgc cagtgcatgt gtcccaggga aagcttttc      240 ctttagttct cacacaacag agcttcttgg aagccctccc cggcgaaggt gctggtggct     300
ctgccttgct ccgtccctga cccgttctca cctccttctt tgccatcagg aggacagtgt     360
ttctcagagc agttctgatg ctggcctggg cagcgaccat gagagtgaca cgctgaccat     420
cggtaaggac tctgggtttt cttattcagg tggtgcctga gcttccccca gctgggcaga     480
gtggaggcag aggaggagag gtgcagaggc tggtggcgct gactcaaggt ttgctgctgg     540 gctgggctg ggtggctgcg ggggtgggag cagcttggtg gcgggttggc ctaatgcttg      600
ctggggtgcc tggggctcgg tttgggagct agcagggcag tgtcccagag agctgagatg     660 attgggttt ggggaatccc ttaggggagt ggacactgaa taccaggat gaggagctga      720 ggccaagcc aggagggtgg gatttgagct tagtacataa gaagagtgag agcccaggag      780
atgaggaaca gccttccaga tttttcttgg gtagcgtgtg taggaggcca gtgtcaccag     840
tagcatatgt ggaacagaag tcttgaccct tgctatctct gcctagtcct aatggctggc     900 tttcccagg aaggcttctg cttccatgga ctgttagatt aaccctttat ttaggtaaat     960
gagggaacct actttataag cataggaaag ggtgaagaat cttttaagat tcctttactc    1020
aagttttctt ttgaagaatc ccagagctta ggcaatagac accagacttt gagcctcagt    1080
tatccattca cccatccacc cacccaccca cccatccttc catcctccca tcctcccatt    1140
cacccatcca cccatccagc tgtccaccca ttctacactg agtacctata atgtgcctgg    1200
ctttggtgat acaaaggtga ataagacata gtcctttcct ttgcccccaa ccctcagacc    1260
agagatgaac atgtggaatg acctaaacac ctggaacagg tgtggtgtat gagcggcagg    1320
cctctgatga gagggtgggg gatggccagc cctcactccg aagcccctct gagttgattg    1380
agccatcttt gcattctggt cctgcagatg tctctgctat ctccaacctc atcaggaagc    1440
atgtgtctga agcccggctg gtggaagaca tagggcatga gctgacctat gtgctgccat    1500
atgaagctgc taaggaggga gcctttgtgg aactctttca tgagattgat gaccggctct    1560
cagacctggg catttctagt tatggcatct cagagacgac cctggaagaa gtaagttaag    1620
tggctgactg tcggaatata tagcaaggcc aaatgtccta aggccagacc agtagcctgc    1680
attgggagca ggattatcat ggagttagtc attgagtttt taggtcatcg acatctgatt    1740
aatgttggcc ccagtgagcc atttaagatg gtagtgggag atagcaggaa agaagtgttt    1800
tcctctgtac cacagtacat gcctgagatt tgtgtgttga aaccagtggt acctaacaca    1860
tttacatccc aaccttaaac tcctatgcac ttatttaccc tttaatgagc ctctttactt    1920
aagtacagtg kgaggaacag cggcatcagg atcacttggg aacttgttag aaattcagca    1980
acttgggccc agctcagacc tactgaatca gaatcaggag caattctctg gtgtgactgt    2040
```

```
gtcacagcca ggtatcaact ggattctcat acataggaaa tgacaaacgt ttatggatgg    2100
atagtctact tgtgccaggt gctgagattt gttttttgtt ttttgatttt tttttaatca    2160
ctgtgacctc atttaattct caaaaaaaga tgaaaaaatg aacactcagg aatgctgaca    2220
tgagattcag aatcagggt  ttggggcttc aaagtccatc ctctctttat ccatgtaatg    2280 cctccccttca gagatacaac atcacagacc ttgaaggctg aaggggatat aaaagctgtc    2340
tggccaagtg gtctccaagc ttgacagtgc agcagaatca cctggggata ttattaaaaa    2400
taaacatact aaggtttggc ttcagggcct gtgaatcaga atttctggag gtgaggcctt    2460
gaagtctgta tttctattgc atactttgga cacagtggtc tatagactag agtttggaaa    2520
tgattgcgct cattcagatt ctcttctgat gtttgaattg ctgccatcat atttctagtg    2580
ctctatttcc tcctgctcat tctgtcttgg ataacttatc atagtactag cctactcaaa    2640
gatttagagc cacagtcctg aaagaagcca cttgactcat tccctgtagg ttcagaataa    2700
atttcttctg cgcagtgtct gtcatagctt ttttaaatt tttttttatt tttgatgaga    2760
ctggagtttt gctcttattg cccaagctgg agtgcagtgg tgcgattttg gctcactgca    2820
acctccacct cccaggttca gcgattctc  ctgcctcagc ctcccaagta gctgagatta    2880
caagcatgtg ctaccacgcc cagctaattt tgtatttta gtagagatgg gttttatcca    2940
tgttggtcag gctggtctcg agctccagac ctcaggtgat ctgcccgcct cggcctccca    3000
aagtgctggg attataggcc tgagccacag cgctcagcca taactttaat ttgaaaatga    3060
ttgtctagct tgatagctct caccactgag gaaatgttct ctggcaaaaa cggcttctct    3120
cccaggtaac tctgagaaag tgttattaag aaatgtggct tctactttct ctgtcttacg    3180
gggctaacat gccactcagt aatataataa tcgtggcagt ggtgactact ctcgtaatgt    3240
tggtgcttat aatgttctca tctctctcat tttccagata ttcctcaagg tggccgaaga    3300
gagtggggtg gatgctgaga cctcaggtaa ctgccttgag ggagaatggc acacttaaga    3360
tagtgccttc tgctggcttt ctcagtgcac gagtattgtt cctttccctt tgaattgttc    3420
tattgcattc tcatttgtag agtgtaggtt tgttgcagat ggggaaggtt tgttttgttg    3480
taaataaaat aaagtatggg attctttcct tgtgccttca gatggtacct tgccagcaag    3540
acgaaacagg cgggccttcg gggacaagca gagctgtctt cgcccgttca ctgaagatga    3600
tgctgctgat ccaaatgatt ctgacataga cccaggtctg ttagggcaag atcaaacagt    3660
gtcctactgt ttgaatgtga aattctctct catgctctca cctgttttct ttggatggcc    3720
tttagccaag gtgatagatc cctacagagt ccaaagagaa gtgaggaaat ggtaaaagcc    3780
acttgttctt tgcagcatcg tgcatgtgat caaacctgaa agagcctatc catatcactt    3840
cctttaaaga cataaagatg gtgcctcaat cctctgaacc catgtattta ttatctttc    3900 tgcggggtcc tagtttcttg tatacattag gtgtttaatt gttgaacaaa tattcattcg    3960
agtagatgag tgattttgaa agagtcagaa aggggaattt gctgttagag ttaattgtac    4020
cctaagactt agatatttga ggctgggcat ggtggctcat gccagtaatc ccagcgcttt    4080
gagaggctga ggtgggtaga tcacctgagg tcaggagttt gagaccagtc tgaccaacaa    4140
ggtgaaaccc cgtctctact aaatacaaaa aattagccga gtgtggtggc acatgcctgt    4200
catcccagct acttgggagg ctgaggcagg agaatcgctt gaacccagga ggcagaggtt    4260
gcagtcagcc acggttgcgc cattgcactc cagactgggc aacaagagtg aaaactccat    4320
ctcaaaaaag aaaaaaaag  aattagatat tttggatgag tgtgtctttg tgtgtttaac    4380
tgagatggag aggagagcta agacatcaaa caaatattgt taagatgtaa aagcacatca    4440
```

```
gttaggtatc attagtttag gacaaggatt tctagaaaat ttttaggaac agaaaacttt    4500
ccagttctct caccccctgct caaagagtgt atggctctta cattatatat aactgcctga   4560
cttcatacag tatcagtact tagatcattt gaaatgtgtc cacgttttac caaaatataa   4620
tagggtgaga agctgagatg ctaattgcca ttgtgtattc tcaaatatgt caagctacgt   4680
acatggcctg tttcatagag tagtctataa gaaattgatg acttgattca tccgaatggc   4740
tggctgtaac acctggttac gcatgaacac ctcttttcag ttgtctcaag acacctttct   4800
tttctgtact tatcagacaa ggactgaaag gcagagactg ctactgttag acattttgag   4860
tcaagctttt ccttggacat agctttgtca tgaaagccct ttacttctga gaaacttcta   4920
gcttcagaca catgccttca agatagttgt tgaagacacc agaagaagga gcatggcaat   4980
gccgaaaaca cctaagataa taggtgacct tcagtgttgg cttcttgcag aatccagaga   5040
gacagacttg ctcagtggga tggatggcaa agggtcctac caggtgaaag gctggaaact   5100
tacacagcaa cagtttgtgg ccctttttgtg aagagactg ctaattgcca gacggagtcg   5160
gaaaggattt tttgctcagg tgagacgtgc tgttttcgcc agagactctg gcttcatggg   5220
tgggctgcag gctctgtgac cagtgaaggc aggatagcat cctggtcaag atatggatgc   5280
cggagccaga tttatctgta tttcaatccc agttctattc cttgccagtt gtgtatccgc   5340
tggcaagtta cttctctatg cctcaatctc ctcatctgta aaatggggat aataatatta   5400
cctgcaatac agggttgtta cgaaaataaa aatgaatagg tgcttagaat ggggcctgac   5460
attagtaagt gctagttttt gtgtgtgtat atgttatttt tattttggag gagaacataa   5520
aaaggacaaa gtgtagaaaa actggttggg tgtattcagc tgtcataaca tgagagttgt   5580
tatgcccaga tgcacttgac atgtgaattt attagaaaca tgattttctt ctgagttgat   5640
gtttaactca aactgataga aaagataggt cagaatatag ttggccaaca gagaagactt   5700
gttagactat tgtctgcatg tcagtgtttg catgctaact tgcttagtta gaaaggttaa   5760 atttttcac tctataaaat caagaaatat agagaaaagg tctgcagaga gtctttcatt    5820
tgatgatgtg gatattgtta agagcgggag tttggagcat acagagctca agttgaatcc   5880
tgactttgct acttattggc tatatgacct tgggcaagct gcttagtctc tctgatcctc   5940
agttaccttt gtttgttgat gatgaccatt gataacacaa ccataaataa tgacaacata   6000
gagatagttc tcattatagt agttgttata cagaattatt cactcaatgt taattttctg   6060
cattgaaatc ccagaacatt agaattgggg gcattatttg aatctttaag gttataagga   6120
atacatttct cagcaataaa tggaaggagt tttgggttaa cttataaagt atacccaagt   6180 cattttttt cagagaagat atggtagaaa gtcttaggag gttgaagaag gaattggata    6240
tttattcttt ctgagactat catgggagat aatgactatg gttgtccatg attggagccg   6300
ttgctgtaga gttggttta ttatagtgta ggatttgaat gggccatgtg ttctcagacc    6360
tcagaataaa aagagaaaac tgaggccagt ggggagcgtg acttcacatg ggtacacttg   6420
tgctagagac agaaccagga ttcaggactt ctggctcctg gtcctgggtt catggcccaa   6480
tgtagtcttt ctcagtcttc aggaggagga agggcaggac ccagtgttct gagtcaccct   6540
gaatgtgagc actatttact tcgtgaactt cttggcttag tgcctctgcc aggtggccat   6600
aacctctggc cttgtgttgc cagagaaaag gtttagtttt caggctccat tgcttcccag   6660
ctgccaagaa tgccttggtg cagcacagtc ataggccctg cattcctcat gccgtgctg    6720 gttggtcggg gaggtgggct ggactcgtag ggatttgccc cttggccttg tttctaacac   6780
ttgccgtttc ctgctgtccc cctgccccct ccactgcctg ggtaaagatt gtcttgccag   6840
```

```
ctgtgtttgt ctgcattgcc cttgtgttca gcctgatcgt gccaccctt  ggcaagtacc     6900 ccagcctgga acttcagccc tggatgtaca acgaacagta cacatttgtc aggtatgttt     6960
gtcttctaca tcccaggagg gggtaagatt cgagcagacc aaagatgttt acgagggcca     7020
agggaatgga cttcagaatt acacggtgga at                                    7052

<210> SEQ ID NO 23
<211> LENGTH: 2534
<212> TYPE: DNA
<213> ORGANISM: Homo sapiens

<400> SEQUENCE: 23
gggaagcatt taaaaaaaaa aaagtatata tatatatata tatatatata tgtaatgtga       60
attggcctct ttttctctaa gcccacattt tcttcttaca tagttcaggt ttactttatt      120
ttttcctttc cggctgctga ccctgtattg cccgtagttg tggaacatag catgtgtttg      180
tgacctgtgc ctgttatttt tgtgctttct agttgtgcat gcaaagagta caagttttc       240 ttgccctttc ttggaaaatc ctgcttgtct gtgccaaagg gataattgtg aaagcacttt      300
tgaaatactt aatgagttga ttttcttcaa attaaaaaaa atatataaat gtatatgtgt      360
atgtacatgt gtgtacacat acacaccttt atacatacag cccatttaaa acaagctcca     420
ctttggagtg ctctacgtca ccctgatgcc gaatacaggg ccagagtctg agatccttct     480
gggtggtttc tgtgttttgt tcatttctgt tttaagagcc tgtcacagag aaatgcttcc     540
taaaatgttt aatttataaa aacatttta tctctcgatt actggtttta atgaattact       600
aagctggctg cctctcatgt acccacagca atgatgctcc tgaggacacg ggaaccctgg     660
aactcttaaa cgccctcacc aaagaccctg gcttcgggac ccgctgtatg gaggaaacc      720 caatcccgtg agtgccactt tagccataag cagggcttct tgtgcttgtt gcctggtttg     780
atttctaata tgctgcattt atcaactgca tgccacattg tgaccgccag catttgccct     840
ttgaattatt attatgtttt atttacaaaa agcgaaggta gtaaccgaac taaattatct     900
aggaacaaac gtttggagag tcttctaaca ccgyscaaag cacgtcatta cagacatttg     960
tttactgatt tagaacctta atatttaatt taaatacgca ctttacactt actgatgaaa    1020
tgcttttcct ttcttctct  cccagcccct gtacttaagt gcttcaatag gctctcatta    1080
tatatgattt ttaggttttg cttatcagct tcttcgcttt tataatctga aaagatggca    1140
tatgaatttt tataaaaagg gacactttct tcttctcaaa ttgtatattt ttattgtact    1200
ttccttcaaa accccctttt aaaagtaag  cagtggataa ataaattcag tgaagcatcc    1260
atatgaccct taagtgagtg taggggaagg gaggtcacca gatcactgtg agtgaagatg    1320
gtggagaggt gaggatctta tgaggccgtg ctcaaggctg gtagaggtgg gttagtgttt    1380
ccaggtttag gcagaatctc agctgaggtc atgaaacaac agtgatctct gaaaaattat    1440
ggcaaggtgg gaaggtgctg gagaattgga gaggggcaa  acttgacttt caagtttcaa    1500
tgggaagata ggtgactctg cacaccacag aacagtgagc atgataacct gtttatacaa    1560
ggttctagag cagatttcta aatggatagc tactgtgtgc ttgtttgttc ttaattagta    1620
ttggatagtt actaaatact tgttagtact tagtacataa tgggtggtaa atcctagcag    1680
ctaatattgg ttcccaaata accagatgac aaggatagag aaggacacag acacggccta    1740
tctggatttc atggtgcctt tgattttcca catgaaggtt gtgtagggaa gatagaagca    1800
tgagatgaga tgataatata gttatctgga ttcatcactg gccagctgaa ccatatgaac    1860
tcatggattg atgctagctt aggaaggctc tgtaggagcc agaactgggc tgagagccag    1920
```

| | |
|---|---|
| cccatagaga caaaagaggc ccggccctga catcagaggg ttcaaacatg atgtctgagc | 1980 |
| cccacctaca gtctgccgga ggtggttgga aggaagagcc tttatcctta caattcttac | 2040 |
| tgaaattcaa attttaggt tttgcaaaaa aatggtggac ctgaaggaaa tttgacagga | 2100 |
| gcatgtctca gctgtattta aatttgtctc agccaatccc cttttgaatg ttcagagtgt | 2160 |
| aagcttcagg agggcagcgc gtcttagtgt gacttttctg gtcagttcag gtgctttaag | 2220 |
| gagacaatta gagatcaatc tggaaaactt catttgaatt tttaatacat aagaaaacaa | 2280 |
| taagaaatag ttaaaaatat atatttatat aatatatata tgtgtgtgtg tgtgtgtgtg | 2340 |
| tgtgtgtgtg tatatatata tatattttat ttatttattt ttttttgaga tggagtctcg | 2400 |
| ctctgttgcc caggctggag tgcagtggct caatcttggc tcactgccac ctctgcctcc | 2460 |
| caggttcaag tgattctcct acctcagcct cctgagtagc tgggattaca agcatgtgcc | 2520 |
| accacactgg ctaa | 2534 |

<210> SEQ ID NO 24
<211> LENGTH: 2841
<212> TYPE: DNA
<213> ORGANISM: Homo sapiens

<400> SEQUENCE: 24

| | |
|---|---|
| tcttgccagt ctctactcat ttttcagcac atcgagcata agatccagac tctttcccag | 60 |
| gcctctctca tctggctcct ctcctcctcc tttatcatta ctcttcttcg tagcttatcc | 120 |
| tactccagcc atgctgtctt cctattattc ctaaaaarta gaaatgcatt tcttcctagg | 180 |
| gcctttgtac ctgcacttgc catcgctttt gctcagaatg ttcttttttgc caagcttttg | 240 |
| cccagcttgt tctccatcat tgttatgttt tggctgaaat gtcttctctt agtaggttca | 300 |
| ttctccccag tcactgtctt tttatttttgc tttattttgg gccatctaag gttatcttat | 360 |
| tagtgtattt gttgttcgtc tcctccatgg gcatacacct ccatgaaggc aggtattttc | 420 |
| accttaggcc ctcgaatata ctggacagca tctggcacgt agtagatgct caacgaatgt | 480 |
| ttgttgtgtg agcaaatggt tggttgattg gattgaactg agttcagtat gtaaatattt | 540 |
| agggcctctt tgcattctat tttacttatg tataaaatga tacataatga tgatataaat | 600 |
| gatgtcacag tgtacaaggc tgttgtggga tcaagcaatc aaatgagatc atgcttgtct | 660 |
| tttccaaatg gtgagggaat agatgcatgt ttgtggttgt tacggaatga tcctgtgctc | 720 |
| ctgaggcaac agaaaggcca ggccatctct ggtaatccta ctcttgctgt cttcccttg | 780 |
| cagagacacg ccctgccagg caggggagga agagtggacc actgccccag ttccccagac | 840 |
| catcatggac ctcttccaga atgggaactg gacaatgcag aacccttcac ctgcatgcca | 900 |
| gtgtagcagc gacaaaatca agaagatgct gcctgtgtgt cccccagggg caggggggct | 960 |
| gcctcctcca caagtgagtc actttcaggg ggtgattggg cagaagggggt gcaggatggg | 1020 |
| ctggtagctt ccgcttggaa gcaggaatga gtgagatatc atgttgggag ggtctgtttc | 1080 |
| agtcttttt gttttttgtt ttttttttctg aggcggagtc ttgctctgtc gcccaggctg | 1140 |
| gagtgctgtg catgatcttg gcctcactgc aacctccacc tcccaggttc aagcgattct | 1200 |
| cctgcctcag cctcctgagt agctgggatt acaggcacgc accaccatgt ctggctaatt | 1260 |
| tttgtgtttt tagtagagat agggtttcgc cgtgttggcc aggctggtct ggaattcctg | 1320 |
| acctcaggtg atccacccgc ctcggcctcc caaagtgctg ggattacagg cgtgagccac | 1380 |
| tacgcccagc cctgtttcag tctttaactc gcttcttgtc ataagaaaaa gcatgtgagt | 1440 |
| tttgagggga gaaggtttgg accacactgt gcccatgcct gtcccacagc agtaaagtca | 1500 |

```
caggacagac tgtggcaggc ctggcttcca atcttggctc tgcaacaaat gagctggtag    1560
cctttgacag gcctgggcct gtttcttcac ctctgaatta gggaggctgg accagaaaac    1620
tcctgtggat cttgtcaact ctggtattct tagagactct gtttgggaag gagtcctgag    1680
ccattttttt tttcttgaga atttcaggaa gaggagtgct tatgatagct ctctgctgct    1740
tttatcagca accaaattgc aggatgagga caagcaattc taaatgagta caggaactaa    1800
aagaaggctt ggttaccact cttgaaaata atagctagtc caggtgcggg gtggctcaca    1860
cctgtaatct cagtattttg ggatgccgag gtggactgat cacctaaggt caggagttcg    1920
aaaccagctt ggccaatgtg gcgaaaccct gtctctacta aaaattcaaa aattagccag    1980
gcatggtggc acatgcctgt aatcccagtt acttgggagg ctgaagcagg agaattgctt    2040
gaacctggga ggtggaggtc gcagggagcc aaaattgcgc cactgtactc cagcctgagc    2100
aacacagcaa aactccatat caaaaaataa aatgaataaa ataacagcta atctagtcat    2160
cagtataact ccagtgaaca gaagatttat taggcatagt gaatgatggt gcttcctaaa    2220
aatctcttga ctacaaagaa tctcatttca atgtttattg tttagatgtt cagaataaat    2280
tcttgggaaa gaccttggct tggtgtaagt gaattaccag tgccgagggc agggtgaacc    2340
aagtctcagt gctggttgac tgagggcagt gtctgggacc tgtagtcagg tttccggtca    2400
cactgtggac atggtcactg ttgtccttga tttgttttct gtttcaattc ttgtctataa    2460
agacccgtat gcttggtttt catgtgatga cagagaaaac aaaacactgc agatatcctt    2520
caggacctga caggaagaaa catttcggat tatctggtga gacgtatgt gcagatcata    2580 gccaaaggt gacttttac taaacttggc ccctgcctta ttattactaa ttagaggaat    2640
taaagaccta caaataacag actgaaacag tgggggaaat gccagattat ggcctgattc    2700
tgtctattgg aagtttagga tattatccca aactagaaaa gatgacgaga gggactgtga    2760
acattcagtt gtcagcttca aggctgaggc agcctggtct agaatgaaaa tagaaatgga    2820
ttcaacgtca aattttgcca c                                             2841
```

<210> SEQ ID NO 25
<211> LENGTH: 852
<212> TYPE: DNA
<213> ORGANISM: Homo sapiens

<400> SEQUENCE: 25

```
gcatgctgga gtgatagtga ccatgagttt ctaagaaaga agcataattt ctccatatgt      60
catccacaat tgaaatatta ttgttaattg aaaaagcttc taggccaggc acggtggctc     120
atgcctgtaa tcccagcact ttaggagcca aggcgggtgg atcacttgag gtcaggagtt     180
tgagaccagc ctggccaaca tggggaaacc ctgtctctac taaaaataca aaataagctg     240
ggcgtggtgg tgcgtgcctg taatcccagc tacttgggag gctgaggcag gagaactgct     300
tgaatctggg aggcggaggt tgcagtgagc tgagttcatg ccattgcatt ccagcctggg     360
caacaagagc gaaaccatct cccaaaagaa aaaaaaaga aagaaaaagc ttctagtttg     420
gttacatctt ggtctataag gtggtttgta aattggttta acccaaggcc tggttctcat     480
ataagtaata gggtatttat gatggagaga aggctggaag aggcctgaac acaggcttct     540
tttctctagc acaaccctac aaggccagct gattctaggg ttatttctgt ccgttcctta     600
tatcctcagg tggatattta ctcctttgc atcattagga ataggctcag tgctttcttt     660
gaactgattt tttgtttctt tgtctctgca gcttaaagaa caagatctgg gtgaatgagt     720
ttaggtaagt tgctgtcttt ctggcacgtt tagctcaggg ggaggatggt gttgtaggtg     780
```

```
tgcttggatt gaagaaagcc ttggggattg tttgtcactc acacacttgt gggtgccatc    840
tcactgtgag ga                                                        852

<210> SEQ ID NO 26
<211> LENGTH: 6289
<212> TYPE: DNA
<213> ORGANISM: Homo sapiens

<400> SEQUENCE: 26
gctttataga gtttctgcct agagcatcat ggctcagtgc ccagcagccc ctccagaggc     60
ctctgaatat ttgatatact gatttccttg aggagaatca gaaatctcct gcaggtgtct    120
agggatttca gtaagtagt gttgtgaggg gaatacctac ttgtactttc cccccaaacc     180
agattcccga ggcttcttaa ggactcaagg acaatttcta ggcatttagc acgggactaa    240
aaaggtctta gaggaaataa gaagcgccaa aaccatctct ttgcactgta tttcaaccca    300
tttgtccttc tgggttttga aggaacaggt gggactgggg acagaagagt tcttgaagcc    360
agtttgtcca tcatggaaaa tgagataggt gatgtggcta cgtcaggggg cccgaaggct    420
ccttgttact gatttccgtc tttttctctct gccttttccc caagggccag gacccctgga    480
tctctgggca gagcagacgc aggcccctat aatagccctc atgctagaaa ggagccggag    540
cctgtgtata aggccagcgc agcctactct ggacagtgca gggttcccac tctcccaact    600
ccccatctgc ttgcctccag acccacattc acacgagc cactgggttg gaggagcatc     660
tgtgagatga acaccattc tttcctcaat gtctcagcta tctaactgtg tgtgtaatca    720
ggccaggtcc tccctgctgg gcagaaacca tgggagttaa gagattgcca acatttatta    780
gaggaagctg acgtgtaact tctgaggcaa aatttagccc tcctttgaac aggaatttga    840
ctcagtgaac cttgtacaca ctcgcactga gtctgctgct gatgatactg tgcaccccac    900
tgtctgggtt ttaatgtcag gctgttcttt taggtatggc ggcttttccc tgggtgtcag    960
taatactcaa gcacttcctc cgagtcaaga agttaatgat gccatcaaac aaatgaagaa   1020
acacctaaag ctggccaagg taaaatatct atcgtaagat gtatcagaaa atgggcatg    1080 tagctgctgg gatataggag tagttggcag gttaaacgga tcacctggca gctcattgtt   1140
ctgaatatgt tggcatacag agccgtcttt ggcatttagc gatttgagcc agacaaaact   1200
gaattactta gttgtacgtt taaaagtgta ggtcaaaaac aaatccagag gccaggagct   1260
gtggctcatg cctgtaatcc tagcactttg ggaggctgaa gcgggtggat cacttgaggt   1320
caggagttcg agaccagcct ggcctacatg acaaaacccc gtatctacta aaaatacaaa   1380
aaaattagct gggcttggtg gcacacacct gtaatcccag ctactgggaa ggctgaggca   1440
ggagaattgc ttgaaccctg taggaagagg ttgtagtgag ccaagatcgc accgttgcac   1500
tccagcctgg gcaacaagag caaaactcca tctcaaaaaa caaattaaat ccagagattt   1560
aaaagctctc agaggctggg cgcggtggct tacacctgtt atcccagcat tttgggatgc   1620
cgaggcgggc aaagcacaag gtcaggagtt tgagaccagc ctggccaaca tagtgaaacc   1680
ctgtctctgc taaaaacata gaaaaattag ccgggcatgg tggcgtgcgc ctgtaatccc   1740
agctactcgg gaggctgagg tgagagaatt rcttgaaccc gggaggcgga ggttgcagtg   1800
agcccagatt gcaccactgc actccagcct gggcgacaga gcaagactcc atctcaaaaa   1860
aagctctcag aacaaccagg tttacaaatt tggtcagttg gtaaataaac tgggtttcaa   1920
acatactttg ctgaaayaat cactgactaa ataggaaatg aatcttttt ttttttttt    1980 taagctggca agctggtctg taggacctga taagtactca cttcatttct ctgtgtctca   2040
```

```
ggtttcccat ttttaggtga gaattaaggg gctctgataa aacagaccct aggattgtgg   2100
acagcagtga tagtcctaga gtccacaagt ctgcttttga gtgatgggcc catgtatctg   2160
gcacatctgc aggcagagcg tggttctggc tcttcagatg atgccggtgg agcactttga   2220
ggagtcctca ccccaccgtg ataaccagac attaaaatct tggggctttg catcccagga   2280
tttctctgtg attccttcta gacttgtggc atcatggcag catcactgct gtagatttct   2340
agtcacttgg ttctcaggag ccgtttattt aatggcttca catttaattt cagtgaacaa   2400
ggtagtggca ttgctcttca cagggccgtc ctgttgtcca caggttccag attgactgtt   2460
gccccttatc tatgtgaaca gtcacaactg aggcaggttt ctgttgttta caggacagtt   2520
ctgcagatcg atttctcaac agcttgggaa gatttatgac aggactggac accagaaata   2580
atgtcaaggt aaaccgctgt ctttgttcta gtagcttttt gatgaacaat aatccttatg   2640
tttcctggag tacttccaac tcatggtaaa gttggcaggg gcattcacaa cagaaaagag   2700
caaactatta actttaccag tgaggcagta cggtgtagtg tagtgattca gagaatttgc   2760
tttgccacca gacataccag gtaaccttga ctaagttact taacctatct aaacctcagt   2820
tycctcatct gtgaaatgga gacagtaatc atagctattt ccaaactgtt gtgagaattc   2880
aatgagttaa aggtataagg tcctcaccac agcgcctgcc cacatagtca gtgatcacta   2940
tgtcctgaac actgtaatta cttcgccata ttctctgatc atagtgtttt gccttggtat   3000
gtgactagaa tttctttctg aggtttatgg gcatggttgg tgggtatgca cctgcctgca   3060
ggagcccggt tgggggcat taccttgtac ctggtatgtt ttctttcagg tgtggttcaa   3120
taacaagggc tggcatgcaa tcagctcttt cctgaatgtc atcaacaatg ccattctccg   3180
ggccaacctg caaaagggag agaacccag ccattatgga attactgctt tcaatcatcc   3240
cctgaatctc accaagcagc agctctcaga ggtggctctg taagtgtggc tgtgtctgta   3300
tagatggagt ggggcaaggg agagggttat ggagaagggg agaaaaatgt gaatctcatt   3360 gtagggaac agctgcagag accgttatat tatgataaat ctggattgat ccaggctctg   3420
ggcagaagtg ataagtttac gaattggctg gttgggcttc ttgaactgca gaagagaaaa   3480
tgacactgat atgtaaaaat cgtaacattt agtgaattca tataaagtga gttcaaaaat   3540
tgttaattaa attataattt aattataagt gtttaatcag tttgatttgt ttaaaaacca   3600 ctgtttttaaa tttggtggaa tatgttttta ttagcttgta tctttaattc ctaaattaag   3660
ctgtgtgtgt gtgtgtgtgt gtgtgtgtgt gtgtgtgtgt gtgtgtgtgt gaagtttaaa   3720
gccaggatga gctagtttaa agtatgcagc ctttggagtc atacagatct gggtttgaat   3780
ctggtctcta aacttatag atgtatgata ttaaatgagg cagttcatgt aaattgccaa   3840
gcccagcact cagcacagag ttgatatttc acacacatta gataccttc ctgtatgtgg   3900 agcatggcag ttcctgtttc tgctttactc ctacaggata ctaatatagg acactaggat   3960 ctttataccaa agacccatg taatgggctt atgagaccat tcttcttata aaaatctgac   4020 agaattttttg tatgtgttag atcaataggc tgcatactgt tattttcaag ttgatttaca   4080
gccagaaata ttaatttatt tgagtagtta cagagtaata tttctgctct catttagttt   4140
tcaagcccca ctagtccttt gtgtgtgaaa atttacaact tactgctctt acaaggtcat   4200
gaacagtgga ccaaagtgaa tgccattaac cactctgact tccttcatta gtttttattgt   4260 gacagtggac tcttttgacc tcagtaatac cagtttggca tttacattgt catattttta   4320
gacttaaaaa tgatcatctt aaccctgaat aaaatgtgtc tggtgaacag atgttttcc   4380 ttggctgtgc ctcagatatc tctgtgtgtg tgtacgtgtg tgtttgtctg tgtgtccatg   4440
```

```
tcctcactga ttgagcccta actgcatcaa agacccctca gattttcaca cgcttttttct      4500 ctccaggatg accacatcag tggatgtcct tgtgtccatc tgtgtcatct ttgcaatgtc      4560
cttcgtccca gccagctttg tcgtattcct gatccaggag cgggtcagca agcaaaaca       4620 cctgcagttc atcagtggag tgaagcctgt catctactgg ctctctaatt ttgtctggga      4680
tatggtaagg acacaggcct gctgtatctt tctgatgtct gtcagggcca tggattgata      4740
tggataagaa agaaagagct ctggctatca tcaggaaatg ttccagctac tctaaagatg      4800
tatgaaaaag aaatagccag aggcaggtga tcactttcat gacaccaaac acagcattgg      4860
gtaccagagt tcatgtcaca ccagagggaa aattctgtac acaatgatga aaattaatac      4920
cactaccact taagttccta tgtgacaact ttcccaagaa tcagagagat acaagtcaaa      4980
actccaagtc aatgcctcta acttctctga tgggttttaa cctccagagt cagaatgttc      5040
tttgccttac taggaaagcc atctgtcatt tagaaaactc tgtacatttt atcagcagct      5100
tatccatcca ttgcaaatat tgttttttgtg ccasccacaa tatattgctt ctatttggac     5160
caatatgggg gatttgaagg aattctgaag ttctaattat atttcaactc tactttacaa      5220
tatctccctg aaatatatct ccctgtaact tctattaatt ataagctaca cagagcaaat      5280
ctaattcttc tcccaccgaa caagtccctg gatatttaaa ataactctc atactctcat       5340 ttaacctgag tattacccag ataagatgat atatgagaat acaccttgta acctccgaag      5400
cactgtacaa atgtgagcaa tgatggtgga gatgatgatg agatctttgc tgtttatacc      5460
aagcccctta gactgtgtca ctcttctgat ccggttgtcc ttgtatggcc atgctgtata      5520
ttgtgaatgt cccgttttca aaagcaaagc caagaattaa ccttgtgttc aggctgtggt      5580
ctgaatggtt atgggtccag agggagttga tctttagctc acacttctat tactgcagca      5640
caaagatttt gcattttgga aggagcaccg tcttactggc aacttagtgg taaaccaaaa      5700
cctccatttc acacaaatga ttgtgaaatt cgggtctcct tcattctata caaattcatt      5760
tgattttttt gaaactaaac tttatattta tccatattaa attacatggg ttttattttt      5820
gttttatctt gattcagtaa ttactccttt cagtaaacac agactgagtg ctgtgtgtct      5880
gacttatgcc aggcataggt gattcagaga tgaaaggtca agtccctgaa cccatctctt      5940
gtcttcctgg gtattatctg tccctccctg ctttagagct cctgaaattt gctagaagca      6000
tgtcttcatc taagttgttg ataaacacat caagtaggat tggactgagg cagagccctg      6060
tagtctgaag ctgcagttct tctagcggct gacaagcccc actatcactt ccctgctggt      6120
gctttgctct gccagctgtg aattctcata attgtcctat cgtcaagtct ttatttctgc      6180
attttactgc ttgatacact gtcaggacag actttaaaat tattctcagt gcgatgaaac      6240
aattctgaca ttcatgttat gagcagttac ctcataaata gattacatg               6289

<210> SEQ ID NO 27
<211> LENGTH: 4244
<212> TYPE: DNA
<213> ORGANISM: Homo sapiens

<400> SEQUENCE: 27
aaattactct gactgggaat ccatcgttca gtaagtttac tgagtgtgac accttggctt       60
gactgttgga aagacagaaa gggcatgtag tttataaaat cagccaaggg gaaaatgctt      120
gtcaaaatgt attgtcgggt attttgatta atagtttatg tggcttcatt aattcagagt      180
tactctccaa tatgtttatc tgcccttct tgtctgataa tggtgaaaac ttgtgtgatg      240
cattgtatat ttgatttagg ggtgaactgg atgtctttgt tttcactttt agtgcaatta      300
```

-continued

| | |
|---|---|
| cgttgtccct gccacactgg tcattatcat cttcatctgc ttccagcaga agtcctatgt | 360 |
| gtcctccacc aatctgcctg tgctagccct tctacttttg ctgtatgggt aagtcacctc | 420 |
| tgagtgaggg agctgcacag tggataaggc atttggtgcc cagtgtcaga aggagggcag | 480 |
| ggactctcag tagacactta tcttttttgtg tctcaacagg tggtcaatca cacctctcat | 540 |
| gtacccagcc tcctttgtgt tcaagatccc cagcacagcc tatgtggtgc tcaccagcgt | 600 |
| gaacctcttc attggcatta atggcagcgt ggccaccttt gtgctggagc tgttcaccga | 660 |
| caatgtgagt catgcagaga gaacactcct gctgggatga gcatctctgg gagccagagg | 720 |
| acagtgttta attgtgatct tattccactt gtcagtggta ttgacactgc tgactgcctt | 780 |
| gtcctgtctt cagagtctgt cttccctgag aaggcaaagc acctttcttt cttgctgtgc | 840 |
| cttacatttt gctggtcaag cctttcagtt tcttttgaca gttttttta cttctttctt | 900 |
| ttttcaatgt tgctcttacc aagagtagcc cctctgcctt ccactttaca catgagagct | 960 |
| gggcgacgca ttcagtccta aggcttttac catcacctct cttggtgttt ttattgtcat | 1020 |
| ctctaagatc aatgccttta gccttgatca taaccttgaa ctctaatctc aaattctcac | 1080 |
| ttgcctagtg gattgctcca tttagatagt atatagatac cccaacctgg atatgtccta | 1140 |
| gttttctttc cccttggaac ttaatgcttt tcttgccatc cctgtcacac tcagtggcac | 1200 |
| taccatccac tcggttgccc aagctggctc ttagagttat cctagatgct tgctttgctg | 1260 |
| ttgcagattt cccacattca actggttatg ttgtcagttc ttccaggtat ggacctctaa | 1320 |
| aataaggctt cctctccatt ccggttgtca ttgcctttgt ccaaacacag cacacaaggc | 1380 |
| cttttacagt tgcacaactc ttcctgtcca tacccaccac acccttttccc agctgtaagc | 1440 |
| ttcagatgag ttgcctccaa ccaccatgct cctgtaggcc tggcttgaaa tgcccttctt | 1500 |
| ctgtcacagg gtctggtagt atatcccttg cccttcaaga tttagctaaa atgtgaagct | 1560 |
| ttccttacct gctgggaggt gttctctctt ttctctgtgc tctcagagtc cttagtccat | 1620 |
| gcctccagta caacgtacat ccacttacat ggtaatttcc tgtttacata cttttcctac | 1680 |
| tcggagtgga gtctgtttct taataatttt gcctctccca tgccctagca cagtgcatcc | 1740 |
| agcgtatagc cccttattca gttggtagat atttggccac tgttgccttg tgggatcata | 1800 |
| agttctgatg tatttgagaa gaatttctaa aattctgaca aaatcctgaa actcaaatat | 1860 |
| tgacccagac atgagcaatt tgcttttcaa atgctaaggg attttaatg gatttgctttt | 1920 |
| aattaaatct agcctgtttc taagctttat tcattatttc tccatactca gagcatttct | 1980 |
| ccagattttc taaagaatag aatttttattg ctacatatca tcagctatgc ctgctgctat | 2040 |
| ttaattggta tctgaattaa aaggtctggt ttgtccctag agaatcaaat ttttttcttca | 2100 |
| ctcccatatt tcagaacttg atacattttt aggataaacc atgaatgaca cccgtttctt | 2160 |
| ctccctcacc ctcccttccc tcccattttt tttttttttt tttttttagaa gctgaataat | 2220 |
| atcaatgata tcctgaagtc cgtgttcttg atcttcccac atttttgcct gggacgaggg | 2280 |
| ctcatcgaca tggtgaaaaa ccaggcaatg gctgatgccc tggaaaggtt tggtgagtga | 2340 |
| agcagtggct gtaggatgct ttaatggaga tggcactctg cataggcctt ggtaccctga | 2400 |
| actttgtttt ggaaagaagc aggtgactaa gcacaggatg ttcccccacc cccatgccca | 2460 |
| gtgacagggc tcatgccaac acagctggtt gtggcatggg ttttgtgaca caaccatttg | 2520 |
| tctgtgtctc tgatagcatt gagaaaagtg aaagggcagt tttgaaggta aggaaaatag | 2580 |
| tgttatttgc ttggatccac tggctcatgc cactgtctgg gttggttaga agcactggaa | 2640 |
| aagtcaaacc ataactttga gaattaggtg atcagggaat cagaaggaaa gatgcaaact | 2700 |

```
ttggctcttt taggcgaatc atgtgcctgc agatgaggtc atttattatc ttttacacag    2760
tctataaaat tataatgtat tacatctttt tctacctttta gaatggttaa aaatatttct    2820
ccggtagcca tatgattatt attcatccat tagataatat agtcaaatgg gccatgttat    2880
ttactgttca tagaagaggg gcttttttgca acttgggcta caaaggagat atgtaaggaa    2940
tttaaggaat ggttacatgg aactagattt aattgaatct agtggtttaa ttgattcact    3000
aggatatatg ctactgaaag gggaatctgc ttaaagtgct ttctgatatt tattattact    3060
aaaacttaga atttattaaa aatactgact gtgaaaatta cttgggtcgt ttgcctttttt   3120 aaaaggattt ttggcatgtc tcattaaaaa aagaaatact agatatcttc agtgaagtta    3180
caaatcgaat acacattggc tctgaaattc tgattgatac tgggtcataa aaagttttcc    3240
caaatcagac ttggaaagtg atcactctct tgttactctt ttttccttgt catgggtgat    3300
agccatttgt gtttattgga agatcggtga attttaagga acataggccc aaatttgagg    3360
aagggccatg gttttttgatc cctccattct gaccggatct ctgcattgtg tctactaggg   3420
gagaatcgct ttgtgtcacc attatcttgg gacttggtgg gacgaaacct cttcgccatg    3480
gccgtggaag gggtggtgtt cttcctcatt actgttctga tccagtacag attcttcatc    3540
aggcccaggt gagcttttttc ttagaacccg tggagcacct ggttgagggt cacagaggag   3600
gcgcacaggg aaaactcac caatgggggt tgcattgaac tgaactcaaa atatgtgata    3660
aaactgattt tcctgatgtg ggcatcccgc agccccctcc ctgcccatcc tggagactgt    3720
ggcaagtagg ttttataata ctacgttaga gactgaatct ttgtcctgaa aaatagtttg    3780
aaaggttcat ttttcttgtt ttttccccca agacctgtaa atgcaaagct atctcctctg    3840
aatgatgaag atgaagatgt gaggcgggaa agacagagaa ttcttgatgg tggaggccag    3900
aatgacatct tagaaatcaa ggagttgacg aaggtgagag agtacaggtt acaatagctc    3960
atcttcagtt ttttttcagct ttatgtgctg taacccagca gtttgctgac ttgcttaata    4020
aaagggcatg tgttcccaaa atgtacatct ataccaaggt tctgtcaatt ttattttaaa    4080
aacaccatgg agacttctta aagaattctt actgagaatt cttttgtgat atgaattccc    4140
attctcgaat actttggttt tatatgctta catttatgtg ttagttatta aaacatacta    4200
atattgtata tctagtcaaa ctgagtagag agataatggt gatt                     4244
```

<210> SEQ ID NO 28
<211> LENGTH: 5023
<212> TYPE: DNA
<213> ORGANISM: Homo sapiens

<400> SEQUENCE: 28

```
ttttaaaata cctgcaatac atatatatgt tgaatagatg aaaaattatg tagatgataa     60
tgaatgatac ggttctaaaa agacaggtta aaaagtaagt tcacttttat tttgagcttc    120
agaatcattc agaagccagt cgccacaaac gcagaccaag gctcttggca catcaaatat    180
gcctatggct tagggttatt gacaagtctt atgttgcagt gtatgtggtt tatagtcctg    240
ccttccacag ttgcttggga gagctgtgag tcactgaggc ttatgaatgt ttacattttg    300
tttgttgcag atatatagaa ggaagcggaa gcctgctgtt gacaggatttt gcgtgggcat   360 tcctcctggt gaggtaaaga cactttgtct atattgcgtt tgtccctatt agttcagact    420
atctctaccc aatcaagcaa cgatgctcgt taagaggtaa aagtggattt taaaggcttc    480
tgtatttatg ccaggatgga gcaattagtc atcgagaaga gagggaccct gtatgtcaag    540
agaatgattt cagagaatcc aatacaattt aagaaaaagc atggggctgg gcgcagtgat    600
```

```
tcactcctgt aatcccagca ctttgggagg ccgaggtggg cggactcacg aggtcaggag    660
attgagacca tcctggccaa catggtgaaa ccccatctct actataaata caaaaattag    720
ctgggcatag tagtgcattc ctgtagtccc agctactcgg gaggctgagg caggagaatt    780
gcttgaacct aggaggggga ggttgcccag attgcgctgc tgcactccag cctggtgaca    840
gagtgagact catgtcaaca acaaaaacag aaaaagcacg cacatctaaa acatgctttt    900
gtgatccatt tgggatggtg atgacattca aatagttttt taaaaataga ttttctcctt    960
tctggtttcc gtttgtgttc ttttatgccc ttttgccaga gtaggtggtg caatttggct   1020
agctggcttt cattactgtt tttcacacat aactttggc ctcaacttga caactcaaat   1080
aatatttata aatacagcca cacttaaaat ggtcccatta tgaaatacat atttaaatat   1140
ctatacgatg tgttaaaacc aagaaaatat ttgattcttc tctgatattt aagaattgaa   1200
ggtttgaggt agttacgtgt tagggcatt tatattcatg tttttagagt ttgcttatac   1260
aacttaatct ttccttttca gtgctttggg ctcctgggag ttaatgggc tggaaaatca   1320 tcaactttca agatgttaac aggagatacc actgttacca gaggagatgc tttccttaac   1380
aaaaataggt gagaaaagaa gtggcttgta ttttgctgca aagactttgt ttttaattta   1440
tttaaagaaa taggttgtta ttttttgatta cagtggtatt tttagagttc ataaaaatgt   1500
tgaaatatag taaagggtaa agaagcacat aaaatcatcc atgatttcaa tatctagaga   1560
taatcacaat ttacatttcc tttcagtctc attctcttct tttaacagct ttattcaggt   1620
ataatttaca tacaatataa tttgcttgtt ttttaagagt ataatttagt gattttttggt   1680 aaattgagag ttttgcaacc atcaccacaa tccagtttta gaacttttcc atcaccccac   1740
atctgtctta tatacacata taaatgtgcc atacaattga gatcatactg tatgtagaat   1800
ttaaaattag tttttattgt taatgagtgt attatgaata tttcccagtg ggttacattt   1860
cctaagatgt ggaattttac attgctacat aaaatccccc tatgtacatg tacctataat   1920
ttatttaata aattccttat aaatgttgga cacattagtt tccattttc actatgtaaa   1980 tatgtccctg tatacatctt ttattattc ctcaggaaca attcctacaa agtaaattgc   2040
cctctctaaa gagcatacaa attgactgag ccaccgttag gccatttct gagactgcac   2100 aggtcacaaa gcaatctgat ctttgggaat acagctacat tttataggct tcttagataa   2160
tgttactcta agtactttaa atatgtgggg cttctctggg cttttttttt tttgagacgg   2220
agtttcactc ttactgccca ggctggagag caatggcgcg accttggctc actgcaacct   2280
ccgcctccca ggttcaagcg attctcctgc ctcagcctcc tgagtagctg agattacagg   2340
tgcccgccac aatgcctgcc taattttttt gtattttcag tagagatggg gtttcaccat   2400
gttggccaga ctggtctcga gctcctgacc tcaggtgatc cacctgcctc agcctcccaa   2460
agttctggga ttacaggcat gagccactgc gcccggcttc tctggactta ttatgtggag   2520
agatagtaca aggcagtggc tttcagagtt ttttgaccat gaccgttgtg ggaaatacat   2580
tttatatctc aacctagtat gtacacacag acatgtagac acatgtataa cctaaagttt   2640
cataaagcag tacctactgt tactaattgt agtgcactct gctatttctt attctaccttt   2700 atactgcgtc attaaaaaag tgctggtcat gacccactaa attatttcc caaaccacta   2760 atgaacaatg actcacaatt tgaacacact ggacagggg atagccaata aaattgaaaa   2820
gagcaaggaa attaatgtat tcatgatctc ctctcctgtc tcttacatttt ttgcagtagc   2880 aatgtaaagg aatcctaaga gaacagacat tctgggaata gcaggcctag cgctgcacaa   2940 ctgcttttcct aggcttgctc ctagtaccaa gctcctgacg catatagcag tggcagtaat   3000
```

```
aaccagccca tagtaaggtt tgtcacaggg actggttgta agaactgatt tgrttggtat    3060
agctgtgagg gcctggcacg gtgtccacgt gtgcctcaat cctaattctg aaaaaggctg    3120
accctggggg tgctaattag atacacagag aggaatgaat gctgccagaa ggccaagttc    3180
atggcaatgc cgctgtggct gaggtgcagt catcagtctg gaacgtgaac actgaacttc    3240
tctcacatgt gattcttcac ttgactggct tcatagaacc ccaaagccac cccaccacca    3300
cataaattgt gtctctaggt tctgtgttgc tcacactcaa aatttctggg ccttctcatt    3360
tggtgcatgt gaatggtgca tatgagtgaa gtctaggatg gggccttagc gttaaagccc    3420
tggggtagtg tgactgagat tgttggtaaa gaatgtgcag tggttggcat gacctcagaa    3480
attctgaaat gggactgcac ctgcagactg aagtgttcag agagccaggg aggtgcaagg    3540 actgggagg gtagaggcag gaaccctgcc tgccaggaag agctagcatc ctgggggcag    3600
aaaggctgtg ctttcaagta gcagcagatg tattggtatc tttgtaatgg agaagcatac    3660
tttacaggaa cattaggcca gattgtctaa ccagagtatc tctacctgct taaaatctaa    3720
gtagttttct tgtcctttgc agtatcttat caaacatcca tgaagtacat cagaacatgg    3780
gctactgccc tcagtttgat gccatcacag agctgttgac tggagagaa cacgtggagt    3840 tctttgccct tttgagagga gtcccagaga aagaagttgg caaggtactg tgggcacctg    3900
aaagccagcc tgtctccttt ggcatcctga caatatatac cttatggctt ttccacacgc    3960
attgacttca ggctgttttt cctcatgaat gcagcagcac aaaatgctgg ttctttgtat    4020
ctgctttcag ggtggaaacc tgtaacggtg gtggggcagg gctgggtggg cagagaggga    4080
gtgctgctcc caccacacga gtcccttctc cctgctttgg ctcctcacca gttgtcaggt    4140
tatgattata gaatcagtc ctactcagtg aaagaacttt catacatgta tgtgtaggac    4200
agcatgataa aattcccaag ccagaccaaa gtcaaggtgc ttttatcac tgtaggttgg    4260 tgagtgggcg attcggaaac tgggcctcgt gaagtatgga gaaaaatatg ctggtaacta    4320
tagtggaggc aacaaacgca agctctctac agccatggct ttgatcggcg ggcctcctgt    4380
ggtgtttctg gtgagtataa ctgtggatgg aaaactgttg ttctggcctg agtggaaaac    4440
atgactgttc aaaagtccta tatgtccagg gctgttgtat gattggcttg tcttccccca    4500
gggacagcag agcaaccttg gaaaagcaga gggaagcttc tcccttggca cacactgggg    4560
tggctgtacc atgcctgcag atgctcccaa atagaggcac tccaagcact tgtttctta    4620 gcgtgattga ggctggatat gtgatttgat ctttctctgg aacattcttt ctaatcatct    4680
ttgtgttcat tccctgaaaa tgaagagtgt ggacacagct ttaaaatccc caaggtagca    4740
actaggtcat agttccttac acacggatag atgaaaaaca gatcagactg ggaagtggcc    4800
cttgaccttt tttcttctgt agataagagc attgatgtta ttacgggaag aagcctttga    4860
ggcttttatg tattccacct cggtctggaa tttgttctg taaggctaac agttgcaata    4920
tactagggta atctgagtga gctggaatta aaaaaaaaaa ggaatttcac cccaatctta    4980
tactgacttc aatagaggtt tcagacaaaa agttgttttg tat                     5023
```

<210> SEQ ID NO 29
<211> LENGTH: 5138
<212> TYPE: DNA
<213> ORGANISM: Homo sapiens
<220> FEATURE:
<221> NAME/KEY: misc_feature
<222> LOCATION: (1)...(5138)
<223> OTHER INFORMATION: n = a, t, c, or g

<400> SEQUENCE: 29

```
ngccnngttn aaaangaaaa tttnnnnnaa attnaanntt annggngnnn tttccccaga      60
aaaaacnaaa angatttccn cccnggggggg nccccenant cnaaaaggcc ccncttnttt    120
gnggngaggg aaagntttt ttggaatttt taatttttgg tcccccaaaa cctattattg     180
agaatttaat tacataaaaa agtactcaga atatttgagt ttcctgcatc aataagacat    240
ttataataat gaccttgttt acaaatgaat ttgaaagtta ctctaattct ttgattcatc    300
aagaaataac tagaatggca agttaaaatt taagctgttt caaagatgct tctgcattta    360
aaaacaaatt tatctttgat tttttttccc cccagcaaat aagacttatt ttattctaat    420
tacaggatga acccaccaca ggcatggatc ccaaagcccg gcggttcttg tggaattgtg    480
ccctaagtgt tgtcaaggag gggagatcag tagtgcttac atctcatagg tccgtagtaa    540
agtcttgggt tcctcactgt gggatgtttt aactttccaa gtagaatatg cgatcatttt    600
gtaaaaatta gaaatacag aaaagcaaag agtaaaacaa ttattacctg aaattatata     660
tgcatattct tacaaaaatg caagcccagt ataaatactg ctcttttttca cttaatatat   720 tgtaaacatt attccaagtc agtgcattta ggtgtcattt cttatagctg gatagtattc    780
cattaggata tactcttatt taactattcc cccttttgta gacatttgga ttatttccaa    840
cttgttcaca attgtaaaca ccactacact gaacagcatc atccctatat ccacatgtac    900
ttgtaacaga atacaattcc ctaggaagct ggaatgctgg aagtcatggt gatgttctca    960
tggttacaga gaatctctct aaaactaaaa cctctttctg ttttaccgca gtatggaaga  1020
atgtgaagct ctttgcacta ggatggcaat catggtcaat ggaaggttca ggtgccttgg  1080
cagtgtccag catctaaaaa ataggtaata aagataattt ctttgggata gtgcctagtg  1140
agaaggcttg atatttattc ttttgtgagt atataaatgg tgcctctaaa ataaagggaa  1200
ataaaactga gcaaaacagt atagtggaaa gaatgagggc tttgaagtcc gaactgcatt  1260
caaattctgt ctttaccatt tactggttct gtgactcttg ggcaagttac ttaactactg  1320
taagagttag tttccctgga agatctacct cctagctttg tgctatagat gaaatgaaaa  1380
aaatttacat gtgccagtac tggtgagagc gcaagctttg gagtcaaaca caatggggtt  1440
tgcatcctgg ccctaccaat tatgagctct gagccatggg caagtgacta actccctggg  1500
cctcagtttc tctgtaacat ctgtcagact tcatgggtcc aggtgaggat taaaggagat  1560
catgtattta cagcacatgg catggtgctt cacataaaat aagtatttag taaatgataa  1620
ctggttcctt ctctcagaaa cttatttctg ggcctgccag gggccgccct ttttcatggc  1680
acaagttggg ttcccagggt tcagtattct tttaaatagt tttctggaga tcctccattt  1740
gggtattttt tcctgctttc aggtttggag atggttatac aatagttgta cgaatagcag  1800
ggtccaaccc ggacctgaag cctgtccagg atttctttgg acttgcattt cctggaagtg  1860
ttcyaaaaga gaaacaccgg aacatgctac aataccagct tccatcttca ttatcttctc  1920
tggccaggat attcagcatc ctctcccaga gcaaaaagcg actccacata gaagactact  1980
ctgtttctca gacaacactt gaccaagtaa gctttgagtg tcaaaacaga tttacttctc  2040
agggtgtgga ttcctgcccc gacactcccg cccataggtc caagagcagt ttgtatcttg  2100
aattggtgct tgaattcctg atctactatt cctagctatg cttttttacta aacctctctg  2160 aacctgaaaa gggagatgat gcctatgtac tctataggat tattgtgaga atttactgta  2220
ataataacca taaaaactac catttagtga gcacctacca tgggccaggc attttacttg  2280
gtgcctaatc ctatttaaat tagataaaaa agtaccaaat aggtcctgac acttaagaag  2340
tactcagtaa atattttctt ccctcttccc tttaatcaag accgtatgtg ccaaagtaaa  2400
```

```
tggatgactg agcagttggt gatgtagggg tgggggggcga tatagaaagt cagttttgg    2460 ccgggcgtgg tggctcatgc ctgtaatccc agcactttgg gaggctgagg agcaggcaga    2520
tcatgaggtc aggagatcca gataatcctg gccaacaggg tgaaacccg tctctactaa    2580 aaatacaaaa attagctggg catggtggtg cgcacttgta gtcccagcta cttgcgaggc    2640
tgaggcagga gaattgctcg aacccaggag gtggaggtta cagtgagcca aggtctcgcc    2700
actgcactcc agcctgggga cagagcaaga ccccatttca aggggggaaa aaagtctat    2760 ttttaagttg ttattgcttt tttcaagtat tcttccctcc ttcacacaca gttttctagt    2820
taatccattt atgtaattct gtatgctcct acttgaccta atttcaacat ctggaaaaat    2880
agaactagaa taaagaatga gcaagttgag tggtatttat aaaggtccat cttaatcttt    2940
taacaggtat ttgtgaactt tgccaaggac caaagtgatg atgaccactt aaaagacctc    3000
tcattacaca aaaccagac agtagtggac gttgcagttc tcacatcttt tctacaggat     3060
gagaaagtga agaaagcta tgtatgaaga atcctgttca tacggggtgg ctgaaagtaa     3120
agaggaacta gactttcctt tgcaccatgt gaagtgttgt ggagaaaaga gccagaagtt    3180
gatgtgggaa gaagtaaact ggatactgta ctgatactat tcaatgcaat gcaattcaat    3240
gcaatgaaaa caaaattcca ttacaggggc agtgcctttg tagcctatgt cttgtatggc    3300
tctcaagtga aagacttgaa tttagttttt tacctatacc tatgtgaaac tctattatgg    3360
aacccaatgg acatatgggt ttgaactcac acttttttttt ttttttttgt tcctgtgtat    3420
tctcattggg gttgcaacaa taattcatca agtaatcatg ccagcgatt attgatcaaa     3480 atcaaaaggt aatgcacatc ctcattcact aagccatgcc atgcccagga gactggtttc    3540
ccggtgacac atccattgct ggcaatgagt gtgccagagt tattagtgcc aagtttttca    3600
gaaagtttga agcaccatgg tgtgtcatgc tcacttttgt gaaagctgct ctgctcagag    3660
tctatcaaca ttgaatatca gttgacagaa tggtgccatg cgtggctaac atcctgcttt    3720
gattccctct gataagctgt tctggtggca gtaacatgca acaaaaatgt gggtgtctcc    3780
aggcacggga aacttggttc cattgttata ttgtcctatg cttcgagcca tgggtctaca    3840
gggtcatcct tatgagactc ttaaatatac ttagatcctg gtaagaggca aagaatcaac    3900
agccaaactg ctggggctgc aactgctgaa gccagggcat gggattaaag agattgtgcg    3960
ttcaaaccta gggaagcctg tgcccatttg tcctgactgt ctgctaacat ggtacactgc    4020
atctcaagat gtttatctga cacaagtgta ttatttctgg cttttttgaat taatctagaa    4080 aatgaaaaga tggagttgta ttttgacaaa aatgtttgta cttttttaatg ttatttggaa    4140 ttttaagttc tatcagtgac ttctgaatcc ttagaatggc ctctttgtag aaccctgtgg    4200
tatagaggag tatggccact gcccactatt tttatttct tatgtaagtt tgcatatcag     4260
tcatgactag tgcctagaaa gcaatgtgat ggtcaggatc tcatgacatt atatttgagt    4320
ttctttcaga tcatttagga tactcttaat ctcacttcat caatcaaata ttttttgagt    4380
gtatgctgta gctgaaagag tatgtacgta cgtataagac tagagagata ttaagtctca    4440
gtacacttcc tgtgccatgt tattcagctc actggtttac aaatataggt tgtcttgtgg    4500
ttgtaggagc ccactgtaac aatactgggc agccttttttt tttttttttt taattgcaac    4560
aatgcaaaag ccagaaaagt ttaagggtca caagtctaaa caatgaattc ttcaacaggg    4620
aaaacagcta gcttgaaaac ttgctgaaaa acacaacttg tgtttatggc atttagtacc    4680
ttcaaataat tggctttgca gatattggat accccattaa atctgacagt ctcaaatttt    4740
tcatctcttc aatcactagt caagaaaaaa tataaaaaca acaaatactt ccatatggag    4800
```

-continued

```
cattttcag agtttctaa cccagtctta tttttctagt cagtaaacat ttgtaaaaat       4860
actgtttcac taatacttac tgttaactgt cttgagagaa aagaaaaata tgagagaact       4920
attgtttggg gaagttcaag tgatctttca atatcattac taacttcttc cactttttcc       4980
agaatttgaa tattaacgct aaggtgtaa gacttcagat ttcaaattaa tctttctata        5040
ttttttaaat ttacagaata ttatataacc cactgctgaa aaagaaacaa atgattgttt       5100
tagaagttaa aggtcaatat tgattttaaa atattaag                              5138
```

<210> SEQ ID NO 30
<211> LENGTH: 20
<212> TYPE: DNA
<213> ORGANISM: Homo sapiens

<400> SEQUENCE: 30
gtgttcctgc agagggcatg                                                    20

<210> SEQ ID NO 31
<211> LENGTH: 20
<212> TYPE: DNA
<213> ORGANISM: Homo sapiens

<400> SEQUENCE: 31
cacttccagt aacagctgac                                                    20

<210> SEQ ID NO 32
<211> LENGTH: 21
<212> TYPE: DNA
<213> ORGANISM: Homo sapiens

<400> SEQUENCE: 32
ctttgcgcat gtccttcatg c                                                  21

<210> SEQ ID NO 33
<211> LENGTH: 21
<212> TYPE: DNA
<213> ORGANISM: Homo sapiens

<400> SEQUENCE: 33
gacatcagcc ctcagcatct t                                                  21

<210> SEQ ID NO 34
<211> LENGTH: 19
<212> TYPE: DNA
<213> ORGANISM: Homo sapiens

<400> SEQUENCE: 34
caacaagcca tgttccctc                                                     19

<210> SEQ ID NO 35
<211> LENGTH: 18
<212> TYPE: DNA
<213> ORGANISM: Homo sapiens

<400> SEQUENCE: 35
catgttccct cagccagc                                                      18

<210> SEQ ID NO 36
<211> LENGTH: 19
<212> TYPE: DNA
<213> ORGANISM: Homo sapiens

<400> SEQUENCE: 36
cagagctcac agcagggac                                              19

<210> SEQ ID NO 37
<211> LENGTH: 21
<212> TYPE: PRT
<213> ORGANISM: Homo sapiens

<400> SEQUENCE: 37

Cys Ser Val Arg Leu Ser Tyr Pro Pro Tyr Glu Gln His Glu Cys His
1               5                   10                  15

Phe Pro Asn Lys Ala
            20

<210> SEQ ID NO 38
<211> LENGTH: 14
<212> TYPE: DNA
<213> ORGANISM: Homo sapiens

<400> SEQUENCE: 38
gcctgtgtgt cccc                                                   14

<210> SEQ ID NO 39
<211> LENGTH: 14
<212> TYPE: DNA
<213> ORGANISM: Homo sapiens
<220> FEATURE:
<221> NAME/KEY: misc_feature
<222> LOCATION: (1)...(14)
<223> OTHER INFORMATION: n = t or c

<400> SEQUENCE: 39
gcctgtgngt cccc                                                   14

<210> SEQ ID NO 40
<211> LENGTH: 45
<212> TYPE: DNA
<213> ORGANISM: Homo sapiens

<400> SEQUENCE: 40
aagaagatgc tgcctgtgtg tcccccaggg gcaggggggc tgcct                 45

<210> SEQ ID NO 41
<211> LENGTH: 15
<212> TYPE: PRT
<213> ORGANISM: Homo sapiens

<400> SEQUENCE: 41

Lys Lys Met Leu Pro Val Cys Pro Pro Gly Ala Gly Gly Leu Pro
1               5                   10                  15

<210> SEQ ID NO 42
<211> LENGTH: 15
<212> TYPE: PRT
<213> ORGANISM: Mus musculus

<400> SEQUENCE: 42

Lys Lys Met Leu Pro Val Cys Pro Pro Gly Ala Gly Gly Leu Pro
1               5                   10                  15

<210> SEQ ID NO 43
<211> LENGTH: 15
<212> TYPE: PRT
<213> ORGANISM: Homo sapiens

<400> SEQUENCE: 43

```
Lys Lys Met Leu Pro Val Arg Pro Pro Gly Ala Gly Gly Leu Pro
1               5                   10                  15

<210> SEQ ID NO 44
<211> LENGTH: 5
<212> TYPE: PRT
<213> ORGANISM: Caenorhabditis elegans

<400> SEQUENCE: 44

Leu Leu Gly Gly Ser
1               5

<210> SEQ ID NO 45
<211> LENGTH: 45
<212> TYPE: DNA
<213> ORGANISM: Homo sapiens

<400> SEQUENCE: 45
aagaagatgc tgcctgtgcg tcccccaggg gcaggggggc tgcct                   45

<210> SEQ ID NO 46
<211> LENGTH: 14
<212> TYPE: DNA
<213> ORGANISM: Homo sapiens

<400> SEQUENCE: 46
gcctacttgc agga                                                     14

<210> SEQ ID NO 47
<211> LENGTH: 14
<212> TYPE: DNA
<213> ORGANISM: Homo sapiens

<400> SEQUENCE: 47
gcctacttgc ggga                                                     14

<210> SEQ ID NO 48
<211> LENGTH: 45
<212> TYPE: DNA
<213> ORGANISM: Homo sapiens

<400> SEQUENCE: 48
tgggggggct tcgcctactt gcaggatgtg gtggagcagg caatc                   45

<210> SEQ ID NO 49
<211> LENGTH: 15
<212> TYPE: PRT
<213> ORGANISM: Homo sapiens

<400> SEQUENCE: 49

Trp Gly Gly Phe Ala Tyr Leu Gln Asp Val Val Glu Gln Ala Ile
1               5                   10                  15

<210> SEQ ID NO 50
<211> LENGTH: 15
<212> TYPE: PRT
<213> ORGANISM: Mus musculus

<400> SEQUENCE: 50

Trp Gly Gly Phe Ala Tyr Leu Gln Asp Val Val Glu Gln Ala Ile
1               5                   10                  15

<210> SEQ ID NO 51
<211> LENGTH: 15
```

```
<212> TYPE: PRT
<213> ORGANISM: Homo sapiens

<400> SEQUENCE: 51

Trp Gly Gly Phe Ala Tyr Leu Arg Asp Val Val Glu Gln Ala Ile
1               5                   10                  15

<210> SEQ ID NO 52
<211> LENGTH: 12
<212> TYPE: PRT
<213> ORGANISM: Caenorhabditis elegans

<400> SEQUENCE: 52

Phe Met Thr Val Gln Arg Ala Val Asp Val Ala Ile
1               5                   10

<210> SEQ ID NO 53
<211> LENGTH: 45
<212> TYPE: DNA
<213> ORGANISM: Homo sapiens

<400> SEQUENCE: 53
tgggggggct cgcctactt gcgggatgtg gtggagcagg caatc                45

<210> SEQ ID NO 54
<211> LENGTH: 25
<212> TYPE: DNA
<213> ORGANISM: Homo sapiens
<220> FEATURE:
<221> NAME/KEY: misc_feature
<222> LOCATION: (1)...(25)
<223> OTHER INFORMATION: n is a, t, c, or g.

<400> SEQUENCE: 54
tcattcctct tgtnngcncn gnncn                                     25

<210> SEQ ID NO 55
<211> LENGTH: 45
<212> TYPE: DNA
<213> ORGANISM: Homo sapiens

<400> SEQUENCE: 55
agtagcctca ttcctcttct tgtgagcgct ggcctgctag tggtc                45

<210> SEQ ID NO 56
<211> LENGTH: 15
<212> TYPE: PRT
<213> ORGANISM: Homo sapiens

<400> SEQUENCE: 56

Ser Ser Leu Ile Pro Leu Leu Val Ser Ala Gly Leu Leu Val Val
1               5                   10                  15

<210> SEQ ID NO 57
<211> LENGTH: 15
<212> TYPE: PRT
<213> ORGANISM: Mus musculus

<400> SEQUENCE: 57

Ser Ser Leu Ile Pro Leu Leu Val Ser Ala Gly Leu Leu Val Val
1               5                   10                  15

<210> SEQ ID NO 58
<211> LENGTH: 14
<212> TYPE: PRT
<213> ORGANISM: Homo sapiens
```

```
<400> SEQUENCE: 58

Ser Ser Leu Ile Pro Leu Val Ser Ala Gly Leu Leu Val Val
1               5                   10

<210> SEQ ID NO 59
<211> LENGTH: 15
<212> TYPE: PRT
<213> ORGANISM: Caenorhabditis elegans

<400> SEQUENCE: 59

Ile Asn Tyr Ala Lys Leu Thr Phe Ala Val Ile Val Leu Thr Ile
1               5                   10                  15

<210> SEQ ID NO 60
<211> LENGTH: 42
<212> TYPE: DNA
<213> ORGANISM: Homo sapiens

<400> SEQUENCE: 60
agtagcctca ttcctcttgt gagcgctggc ctgctagtgg tc                     42

<210> SEQ ID NO 61
<211> LENGTH: 25
<212> TYPE: DNA
<213> ORGANISM: Homo sapiens
<220> FEATURE:
<221> NAME/KEY: misc_feature
<222> LOCATION: (1)...(25)
<223> OTHER INFORMATION: n is a, t, c, or g.

<400> SEQUENCE: 61
tgatgaagat gananncngn ngcga                                        25

<210> SEQ ID NO 62
<211> LENGTH: 36
<212> TYPE: DNA
<213> ORGANISM: Homo sapiens

<400> SEQUENCE: 62
aatgatgaag atgaagatgt gaggcgggaa agacag                            36

<210> SEQ ID NO 63
<211> LENGTH: 12
<212> TYPE: PRT
<213> ORGANISM: Homo sapiens

<400> SEQUENCE: 63

Asn Asp Glu Asp Glu Asp Val Arg Arg Glu Arg Gln
1               5                   10

<210> SEQ ID NO 64
<211> LENGTH: 12
<212> TYPE: PRT
<213> ORGANISM: Mus musculus

<400> SEQUENCE: 64

Asn Asp Glu Asp Glu Asp Val Arg Arg Glu Arg Gln
1               5                   10

<210> SEQ ID NO 65
<211> LENGTH: 10
<212> TYPE: PRT
<213> ORGANISM: Homo sapiens

<400> SEQUENCE: 65
```

```
Asn Asp Glu Asp Val Arg Arg Glu Arg Gln
1               5                   10
```

```
<210> SEQ ID NO 66
<211> LENGTH: 15
<212> TYPE: PRT
<213> ORGANISM: Caenorhabditis elegans

<400> SEQUENCE: 66
```

```
Asp Glu Arg Asp Val Glu Asp Ser Asp Val Ile Ala Glu Lys Ser
1               5                   10                  15
```

```
<210> SEQ ID NO 67
<211> LENGTH: 30
<212> TYPE: DNA
<213> ORGANISM: Homo sapiens

<400> SEQUENCE: 67
aatgatgaag atgtgaggcg ggaaagacag                                         30

<210> SEQ ID NO 68
<211> LENGTH: 14
<212> TYPE: DNA
<213> ORGANISM: Homo sapiens

<400> SEQUENCE: 68
agttgtacga atag                                                         14

<210> SEQ ID NO 69
<211> LENGTH: 14
<212> TYPE: DNA
<213> ORGANISM: Homo sapiens
<220> FEATURE:
<221> NAME/KEY: misc_feature
<222> LOCATION: (1)...(14)
<223> OTHER INFORMATION: n is t or c.

<400> SEQUENCE: 69
agttgtanga atag                                                         14

<210> SEQ ID NO 70
<211> LENGTH: 20
<212> TYPE: DNA
<213> ORGANISM: Homo sapiens

<400> SEQUENCE: 70
ggctggatta gcagtcctca                                                   20

<210> SEQ ID NO 71
<211> LENGTH: 20
<212> TYPE: DNA
<213> ORGANISM: Homo sapiens

<400> SEQUENCE: 71
ggatttccca gatcccagtg                                                   20

<210> SEQ ID NO 72
<211> LENGTH: 20
<212> TYPE: DNA
<213> ORGANISM: Homo sapiens

<400> SEQUENCE: 72
gacagacttg gcatgaagca                                                   20
```

```
<210> SEQ ID NO 73
<211> LENGTH: 20
<212> TYPE: DNA
<213> ORGANISM: Homo sapiens

<400> SEQUENCE: 73
gcacttggca gtcacttctg                                              20

<210> SEQ ID NO 74
<211> LENGTH: 20
<212> TYPE: DNA
<213> ORGANISM: Homo sapiens

<400> SEQUENCE: 74
cgtttctcca ctgtcccatt                                              20

<210> SEQ ID NO 75
<211> LENGTH: 20
<212> TYPE: DNA
<213> ORGANISM: Homo sapiens

<400> SEQUENCE: 75
acttcaagga cccagcttcc                                              20

<210> SEQ ID NO 76
<211> LENGTH: 24
<212> TYPE: DNA
<213> ORGANISM: Homo sapiens

<400> SEQUENCE: 76
tcggtttctt gtttgttaaa ctca                                         24

<210> SEQ ID NO 77
<211> LENGTH: 20
<212> TYPE: DNA
<213> ORGANISM: Homo sapiens

<400> SEQUENCE: 77
tcccaaggct ttgagatgac                                              20

<210> SEQ ID NO 78
<211> LENGTH: 19
<212> TYPE: DNA
<213> ORGANISM: Homo sapiens

<400> SEQUENCE: 78
ggctccaaag cccttgtaa                                               19

<210> SEQ ID NO 79
<211> LENGTH: 20
<212> TYPE: DNA
<213> ORGANISM: Homo sapiens

<400> SEQUENCE: 79
gctgctgtga tggggtatct                                              20

<210> SEQ ID NO 80
<211> LENGTH: 25
<212> TYPE: DNA
<213> ORGANISM: Homo sapiens

<400> SEQUENCE: 80
tttgtaaatt ttgtagtgct cctca                                        25
```

```
<210> SEQ ID NO 81
<211> LENGTH: 20
<212> TYPE: DNA
<213> ORGANISM: Homo sapiens

<400> SEQUENCE: 81
tagtcagccc ttgcctccta                                               20

<210> SEQ ID NO 82
<211> LENGTH: 20
<212> TYPE: DNA
<213> ORGANISM: Homo sapiens

<400> SEQUENCE: 82
aaagggcttt ggtaagggta                                               20

<210> SEQ ID NO 83
<211> LENGTH: 20
<212> TYPE: DNA
<213> ORGANISM: Homo sapiens

<400> SEQUENCE: 83
gatgtggtgc tccctctagc                                               20

<210> SEQ ID NO 84
<211> LENGTH: 20
<212> TYPE: DNA
<213> ORGANISM: Homo sapiens

<400> SEQUENCE: 84
caagtgagtg cttgggattg                                               20

<210> SEQ ID NO 85
<211> LENGTH: 21
<212> TYPE: DNA
<213> ORGANISM: Homo sapiens

<400> SEQUENCE: 85
gcaaattcaa atttctccag g                                             21

<210> SEQ ID NO 86
<211> LENGTH: 20
<212> TYPE: DNA
<213> ORGANISM: Homo sapiens

<400> SEQUENCE: 86
tcaaggagga aatggacctg                                               20

<210> SEQ ID NO 87
<211> LENGTH: 20
<212> TYPE: DNA
<213> ORGANISM: Homo sapiens

<400> SEQUENCE: 87
ctgaaagttc aagcgcagtg                                               20

<210> SEQ ID NO 88
<211> LENGTH: 20
<212> TYPE: DNA
<213> ORGANISM: Homo sapiens

<400> SEQUENCE: 88
tgcagactga atggagcatc                                               20
```

```
<210> SEQ ID NO 89
<211> LENGTH: 20
<212> TYPE: DNA
<213> ORGANISM: Homo sapiens

<400> SEQUENCE: 89
gccaggggac actgtattct                                              20

<210> SEQ ID NO 90
<211> LENGTH: 20
<212> TYPE: DNA
<213> ORGANISM: Homo sapiens

<400> SEQUENCE: 90
aggtcctctg ccttcactca                                              20

<210> SEQ ID NO 91
<211> LENGTH: 20
<212> TYPE: DNA
<213> ORGANISM: Homo sapiens

<400> SEQUENCE: 91
ccagtgctta cccctgctaa                                              20

<210> SEQ ID NO 92
<211> LENGTH: 21
<212> TYPE: DNA
<213> ORGANISM: Homo sapiens

<400> SEQUENCE: 92
cacacaacag agcttcttgg a                                            21

<210> SEQ ID NO 93
<211> LENGTH: 20
<212> TYPE: DNA
<213> ORGANISM: Homo sapiens

<400> SEQUENCE: 93
acctggaaca ggtgtggtgt                                              20

<210> SEQ ID NO 94
<211> LENGTH: 21
<212> TYPE: DNA
<213> ORGANISM: Homo sapiens

<400> SEQUENCE: 94
gggctaacat gccactcagt a                                            21

<210> SEQ ID NO 95
<211> LENGTH: 20
<212> TYPE: DNA
<213> ORGANISM: Homo sapiens

<400> SEQUENCE: 95
gtttgttgca gatggggaag                                              20

<210> SEQ ID NO 96
<211> LENGTH: 20
<212> TYPE: DNA
<213> ORGANISM: Homo sapiens

<400> SEQUENCE: 96
caccagaaga aggagcatgg                                              20
```

```
<210> SEQ ID NO 97
<211> LENGTH: 20
<212> TYPE: DNA
<213> ORGANISM: Homo sapiens

<400> SEQUENCE: 97
ctggactcgt agggatttgc                                               20

<210> SEQ ID NO 98
<211> LENGTH: 21
<212> TYPE: DNA
<213> ORGANISM: Homo sapiens

<400> SEQUENCE: 98
gcctgtcaca gagaaatgct t                                             21

<210> SEQ ID NO 99
<211> LENGTH: 21
<212> TYPE: DNA
<213> ORGANISM: Homo sapiens

<400> SEQUENCE: 99
ttacggaatg atcctgtgct c                                             21

<210> SEQ ID NO 100
<211> LENGTH: 20
<212> TYPE: DNA
<213> ORGANISM: Homo sapiens

<400> SEQUENCE: 100
agtcaggttt ccggtcacac                                               20

<210> SEQ ID NO 101
<211> LENGTH: 22
<212> TYPE: DNA
<213> ORGANISM: Homo sapiens

<400> SEQUENCE: 101
ccgttcctta tatcctcagg tg                                            22

<210> SEQ ID NO 102
<211> LENGTH: 21
<212> TYPE: DNA
<213> ORGANISM: Homo sapiens

<400> SEQUENCE: 102
ccttgtacac actcgcactg a                                             21

<210> SEQ ID NO 103
<211> LENGTH: 20
<212> TYPE: DNA
<213> ORGANISM: Homo sapiens

<400> SEQUENCE: 103
tgttgtccac aggttccaga                                               20

<210> SEQ ID NO 104
<211> LENGTH: 20
<212> TYPE: DNA
<213> ORGANISM: Homo sapiens

<400> SEQUENCE: 104
tgaggtttat gggcatggtt                                               20
```

```
<210> SEQ ID NO 105
<211> LENGTH: 20
<212> TYPE: DNA
<213> ORGANISM: Homo sapiens

<400> SEQUENCE: 105
atgtttttcc ttggctgtgc                                              20

<210> SEQ ID NO 106
<211> LENGTH: 20
<212> TYPE: DNA
<213> ORGANISM: Homo sapiens

<400> SEQUENCE: 106
atctgccctt tcttgtctga                                              20

<210> SEQ ID NO 107
<211> LENGTH: 20
<212> TYPE: DNA
<213> ORGANISM: Homo sapiens

<400> SEQUENCE: 107
agggagctgc acagtggata                                              20

<210> SEQ ID NO 108
<211> LENGTH: 24
<212> TYPE: DNA
<213> ORGANISM: Homo sapiens

<400> SEQUENCE: 108
tcactcccat atttcagaac ttga                                         24

<210> SEQ ID NO 109
<211> LENGTH: 22
<212> TYPE: DNA
<213> ORGANISM: Homo sapiens

<400> SEQUENCE: 109
tgtttattgg aagatcggtg aa                                           22

<210> SEQ ID NO 110
<211> LENGTH: 25
<212> TYPE: DNA
<213> ORGANISM: Homo sapiens

<400> SEQUENCE: 110
cgttagagac tgaatctttg tcctg                                        25

<210> SEQ ID NO 111
<211> LENGTH: 20
<212> TYPE: DNA
<213> ORGANISM: Homo sapiens

<400> SEQUENCE: 111
agtcctgcct tccacagttg                                              20

<210> SEQ ID NO 112
<211> LENGTH: 21
<212> TYPE: DNA
<213> ORGANISM: Homo sapiens

<400> SEQUENCE: 112
ggtagttacg tgttaggggc a                                            21
```

```
<210> SEQ ID NO 113
<211> LENGTH: 21
<212> TYPE: DNA
<213> ORGANISM: Homo sapiens

<400> SEQUENCE: 113
caggaacatt aggccagatt g                                      21

<210> SEQ ID NO 114
<211> LENGTH: 23
<212> TYPE: DNA
<213> ORGANISM: Homo sapiens

<400> SEQUENCE: 114
catgtatgtg taggacagca tga                                    23

<210> SEQ ID NO 115
<211> LENGTH: 21
<212> TYPE: DNA
<213> ORGANISM: Homo sapiens

<400> SEQUENCE: 115
ctgtttcaaa gatgcttctg c                                      21

<210> SEQ ID NO 116
<211> LENGTH: 20
<212> TYPE: DNA
<213> ORGANISM: Homo sapiens

<400> SEQUENCE: 116
cctaggaagc tggaatgctg                                        20

<210> SEQ ID NO 117
<211> LENGTH: 20
<212> TYPE: DNA
<213> ORGANISM: Homo sapiens

<400> SEQUENCE: 117
gggttcccag ggttcagtat                                        20

<210> SEQ ID NO 118
<211> LENGTH: 23
<212> TYPE: DNA
<213> ORGANISM: Homo sapiens

<400> SEQUENCE: 118
cttgacctaa tttcaacatc tgg                                    23

<210> SEQ ID NO 119
<211> LENGTH: 20
<212> TYPE: DNA
<213> ORGANISM: Homo sapiens

<400> SEQUENCE: 119
atccccaact caaaaccaca                                        20

<210> SEQ ID NO 120
<211> LENGTH: 21
<212> TYPE: DNA
<213> ORGANISM: Homo sapiens

<400> SEQUENCE: 120
aagtccaatt tagcccacgt t                                      21
```

```
<210> SEQ ID NO 121
<211> LENGTH: 20
<212> TYPE: DNA
<213> ORGANISM: Homo sapiens

<400> SEQUENCE: 121
ccagccattc aaaattctcc                                              20

<210> SEQ ID NO 122
<211> LENGTH: 20
<212> TYPE: DNA
<213> ORGANISM: Homo sapiens

<400> SEQUENCE: 122
ggtgcaggtc aatttccaat                                              20

<210> SEQ ID NO 123
<211> LENGTH: 20
<212> TYPE: DNA
<213> ORGANISM: Homo sapiens

<400> SEQUENCE: 123
ccccttcacc accattacaa                                              20

<210> SEQ ID NO 124
<211> LENGTH: 20
<212> TYPE: DNA
<213> ORGANISM: Homo sapiens

<400> SEQUENCE: 124
tgtccaagga aaagcctcac                                              20

<210> SEQ ID NO 125
<211> LENGTH: 20
<212> TYPE: DNA
<213> ORGANISM: Homo sapiens

<400> SEQUENCE: 125
aggacctctt gccagactca                                              20

<210> SEQ ID NO 126
<211> LENGTH: 20
<212> TYPE: DNA
<213> ORGANISM: Homo sapiens

<400> SEQUENCE: 126
aggagatgac acaggccaag                                              20

<210> SEQ ID NO 127
<211> LENGTH: 20
<212> TYPE: DNA
<213> ORGANISM: Homo sapiens

<400> SEQUENCE: 127
cgcacacctc tgaagctacc                                              20

<210> SEQ ID NO 128
<211> LENGTH: 20
<212> TYPE: DNA
<213> ORGANISM: Homo sapiens

<400> SEQUENCE: 128
acctcactca cacctgggaa                                              20
```

```
<210> SEQ ID NO 129
<211> LENGTH: 20
<212> TYPE: DNA
<213> ORGANISM: Homo sapiens

<400> SEQUENCE: 129
gcctcctgcc tgaaccttat                                                   20

<210> SEQ ID NO 130
<211> LENGTH: 23
<212> TYPE: DNA
<213> ORGANISM: Homo sapiens

<400> SEQUENCE: 130
caaaatcatg acaccaagtt gag                                               23

<210> SEQ ID NO 131
<211> LENGTH: 20
<212> TYPE: DNA
<213> ORGANISM: Homo sapiens

<400> SEQUENCE: 131
catgcacatg cacacacata                                                   20

<210> SEQ ID NO 132
<211> LENGTH: 20
<212> TYPE: DNA
<213> ORGANISM: Homo sapiens

<400> SEQUENCE: 132
ccttagcccg tgttgagcta                                                   20

<210> SEQ ID NO 133
<211> LENGTH: 21
<212> TYPE: DNA
<213> ORGANISM: Homo sapiens

<400> SEQUENCE: 133
tgcttttatt cagggactcc a                                                 21

<210> SEQ ID NO 134
<211> LENGTH: 20
<212> TYPE: DNA
<213> ORGANISM: Homo sapiens

<400> SEQUENCE: 134
cccatgcact gcagagattc                                                   20

<210> SEQ ID NO 135
<211> LENGTH: 19
<212> TYPE: DNA
<213> ORGANISM: Homo sapiens

<400> SEQUENCE: 135
aaggcaggag acatcgctt                                                    19

<210> SEQ ID NO 136
<211> LENGTH: 20
<212> TYPE: DNA
<213> ORGANISM: Homo sapiens

<400> SEQUENCE: 136
gggatcagca tggtttccta                                                   20
```

```
<210> SEQ ID NO 137
<211> LENGTH: 20
<212> TYPE: DNA
<213> ORGANISM: Homo sapiens

<400> SEQUENCE: 137
gcttaagtcc cactcctccc                                              20

<210> SEQ ID NO 138
<211> LENGTH: 20
<212> TYPE: DNA
<213> ORGANISM: Homo sapiens

<400> SEQUENCE: 138
attttcctcc gcatgtgtgt                                              20

<210> SEQ ID NO 139
<211> LENGTH: 20
<212> TYPE: DNA
<213> ORGANISM: Homo sapiens

<400> SEQUENCE: 139
tcacagaagc ctagccatga                                              20

<210> SEQ ID NO 140
<211> LENGTH: 20
<212> TYPE: DNA
<213> ORGANISM: Homo sapiens

<400> SEQUENCE: 140
aacagagcag ggagatggtg                                              20

<210> SEQ ID NO 141
<211> LENGTH: 20
<212> TYPE: DNA
<213> ORGANISM: Homo sapiens

<400> SEQUENCE: 141
tctgcacctc tcctcctctg                                              20

<210> SEQ ID NO 142
<211> LENGTH: 20
<212> TYPE: DNA
<213> ORGANISM: Homo sapiens

<400> SEQUENCE: 142
actggggcca acattaatca                                              20

<210> SEQ ID NO 143
<211> LENGTH: 20
<212> TYPE: DNA
<213> ORGANISM: Homo sapiens

<400> SEQUENCE: 143
cttccccatc tgcaacaaac                                              20

<210> SEQ ID NO 144
<211> LENGTH: 20
<212> TYPE: DNA
<213> ORGANISM: Homo sapiens

<400> SEQUENCE: 144
gctaaaggcc atccaaagaa                                              20
```

```
<210> SEQ ID NO 145
<211> LENGTH: 20
<212> TYPE: DNA
<213> ORGANISM: Homo sapiens

<400> SEQUENCE: 145
tcaagtgcat ctgggcataa                                               20

<210> SEQ ID NO 146
<211> LENGTH: 20
<212> TYPE: DNA
<213> ORGANISM: Homo sapiens

<400> SEQUENCE: 146
tctgaagtcc attcccttgg                                               20

<210> SEQ ID NO 147
<211> LENGTH: 20
<212> TYPE: DNA
<213> ORGANISM: Homo sapiens

<400> SEQUENCE: 147
caatgtggca tgcagttgat                                               20

<210> SEQ ID NO 148
<211> LENGTH: 19
<212> TYPE: DNA
<213> ORGANISM: Homo sapiens

<400> SEQUENCE: 148
gaagctacca gcccatcct                                                19

<210> SEQ ID NO 149
<211> LENGTH: 20
<212> TYPE: DNA
<213> ORGANISM: Homo sapiens

<400> SEQUENCE: 149
catttccccc actgtttcag                                               20

<210> SEQ ID NO 150
<211> LENGTH: 20
<212> TYPE: DNA
<213> ORGANISM: Homo sapiens

<400> SEQUENCE: 150
ccaaggcttt cttcaatcca                                               20

<210> SEQ ID NO 151
<211> LENGTH: 20
<212> TYPE: DNA
<213> ORGANISM: Homo sapiens

<400> SEQUENCE: 151
gatccgttta acctgccaac                                               20

<210> SEQ ID NO 152
<211> LENGTH: 19
<212> TYPE: DNA
<213> ORGANISM: Homo sapiens

<400> SEQUENCE: 152
atgcccctgc caactttac                                                19
```

```
<210> SEQ ID NO 153
<211> LENGTH: 20
<212> TYPE: DNA
<213> ORGANISM: Homo sapiens

<400> SEQUENCE: 153
ctctgcagct gttccctac                                                  20

<210> SEQ ID NO 154
<211> LENGTH: 20
<212> TYPE: DNA
<213> ORGANISM: Homo sapiens

<400> SEQUENCE: 154
tatcaatcca tggccctgac                                                 20

<210> SEQ ID NO 155
<211> LENGTH: 20
<212> TYPE: DNA
<213> ORGANISM: Homo sapiens

<400> SEQUENCE: 155
agagtccctg ccctccttct                                                 20

<210> SEQ ID NO 156
<211> LENGTH: 20
<212> TYPE: DNA
<213> ORGANISM: Homo sapiens

<400> SEQUENCE: 156
aaggcagtca gcagtgtcaa                                                 20

<210> SEQ ID NO 157
<211> LENGTH: 20
<212> TYPE: DNA
<213> ORGANISM: Homo sapiens

<400> SEQUENCE: 157
ggggaacatc ctgtgcttag                                                 20

<210> SEQ ID NO 158
<211> LENGTH: 20
<212> TYPE: DNA
<213> ORGANISM: Homo sapiens

<400> SEQUENCE: 158
ccattggtga gtgtttccct                                                 20

<210> SEQ ID NO 159
<211> LENGTH: 20
<212> TYPE: DNA
<213> ORGANISM: Homo sapiens

<400> SEQUENCE: 159
agtcagcaaa ctgctgggtt                                                 20

<210> SEQ ID NO 160
<211> LENGTH: 20
<212> TYPE: DNA
<213> ORGANISM: Homo sapiens

<400> SEQUENCE: 160
attgctccat cctggcataa                                                 20
```

-continued

```
<210> SEQ ID NO 161
<211> LENGTH: 23
<212> TYPE: DNA
<213> ORGANISM: Homo sapiens

<400> SEQUENCE: 161
tcatggatga ttttatgtgc ttc                                              23

<210> SEQ ID NO 162
<211> LENGTH: 20
<212> TYPE: DNA
<213> ORGANISM: Homo sapiens

<400> SEQUENCE: 162
gcgtgtggaa aagccataag                                                  20

<210> SEQ ID NO 163
<211> LENGTH: 20
<212> TYPE: DNA
<213> ORGANISM: Homo sapiens

<400> SEQUENCE: 163
gccaatcata caacagccct                                                  20

<210> SEQ ID NO 164
<211> LENGTH: 23
<212> TYPE: DNA
<213> ORGANISM: Homo sapiens

<400> SEQUENCE: 164
tgatcgcata ttctacttgg aaa                                              23

<210> SEQ ID NO 165
<211> LENGTH: 22
<212> TYPE: DNA
<213> ORGANISM: Homo sapiens

<400> SEQUENCE: 165
tccctttatt ttagaggcac ca                                               22

<210> SEQ ID NO 166
<211> LENGTH: 21
<212> TYPE: DNA
<213> ORGANISM: Homo sapiens

<400> SEQUENCE: 166
gatcaggaat tcaagcacca a                                                21

<210> SEQ ID NO 167
<211> LENGTH: 24
<212> TYPE: DNA
<213> ORGANISM: Homo sapiens

<400> SEQUENCE: 167
tgggttccat aatagagttt caca                                             24

<210> SEQ ID NO 168
<211> LENGTH: 22
<212> TYPE: DNA
<213> ORGANISM: Homo sapiens

<400> SEQUENCE: 168
tgtcagctgt tactggaagt gg                                               22
```

-continued

```
<210> SEQ ID NO 169
<211> LENGTH: 22
<212> TYPE: DNA
<213> ORGANISM: Homo sapiens

<400> SEQUENCE: 169
tgtcagctgc tgctggaagt gg                                                  22

<210> SEQ ID NO 170
<211> LENGTH: 21
<212> TYPE: DNA
<213> ORGANISM: Homo sapiens

<400> SEQUENCE: 170
aggagctggc cgaagccaca a                                                   21

<210> SEQ ID NO 171
<211> LENGTH: 21
<212> TYPE: DNA
<213> ORGANISM: Homo sapiens

<400> SEQUENCE: 171
aggagctggc tgaagccaca a                                                   21

<210> SEQ ID NO 172
<211> LENGTH: 21
<212> TYPE: DNA
<213> ORGANISM: Homo sapiens

<400> SEQUENCE: 172
aatgatgcca ccaaacaaat g                                                   21

<210> SEQ ID NO 173
<211> LENGTH: 21
<212> TYPE: DNA
<213> ORGANISM: Homo sapiens

<400> SEQUENCE: 173
aatgatgcca tcaaacaaat g                                                   21

<210> SEQ ID NO 174
<211> LENGTH: 21
<212> TYPE: DNA
<213> ORGANISM: Homo sapiens

<400> SEQUENCE: 174
gaggtggctc cgatgaccac a                                                   21

<210> SEQ ID NO 175
<211> LENGTH: 21
<212> TYPE: DNA
<213> ORGANISM: Homo sapiens

<400> SEQUENCE: 175
gaggtggctc tgatgaccac a                                                   21

<210> SEQ ID NO 176
<211> LENGTH: 21
<212> TYPE: DNA
<213> ORGANISM: Homo sapiens

<400> SEQUENCE: 176
ttccttaaca gaaatagtat c                                                   21
```

```
<210> SEQ ID NO 177
<211> LENGTH: 21
<212> TYPE: DNA
<213> ORGANISM: Homo sapiens

<400> SEQUENCE: 177
ttccttaaca aaatagtat c                                              21

<210> SEQ ID NO 178
<211> LENGTH: 21
<212> TYPE: DNA
<213> ORGANISM: Homo sapiens

<400> SEQUENCE: 178
ggaagtgttc caaaagagaa a                                             21

<210> SEQ ID NO 179
<211> LENGTH: 21
<212> TYPE: DNA
<213> ORGANISM: Homo sapiens

<400> SEQUENCE: 179
ggaagtgttc taaaagagaa a                                             21

<210> SEQ ID NO 180
<211> LENGTH: 21
<212> TYPE: DNA
<213> ORGANISM: Homo sapiens

<400> SEQUENCE: 180
agtaaagagg gactagactt t                                             21

<210> SEQ ID NO 181
<211> LENGTH: 21
<212> TYPE: DNA
<213> ORGANISM: Homo sapiens

<400> SEQUENCE: 181
agtaaagagg aactagactt t                                             21

<210> SEQ ID NO 182
<211> LENGTH: 21
<212> TYPE: DNA
<213> ORGANISM: Homo sapiens

<400> SEQUENCE: 182
gcctacttgc aggatgtggt g                                             21

<210> SEQ ID NO 183
<211> LENGTH: 21
<212> TYPE: DNA
<213> ORGANISM: Homo sapiens

<400> SEQUENCE: 183
gcctacttgc gggatgtggt g                                             21

<210> SEQ ID NO 184
<211> LENGTH: 23
<212> TYPE: DNA
<213> ORGANISM: Homo sapiens

<400> SEQUENCE: 184
cctcattcct cttcttgtga gcg                                           23
```

```
<210> SEQ ID NO 185
<211> LENGTH: 20
<212> TYPE: DNA
<213> ORGANISM: Homo sapiens

<400> SEQUENCE: 185
cctcattcct cttgtgagcg                                              20

<210> SEQ ID NO 186
<211> LENGTH: 21
<212> TYPE: DNA
<213> ORGANISM: Homo sapiens

<400> SEQUENCE: 186
gcaggactac gtgggcttca c                                            21

<210> SEQ ID NO 187
<211> LENGTH: 21
<212> TYPE: DNA
<213> ORGANISM: Homo sapiens

<400> SEQUENCE: 187
gcaggactac atgggcttca c                                            21

<210> SEQ ID NO 188
<211> LENGTH: 21
<212> TYPE: DNA
<213> ORGANISM: Homo sapiens

<400> SEQUENCE: 188
aaaagtctac cgagatggga t                                            21

<210> SEQ ID NO 189
<211> LENGTH: 21
<212> TYPE: DNA
<213> ORGANISM: Homo sapiens

<400> SEQUENCE: 189
aaaagtctac tgagatggga t                                            21

<210> SEQ ID NO 190
<211> LENGTH: 21
<212> TYPE: DNA
<213> ORGANISM: Homo sapiens

<400> SEQUENCE: 190
ggccagatca cctccttcct g                                            21

<210> SEQ ID NO 191
<211> LENGTH: 21
<212> TYPE: DNA
<213> ORGANISM: Homo sapiens

<400> SEQUENCE: 191
ggccagatca tctccttcct g                                            21

<210> SEQ ID NO 192
<211> LENGTH: 21
<212> TYPE: DNA
<213> ORGANISM: Homo sapiens

<400> SEQUENCE: 192
acacaccaca tggatgaagc g                                            21
```

```
<210> SEQ ID NO 193
<211> LENGTH: 21
<212> TYPE: DNA
<213> ORGANISM: Homo sapiens

<400> SEQUENCE: 193
acacaccaca cggatgaagc g                                              21

<210> SEQ ID NO 194
<211> LENGTH: 21
<212> TYPE: DNA
<213> ORGANISM: Homo sapiens

<400> SEQUENCE: 194
cctggaagaa gtaagttaag t                                              21

<210> SEQ ID NO 195
<211> LENGTH: 21
<212> TYPE: DNA
<213> ORGANISM: Homo sapiens

<400> SEQUENCE: 195
cctggaagaa ctaagttaag t                                              21

<210> SEQ ID NO 196
<211> LENGTH: 21
<212> TYPE: DNA
<213> ORGANISM: Homo sapiens

<400> SEQUENCE: 196
gctgcctgtg tgtcccccag g                                              21

<210> SEQ ID NO 197
<211> LENGTH: 21
<212> TYPE: DNA
<213> ORGANISM: Homo sapiens

<400> SEQUENCE: 197
gctgcctgtg cgtcccccag g                                              21

<210> SEQ ID NO 198
<211> LENGTH: 22
<212> TYPE: DNA
<213> ORGANISM: Homo sapiens

<400> SEQUENCE: 198
tagccattat ggaattactg ct                                             22

<210> SEQ ID NO 199
<211> LENGTH: 21
<212> TYPE: DNA
<213> ORGANISM: Homo sapiens

<400> SEQUENCE: 199
tagccattat caattactgc t                                              21

<210> SEQ ID NO 200
<211> LENGTH: 26
<212> TYPE: DNA
<213> ORGANISM: Homo sapiens

<400> SEQUENCE: 200
gatgaagatg aagatgtgag gcggga                                         26
```

```
<210> SEQ ID NO 201
<211> LENGTH: 20
<212> TYPE: DNA
<213> ORGANISM: Homo sapiens

<400> SEQUENCE: 201
gatgaagatg tgaggcggga                                            20

<210> SEQ ID NO 202
<211> LENGTH: 21
<212> TYPE: DNA
<213> ORGANISM: Homo sapiens

<400> SEQUENCE: 202
aatagttgta cgaatagcag g                                          21

<210> SEQ ID NO 203
<211> LENGTH: 21
<212> TYPE: DNA
<213> ORGANISM: Homo sapiens

<400> SEQUENCE: 203
aatagttgta tgaatagcag g                                          21

<210> SEQ ID NO 204
<211> LENGTH: 21
<212> TYPE: DNA
<213> ORGANISM: Homo sapiens

<400> SEQUENCE: 204
acacgctggg ggtgctggct g                                          21

<210> SEQ ID NO 205
<211> LENGTH: 21
<212> TYPE: DNA
<213> ORGANISM: Homo sapiens

<400> SEQUENCE: 205
acacgctggg cgtgctggct g                                          21

<210> SEQ ID NO 206
<211> LENGTH: 20
<212> TYPE: DNA
<213> ORGANISM: Homo sapiens

<400> SEQUENCE: 206
gaccagccac ggcgtccctg                                            20

<210> SEQ ID NO 207
<211> LENGTH: 21
<212> TYPE: DNA
<213> ORGANISM: Homo sapiens

<400> SEQUENCE: 207
gaccagccac gggcgtccct g                                          21

<210> SEQ ID NO 208
<211> LENGTH: 22
<212> TYPE: DNA
<213> ORGANISM: Homo sapiens

<400> SEQUENCE: 208
cattttctta gaaaagagag gt                                         22
```

```
<210> SEQ ID NO 209
<211> LENGTH: 22
<212> TYPE: DNA
<213> ORGANISM: Homo sapiens

<400> SEQUENCE: 209
cattttctta gagaagagag gt                                              22

<210> SEQ ID NO 210
<211> LENGTH: 21
<212> TYPE: DNA
<213> ORGANISM: Homo sapiens

<400> SEQUENCE: 210
gaaaattagt atgtaaggaa g                                               21

<210> SEQ ID NO 211
<211> LENGTH: 21
<212> TYPE: DNA
<213> ORGANISM: Homo sapiens

<400> SEQUENCE: 211
gaaaattagt ctgtaaggaa g                                               21

<210> SEQ ID NO 212
<211> LENGTH: 25
<212> TYPE: DNA
<213> ORGANISM: Homo sapiens

<400> SEQUENCE: 212
cctccgcctg ccaggttcag cgatt                                           25

<210> SEQ ID NO 213
<211> LENGTH: 25
<212> TYPE: DNA
<213> ORGANISM: Homo sapiens

<400> SEQUENCE: 213
cctccgcctg ccgggttcag cgatt                                           25

<210> SEQ ID NO 214
<211> LENGTH: 25
<212> TYPE: DNA
<213> ORGANISM: Homo sapiens

<400> SEQUENCE: 214
tatgtgctga ccatgggagc ttgtt                                           25

<210> SEQ ID NO 215
<211> LENGTH: 25
<212> TYPE: DNA
<213> ORGANISM: Homo sapiens

<400> SEQUENCE: 215
tatgtgctga ccgtgggagc ttgtt                                           25

<210> SEQ ID NO 216
<211> LENGTH: 21
<212> TYPE: DNA
<213> ORGANISM: Homo sapiens

<400> SEQUENCE: 216
gtgacaccca acggagtagg g                                               21
```

```
<210> SEQ ID NO 217
<211> LENGTH: 21
<212> TYPE: DNA
<213> ORGANISM: Homo sapiens

<400> SEQUENCE: 217
gtgacaccca gcggagtagg g                                      21

<210> SEQ ID NO 218
<211> LENGTH: 21
<212> TYPE: DNA
<213> ORGANISM: Homo sapiens

<400> SEQUENCE: 218
agtatccctt gttcacgaga a                                      21

<210> SEQ ID NO 219
<211> LENGTH: 25
<212> TYPE: DNA
<213> ORGANISM: Homo sapiens

<400> SEQUENCE: 219
agtatccctc ccttgttcac gagaa                                  25

<210> SEQ ID NO 220
<211> LENGTH: 21
<212> TYPE: DNA
<213> ORGANISM: Homo sapiens

<400> SEQUENCE: 220
ctgggttcct gtatcacaac c                                      21

<210> SEQ ID NO 221
<211> LENGTH: 21
<212> TYPE: DNA
<213> ORGANISM: Homo sapiens

<400> SEQUENCE: 221
ctgggttcct atatcacaac c                                      21

<210> SEQ ID NO 222
<211> LENGTH: 21
<212> TYPE: DNA
<213> ORGANISM: Homo sapiens

<400> SEQUENCE: 222
ggcctaccaa gggagaaact g                                      21

<210> SEQ ID NO 223
<211> LENGTH: 21
<212> TYPE: DNA
<213> ORGANISM: Homo sapiens

<400> SEQUENCE: 223
ggcctaccaa aggagaaact g                                      21

<210> SEQ ID NO 224
<211> LENGTH: 20
<212> TYPE: DNA
<213> ORGANISM: Homo sapiens

<400> SEQUENCE: 224
tttaaagggg gtgattagga                                        20
```

```
<210> SEQ ID NO 225
<211> LENGTH: 20
<212> TYPE: DNA
<213> ORGANISM: Homo sapiens

<400> SEQUENCE: 225
tttaaagggg ttgattagga                                              20

<210> SEQ ID NO 226
<211> LENGTH: 22
<212> TYPE: DNA
<213> ORGANISM: Homo sapiens

<400> SEQUENCE: 226
gaagaaattt gttttttttga tt                                          22

<210> SEQ ID NO 227
<211> LENGTH: 22
<212> TYPE: DNA
<213> ORGANISM: Homo sapiens

<400> SEQUENCE: 227
gaagaaattt ttttttttga tt                                           22

<210> SEQ ID NO 228
<211> LENGTH: 21
<212> TYPE: DNA
<213> ORGANISM: Homo sapiens

<400> SEQUENCE: 228
gcgggcatcc cgagggaggg g                                            21

<210> SEQ ID NO 229
<211> LENGTH: 21
<212> TYPE: DNA
<213> ORGANISM: Homo sapiens

<400> SEQUENCE: 229
gcgggcatcc tgagggaggg g                                            21

<210> SEQ ID NO 230
<211> LENGTH: 21
<212> TYPE: DNA
<213> ORGANISM: Homo sapiens

<400> SEQUENCE: 230
agggaggggg gctgaagatc a                                            21

<210> SEQ ID NO 231
<211> LENGTH: 21
<212> TYPE: DNA
<213> ORGANISM: Homo sapiens

<400> SEQUENCE: 231
agggaggggg actgaagatc a                                            21

<210> SEQ ID NO 232
<211> LENGTH: 20
<212> TYPE: DNA
<213> ORGANISM: Homo sapiens

<400> SEQUENCE: 232
aggagccaaa cgctcattgt                                              20
```

```
<210> SEQ ID NO 233
<211> LENGTH: 21
<212> TYPE: DNA
<213> ORGANISM: Homo sapiens

<400> SEQUENCE: 233
aggagccaaa gcgctcattg t                                              21

<210> SEQ ID NO 234
<211> LENGTH: 21
<212> TYPE: DNA
<213> ORGANISM: Homo sapiens

<400> SEQUENCE: 234
aagccactgt ttttaaccag t                                              21

<210> SEQ ID NO 235
<211> LENGTH: 21
<212> TYPE: DNA
<213> ORGANISM: Homo sapiens

<400> SEQUENCE: 235
aagccactgt atttaaccag t                                              21

<210> SEQ ID NO 236
<211> LENGTH: 21
<212> TYPE: DNA
<213> ORGANISM: Homo sapiens

<400> SEQUENCE: 236
cgtgggcttc acactcaaga t                                              21

<210> SEQ ID NO 237
<211> LENGTH: 21
<212> TYPE: DNA
<213> ORGANISM: Homo sapiens

<400> SEQUENCE: 237
cgtgggcttc ccactcaaga t                                              21

<210> SEQ ID NO 238
<211> LENGTH: 21
<212> TYPE: DNA
<213> ORGANISM: Homo sapiens

<400> SEQUENCE: 238
tcacactcaa gatcttcgct g                                              21

<210> SEQ ID NO 239
<211> LENGTH: 21
<212> TYPE: DNA
<213> ORGANISM: Homo sapiens

<400> SEQUENCE: 239
tcacactcaa catcttcgct g                                              21

<210> SEQ ID NO 240
<211> LENGTH: 21
<212> TYPE: DNA
<213> ORGANISM: Homo sapiens

<400> SEQUENCE: 240
gcagcctcac ccgctcttcc c                                              21
```

-continued

```
<210> SEQ ID NO 241
<211> LENGTH: 21
<212> TYPE: DNA
<213> ORGANISM: Homo sapiens

<400> SEQUENCE: 241
gcagcctcac tcgctcttcc c                                              21

<210> SEQ ID NO 242
<211> LENGTH: 21
<212> TYPE: DNA
<213> ORGANISM: Homo sapiens

<400> SEQUENCE: 242
agaagagaat atcagaaatc t                                              21

<210> SEQ ID NO 243
<211> LENGTH: 21
<212> TYPE: DNA
<213> ORGANISM: Homo sapiens

<400> SEQUENCE: 243
agaagagaat gtcagaaatc t                                              21

<210> SEQ ID NO 244
<211> LENGTH: 21
<212> TYPE: DNA
<213> ORGANISM: Homo sapiens

<400> SEQUENCE: 244
gcgcagtgcc ctgtgtcctt a                                              21

<210> SEQ ID NO 245
<211> LENGTH: 21
<212> TYPE: DNA
<213> ORGANISM: Homo sapiens

<400> SEQUENCE: 245
gcgcagtgcg ctgtgtcctt a                                              21

<210> SEQ ID NO 246
<211> LENGTH: 21
<212> TYPE: DNA
<213> ORGANISM: Homo sapiens

<400> SEQUENCE: 246
gatctaaggt tgtcattctg g                                              21

<210> SEQ ID NO 247
<211> LENGTH: 21
<212> TYPE: DNA
<213> ORGANISM: Homo sapiens

<400> SEQUENCE: 247
gatctaaggt ggtcattctg g                                              21

<210> SEQ ID NO 248
<211> LENGTH: 23
<212> TYPE: DNA
<213> ORGANISM: Homo sapiens

<400> SEQUENCE: 248
ctcttctgtt agcacagaag aga                                            23
```

-continued

```
<210> SEQ ID NO 249
<211> LENGTH: 23
<212> TYPE: DNA
<213> ORGANISM: Homo sapiens

<400> SEQUENCE: 249
ctcttctgtt atcacagaag aga                                           23

<210> SEQ ID NO 250
<211> LENGTH: 21
<212> TYPE: DNA
<213> ORGANISM: Homo sapiens

<400> SEQUENCE: 250
cattctaggg atcatagcca t                                             21

<210> SEQ ID NO 251
<211> LENGTH: 21
<212> TYPE: DNA
<213> ORGANISM: Homo sapiens

<400> SEQUENCE: 251
cattctaggg gtcatagcca t                                             21

<210> SEQ ID NO 252
<211> LENGTH: 22
<212> TYPE: DNA
<213> ORGANISM: Homo sapiens

<400> SEQUENCE: 252
aagtacagtg ggaggaacag cg                                            22

<210> SEQ ID NO 253
<211> LENGTH: 22
<212> TYPE: DNA
<213> ORGANISM: Homo sapiens

<400> SEQUENCE: 253
aagtacagtg tgaggaacag cg                                            22

<210> SEQ ID NO 254
<211> LENGTH: 22
<212> TYPE: DNA
<213> ORGANISM: Homo sapiens

<400> SEQUENCE: 254
attcctaaaa aatagaaatg ca                                            22

<210> SEQ ID NO 255
<211> LENGTH: 22
<212> TYPE: DNA
<213> ORGANISM: Homo sapiens

<400> SEQUENCE: 255
attcctaaaa agtagaaatg ca                                            22

<210> SEQ ID NO 256
<211> LENGTH: 21
<212> TYPE: DNA
<213> ORGANISM: Homo sapiens

<400> SEQUENCE: 256
ggcccctgcc ttattattac t                                             21
```

```
<210> SEQ ID NO 257
<211> LENGTH: 21
<212> TYPE: DNA
<213> ORGANISM: Homo sapiens

<400> SEQUENCE: 257
ggcccctgcc gtattattac t                                              21

<210> SEQ ID NO 258
<211> LENGTH: 22
<212> TYPE: DNA
<213> ORGANISM: Homo sapiens

<400> SEQUENCE: 258
tgagagaatt acttgaaccc gg                                             22

<210> SEQ ID NO 259
<211> LENGTH: 22
<212> TYPE: DNA
<213> ORGANISM: Homo sapiens

<400> SEQUENCE: 259
tgagagaatt gcttgaaccc gg                                             22

<210> SEQ ID NO 260
<211> LENGTH: 21
<212> TYPE: DNA
<213> ORGANISM: Homo sapiens

<400> SEQUENCE: 260
tttgctgaaa caatcactga c                                              21

<210> SEQ ID NO 261
<211> LENGTH: 21
<212> TYPE: DNA
<213> ORGANISM: Homo sapiens

<400> SEQUENCE: 261
tttgctgaaa taatcactga c                                              21

<210> SEQ ID NO 262
<211> LENGTH: 22
<212> TYPE: DNA
<213> ORGANISM: Homo sapiens

<400> SEQUENCE: 262
aacctcagtt ccctcatctg tg                                             22

<210> SEQ ID NO 263
<211> LENGTH: 22
<212> TYPE: DNA
<213> ORGANISM: Homo sapiens

<400> SEQUENCE: 263
aacctcagtt tcctcatctg tg                                             22

<210> SEQ ID NO 264
<211> LENGTH: 21
<212> TYPE: DNA
<213> ORGANISM: Homo sapiens

<400> SEQUENCE: 264
ctggacacca gaaataatgt c                                              21
```

```
<210> SEQ ID NO 265
<211> LENGTH: 21
<212> TYPE: DNA
<213> ORGANISM: Homo sapiens

<400> SEQUENCE: 265
ctggacacca aaataatgt c                                              21

<210> SEQ ID NO 266
<211> LENGTH: 21
<212> TYPE: DNA
<213> ORGANISM: Homo sapiens

<400> SEQUENCE: 266
tcctatgtgt cctccaccaa t                                             21

<210> SEQ ID NO 267
<211> LENGTH: 21
<212> TYPE: DNA
<213> ORGANISM: Homo sapiens

<400> SEQUENCE: 267
tcctatgtgt gctccaccaa t                                             21

<210> SEQ ID NO 268
<211> LENGTH: 21
<212> TYPE: DNA
<213> ORGANISM: Homo sapiens

<400> SEQUENCE: 268
aagaagtggc ttgtattttg c                                             21

<210> SEQ ID NO 269
<211> LENGTH: 21
<212> TYPE: DNA
<213> ORGANISM: Homo sapiens

<400> SEQUENCE: 269
aagaagtggc ctgtattttg c                                             21

<210> SEQ ID NO 270
<211> LENGTH: 23
<212> TYPE: DNA
<213> ORGANISM: Homo sapiens

<400> SEQUENCE: 270
aactgatttg attggtatag ctg                                           23

<210> SEQ ID NO 271
<211> LENGTH: 23
<212> TYPE: DNA
<213> ORGANISM: Homo sapiens

<400> SEQUENCE: 271
aactgatttg gttggtatag ctg                                           23

<210> SEQ ID NO 272
<211> LENGTH: 21
<212> TYPE: DNA
<213> ORGANISM: Homo sapiens

<400> SEQUENCE: 272
cagggtccaa cccggacctg a                                             21
```

```
<210> SEQ ID NO 273
<211> LENGTH: 21
<212> TYPE: DNA
<213> ORGANISM: Homo sapiens

<400> SEQUENCE: 273
cagggtccaa tccggacctg a                                              21

<210> SEQ ID NO 274
<211> LENGTH: 22
<212> TYPE: DNA
<213> ORGANISM: Homo sapiens

<400> SEQUENCE: 274
ttgggaggct aaggcaggag aa                                             22

<210> SEQ ID NO 275
<211> LENGTH: 22
<212> TYPE: DNA
<213> ORGANISM: Homo sapiens

<400> SEQUENCE: 275
ttgggaggct gaggcaggag aa                                             22

<210> SEQ ID NO 276
<211> LENGTH: 15
<212> TYPE: DNA
<213> ORGANISM: Gallus gallus

<400> SEQUENCE: 276 accagggaa tctcc                                                      15

<210> SEQ ID NO 277
<211> LENGTH: 15
<212> TYPE: DNA
<213> ORGANISM: Gallus gallus

<400> SEQUENCE: 277
accagggaaa tctcc                                                     15

<210> SEQ ID NO 278
<211> LENGTH: 45
<212> TYPE: DNA
<213> ORGANISM: Gallus gallus

<400> SEQUENCE: 278
cgctacccaa caccagggga atctcctggt attgttggaa acttc                    45

<210> SEQ ID NO 279
<211> LENGTH: 15
<212> TYPE: PRT
<213> ORGANISM: Homo sapiens

<400> SEQUENCE: 279

Arg Tyr Pro Thr Pro Gly Glu Ala Pro Gly Val Val Gly Asn Phe
1               5                   10                  15

<210> SEQ ID NO 280
<211> LENGTH: 15
<212> TYPE: PRT
<213> ORGANISM: Mus musculus

<400> SEQUENCE: 280

Arg Tyr Pro Thr Pro Gly Glu Ala Pro Gly Val Val Gly Asn Phe
1               5                   10                  15
```

```
<210> SEQ ID NO 281
<211> LENGTH: 15
<212> TYPE: PRT
<213> ORGANISM: Gallus gallus

<400> SEQUENCE: 281

Arg Tyr Pro Thr Pro Gly Glu Ser Pro Gly Ile Val Gly Asn Phe
1               5                   10                  15

<210> SEQ ID NO 282
<211> LENGTH: 15
<212> TYPE: PRT
<213> ORGANISM: Gallus gallus

<400> SEQUENCE: 282

Arg Tyr Pro Thr Pro Gly Lys Ser Pro Gly Ile Val Gly Asn Phe
1               5                   10                  15

<210> SEQ ID NO 283
<211> LENGTH: 45
<212> TYPE: DNA
<213> ORGANISM: Gallus gallus

<400> SEQUENCE: 283
cgctacccaa caccagggaa atctcctggt attgttggaa acttc              45

<210> SEQ ID NO 284
<211> LENGTH: 19
<212> TYPE: DNA
<213> ORGANISM: Homo sapiens

<400> SEQUENCE: 284
gcgtcaggga tggggacag                                           19

<210> SEQ ID NO 285
<211> LENGTH: 20
<212> TYPE: DNA
<213> ORGANISM: Homo sapiens

<400> SEQUENCE: 285
gcgtcaggga ttggggacag                                          20

<210> SEQ ID NO 286
<211> LENGTH: 17
<212> TYPE: DNA
<213> ORGANISM: Homo sapiens

<400> SEQUENCE: 286
ccacttcggt ctccatg                                             17

<210> SEQ ID NO 287
<211> LENGTH: 17
<212> TYPE: DNA
<213> ORGANISM: Homo sapiens

<400> SEQUENCE: 287
ccacttcgat ctccatg                                             17
```

POLYNUCLEOTIDE ENCODING AN ATP BINDING CASSETTE TRANSPORTER 1 (ABC1) POLYPEPTIDE

This application is a continuation of U.S. Ser. No. 10/452,510, filed 2 Jun. 2003, now abandoned which is a divisional of U.S. Ser. No. 09/526,193, filed 15 Mar. 2000, now U.S. Pat. No. 6,617,122, which claims priority from U.S. Provisional Application No. 60/124,702, filed Mar. 15, 1999, U.S. Provisional Application No. 60/138,048, filed Jun. 8, 1999, U.S. Provisional Application No. 60/139,600, filed Jun. 17, 1999, and U.S. Provisional Application No. 60/151,977, filed Sep. 1, 1999.

BACKGROUND OF THE INVENTION

Low HDL cholesterol (HDL-C), or hypoalphalipoproteinemia, is a blood lipid abnormality which correlates with a high risk of cardiovascular disease (CVD), in particular coronary artery disease (CAD), but also cerebrovascular disease, coronary restenosis, and peripheral vascular disease. HDL, or 'good cholesterol' levels are influenced by both environmental and genetic factors.

Epidemiological studies have consistently demonstrated that plasma HDL-C) concentration is inversely related to the incidence of CAD. HDL-C levels are a strong graded and independent cardiovascular risk factor. Protective effects of an elevated HDL-C persist until 80 years of age. A low HDL-C is associated with an increased CAD risk even with normal (<5.2 mmol/l) total plasma cholesterol levels. Coronary disease risk is increased by 2% in men and 3% in women for every 1 mg/dL (0.026 mmol/l) reduction in HDL-C and in the majority of studies this relationship is statistically significant even after adjustment for other lipid and non-lipid risk factors. Decreased HDL-C levels are the most common lipoprotein abnormality seen in patients with premature CAD. Four percent of patients with premature CAD with have an isolated form of decreased HDL-C levels with no other lipoprotein abnormalities while 25% have low HDL levels with accompanying hypertriglyceridemia.

Even in the face of other dyslipidemias or secondary factors, HDL-C levels are important predictors of CAD. In a cohort of diabetics, those with isolated low HDL cholesterol had a 65% increased death rate compared to diabetics with normal HDL cholesterol levels (>0.9 mmol/l). Furthermore, it has been shown that even within high risk populations, such as those with familial hypercholesterolemia, HDL cholesterol level is an important predictor of CAD. Low HDL cholesterol levels thus constitute a major, independent, risk for CAD.

These findings have led to increased attention to HDL cholesterol levels as a focus for treatment, following the recommendations of the National Cholesterol Education Program. These guidelines suggest that HDL cholesterol values below 0.9 mmol/l confer a significant risk for men and women. As such, nearly half of patients with CAD would have low HDL cholesterol. It is therefore crucial that we obtain a better understanding of factors which contribute to this phenotype. In view of the fact that pharmacological intervention of low HDL cholesterol levels has so far proven unsatisfactory, it is also important to understand the factors that regulate these levels in the circulation as this understanding may reveal new therapeutic targets.

Absolute levels of HDL cholesterol may not always predict risk of CAD. In the case of CETP deficiency, individuals display an increased risk of developing CAD, despite increased HDL cholesterol levels. What seems to be important in this case is the functional activity of the reverse cholesterol transport pathway, the process by which intracellular cholesterol is trafficked out of the cell to acceptor proteins such as ApoAI or HDL. Other important genetic determinants of HDL cholesterol levels, and its inverse relation with CAD, may reside in the processes leading to HDL formation and intracellular cholesterol trafficking and efflux. To date, this process is poorly understood, however, and clearly not all of the components of this pathway have been identified. Thus, defects preventing proper HDL-mediated cholesterol efflux may be important predictors of CAD. Therefore it is critical to identify and understand novel genes involved in the intracellular cholesterol trafficking and efflux pathways.

HDL particles are central to the process of reverse cholesterol transport and thus to the maintenance of tissue cholesterol homeostasis. This process has multiple steps which include the binding of HDL to cell surface components, the acquisition of cholesterol by passive absorption, the esterification of this cholesterol by LCAT and the subsequent transfer of esterified cholesterol by CETP, to VLDL and chylomicron remnants for liver uptake. Each of these steps is known to impact the plasma concentration of HDL.

Changes in genes for ApoAI-CIII, lipoprotein lipase, CETP, hepatic lipase, and LCAT all contribute to determination of HDL-C levels in humans. One rare form of genetic HDL deficiency is Tangier disease (TD), diagnosed in approximately 40 patients world-wide, and associated with almost complete absence of HDL cholesterol (HDL-C) levels (listed in OMIM as an autosomal recessive trait (OMIM 205400)). These patients have very low HDL cholesterol and ApoAI levels, which have been ascribed to hypercatabolism of nascent HDL and ApoAI, due to a delayed acquisition of lipid and resulting failure of conversion to mature HDL. TD patients accumulate cholesterol esters in several tissues, resulting in characteristic features, such as enlarged yellow tonsils, hepatosplenomegaly, peripheral neuropathy, and cholesterol ester deposition in the rectal mucosa. Defective removal of cellular cholesterol and phospholipids by ApoAI as well as a marked deficiency in HDL mediated efflux of intracellular cholesterol has been demonstrated in TD fibroblasts. Even though this is a rare disorder, defining its molecular basis could identify pathways relevant for cholesterol regulation in the general population. The decreased availability of free cholesterol for efflux in the surface membranes of cells in Tangier Disease patients appears to be due to a defect in cellular lipid metabolism or trafficking. Approximately 45% of Tangier patients have signs of premature CAD, suggesting a strong link between decreased cholesterol efflux, low HDL cholesterol and CAD. As increased cholesterol is observed in the rectal mucosa of persons with TD, the molecular mechanism responsible for TD may also regulate cholesterol adsorption from the gastrointestinal (GI) tract.

A more common form of genetic HDL deficiency occurs in patients who have low plasma HDL cholesterol usually below the 5th percentile for age and sex (OMIM 10768), but an absence of clinical manifestations specific to Tangier disease (Marcil et al., Arterioscler. Thromb. Vasc. Biol. 19:159-169, 1999; Marcil et al., Arterioscler. Thromb. Vasc. Biol. 15:1015-1024, 1995). These patients have no obvious environmental factors associated with this lipid phenotype, and do not have severe hypertriglyceridemia nor have known causes of severe HDL deficiency (mutations in ApoAI, LCAT, or LPL deficiency) and are not diabetic. The pattern of inheritance of this condition is most consistent with a Mendelian dominant trait (OMIM 10768).

The development of drugs that regulate cholesterol metabolism has so far progressed slowly. Thus, there is a need for a better understanding of the genetic components of the cholesterol efflux pathway. Newly-discovered components can then serve as targets for drug design.

Low HDL levels are likely to be due to multiple genetic factors. The use of pharmacogenomics in the aid of designing treatment tailored to the patient makes it desirable to identify polymorphisms in components of the cholesterol efflux pathway. An understanding of the effect of these polymorphisms on protein function would allow for the design of a therapy that is optimal for the patient.

SUMMARY OF THE INVENTION

In a first aspect, the invention features a substantially pure ABC1 polypeptide having ABC1 biological activity. Preferably, the ABC1 polypeptide is human ABC1 (e.g., one that includes amino acids 1 to 60 or amino acids 61 to 2261 of SEQ ID NO: 1). In one preferred embodiment, the ABC1 is polypeptide includes amino acids 1 to 2261 of SEQ ID NO: 1.

Specifically excluded from the polypeptides of the invention are the polypeptide having the exact amino acid sequence as GenBank accession number CAA10005.1 and the nucleic acid having the exact sequence as AJ012376.1. Also excluded is protein having the exact amino acid sequence as GenBank accession number X75926.

In a related aspect, the invention features a substantially pure ABC1 polypeptide that includes amino acids 1 to 2261 of SEQ ID NO: 1.

In another aspect, the invention features a substantially pure nucleic acid molecule encoding an ABC1 polypeptide having ABC1 biological activity (e.g., a nucleic acid molecule that includes nucleotides 75 to 254 or nucleotides 255 to 6858 of SEQ ID NO: 2). In one preferred embodiment, the nucleic acid molecule includes nucleotides 75 to 6858 of SEQ ID NO: 2.

In a related aspect, the invention features an expression vector, a cell, or a non-human mammal that includes the nucleic acid molecule of the invention.

In yet another aspect, the invention features a substantially pure nucleic acid molecule that includes nucleotides 75 to 254 of SEQ ID NO: 2, nucleotides 255 to 6858 of SEQ ID NO: 2, or nucleotides 75 to 6858 of SEQ ID NO: 2.

In still another aspect, the invention features a substantially pure nucleic acid molecule that includes at least fifteen nucleotides corresponding to the 5' or 3' untranslated region from a human ABC1 gene. Preferably, the 3' untranslated region includes nucleotides 7015-7860 of SEQ ID NO: 2.

In a related aspect, the invention features a substantially pure nucleic acid molecule that hybridizes at high stringency to a probe comprising nucleotides 7015-7860 of SEQ ID NO: 2.

In another aspect, the invention features a method of treating a human having low HDL cholesterol or a cardiovascular disease, including administering to the human an ABC1 polypeptide, or cholesterol-regulating fragment thereof, or a nucleic acid molecule encoding an ABC1 polypeptide, or cholesterol-regulating fragment thereof. In a preferred embodiment, the human has a low HDL cholesterol level relative to normal. Preferably, the ABC1 polypeptide is wild-type ABC1, or has a mutation that increases its stability or its biological activity. A preferred biological activity is regulation of cholesterol.

In a related aspect, the invention features a method of preventing or treating cardiovascular disease, including introducing into a human an expression vector comprising an ABC1 nucleic acid molecule operably linked to a promoter and encoding an ABC1 polypeptide having ABC1 biological activity.

In another related aspect, the invention features a method of preventing or ameliorating the effects of a disease-causing mutation in an ABC1 gene, including introducing into a human an expression vector comprising an ABC1 nucleic acid molecule operably linked to a promoter and encoding an ABC1 polypeptide having ABC1 biological activity.

In still another aspect, the invention features a method of treating or preventing cardiovascular disease, including administering to an animal (e.g., a human) a compound that mimes the activity of wild-type ABC1 or modulates the biological activity of ABC1.

One preferred cardiovascular disease that can be treated using the methods of the invention is coronary artery disease. Others include cerebrovascular disease and peripheral vascular disease.

The discovery that the ABC1 gene and protein are involved in cholesterol transport that affects serum HDL levels allows the ABC1 protein and gene to be used in a variety of diagnostic tests and assays for identification of HDL-increasing or CVD-inhibiting drugs. In one family of such assays, the ability of domains of the ABC1 protein to bind ATP is utilized; compounds that enhance this binding are potential HDL-increasing drugs. Similarly, the anion transport capabilities and membrane pore-forming functions in cell membranes can be used for drug screening.

ABC1 expression can also serve as a diagnostic tool for low HDL or CVD; determination of the genetic subtyping of the ABC1 gene sequence can be used to subtype low HDL individuals or families to determine whether the low HDL phenotype is related to ABC1 function. This diagnostic process can lead to the tailoring of drug treatments according to patient genotype (referred to as pharmacogenomics), including prediction of the patient's response (e.g., increased or decreased efficacy or undesired side effects upon administration of a compound or drug.

Antibodies to an ABC1 polypeptide can be used both as therapeutics and diagnostics. Antibodies are produced by immunologically challenging a B-cell-containing biological system, e.g., an animal such as a mouse, with an ABC1 polypeptide to stimulate production of anti-ABC1 protein by the B-cells, followed to by isolation of the antibody from the biological system. Such antibodies can be used to measure ABC1 polypeptide in a biological sample such as serum, by contacting the sample with the antibody and then measuring immune complexes as a measure of the ABC1 polypeptide in the sample. Antibodies to ABC1 can also be used as therapeutics for the modulation of ABC1 biological activity.

Thus, in another aspect, the invention features a purified antibody that specifically binds to ABC1.

In yet another aspect, the invention features a method for determining whether a candidate compound modulates ABC1 biological activity, comprising: (a) providing an ABC1 polypeptide; (b) contacting the ABC1 polypeptide with the candidate compound; and (c) measuring ABC1 biological activity, wherein altered ABC1 biological activity, relative to an ABC1 polypeptide not contacted with the compound, indicates that the candidate compound modulates ABC1 biological activity. Preferably, the ABC1 polypeptide is in a cell or is in a cell-free assay system.

In still another aspect, the invention features a method for determining whether a candidate compound modulates ABC1 expression. The method includes (a) providing a nucleic acid molecule comprising an ABC1 promoter operably linked to a reporter gene; (b) contacting the nucleic acid molecule with the candidate compound; and (c) measuring reporter gene expression, wherein altered reporter gene expression, relative to a nucleic acid molecule not contacted with the compound, indicates that the candidate compound modulates ABC1 expression.

In another aspect, the invention features a method for determining whether candidate compound is useful for modulating cholesterol levels, the method including the steps of: (a) providing an ABC1 polypeptide; (b) contacting the polypeptide with the candidate compound; and (c) measuring binding of the ABC1 polypeptide, wherein binding of the ABC1 polypeptide indicates that the candidate compound is useful for modulating cholesterol levels.

In a related aspect, the invention features method for determining whether a candidate compound mimics ABC1 biological activity. The method includes (a) providing a cell that is not expressing an ABC1 polypeptide; (b) contacting the cell with the candidate compound; and (c) measuring ABC1 biological activity of the cell, wherein altered ABC1 biological activity, relative to a cell not contacted with the compound, indicates that the candidate compound modulates ABC1 biological activity. Preferably, the cell has an ABC1 null mutation. In one preferred embodiment, the cell is in a mouse or a chicken (e.g., a WHAM chicken) in which its ABC1 gene has been mutated.

In still another aspect, the invention features a method for determining whether a candidate compound is useful for the treatment of low HDL cholesterol. The method includes (a) providing an ABC transporter (e.g., ABC1); (b) contacting the transporter with the candidate compound; and (c) measuring ABC transporter biological activity, wherein increased ABC transporter biological activity, relative to a transporter not contacted with the compound, indicates that the candidate compound is useful for the treatment of low HDL cholesterol. Preferably the ABC transporter is in a cell or a cell free assay system.

In yet another aspect, the invention features a method for determining whether candidate compound is useful for modulating cholesterol levels. The method includes (a) providing a nucleic acid molecule comprising an ABC transporter promoter operably linked to a reporter gene; (b) contacting the nucleic acid molecule with the candidate compound; and (c) measuring expression of the reporter gene, wherein increased expression of the reporter gene, relative to a nucleic acid molecule not contacted with the compound, indicates that the candidate compound is useful for modulating cholesterol levels.

In still another aspect, the invention features a method for determining whether a candidate compound increases the stability or decreases the regulated catabolism of an ABC transporter polypeptide. The method includes (a) providing an ABC transporter polypeptide; (b) contacting the transporter with the candidate compound; and (c) measuring the half-life of the ABC transporter polypeptide, wherein an increase in the half-life, relative to a transporter not contacted with the compound, indicates that the candidate compound increases the stability or decreases the regulated catabolism of an ABC transporter polypeptide. Preferably the ABC transporter is in a cell or a cell free assay system.

In a preferred embodiment of the screening methods of the present invention, the cell is in an animal. The preferred ABC transporters are ABC1, ABC2, ABCR, and ABC8, and the preferred biological activity is transport of cholesterol (e.g., HDL cholesterol or LDL cholesterol) or interleukin-1, or is binding or hydrolysis of ATP by the ABC1 polypeptide.

Preferably, the ABC1 polypeptide used in the screening methods includes amino acids 1-60 of SEQ ID NO: 1. Alternatively, the ABC1 polypeptide can include a region encoded by a nucleotide sequence that hybridizes under high stringency conditions to nucleotides 75 to 254 of SEQ ID NO: 2.

In another aspect, the invention features a method for determining whether a patient has an increased risk for cardiovascular disease. The method includes determining whether an ABC1 gene of the patient has a mutation, wherein a mutation indicates that the patient has an increased risk for cardiovascular disease.

In related aspect, the invention features a method for determining whether a patient has an increased risk for cardiovascular disease. The method includes determining whether an ABC1 gene of the patient has a polymorphism, wherein to a polymorphism indicates that the patient has an increased risk for cardiovascular disease.

In another aspect, the invention features a method for determining whether a patient has an increased risk for cardiovascular disease. The method includes measuring ABC1 biological activity in the patient, wherein increased or decreased levels in the ABC1 biological activity, relative to normal levels, indicates that the patient has an increased risk for cardiovascular disease.

In still another aspect, the invention features a method for determining whether a patient has an increased risk for cardiovascular disease. The method includes measuring ABC1 expression in the patient, wherein decreased levels in the ABC1 expression relative to normal levels, indicates that the patient has an increased risk for cardiovascular disease. Preferably, the ABC1 expression is determined by measuring levels of ABC1 polypeptide or ABC1 RNA.

In another aspect, the invention features a non-human mammal having a transgene comprising a nucleic acid molecule encoding a mutated ABC1 polypeptide. In one embodiment, the mutation is a dominant-negative mutation.

In a related aspect, the invention features a non-human mammal, having a transgene that includes a nucleic acid molecule encoding an ABC1 polypeptide having ABC1 biological activity.

In another related aspect, the invention features a cell from a non-human mammal having a transgene that includes a nucleic acid molecule encoding an ABC1 polypeptide having ABC1 biological activity.

In still another aspect, the invention features a method for determining whether a candidate compound decreases the inhibition of a dominant-negative ABC1 polypeptide. The method includes (a) providing a cell expressing a dominant-negative ABC1 polypeptide; (b) contacting the cell with the candidate compound; and (c) measuring ABC1 biological activity of the cell, wherein an increase in the ABC1 biological activity, relative to a cell not contacted with the compound, indicates that the candidate compound decreases the inhibition of a dominant-negative ABC1 polypeptide.

By "polypeptide" is meant any chain of more than two amino acids, regardless of post-translational modification such as glycosylation or phosphorylation.

By "substantially identical" is meant a polypeptide or nucleic acid exhibiting at least 50%, preferably 85%, more preferably 90%, and most preferably 95% identity to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "high stringency conditions" is meant hybridization in 2×SSC at 40° C. with a DNA probe length of at least 40 nucleotides. For other definitions of high stringency conditions, see F. Ausubel et al., *Current Protocols in Molecular Biology*, pp. 6.3.1-6.3.6, John Wiley & Sons, New York, N.Y., 1994, hereby incorporated by reference.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is an ABC1 polypeptide that is at least 75%, more preferably at least 90%, and most preferably at least 99%, by weight, pure. A substantially pure ABC1 polypeptide may be obtained, for example, by extraction from a natural source (e.g., a pancreatic cell), by expression of a recombinant nucleic acid encoding a ABC1 polypeptide, or by chemically synthesizing the protein. Purity can be measured by any appropriate method, e.g., by column chromatography, polyacrylamide gel electrophoresis, or HPLC analysis.

A polypeptide is substantially free of naturally associated components when it is separated from those contaminants that accompany it in its natural state. Thus, a polypeptide which is chemically synthesized or produced in a cellular system different from the cell from which it naturally originates will be substantially free from its naturally associated components. Accordingly, substantially pure polypeptides include those which naturally occur in eukaryotic organisms but are synthesized in *E. coli* or other prokaryotes.

By "substantially pure nucleic acid" is meant nucleic acid that is free of the genes which, in the naturally-occurring genome of the organism from which the nucleic acid of the invention is derived, flank the nucleic acid. The term therefore includes, for example, a recombinant nucleic acid that is incorporated into a vector; into an autonomously replicating plasmid or virus; into the genomic nucleic acid of a prokaryote or a eukaryote cell; or that exists as a separate molecule (e.g., a cDNA or a genomic or cDNA fragment produced by PCR or restriction endonuclease digestion) independent of other sequences. It also is includes a recombinant nucleic acid that is part of a hybrid gene encoding additional polypeptide sequence.

By "modulates" is meant increase or decrease. Preferably, a compound that modulates cholesterol levels (e.g., HDL-cholesterol levels, LDL-cholesterol levels, or total cholesterol levels), or ABC1 biological activity, expression, stability, or degradation does so by at least 10%, more preferably by at least 25%, and most preferably by at least 50%.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody. A purified antibody may be obtained, for example, by affinity chromatography using recombinantly-produced protein or conserved motif peptides and standard techniques.

By "specifically binds" is meant an antibody that recognizes and binds to, for example, a human ABC1 polypeptide but does not substantially recognize and bind to other non-ABC1 molecules in a sample, e.g., a biological sample, that naturally includes protein. A preferred antibody binds to the ABC1 polypeptide sequence of FIG. 9A (SEQ ID NO: 1).

By "polymorphism" is meant that a nucleotide or nucleotide region is characterized as occurring in several different forms. A "mutation" is a form of a polymorphism in which the expression level, stability, function, or biological activity of the encoded protein is substantially altered.

By "ABC transporter" or "ABC polypeptide" is meant any transporter that hydrolyzes ATP and transports a substance across a membrane. Preferably, an ABC transporter polypeptide includes an ATP Binding Cassette and a is transmembrane region. Examples of ABC transporters include, but are not limited to, ABC1, ABC2, ABCR, and ABC8.

By "ABC1 polypeptide" is meant a polypeptide having substantial identity to an ABC1 polypeptide having the amino acid sequence of SEQ ID NO: 1.

By "ABC biological activity" or "ABC1 biological activity" is meant hydrolysis or binding of ATP, transport of a compound (e.g., cholesterol, interleukin-1) or ion across a membrane, or regulation of cholesterol or phospholipid levels (e.g., either by increasing or decreasing HDL-cholesterol or LDL-cholesterol levels).

The invention provides screening procedures for identifying therapeutic compounds (cholesterol-modulating or anti-CVD pharmaceuticals) which can be used in human patients. Compounds that modulate ABC biological activity (e.g., ABC1 biological activity) are considered useful in the invention, as are compounds that modulate ABC concentration, protein stability, regulated catabolism, or its ability to bind other proteins or factors. In general, the screening methods of the invention involve screening any number of compounds for therapeutically active agents by employing any number of in vitro or in vivo experimental systems. Exemplary methods useful for the identification of such compounds are detailed below.

The methods of the invention simplify the evaluation, identification and development of active agents for the treatment and prevention of low HDL and CVD. In general, the screening methods provide a facile means for selecting natural product extracts or compounds of interest from a large population which are further evaluated and condensed to a few active and selective materials. Constitutes of this pool are then purified and evaluated in the methods of the invention to determine their HDL-raising or anti-CVD activities or both.

Other features and advantages of the invention will be apparent from the following description of the preferred embodiments thereof, and from the claims.

Figure 3:
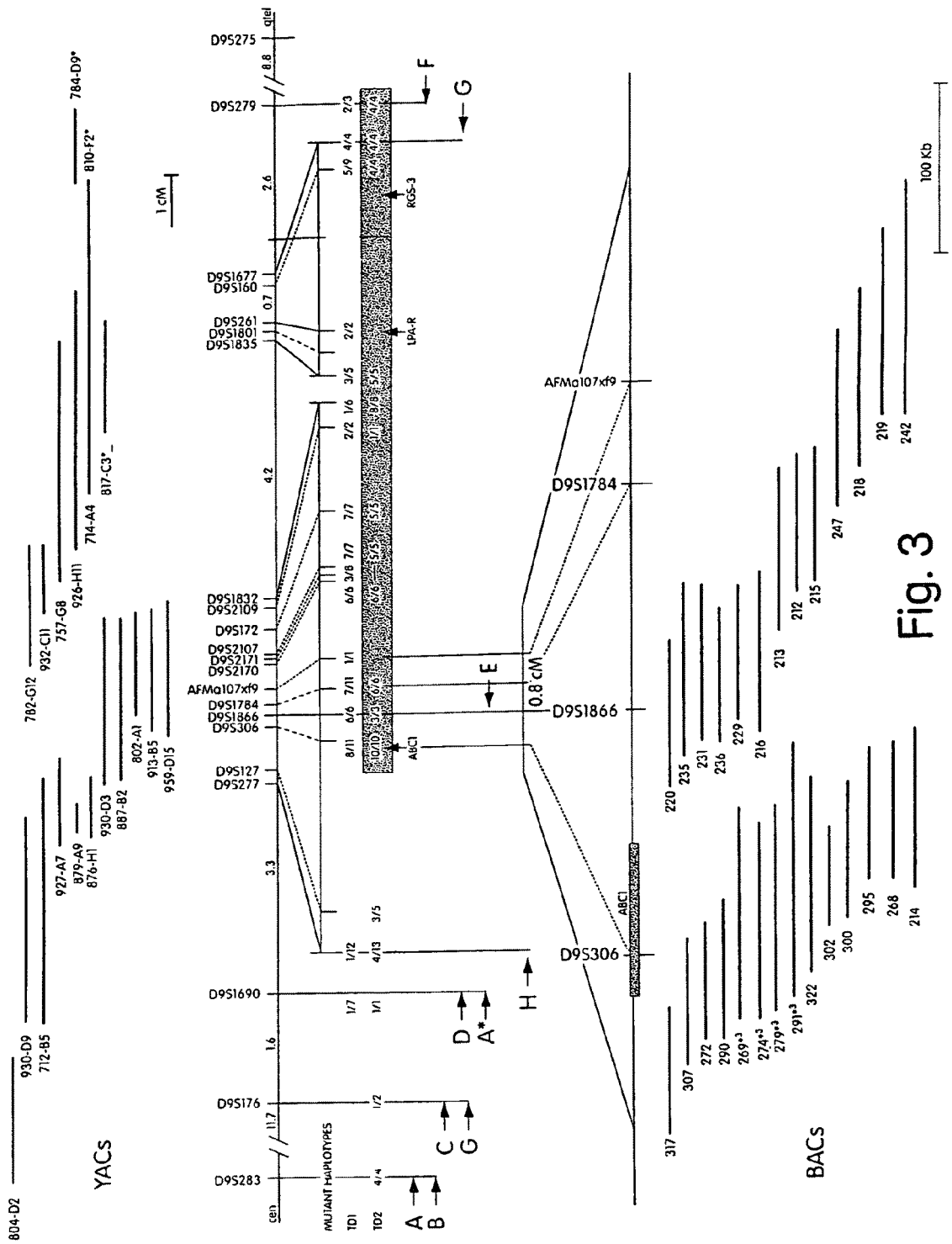

Each individual's ID number, age at the time of lipid measurement, triglyceride level and HDL cholesterol level followed by their percentile ranking for age and sex are listed below the pedigree symbol. Markers spanning the 9q31.1 region are displayed to the left of the pedigree. The affected allele is represented by the darkened bars which illustrate the mapping of the limits of the shared haplotype region as seen in FIG. 3. Parentheses connote inferred marker data, questions marks indicate unknown genotypes, and large arrows show the probands.

Figure 1B:
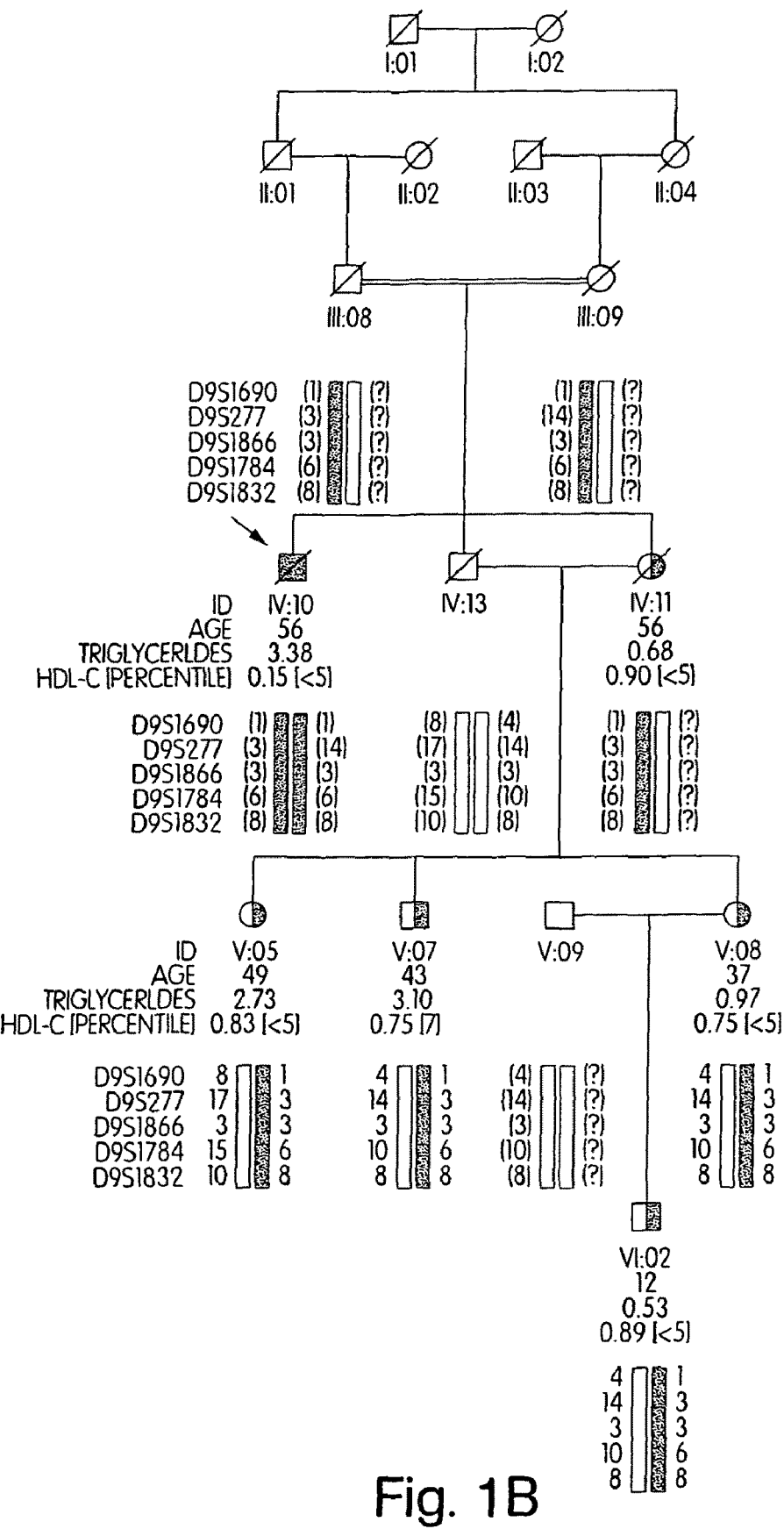
FIGS. 1A and 1B are schematic illustrations showing two pedigrees with Tangier Disease, (TD-1 and TD-2). Square and circle symbols represent males and females, respectively. Diagonal lines are placed through the symbols of all deceased individuals. A shaded symbol on both alleles indicates the probands with Tangier Disease. Individuals with half shaded symbols have HDL-C levels at or below the 10th percentile for age and sex, while those with quarter shaded symbols have HDL-C between the 11th and 20th percentiles.
Figure 1C:
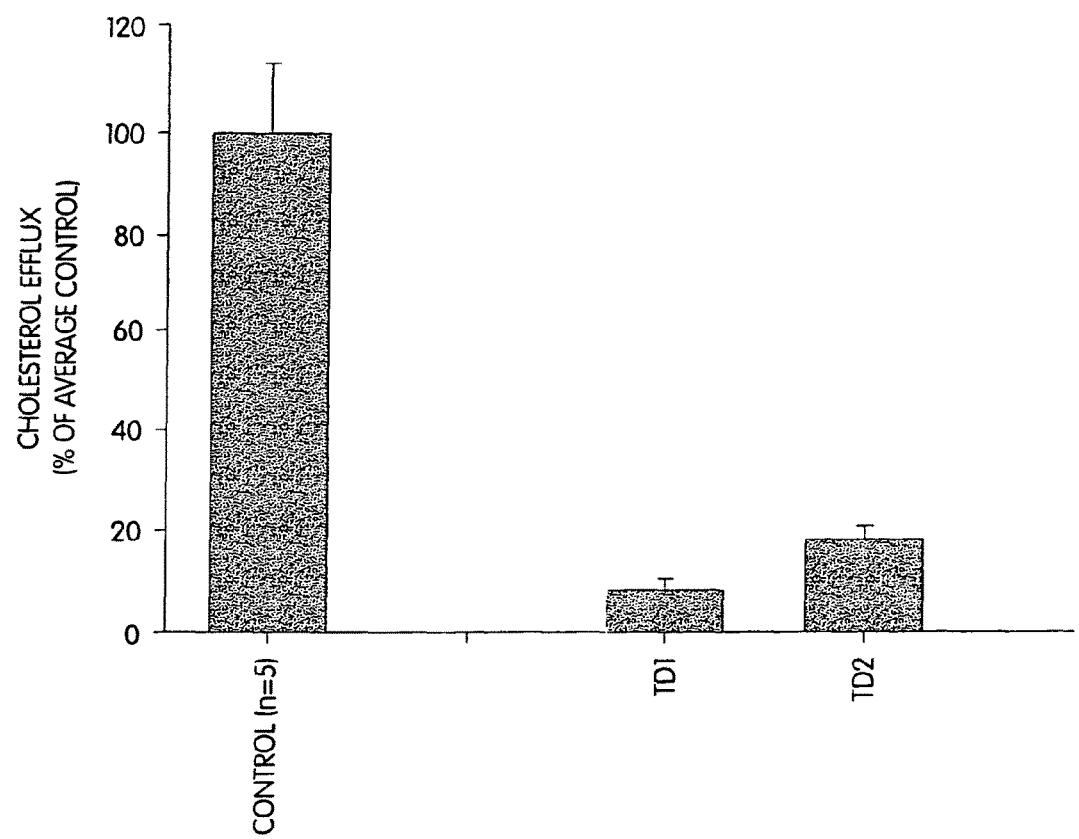
Figure 2C:
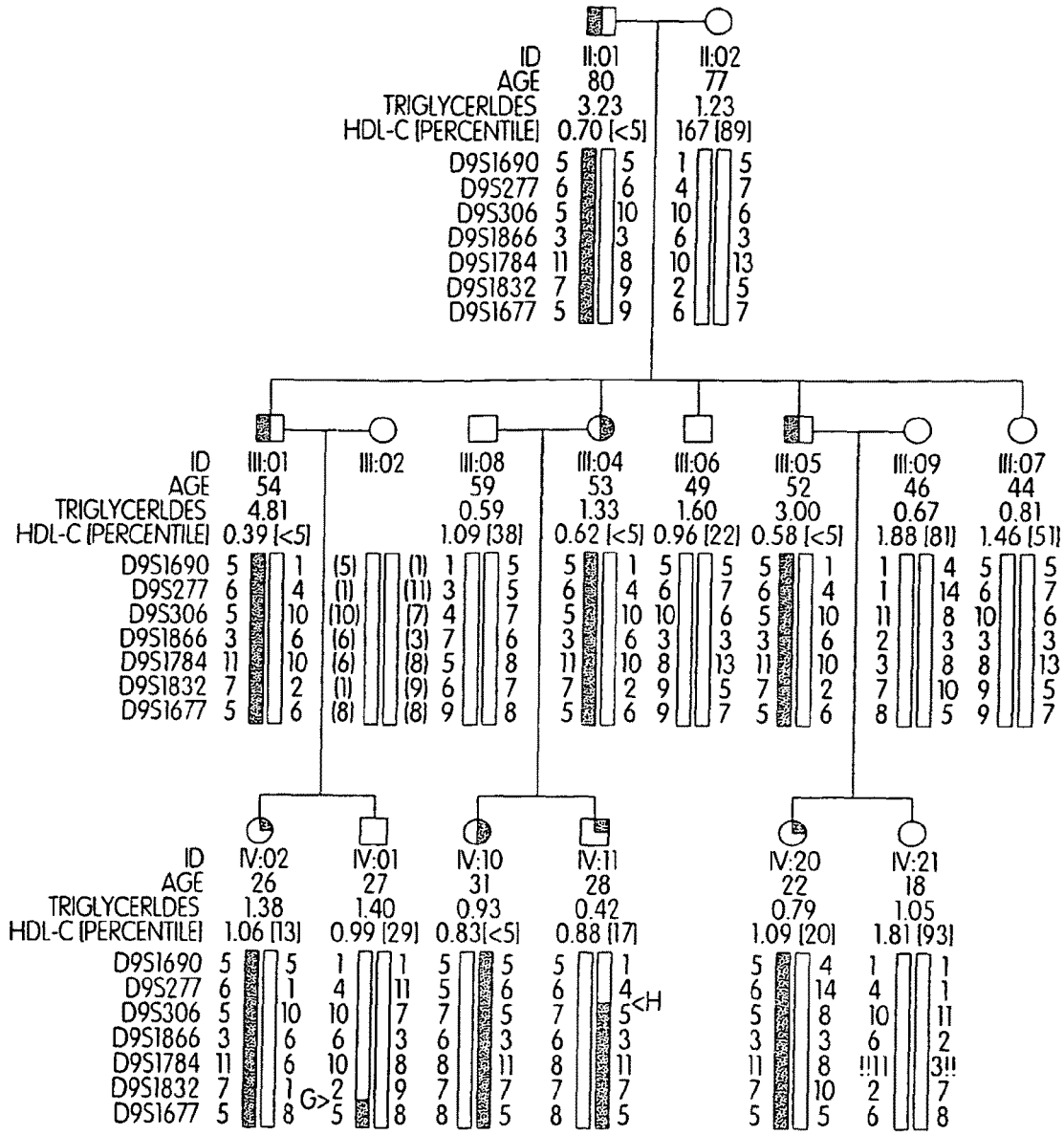
Figure 2D:
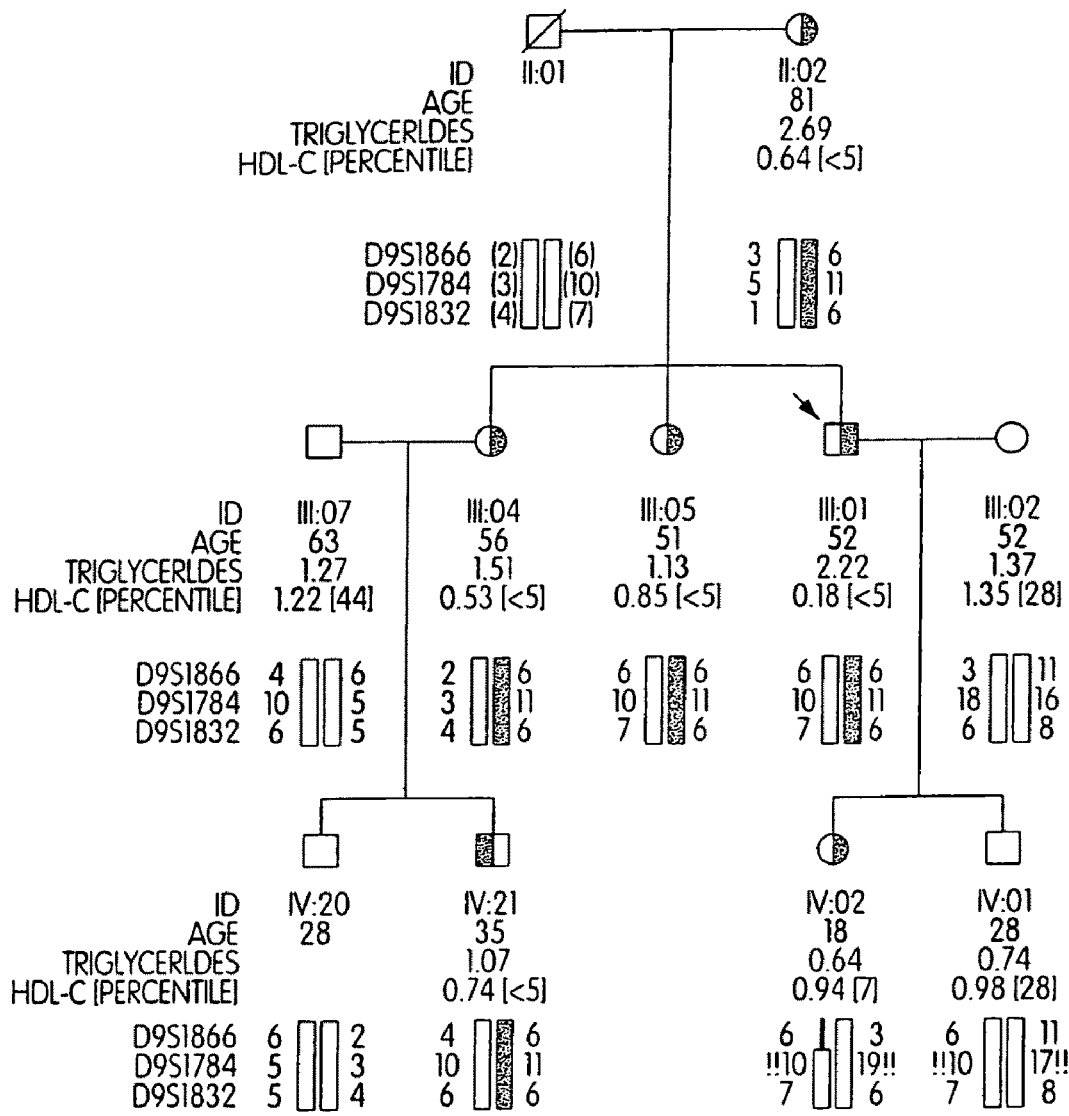

FIG. 1C shows ApoAI (10 μg/mL)—mediated cellular cholesterol efflux in control fibroblasts (n=5, normalized to 100%) and two subjects with Tangier disease (TD). Cells were $^3$H-cholesterol (0.2 μCi/mL) labeled during growth and cholesterol (20 μg/mL) loaded in growth arrest. Cholesterol efflux is determined as $^3$H medium/(3H cell+$^3$H medium)

FIG. 2A-2D are schematic illustrations showing four French Canadian pedigrees with FHA (FHA-1 to -4). The notations are as in FIG. 1. Exclamation points on either side of a genotype (as noted in Families FHA-3 and FHA-4) are is used when the marker data appears to be inconsistent due to potential microsatellite repeat expansions. A bar that becomes a single thin line suggests that the haplotype is indeterminate at that marker.

FIG. 3 shows a schematic illustration showing a genetic and physical map of 9q31 spanning 35 cM. YACs from the region of 9q22-34 were identified and a YAC contig spanning this region was constructed. A total of 22 polymorphic CA microsatellite markers were mapped to the contig and used in haplotype analysis in TD-1 and TD-2. The mutant haplotypes for probands in TD-1 and -2 indicate a significant region of homozygosity in TD-2, while the proband in TD-1 has 2 different mutant haplotypes. The candidate region can be narrowed to the region of homozygosity for CA markers in proband 2. A critical crossover at D9S1690 in TD-1 (A)* also provides a centromeric boundary for the region containing the gene. Three candidate genes in this region (ABC1, LPA-R and RGS-3) are shown. Meiotic recombinations in the FHA families (A-H) refine the minimal critical region to 1.2 cM between D9S277 and D9S1866. The heterozygosity of the TD-2 proband at D9S127, which ends a continuous region of homozygosity in TD-2, further refines the region to less than 1 cM. This is the region to which ABC1 has been mapped. Isolated YAC DNA and selected markers from the region were used to probe high-density BAC grid filters, selecting BACs which via STS-content mapping produced an 800 Kb contig. Four BACs containing ABC1 were sequenced using high-throughput methods.

Figure 4A:
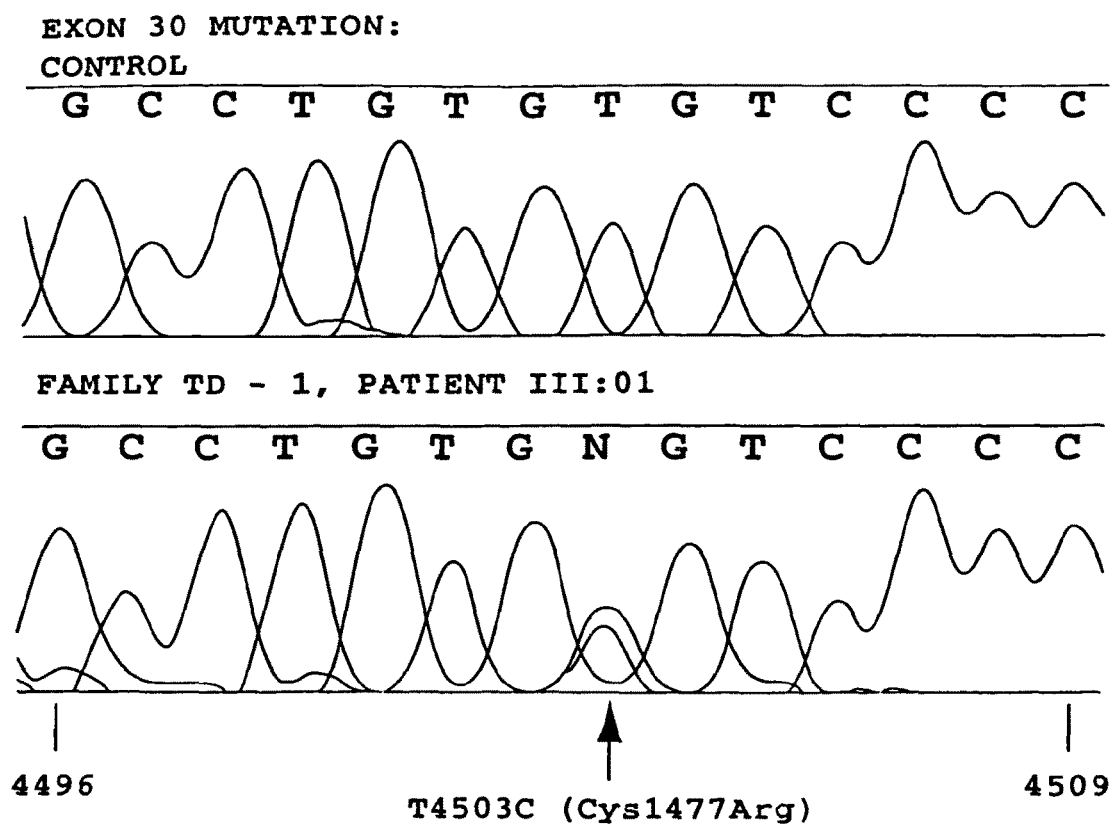

FIG. 4A shows sequence (SEQ ID NO: 39) of one mutation in family TD-1. Patient III-01 is heterozygous for a T to C transition at nucleotide 4503 of the cDNA; the control (SEQ ID NO: 38) is homozygous for T at this position. This mutation corresponds to a cysteine to arginine substitution in the ABC1 protein (C1477R).

FIG. 4B shows the amino acid sequence conservation of residue 1477 in mouse and human, but not a related C. elegans gene. A change from cysteine to arginine likely has an important effect on the protein secondary and tertiary structure, as noted by its negative scores in most substitution matrices (Schuler et al., A Practical Guide to the Analysis of Genes and Proteins, eds. Baxevanis, A. D. & Ouellette, B. F. F. 145:171, 1998). The DNA sequences of the normal and mutant genes are shown above and below the amino acid sequences, respectively. The sequences shown are from top to bottom: wt sequence (SEQ ID NO: 40), human ABC1 (SEQ ID NO: 41), mouse ABC1 (SEQ ID NO: 42), Patient (SEQ ID NO: 43), CAEEL-ABC (SEQ ID NO: 44) and Patient (SEQ ID NO: 45).

Figure 4C:
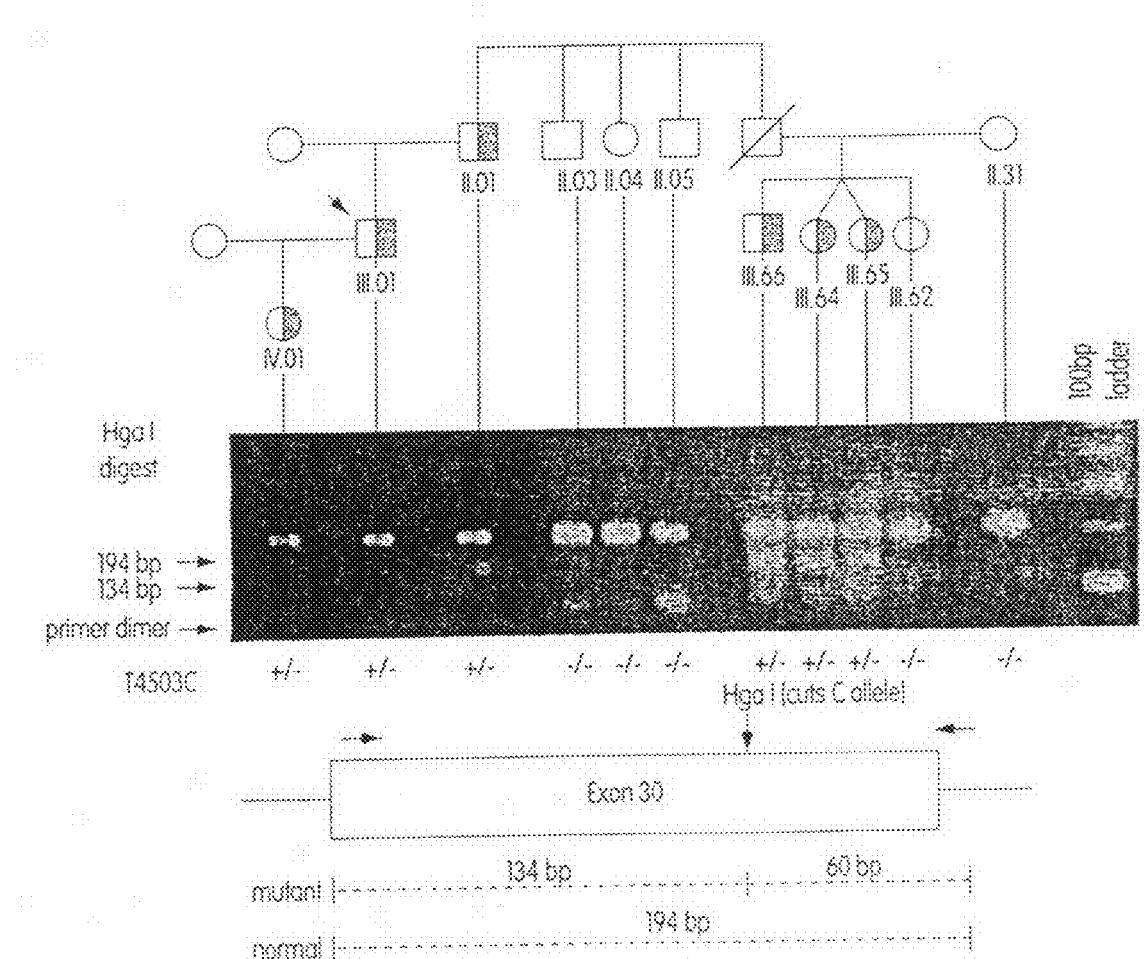

FIG. 4C shows the segregation of the T4503C mutation in TD-1. The presence of the T4503C mutation (+) was assayed by restriction enzyme digestion with Hgal, which cuts only the mutant (C) allele (Õ). Thus, in the absence of the mutation, only the 194 bp PCR product (amplified between ø and Ø) is observed, while in its presence the PCR product is cleaved into fragments of 134 bp and 60 bp. The proband (individual III.01) was observed to be heterozygous for this mutation (as indicated by both the 194 bp and 134 bp bands), as were his daughter, father, and three paternal cousins. A fourth cousin and three of the father's siblings were not carriers of this mutation.

Figure 4D:
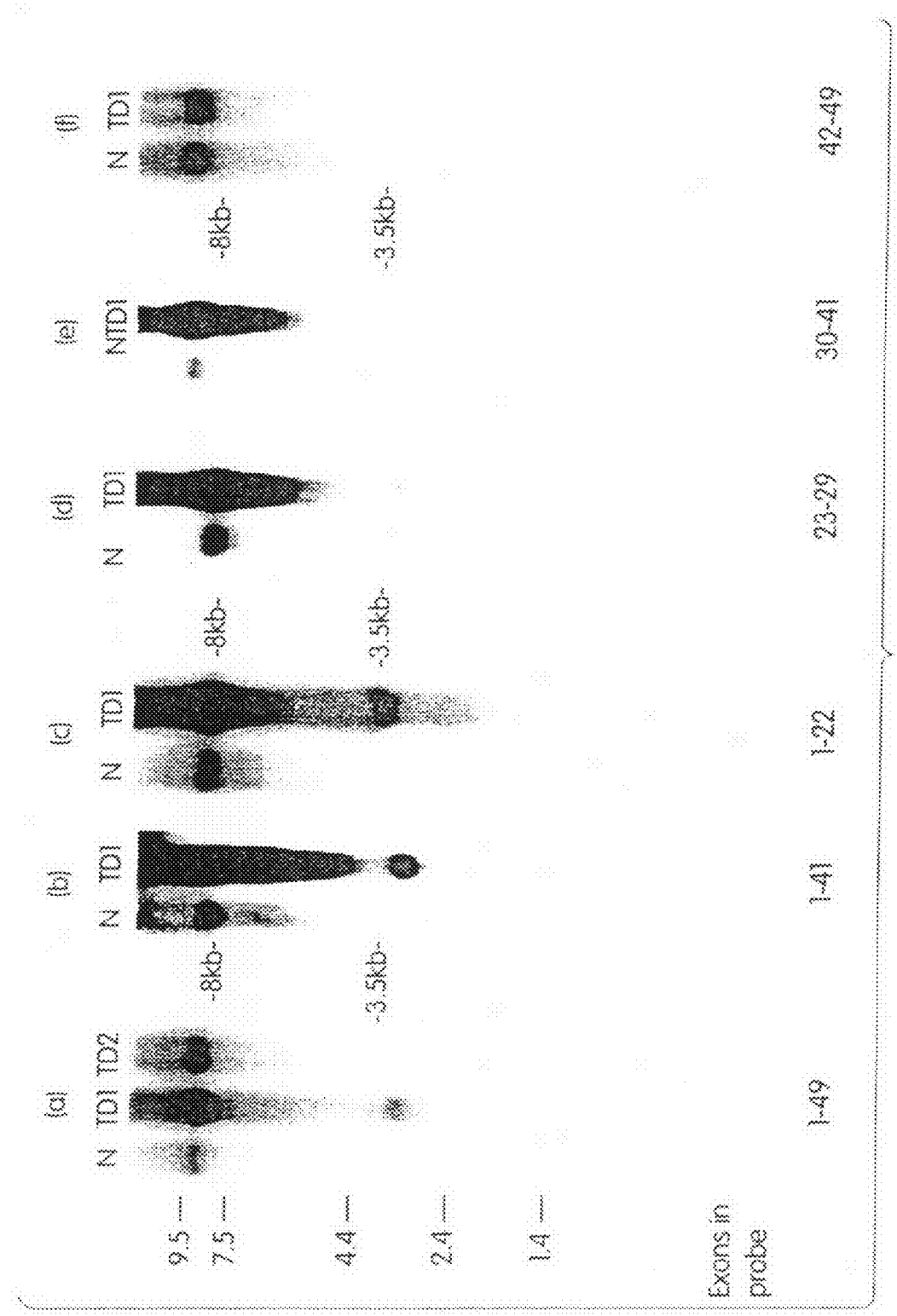

FIG. 4D shows Northern blot analysis with probes spanning the complete ABC1 gene reveal the expected ~8 Kb transcript and, in addition, a ~3.5 kb truncated transcript only seen in the proband TD-1 and not in TD-2 or control. This was detected by probes spanning exons 1-49 (a), 1-41 (b), 1-22 (c), and 23-29 (d), but not with probes spanning exons 30-41 (e) or 42-49 (f).

Figure 5A:
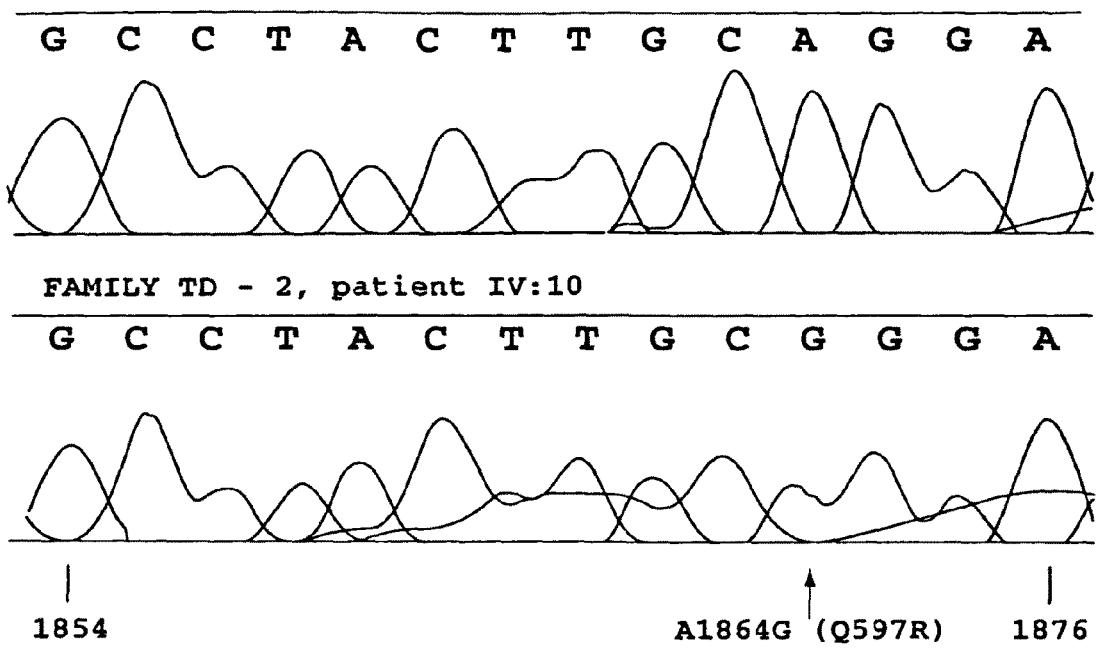

FIG. 5A shows the sequence (SEQ ID NO: 47) of the mutation in family TD-2. Patient IV-10 is homozygous for an A to G transition at nucleotide 1864 of the cDNA (SEQ ID NO: 2); the control (SEQ ID NO: 46) is homozygous for A at this position. This mutation corresponds to a glutamine to arginine substitution in the ABC1 protein (Q597R).

FIG. 5B shows that the glutamine amino acid, which is mutated in the TD-2 proband, is conserved in human and mouse ABC1 as well as in an ABC orthologue from C. elegans, revealing the specific importance of this residue in the structure/function of this ABC protein in both worms and mammals. The DNA sequences of the normal and mutant proteins are shown above and below the amino acid sequences, respectively. The sequences shown are from top to bottom: wt sequence (SEQ ID NO: 48), human ABC1 (SEQ ID NO: 288), mouse ABC1 (SEQ ID NO: 289), Patient (SEQ ID NO: 290), CAEEL-ABC (SEQ ID NO: 52) and Patient (SEQ ID NO: 53).

Figure 5C:
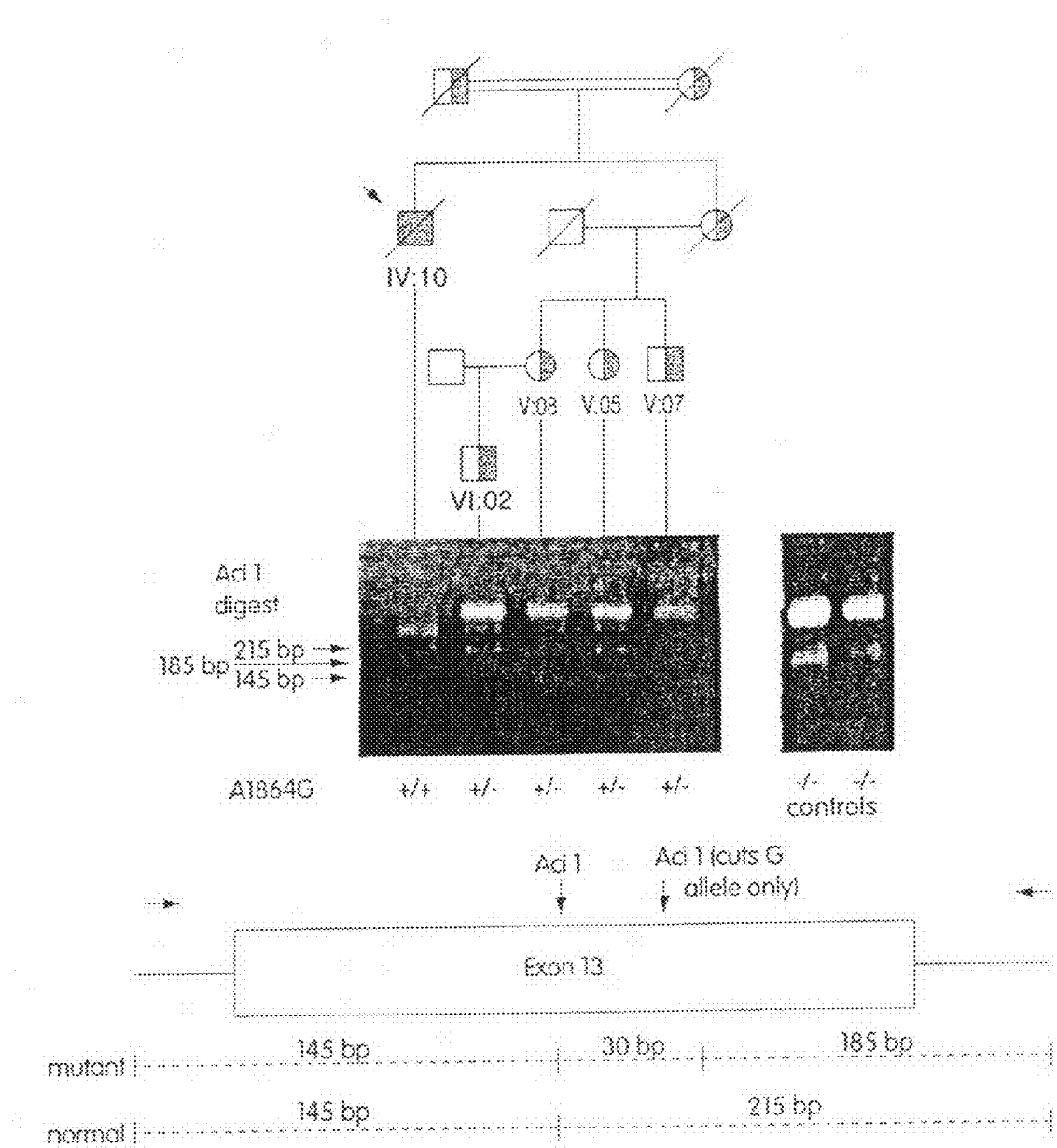

FIG. 5C shows the segregation of the A1864G mutation in TD-2. The presence of the A1864G mutation (indicated by +) was assayed by restriction enzyme digestion with AciI. The 360 bp PCR product has one invariant AciI recognition site (Õ), and a second one is created by the A1864G mutation. The wild-type allele is thus cleaved to fragments of 215 bp and 145 bp, while the mutant allele (G-allele) is cleaved to fragments of 185 bp, 145 bp and 30 bp. The proband (individual IV-10), the product of a consanguineous mating, was homozygous for the A1864G mutation (+/+), as evidenced by the presence of only the 185 bp and 145 bp bands, while four other family members for whom DNA was tested are heterozygous carriers of this mutation (both the 215 bp and 185 bp fragments were present). Two unaffected individuals (−/−), with only the 215 bp and 145 bp bands are shown for comparison.

Figure 6A:
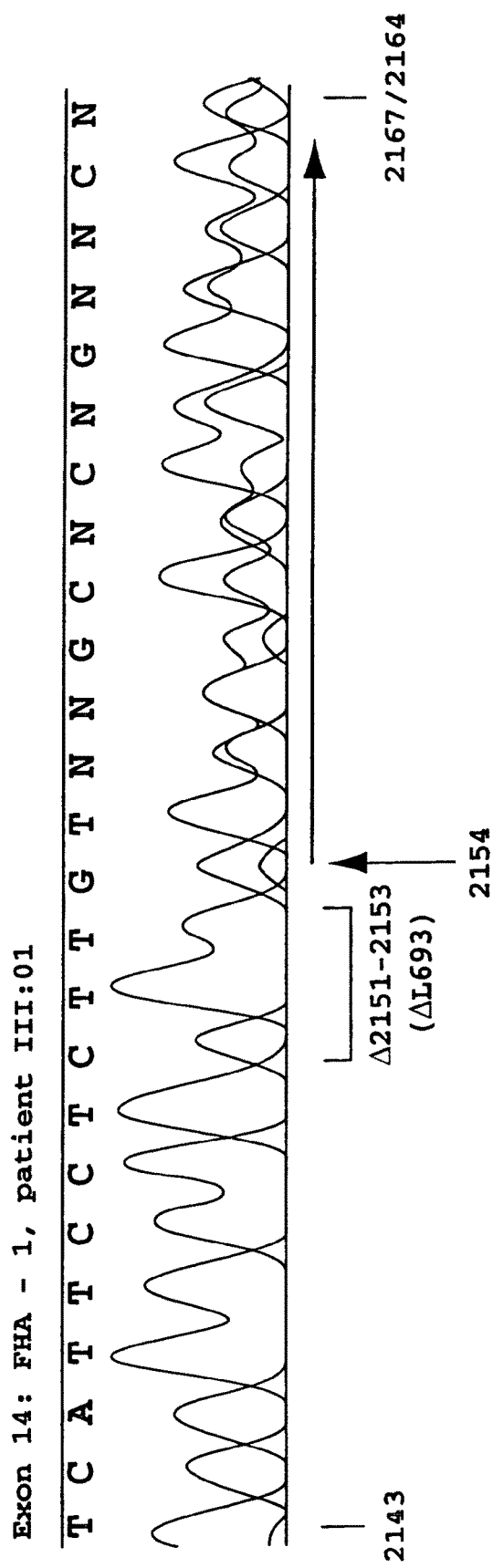

FIG. 6A shows a sequence (SEQ ID NO: 55) of the mutation in family FHA-1. Patient III-01 is heterozygous for a deletion of nucleotides 2151-2153 of the cDNA (SEQ ID NO: 2). This deletion was detected as a superimposed sequence starting at the first nucleotide after the deletion. This corresponds to deletion of leucine 693 in the ABC1 protein (SEQ ID NO: 1).

FIG. 6B is an alignment of the human and mouse wild-type amino acid sequences, showing that the human and mouse sequences are identical in the vicinity of L693. L693 is also conserved in C. elegans. This highly conserved residue lies within a predicted transmembrane domain. The DNA sequences of the normal and mutant proteins are shown above and below the amino acid sequences, respectively. The sequences shown are from top to bottom: wt sequence (SEQ ID NO: 55), human ABC1 (SEQ ID NO: 56), mouse ABC1 (SEQ ID NO: 57), Patient (SEQ ID NO: 58), CAEEL-ABC (SEQ ID NO: 59) and Patient (SEQ ID NO: 60).

Figure 6C:
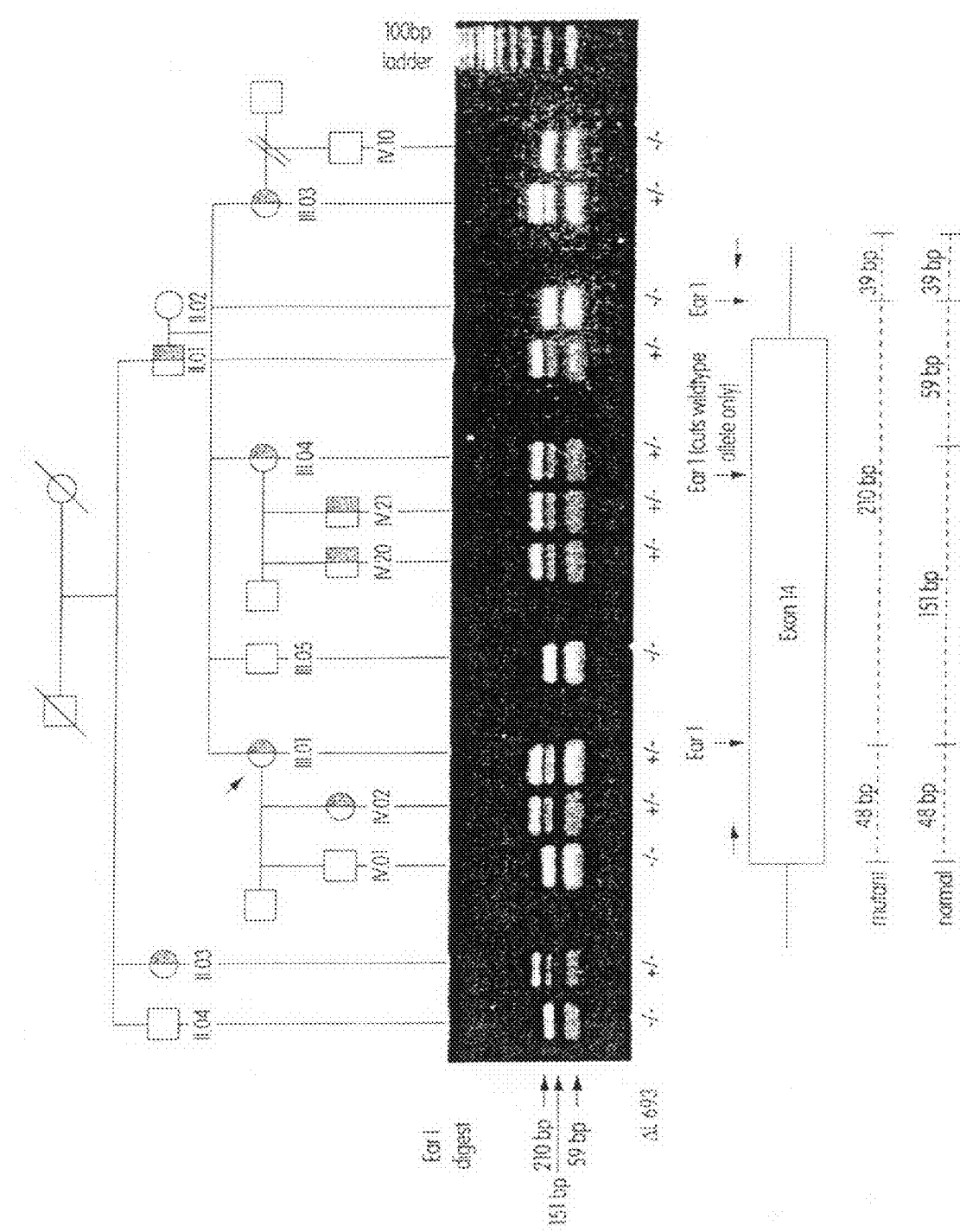

FIG. 6C shows segregation of the L693 mutation in FHA-1, as assayed by EarI restriction digestion. Two invariant EarI restriction sites (indicated by Õ) are present within the 297 bp PCR product located between the horizontal arrows (øØ) while a third site is present in the wild-type allele only. The presence of the mutant allele is thus distinguished by the presence of a 210 bp fragment (+), while the normal allele produces a 151 bp fragment (−). The proband of this family (III.01) is heterozygous for this mutation, as indicated by the presence of both the 210 and 151 bp bands.

Figure 6D:
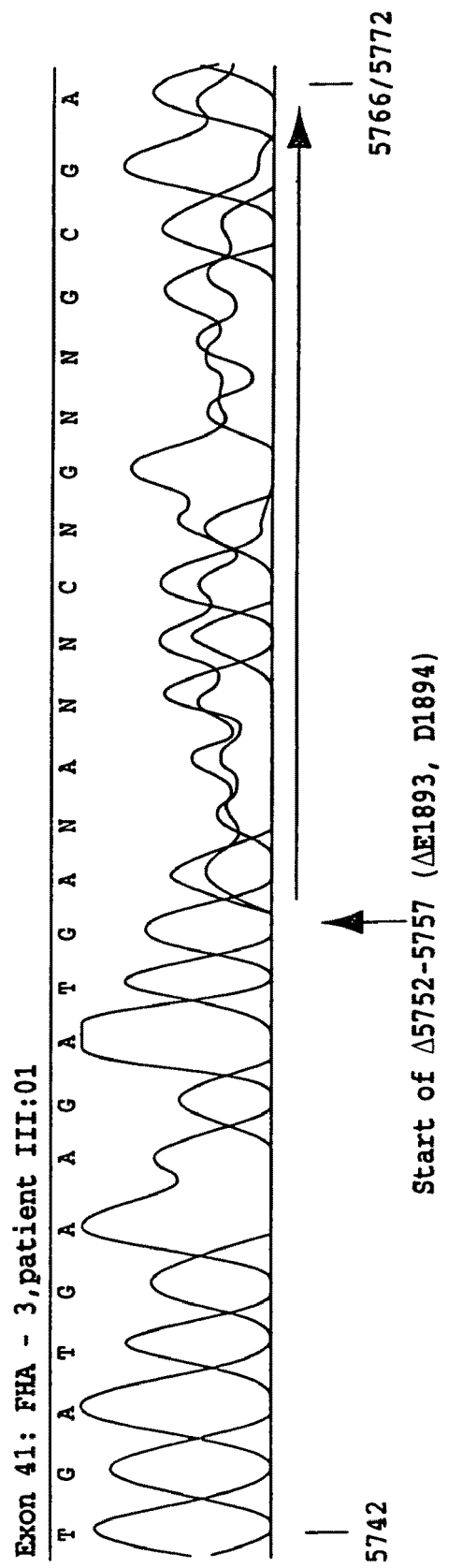

FIG. 6D shows a sequence (SEQ ID NO: 61) of the mutation in family FHA-3. Patient III-01 is heterozygous for a deletion of nucleotides 5752-5757 of the cDNA (SEQ ID NO: 2). This deletion was detected as a superimposed sequence starting at the first nucleotide after the deletion. This corresponds to deletion of glutamic acid 1893 and aspartic acid 1894 in the ABC1 protein (SEQ ID NO: 1).

Figure 6E:
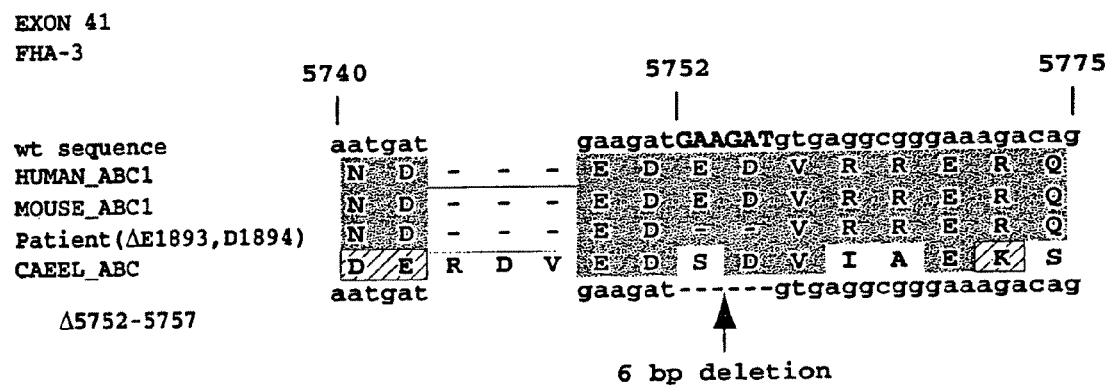

FIG. 6E is an alignment of the human and mouse wild-type amino acid sequences, showing that the human and mouse sequences are identical in the vicinity of 5752-5757. This region is highly conserved in C. elegans. The DNA sequences of the normal and mutant proteins are shown above and below the amino acid sequences, respectively. The sequences shown are from top to bottom: wt sequence (SEQ ID NO: 62), human ABC1 (SEQ ID NO: 63), mouse ABC1 (SEQ ID NO: 64), Patient (SEQ ID NO: 65), CAEEL-ABC (SEQ ID NO: 66) and deletion (SEQ ID NO: 67).

FIG. 6F shows a sequence (SEQ ID NO: 69) of the mutation in family FHA-2. Patient III-01 is heterozygous for a for a C to T transition at nucleotide 6504 of the cDNA (SEQ ID NO: 2). This alteration converts an arginine at position 2144 of SEQ ID NO: 1 to a STOP codon, causing truncation of the last 118 amino acids of the ABC1 protein. The control sequence at the top is SEQ ID NO: 68.

Figure 7A:
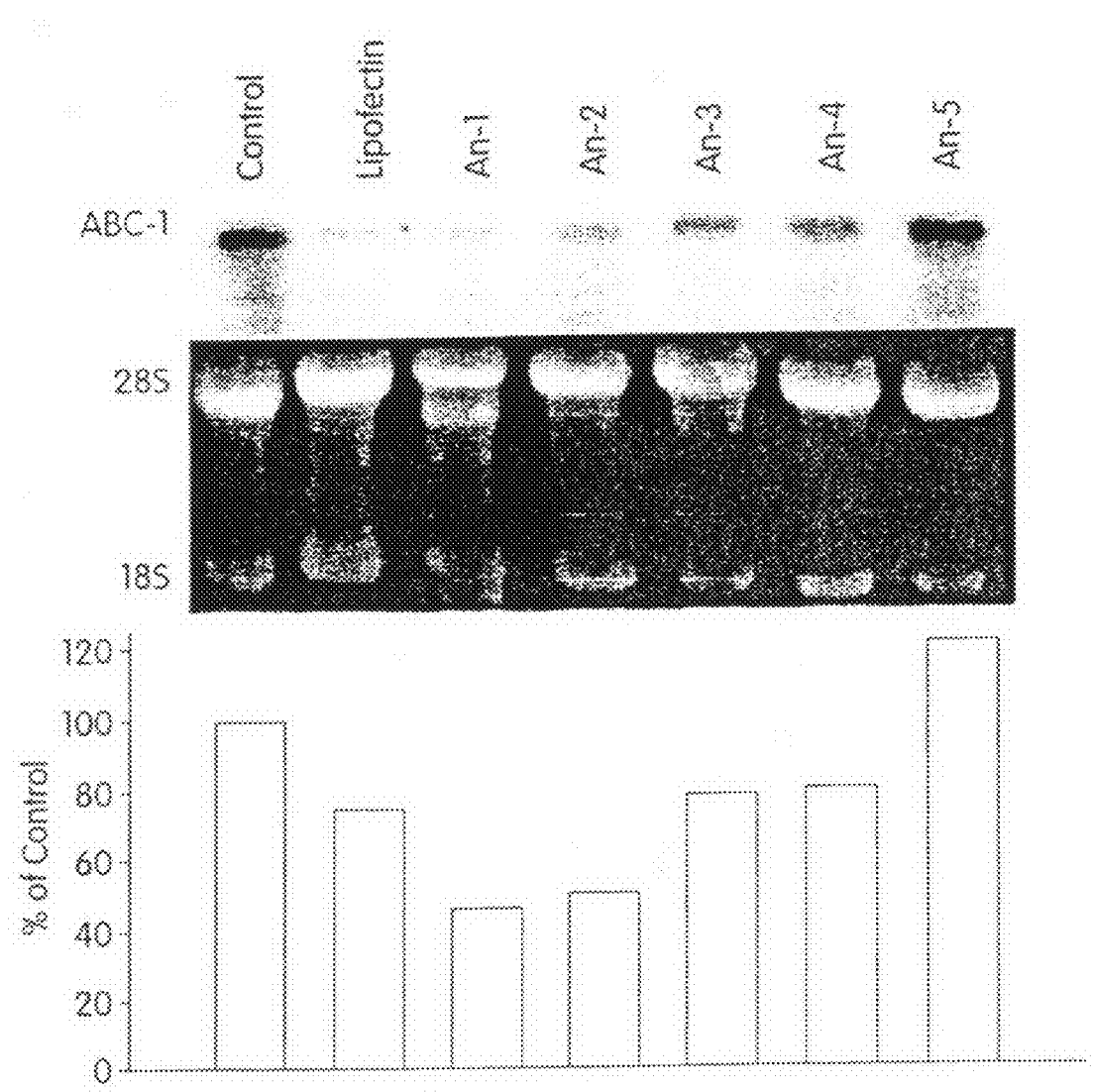
Figure 7B:
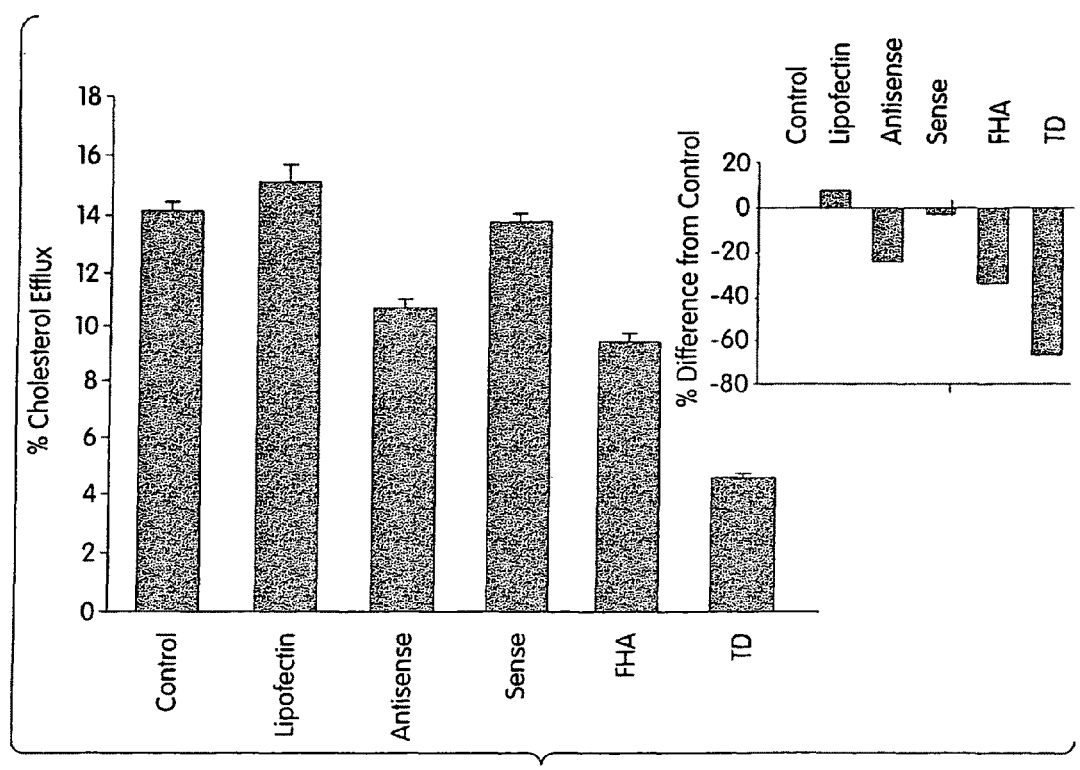

FIGS. 7A and 7B show cholesterol efflux from human skin fibroblasts treated with ABC1 antisense oligonucleotides. Fibroblasts from a control subject to were labeled with $^3$H cholesterol (0.2 µCi/mL) during growth for 48 hours and transfected with 500 nM ABC1 antisense AN-1 (5'-GCA GAG GGC ATG GCT TTA TTT G-3'; SEQ ID NO: 3) with 7.5 µg lipofectin for 4 hours. Following transfection, cells were cholesterol loaded (20 µg/mL) for 12 hours and allowed to equilibrate for 6 hours. Cells were either then harvested for total RNA and 10 µg was used for Northern blot analysis. Cholesterol efflux experiments were carried out as described herein. FIG. 7A: AN-1 was the oligonucleotide that resulted in a predictable decrease in ABC1 RNA transcript levels. FIG. 7B: A double antisense transfection method was used. In this method, cells were labeled and transfected with AN-1 as above, allowed to recover for 20 hours, cholesterol loaded for 24 hours, and then re-transfected with AN-1. Twenty hours after the second transfection, the cholesterol efflux as measured. A ~50% decrease in ABC1 transcript levels was associated with a significant decrease in cholesterol efflux intermediate between that seen in wild-type and TD fibroblasts.

Figure 7C:
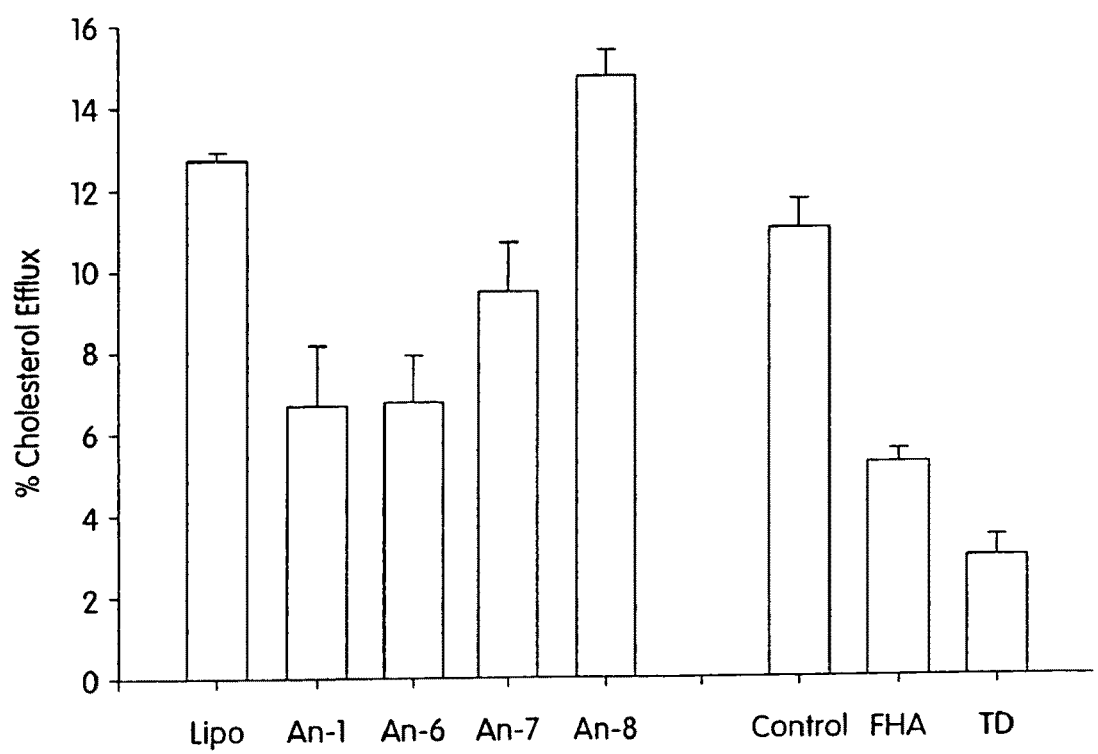

FIG. 7C shows show cholesterol efflux from human skin fibroblasts treated with antisense oligonucleotides directed to the region encoding the amino-terminal 60 amino acids. Note that the antisense oligonucleotide AN-6, which is directed to the previously unrecognized translation start site, produces a substantial decrease in cellular cholesterol efflux.

Figure 8:
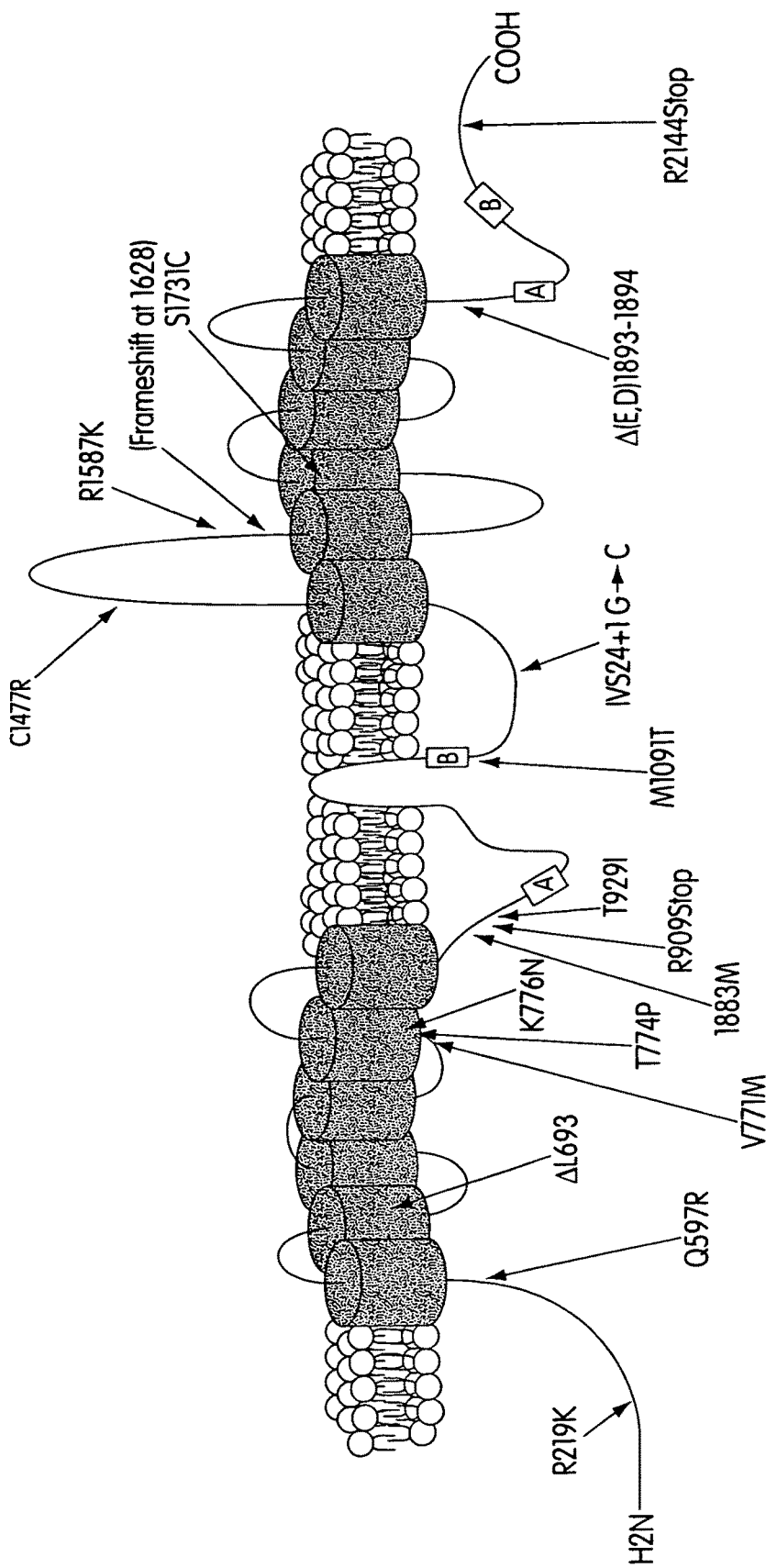

FIG. 8 is a schematic illustration showing predicted topology, mutations, and polymorphisms of ABC1 in Tangier disease and FHA. The two transmembrane and ATP binding domains are indicated. The locations of mutations are indicated by the arrows with the amino acid changes, which are predicted from the human ABC1 cDNA sequence. These mutations occur in different regions of the ABC1 protein.

FIG. 9A shows the amino acid sequence of the human ABC1 protein (SEQ ID NO: 1).

FIGS. 9B-9E show the nucleotide sequence of the human ABC1 cDNA (SEQ ID NO: 2).

FIG. 10 shows the 5' and 3' nucleotide sequences suitable for use as 5' and 3' PCR primers, respectively, for the amplification of the indicated ABC1 exon.

FIG. 11 shows a summary of alterations found in ABC1, including sequencing errors, mutations, and polymorphisms.

FIG. 12 shows a series of genomic contigs (SEQ ID NOS. 14-29) containing the ABC1 promoter (SEQ ID NO: 14), as well as exons 1-49 (and flanking intronic sequence) of ABC1. The exons (capitalized letters) are found in the contigs as follows: SEQ ID NO: 14—exon 1; SEQ ID NO: 15—exon 2; SEQ ID NO: 16—exon 3; SEQ ID NO: 17—exon 4; SEQ ID NO: 18—exon 5; SEQ ID NO: 19-exon 6; SEQ ID NO: 20—exons 7 and 8; SEQ ID NO: 21—exons 9 through 22; SEQ ID NO: 22—exons 23 through 28; SEQ ID NO: 23—exon 29; SEQ ID NO: 24—exons 30 and 31; SEQ ID NO: 25—exon 32; SEQ ID NO: 26-exons 33 through 36; SEQ ID NO: 27—exons 37 through 41; SEQ ID NO: 28—exons 42-45; SEQ ID NO: 29—exons 46-49.

Figure 13:
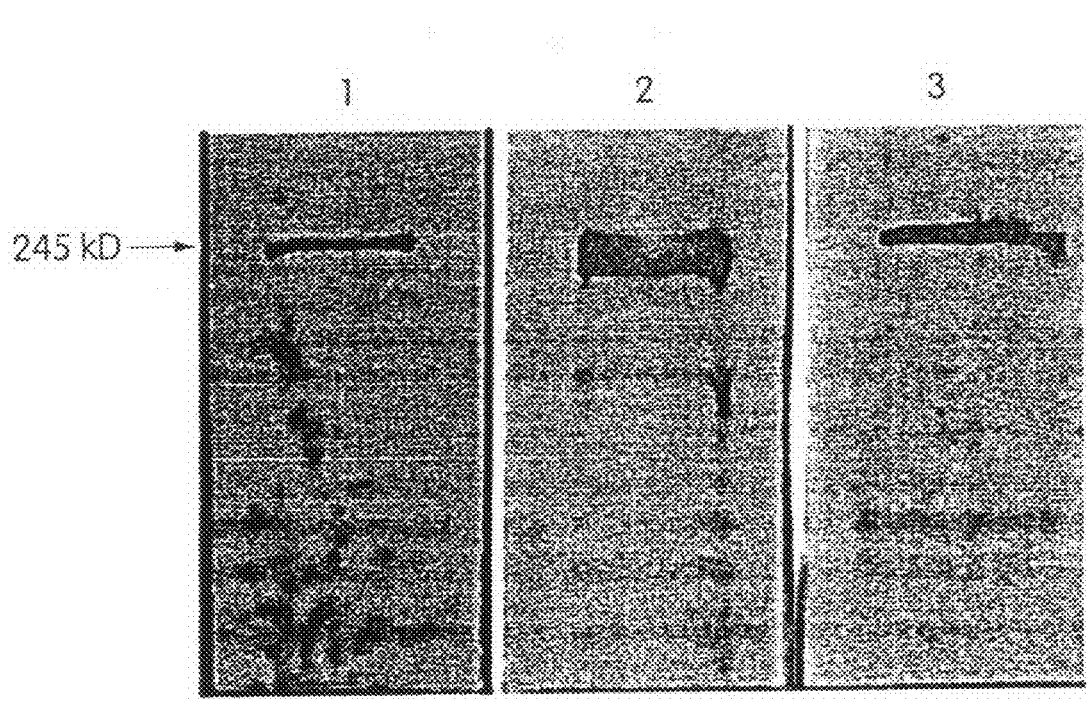

FIG. 13 is a series of illustrations showing that the amino-terminal 60 amino acid region of ABC1 is protein-coding. Lysates of normal human fibroblasts were immunoblotted in parallel with a rabbit polyclonal antibody to amino acids 1-20 of human ABC1 (1); a rabbit polyclonal antibody to amino acids 1430-1449 of human ABC1 (2); and a mouse monoclonal antibody to amino acids 2236-2259 of human ABC1. The additional bands detected in lane 2 may be due to a lack of specificity of that antibody or the presence of degradation products of ABC1.

FIG. 14 is a schematic illustration showing that the WHAM chicken contains a non-conservative substitution (G265A) resulting in an amino acid change (E89K). The control sequence is shown at the top (SEQ ID NO: 276) while the WHAM mutation is shown at the bottom (SEQ ID NO: 277).

Figure 15:
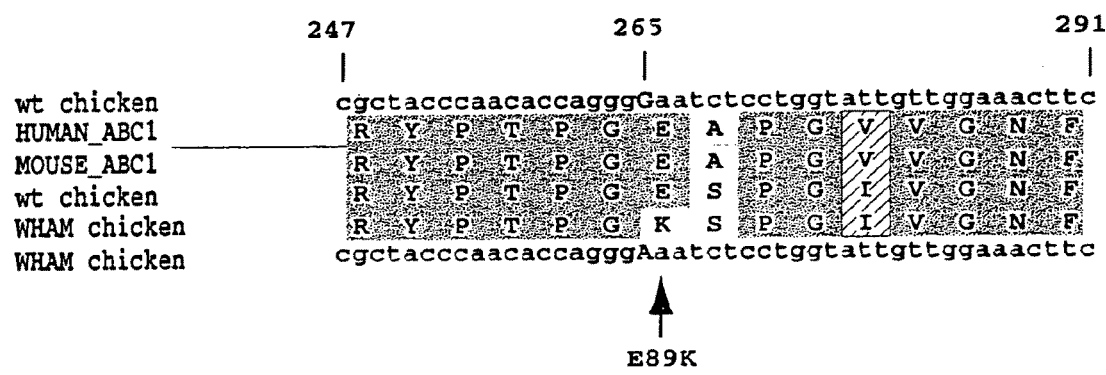

FIG. 15 is a schematic illustration showing that the mutation in the WHAM chicken is at an amino acid that is conserved among human, mouse, and chicken. The sequences shown are from top to bottom: wt chicken nucleotide (SEQ ID NO: 278), human ABC1 (SEQ ID NO: 279), mouse ABC1 (SEQ ID NO: 280), wt chicken amino acid (SEQ ID NO: 281), WHAM chicken nucleotide (SEQ ID NO: 282) and WHAM chicken nucleotide (SEQ ID NO: 283).

Figure 16B:
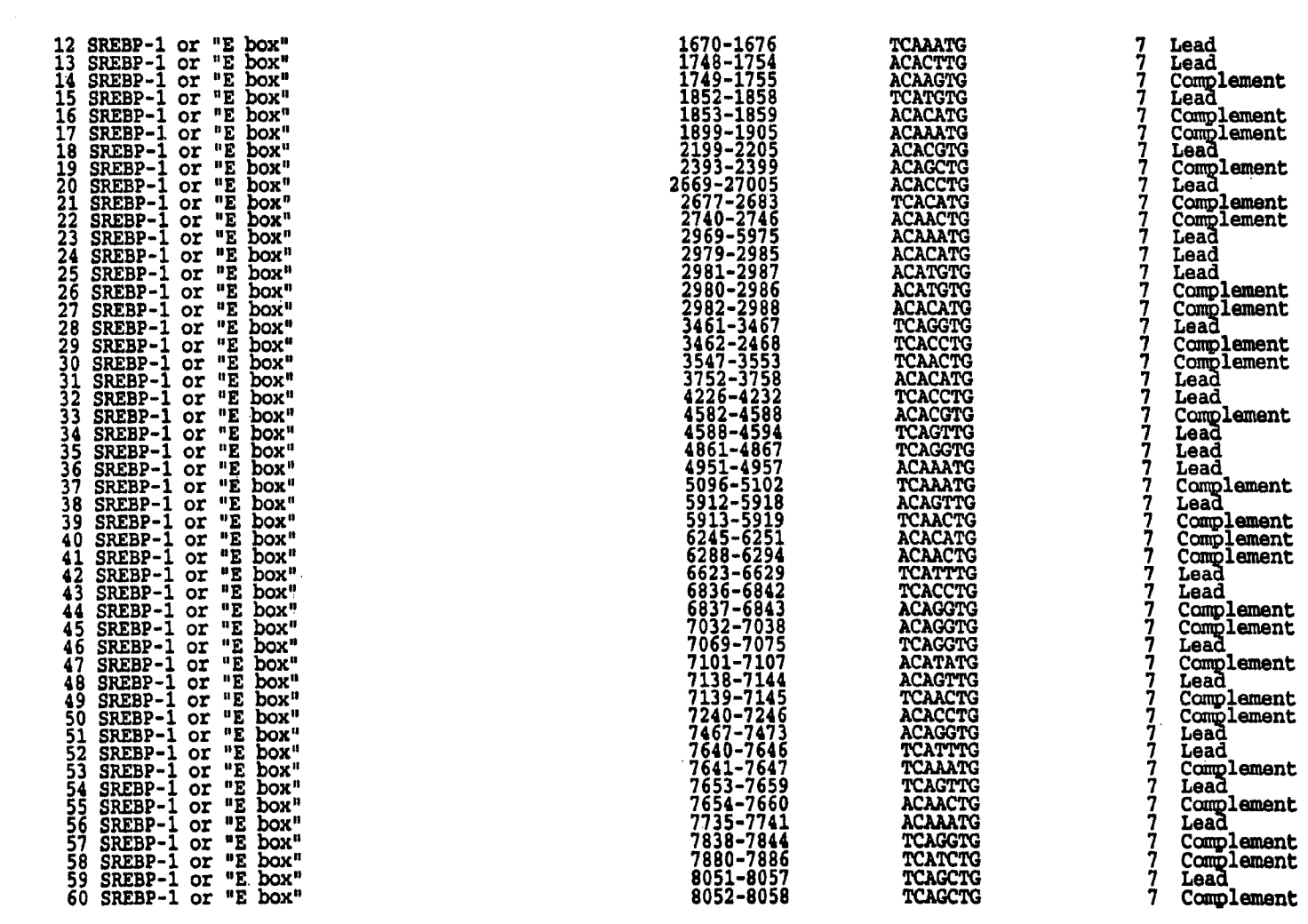

FIG. 16 show a summary of locations of consensus transcription factor binding sites in the human ABC1 promoter (nucleotides 1-8238 of SEQ ID NO: 14). The abbreviations are as follows: PPRE=peroxisome proliferator-activated receptor. SRE=steroid response element-binding protein site. ROR=RAR-related orphan receptor.

DETAILED DESCRIPTION

Genes play a significant role influencing HDL levels. Tangier disease (TD) was the first reported genetic HDL deficiency. The molecular basis for TD is unknown, but has been mapped to 9q31 in three families. We have identified two additional probands and their families, and confirmed linkage and refined the locus to a limited genomic region. Mutations in the ABC1 gene accounting for all four alleles in these two families were detected. A more frequent cause of low HDL levels is a distinct disorder, familial HDL deficiency (FHA).

On the basis of independent linkage, meiotic recombinants and disease associated haplotypes, FHA was localized to a small genomic region encompassing the ABC1 gene. A mutation in a conserved residue in ABC1 segregated with FHA. Antisense reduction of the ABC1 transcript in fibroblasts was associated with a significant decrease in cholesterol efflux.

Cholesterol is normally assembled with intracellular lipids and secreted, but in TD the process is diverted and cholesterol is degraded in lysosomes. This disturbance in intracellular trafficking of cholesterol results in an increase in intracellular cholesterol ester accumulation associated with morphological changes of lysosomes and the Golgi apparatus and cholesteryl ester storage in histiocytes, Schwann cells, smooth muscle cells, mast cells and fibroblasts.

The clinical and biochemical heterogeneity in patients with TD has led to the possibility that genetic heterogeneity may also underlie this disorder. Considering this, we initially performed linkage analysis on these two families of different ancestries (TD-1 is Dutch, TD-2 is British; Frohlich et al., Clin. Invest. Med. 10:377-382, 1987) and confirmed that the genetic mutations underlying TD in these families were localized to the same 9q31 region, to which a large family with TD had been assigned (Rust et al., Nature Genetics 20:96-98, 1998). Detailed haplotype analysis, together with the construction of a physical map, refined the localization of this gene. Mutations in the ABC1 gene were found in TD.

FHA is much more common than TD, although its precise frequency is not known. While TD has been described to date in only 40 families, we have identified more than 40 FHA families in the Netherlands and Quebec alone. After initial suggestions of linkage to 9q31, thirteen polymorphic markers spanning approximately 10 cM in this region were typed and demonstrated the highest LOD score at D9S277. Analysis of the homozygosity of markers in the TD-2 proband, who was expected to be homozygous for markers close to TD due to his parents' consanguinity, placed the TD gene distal to D9S127. Combined genetic data from TD and FHA families pointed to the same genomic segment spanning approximately 1,000 kb between D9S127 and D9S1866. The ABC1 transporter gene was contained within the minimal genomic region. RT-PCR analysis in one family demonstrated a deletion of leucine at residue 693 (693) in the first transmembrane domain of ABC1, which segregated with the phenotype of HDL deficiency in this family.

ABC1 is part of the ATP-binding cassette (ABC transporter) superfamily, which is involved in energy-dependent transport of a wide variety of substrates across membranes (Dean et al., Curr. Opin. Gen. Dev. 5:779-785, 1995). These proteins have characteristic motifs conserved throughout evolution which distinguish this class of proteins from other ATP binding proteins. In humans these genes essentially encode two ATP binding segments and two transmembrane domains (Dean et al., Curr. Opin. Gen. Dev. 5:779-785, 1995). We have now shown that the ABC1 transporter is crucial for intracellular cholesterol transport.

We have demonstrated that reduction of the ABC1 transcript using oligonucleotide antisense approaches results in decreased efflux, clearly demonstrating the link between alterations in this gene and its functional effects. TD and FHA now join the growing list of genetic diseases due to defects in the ABC group of proteins including cystic fibrosis (Zielenski, et al., Annu. Rev. Genet. 29:777-807, 1995), adrenoleukodystrophy (Mosser et al., Nature 361: 726-730, 1993), Zellweger syndrome (Gartner et al., Nat. Genet. 1:23, 1992), progressive familial intrahepatic cholestatis (Bull et al., Nat. Genet. 18:219-224, 1998), and different eye disorders including Stargardt disease (Allikmets et al., Nat. Genet. 15:236-246, 1997), autosomal recessive retinitis pigmentosa (Allikmets et al., Science 277:1805-1807, 1997), and cone-rod dystrophy (Cremers et al., Hum. Mol. Genet. 7:355-362, 1998).

Patients with TD have been distinguished from patients with FHA on the basis that Tangier disease was an autosomal recessive disorder (OMIM 20540) while FHA is inherited as an autosomal dominant trait (OMIM 10768). Furthermore, patients with TD have obvious evidence for intracellular cholesterol accumulation which is not seen in FHA patients. It is now evident that heterozygotes for TD do have reduced HDL levels and that the same mechanisms underlie the HDL deficiency and cholesterol efflux defects seen in heterozygotes for TD as well as FHA. Furthermore, the more severe phenotype in TD represents loss of function from both alleles of the ABC1 gene.

ABC1 is activated by protein kinases, presumably via phosphorylation, which also provides one explanation for the essential role of activation of protein kinase C in promoting cholesterol efflux (Drobnick et al., Arterioscler. Thromb. Vasc. Biol. 15: 1369-1377, 1995). Brefeldin, which inhibits trafficking between the endoplasmic reticulum and the Golgi, significantly inhibits cholesterol efflux, essentially reproducing the effect of mutations in ABC1, presumably through the inhibition of ABC1 biological activity. This finding has significance for the understanding of mechanisms leading to premature atherosclerosis. TD homozygotes develop premature coronary artery disease, as seen in the proband of TD-1 (III-01) who had evidence for coronary artery disease at 38 years. This is particular noteworthy as TD patients, in addition to exhibiting significantly reduced HDL, also have low LDL cholesterol, and yet they develop atherosclerosis despite this. This highlights the importance of HDL intracellular transport as an important mechanism in atherogenesis. There is significant evidence that heterozygotes for TD are also at increased risk for premature vascular disease (Schaefer et al., Ann. Int. Med. 93:261-266, 1980; Serfaty-Lacrosniere et al., Atherosclerosis 107:85-98, 1994). There is also preliminary evidence for premature atherosclerosis in some probands with FHA (FIG. 2B), e.g., the proband in FHA-2 (III-01) had a coronary artery bypass graft at 46 years while the proband in FHA-3 (FIG. 2C) had evidence for CAD around 50 years of age. The TD-1 proband had more severe efflux deficiency than the TD-2 proband (FIG. 1C). Interestingly, the TD-2 proband had no evidence for CAD by 62 when he died of unrelated causes, providing preliminary evidence for a relationship between the degree of cholesterol efflux (mediated in part by the nature of the mutation) and the likelihood of atherosclerosis.

The ABC1 gene plays a crucial role in cholesterol transport and, in particular, intracellular cholesterol trafficking in monocytes and fibroblasts. It also appears to play a significant role in other tissues such as the nervous system, GI tract, and the cornea. Completely defective intracellular cholesterol transport results in peripheral neuropathy, corneal opacities, and deposition of cholesterol esters in the rectal mucosa.

HDL deficiency is heterogeneous in nature. The delineation of the genetic basis of TD and FHA underlies the importance of this particular pathway in intracellular cholesterol transport, and its role in the pathogenesis of atherosclerosis. Unraveling of the molecular basis for TD and FHA defines a key step in a poorly defined pathway of cholesterol efflux from cells and could lead to new approaches to treatment of patients with HDL deficiency in the general population.

HDL has been implicated in numerous other biological processes, including but not limited to: prevention of lipoprotein oxidation; absorption of endotoxins; protection against *Trypanosoma brucei* infection; modulation of endothelial cells; and prevention of platelet aggregation (see Genest et al., J. Invest. Med. 47: 31-42, 1999, hereby incorporated by reference). Any compound that modulates HDL levels may be useful in modulating one or more of the foregoing processes. The present discovery that ABC1 functions to regulate HDL levels links, for the first time, ABC1 with the foregoing processes.

The following examples are to illustrate the invention. They are not meant to limit the invention in any way.

Analysis of TD Families
Studies of Cholesterol Efflux

Both probands had evidence of marked deficiency of cholesterol efflux similar to that previously demonstrated in TD patients (FIG. 1C). TD-1 is of Dutch descent while TD-2 is of British descent.

Linkage Analysis and Establishment of a Physical Map

Multiple DNA markers were genotyped in the region of 9q31 to which linkage to TD had been described (Rust et al., Nat. Genet. 20, 96-98, 1998). Two point linkage analysis gave a maximal peak LOD score of 6.49 at D9S1832 (Table 1) with significant evidence of linkage to all markers in a ~10 cM interval. Recombination with the most proximal marker, D9S1690 was seen in II-09 in Family TD-1 (A* in FIG. 3) providing a centromeric boundary for the disease gene. Multipoint linkage analysis of these data did not increase the precision of the positioning of the disease trait locus.

A physical map spanning approximately 10 cM in this region was established with the development of a YAC contig (FIG. 3). In addition, 22 other polymorphic multi-allelic markers which spanned this particular region were mapped to the contig (FIG. 3) and a subset of these were used in construction of a haplotype for further analysis (FIGS. 1A and 1B; Table 2). The condensed haplotype in these families is shown in FIGS. 1A and 1B.

While the family of Dutch decent did not demonstrate any consanguinity, the proband in TD-2 was the offspring of a first-cousin consanguineous marriage (FIG. 1B). We postulated, therefore, that it was most likely that this proband would be homozygous for the mutation while the proband in the Dutch family was likely to be a compound heterozygote. The Dutch proband shows completely different mutation bearing haplotypes, supporting this hypothesis (FIG. 3).

The TD-2 proband was homozygous for all markers tested (FIG. 1B) distal to D9S127 but was heterozygous at D9S127 and DNA markers centromeric to it (FIG. 3). This suggested that the gene for TD was likely located to the genomic region telomeric of D9S127 and encompassed by the markers demonstrating homozygosity (FIG. 3).

TABLE 1

Two Point Linkage Analysis of TD-1 and TD-2

| Marker Locus | LOD Score at recombination fraction | | | | | | |
|---|---|---|---|---|---|---|---|
| | 0 | 0.01 | 0.05 | 0.10 | 0.20 | 0.30 | 0.40 |
| D9S1690 | -infini | 4.25 | 4.52 | 4.26 | 3.39 | 2.30 | 1.07 |
| D9S277 | 6.22 | 6.11 | 5.67 | 5.10 | 3.90 | 2.60 | 1.17 |
| D9S1866 | 4.97 | 4.87 | 4.49 | 4.00 | 2.96 | 1.85 | 0.70 |
| D9S1784 | 5.50 | 5.40 | 5.00 | 4.47 | 3.36 | 2.17 | 0.92 |
| D9S1832 | 6.49 | 6.37 | 5.91 | 5.31 | 4.05 | 2.69 | 1.21 |
| D9S1677 | 4.60 | 4.51 | 4.18 | 3.76 | 2.88 | 1.93 | 0.93 |

Results of pairwise linkage analysis using MLINK. Values correspond to LOD score for linkage between the disease locus and a marker locus for specified values of the recombination fraction.

TABLE 2

Microsatellite markers used in this study

| Genetic Markers | Type | Hetero-zygocity | Number of alleles | Allele frequency size.bp (proportion |
|---|---|---|---|---|
| D9S283 | CA | 0.80 | 10 | 179(0.04); 181(0.34); 183(0.19); 185(0.20); 189(0.05); 193(0.04); 197(0.07); 199(0.02); 201(0.04); 203(0.04) |
| D9S176 | CA | 0.82 | 9 | 129(0.03); 131(0.06); 133(0.26); 135(0.12); 137(0.25); 139(0.03); 141(0.01); 145(0.05); 147(0.05) |
| D9S1690 | CA | 0.79 | 8 | 225(0.38); 227(0.14); 229(0.04); 231(0.12); 233(0.05); 235(0.16); 237(0.05); 239(0.05) |
| D9S277 | CA | 0.89 | 15 | 167(0.07); 171(0.02); 173(0.15); 175(0.11); 177(0.07); 179(0.04); 181(0.17); 183(0.06); 185(0.02); 187(0.02); 189(0.13); 191(0.13); 193(0.02); 197(0.00); 199(0.00) |
| D9S127 | CA | 0.72 | 6 | 149(0.11); 151(0.07); 153(0.25); 155(0.03); 157(0.45); 159(0.06) |
| D9S306 | CA | 0.87 | 13 | 102(0.06); 104(0.01); 110(0.03); 112(0.08); 114(0.16); 116(0.15); 118(0.11); 120(0.23); 122(0.06); 124(0.06); 126(0.03); 134(0.02); 136(0.01) |
| D9S1866 | CA | 0.62 | 11 | 248(0.06); 252(0.04); 254(0.01); 256(58); 258(0.03); 260(0.06); 262(0.02); 264(0.12); 266(0.06); 268(0.03); 270(0.01) |
| D9S1784 | CA | 0.86 | 15 | 174(0.10); 176(0.02); 178(0.00); 180(0.08); 182(0.11); 184(0.22); 136(0.15); 158(0.06); 190(0.04); 192(0.07); 194(0.08); 196(0.07); 198(0.01); 200(0.01); 202(0.01) |
| AFMa107xf9 | CA | n.a. | n.a. | n.a. |
| D9S2170 | CA | n.a. | n.a. | n.a. |
| D9S2171 | CA | n.a. | n.a. | n.a. |
| D9S2107 | CA | 0.63 | 5 | n.a. |
| D9S172 | CA | 0.54 | 5 | 291(0.00); 297(0.05); 299(0.32); 303(0.62); 305(0.02) |
| D9S2109 | CA | 0.51 | 3 | 1(0.42); 2(0.56); 3(0.02) |

TABLE 2-continued

Microsatellite markers used in this study

| Genetic Markers | Type | Hetero-zygocity | Number of alleles | Allele frequency[f] size.bp (proportion |
|---|---|---|---|---|
| D9S1832 | CA | 0.88 | 12 | 161(0.04); 163(0.02); 167(0.02); 169(0.04); 171(0.10); 173(0.09); 175(0.15); 177(0.28); 179(0.19); 181(0.04); 183(0.01); 185(0.01) |
| D9S1835 | CA | 0.48 | 4 | 110(0.02); 112(0.23); 116(0.68); 118(0.07) |
| D9S1801 | CA | 0.77 | 10 | 166(0.10); 172(0.04); 174(0.02); 182(0.02); 184(0.19); 186(0.40); 188(0.15); 190(0.04); 192(0.02); 194(0.02) |
| D9S261 | CA | 0.63 | 7 | 90(0.02); 92(0.52); 94(0.02); 98(0.02); 100(0.10); 102(0.04); 104(0.08) |
| D9S160 | CA | 0.62 | 6 | 136(0.25); 138(0.53); 140(0.01); 142(0.12); 144(0.00); 146(0.07) |
| D9S1677 | CA | 0.81 | 10 | 251(0.27); 257(0.27); 259(0.07); 261(0.09); 263(0.27); 265(0.14); 267(0.02); 267(0.02); 271(0.04); 273(0.02) |
| D9S279 | CA | 0.78 | 6 | 244(0.09); 246(0.18); 248(0.29); 250(0.29); 252(0.07); 254(0.09) |
| D9S275 | CA | 0.62 | 4 | 190(0.31); 196(0.07); 198(0.52); 200(0.09); |

[f] In a Caucasian population of French Canadian or French descent (J. Weissenbach, Personal Communication 1993).
n.a. = not assessed
These polymorphic microsatellite markers were used for DNA typing in the region of 9q31 seen in FIG. 3. The majority come from the last version of the Généthon human linkage map. The frquency of heterozygosity, the number of alleles as well as the allele frequency of each marker are presented.

Mutation Detection

Based on the defect in intracellular cholesterol transport in patients with TD, we reviewed the EST database for genes in this region which might be relevant to playing a role in this process. One gene that we reviewed as a candidate was the lysophosphatidic acid (LPA) receptor (EDG2) which mapped near D9S1801 (FIG. 3). This receptor binds LPA and stimulates phospholipase-C (PLC), and is expressed in fibroblasts. It has previously been shown that the coordinate regulation of PLC that is necessary for normal HDL3 mediated cholesterol efflux is impaired in TD (Walter et al., J. Clin. Invest. 98:2315-2323, 1996). Therefore this gene represented an excellent candidate for the TD gene. Detailed assessment of this gene, using Northern blot and RT-PCR and sequencing analysis, revealed no changes segregating with the mutant phenotype in this family, in all likelihood excluding this gene as the cause for TD. Polymorphisms were detected, however, in the RT-PCR product, indicating expression of transcripts from both alleles.

The second candidate gene (RGS3) encodes a member of a family regulating G protein signaling which could also be involved in influencing cholesterol efflux (Mendez et al., Trans. Assoc. Amer. Phys. 104:48-53, 1991). This gene mapped 0.7 cM telomeric to the LPA-receptor (FIG. 3), and is expressed in fibroblasts. It was assessed by exon-specific amplification, as its genomic organization was published (Chatterjee et al., Genomics 45:429-433, 1997). No significant sequence changes were detected.

The ABC1 transporter gene had previously been mapped to 9q31, but its precise physical location had not been determined (Luciani et al., Genomics 21:150-159, 1994). The ABC1 gene is a member of the ATP binding cassette transporters which represents a super family of highly conserved proteins involved in membrane transport of diverse substrates including amino acids, peptides, vitamins and steroid hormones (Luciani et al., Genomics 21:150-159, to 1994; Dean et al., Curr. Opin. Gen. Dev. 5:779-785, 1995). Primers to the 3'UTR of this gene mapped to YACs spanning D9S306 (887-B2 and 930-D3) compatible with it being a strong candidate for TD. We initiated large scale genomic sequencing of BACs spanning approximately 800 kb around marker D9S306 (BACs 269, 274, 279 and 291) (FIG. 3). The ABC1 gene was revealed encompassing 49 exons and a minimum of 75 Kb of genomic sequence. In view of the potential function of a gene in this family as a cholesterol transporter, its expression in fibroblasts and localization to the minimal genomic segment underlying TD, we formally assessed ABC1 as a candidate.

Patient and control total fibroblast RNA was used in Northern blot analysis and RT-PCR and sequence analyses. RT-PCR and sequence analysis of TD-1 revealed a heterozygous T to C substitution (FIG. 4A) in the TD-1 proband, which would result in a substitution of arginine for cysteine at a conserved residue between mouse and man (FIG. 4B). This mutation, confirmed by sequencing exon 30 of the ABC1 gene, exhibited complete segregation with the phenotype on one side of this family (FIG. 4C). This substitution creates a Hgal site, allowing for RFLP analysis of amplified genomic DNA and confirmation of the mutation (FIG. 4C). The point mutation in exon 30 was not seen on over 200 normal chromosomes from unaffected persons of Dutch decent, and 250 chromosomes of Western European decent, indicating it is unlikely to be a polymorphism. Northern blot analysis of fibroblast RNA from this patient, using a cDNA encompassing exons 1 to 49 of the gene, revealed a normal sized ~8 Kb transcript and a truncated mutant transcript which was not visible in control RNA or in RNA from other patients with HDL deficiency (FIG. 4D). Additionally, Northern blot analysis using clones encompassing discrete regions of the cDNA revealed that the mutant transcript was detected with a cDNA compassing exons 1 to 49 (a), 1 to 41 (b), 1 to 22 (c), much more faintly with a probe spanning exon 23 to 29 (d) and not seen with probes encompassing exons 30 to 42 (e), but not seen with cDNA fragment spanning exons 30 to 49 (f). This was repeated on multiple filters with control RNA, RNA from other patients with HDL deficiency to and the other TD proband, and only in TD-1 was the truncated transcript observed. Sequence analysis of the coding region did not reveal an alteration in sequence that could account for this finding. Furthermore, DNA analysis by Southern blot did not reveal any major rearrangements. Completion of exon sequencing in genomic DNA showed that this mutation was a G to C is transversion at position (+1) of intron 24, (FIG. 11) affecting a splice donor site and causing aberrant splicing.

RT-PCR analysis of fibroblast RNA encoding the ABC1 gene from the proband in TD-2 (FIG. 1B) revealed a homozygous nucleotide change of A to G at nucleotide 1864 of SEQ ID NO: 2 in exon 13 (FIG. 5A), resulting in a substitution of arginine for glutamine at residue 597 of SEQ ID NO: 1 (FIG. 5B), occurring just proximal to the first predicted transmembrane domain of ABC1 (FIG. 8) at a residue conserved in mouse and as well as a C. elegans homolog. This mutation creates a second AciI site within exon 13. Segregation analysis of the mutation in this family revealed complete concordance between the mutation and the low HDL phenotype as predicted (FIG. 5C). The proband in TD-2 is homozygous for this mutation, consistent with our expectation of a disease causing mutation in this consanguineous family.

Analysis of FHA Families

Linkage Analysis and Refinement of the Minimal Genomic Region Containing the Gene for FHA Data from microsatellite typing of individual family members from the four pedigrees of French Canadian origin were analyzed (FIG. 2). A maximum LOD score of 9.67 at a recombination fraction of 0.0 was detected at D9S277 on chromosome 9q31 (FIG. 3; Table 3). Thereafter, 22 markers were typed in a region spanning 10 cM around this locus in these families (FIGS. 2 and 3). The frequency for these markers were estimated from a sample of unrelated and unaffected subjects of French ancestry (Table 2).

TABLE 3

Two Point Linkage Analysis of FHA

| Marker Locus | LOD Score at recombination fraction | | | | | | |
|---|---|---|---|---|---|---|---|
| | 0 | 0.01 | 0.05 | 0.10 | 0.20 | 0.30 | 0.40 |
| D9S283 | -infini | -2.57 | 0.51 | 1.48 | 1.84 | 1.48 | 0.76 |
| D9S176 | -infini | 1.42 | 3.07 | 3.39 | 3.05 | 2.22 | 1.12 |
| D9S1690 | -infini | 3.11 | 4.04 | 4.04 | 3.33 | 2.24 | 0.96 |
| D9S277 | 9.67 | 9.51 | 8.89 | 8.06 | 6.29 | 4.30 | 2.10 |
| D9S306 | 5.60 | 5.51 | 5.13 | 4.62 | 3.55 | 2.36 | 1.11 |
| D9S1866 | -infini | 7.24 | 7.35 | 6.87 | 5.50 | 3.82 | 1.91 |
| D9S1784 | -infini | 8.85 | 7.76 | 9.03 | 7.09 | 4.78 | 2.25 |
| D9S172 | -infini | 2.63 | 3.00 | 2.87 | 2.26 | 1.50 | 0.67 |
| D9S1832 | -infini | 5.20 | 5.97 | 5.75 | 4.59 | 3.02 | 1.30 |
| D9S1801 | 0.14 | 0.13 | 0.11 | 0.09 | 0.06 | 0.03 | 0..01 |
| D9S1677 | -infini | 7.83 | 7.90 | 7.38 | 5.90 | 4.08 | 2.01 |
| D9S279 | -infini | 3.43 | 3.80 | 3.66 | 3.01 | 2.12 | 1.05 |
| D9S275 | -infini | 2.57 | 2.98 | 2.91 | 2.41 | 1.69 | 0.81 |

Results of pairwise linkage analysis using MLINK. Values correspond to LOD score for linkage between the disease locus and a marker locus for specified values of the recombination fraction.

TD and FHA have thus far been deemed distinct with separate clinical and biochemical characteristics. Even though the genes for these disorders mapped to the same region, it was uncertain whether FHA and TD were due to mutations in the same gene or, alternatively, due to mutations in genes in a similar region.

Refinement of the region containing the gene for FHA was possible by examining haplotype sharing and identification of critical recombination events (FIG. 2). Seven separate meiotic recombination events were seen in these families ("A" through "G" in FIGS. 2 and 3), clearly indicating that the minimal genomic region containing the potential disease gene was a region of approximately 4.4 cM genomic DNA spanned by marker D9S1690 and D9S1866 (FIGS. 2 and 3). This region is consistent with the results of two point linkage analysis which revealed maximal LOD scores with markers D9S277 and D9S306 and essentially excluded the region centromeric to D9S1690 or telomeric to is D9S1866. An 8th meiotic recombination event ("H" in FIG. 3) further refined the FHA region to distal to D9S277.

As described herein, the ABC1 gene mapped within this interval. The overlapping genetic data strongly suggested that FHA may in fact be allelic to TD. Utilization of sets of genetic data from FHA and TD provided a telomeric boundary at D9S1866 (meiotic recombinant) (FIG. 3) and a centromeric marker at D9S127 based on the homozygosity data of TD-2. This refined the locus to approximately 1 Mb between D9S127 and D9S1866. The ABC1 gene mapped within this minimal region (FIG. 3).

Mutation Detection in FHA

Mutation assessment of the ABC1 gene was undertaken in FHA-1 (FIG. 2A). Using primers that spanned overlapping segments of the mRNA we performed RT-PCR analysis and subjected these fragments to mutational analysis. A deletion of three nucleotides is evident in the RT-PCR sequence of FHA-1 III.01 (FIG. 6A), resulting in a loss of nucleotides 2151-2153 of SEQ ID NO: 2 and deletion of a leucine (L693) at amino acid position 693 of SEQ ID NO: 1 (FIG. 6A). This leucine is conserved in mouse and C. elegans (FIG. 6B). The alteration was detected in the RT-PCR products as well as in genomic sequence from exon 14 specific amplification. This mutation results in a loss of an EarI restriction site. Analysis of genomic DNA from the family indicated that the mutation segregated completely with the phenotype of HDL deficiency. The loss of the EarI site results in a larger fragment being remaining in persons heterozygous for this mutation (FIG. 6C). This mutation maps to the first putative transmembrane domain of ABC1 (FIG. 8) and was not seen in 130 chromosomes to from persons of French Canadian descent nor seen in over 400 chromosomes from persons of other Western European ancestry.

A mutation has also been found in patient genomic DNA in pedigree FHA-3 from Quebec. The alteration, a 6 bp deletion of nucleotides 5752-5757 of SEQ ID NO: 2 within exon 41, results in a deletion of amino acids 1893 (Glu) and 1894 (Asp) of SEQ ID NO: 1. The deletion was detected as a double, superimposed, sequence starting from the point of the deletion (FIG. 6D), and was detected in sequence reads in both directions. The deletion can be detected on 3% agarose or 10% polyacrylamide gels, and segregates with disease in FHA-3. It was not seen in 128 normal chromosomes of French-Canadian origin or in 434 other control chromosomes. Amino acids 1893 and 1894 are in a region of the ABC1 protein that is conserved between human, mouse, and C. elegans (FIG. 6E), implying that it is of functional importance.

An additional mutation has been found in patient genomic DNA in pedigree FHA-2 from Quebec (FIG. 6F). The alteration, a C to T transition at position 6504 of SEQ ID NO: 2, converts an arginine at position 2144 of SEQ ID NO: 1 to a STOP codon, causing truncation of the last 118 amino acids of the ABC1 protein. This alteration segregates with disease in family FHA-2.

A summary of all mutations and polymorphisms found in ABC1 is shown in FIG. 11. Each variant indicated as a mutation segregates with low HDL in its family, and was not seen in several hundred control chromosomes.

Functional Relationship Between Changes in ABC1 Transcript Levels and Cholesterol Efflux Antisense approaches were undertaken to decrease the ABC1 transcript and assess the effect of alteration of the transcript on intracellular cholesterol transport. The use of antisense primers to the 5' end of ABC1 clearly resulted in a decrease to approximately 50% of normal RNA levels (FIG.

7A). This would be expected to mimic in part the loss of function due to mutations on one allele, similar to that seen in heterozygotes for TD and patients with FHA. Importantly, reduction in the mRNA for the ABC1 gene resulted in a significant reduction in cellular cholesterol efflux (FIG. 7B), further establishing the role of this protein in is reverse cholesterol transport and providing evidence that the mutations detected are likely to constitute loss of function mutations. Furthermore, these data support the functional importance of the first 60 amino acids of the protein. Antisense oligonucleotide AN-6 is directed to the novel start codon 5' to the one indicated in AJ012376.1; this antisense oligonucleotide effectively suppresses efflux.

The above-described results were obtained using the following materials and methods.

Patient Selection

The probands in TD families had previously been diagnosed as suffering from TD based on clinical and biochemical data. Study subjects with FHA were selected from the Cardiology Clinic of the Clinical Research Institute of Montreal. The main criterion was an HDL-C level <5th percentile for age and gender, with a plasma concentration of triglycerides <95th percentile in the proband and a first-degree relative with the same lipid abnormality. In addition, the patients did not have diabetes.

Biochemical Studies

Blood was withdrawn in EDTA-containing tubes for plasma lipid, lipoprotein cholesterol, ApoAI, and triglyceride analyses, as well as storage at.

−80° C. Leukocytes were isolated from the buffy coat for DNA extraction.

Lipoprotein measurement was performed on fresh plasma as described elsewhere (Rogler et al., Arterioscler. Thromb. Vasc. Biol. 15:683-690, 1995). The laboratory participates and meets the criteria of the Lipid Research Program Standardization Program. Lipids, cholesterol and triglyceride levels were determined in total plasma and plasma at density d<1.006 g/mL (obtained after preparative ultracentrifugation) before and after precipitation with dextran manganese. Apolipoprotein measurement was performed by nephelometry for is ApoB and ApoAI.

Linkage Analysis

Linkage between the trait locus and microsatellite loci was analyzed using the FASTLINK version (4.0 P). FASTLINK/MLINK was used for two-point linkage analysis assuming an autosomal dominant trait with complete penetrance. In FHA and TD heterozygotes, the phenotype was HDL deficiency <5th percentile for age and sex. The disease allele frequency was estimated to be 0.005. Marker allele frequencies were estimated from the genotypes of the founders in the pedigrees using NEWPREP. Multipoint linkage analysis was carried out using FASTLINK/LINKMAP.

Genomic Clone Assembly and Physical Map Construction of the 9q31 Region

Using the Whitehead Institute/MIT Center for Genome Research map as a reference, the genetic markers of interest at 9q31 were identified within YAC contigs. Additional markers that mapped to the approximate 9q31 interval from public databases and the literature were then assayed against the YAC clones by PCR and hybridization analysis. The order of markers was based on their presence or absence in the anchored YAC contigs and later in the BAC contig. Based on the haplotype analysis, the region between D9S277 and D9S306 was targeted for higher resolution physical mapping studies using bacterial artificial chromosomes (BACs). BACs within the region of interest were isolated by hybridization of DNA marker probes and whole YACs to high-density filters containing clones from the RPCI-11 human BAC library (FIG. 3).

Sequence Retrieval and Alignment

The human ABC1 mRNA sequence was retrieved from GenBank using the Entrez nucleotide query (Baxevanis et al., A Practical Guide to the Analysis of Genes and Proteins, eds. Baxevanis, A. D. & Ouellette, B. F. F. 98:120, 1998) as GenBank accession number AJ012376.1. The version of the protein sequence we used as wild-type (normal) was CAA10005.1.

We identified an additional 60 amino acids in-frame with the previously-believed start methionine (FIG. 9A). Bioinformatic analysis of the additional amino acids indicates the presence of a short stretch of basic amino acid residues, followed by a hydrophobic stretch, then several polar residues. This may represent a leader sequence, or another transmembrane or membrane-associated region of the ABC1 protein. In order to differentiate among the foregoing possibilities, antibodies directed to the region of amino acids 1-60 are raised against and used to determine the physical relationship of amino acids 1-60 in relation to the cell membrane. Other standard methods can also be employed, including, for example, expression of fusion proteins and cell fractionation.

We also identified six errors in the previously-reported nucleotide sequence (at positions 839, 4738, 5017, 5995, 6557, and 6899 of SEQ ID NO: 2; FIG. 11). Hence, the sequence of the ABC1 polypeptide of FIG. 9A differs from CAA10005.1 as follows: Thr_Ile at position 1554; Pro_Leu at position 1642; Arg_Lys at position 1973; and Pro_Leu at position 2167. We also identified 5' and 3' UTR sequence (FIGS. 9B-9E).

The mouse ABC1 sequence used has accession number X75926. It is very likely that this mouse sequence is incomplete, as it lacks the additional 60 amino acids described herein for human ABC1.

Version 1.7 of ClustalW was used for multiple sequence alignments with BOXSHADE for graphical enhancement (www.isrec.isb-sib.ch:8080/software/BOX_form.html) with the default parameter. A *Caenorhabditis elegans* ABC1 orthologue was identified with BLAST (version 2.08) using CAA1005.1 (see above) as a query, with the default parameter except for doing an organism filter for *C. elegans*. The selected protein sequence has accession version number AAC69223.1 with a score of 375, and an E value of 103.

Genomic DNA Sequencing

BAC DNA was extracted from bacterial cultures using NucleoBond Plasmid Maxi Kits (Clontech, Palo Alto, Calif.). For DNA sequencing, a sublibrary was first constructed from each of the BAC DNAs (Rowen et al., Automated DNA Sequencing and Analysis, eds. Adams, M. D., Fields, C. & Venter, J. C., 1994). In brief, the BAC DNA was isolated and randomly sheared by nebulization. The sheared DNA was then size fractionated by agarose gel electrophoresis and fragments above 2 kb were collected, treated with Mung Bean nuclease followed by T4 DNA polymerase and klenow enzyme to ensure blunt-ends, and cloned into SmaI-cut M13 mp 19. Random clones were sequenced with an AB1373 or 377 sequencer and fluorescently labeled primers (Applied BioSystems, Foster City, Calif.). DNAStar software was used for gel trace analysis and contig assembly. All DNA sequences were examined against available public databases primarily using BLASTn with RepeatMasker (University of Washington).

Reverse Transcription (RT)-PCR Amplification and Sequence Analysis

Total RNA was isolated from the cultured fibroblasts of TD and FHA patients, and reverse transcribed with a CDS primer containing oligo d(T)18 using 250 units of SuperScript II reverse transcriptase (Life Technologies, Inc., Rockville, Md.) as described (Zhang et al., J. Biol. Chem. 27:1776-1783, 1996). cDNA was amplified with Taq DNA polymerase using primers derived from the published human ABC1 cDNA sequence (Luciani et al., Genomics 21:150-159, 1994). Six sets of primer pairs were designed to amplify each cDNA sample, generating six DNA fragments which are sequentially overlapped covering 135 to 7014 bp of the full-length human ABC1 cDNA. The nucleotides are numbered according to the order of the published human cDNA sequence (AJ012376.1). Primer pairs (1): 135-158 (f) and 1183-1199 (r); (2): 1080-1107 (f) and 2247-2273 (r); (3): 2171-2197 (f) and 3376-3404 (r); (4): 3323-3353 (f) and 4587-4617 (r); (5) 4515-4539 (f) and 5782-5811 (r); (6): 5742-5769 (f) and 6985-7014 (r). RT-PCR products were purified by Qiagen spin columns. Sequencing was carried out in a Model 373A Automated DNA sequencer (Applied Biosystems) using Taq di-deoxy terminator cycle sequencing and Big Dye Kits according to the manufacturer's protocol.

Northern Blot Analysis

Northern transfer and hybridizations were performed essentially as described (Zhang et al., J. Biol. Chem. 27:1776-1783, 1996). Briefly, 20 μg of total fibroblast RNA samples were resolved by electrophoresis in a denaturing agarose (1.2%; w/v) gel in the presence of 7% formaldehyde, and transferred to nylon membranes. The filters were probed with $^{32}$P-labeled human ABC1 cDNA as indicated. Pre-hybridization and hybridizations were carried out in an ExpressHyb solution (ClonTech) at 68° C. according to the manufacturer's protocol.

Detection of the Mutations in TD

Genotyping for the T4503C and A1864G variants was performed by PCR amplification of exon 30 followed by restriction digestion with HgaI and amplification of exon 13 followed by digestion with AciI, respectively. PCR was carried out in a total volume of 50 μL with 1.5 mM MgCl$_2$, 187.5 nM of each dNTP, 2.5 U Taq polymerase and 15 μmol of each primer (forward primer in exon 30: 5'-CTG CCA GGC AGG GGA GGA AGA GTG-3' (SEQ ID NO: 4); reverse primer spanning the junction of exon 30 and intron 30: 5'-GAA AGT GAC TCA CTT GTG GAG GA-3' (SEQ ID NO: 5); forward primer in intron 12: 5'-AAA GGG GCT TGG TAA GGG TA-3' (SEQ ID NO: 6); reverse in intron 13: 5'-CAT GCA CAT GCA CAC ACA TA-3' (SEQ ID NO: 7)). Following an initial denaturation of 3 minutes at 95° C., 35 cycles consisting of 95° C. 10 seconds, 58° C. 30 seconds, 72° C. 30 seconds were performed, with a final extension of 10 minutes at 72° C. For detection of the T4503C mutation, 15 μL of exon 30 PCR product was incubated with 4 U HgaI in a total volume of 25 μL, for 2 hours at 37° C., and the is resulting fragments were separated on a 1.5% agarose gel. The presence of the T4503C mutation creates a restriction site for HgaI, and thus the 194 bp PCR product will be cut into fragments of 134 and 60 bp in the presence of the T4503C variant, but not in its absence. For detection of the A1864G mutation, 15 μL of exon 13 PCR products were digested with 8 U AciI for three hours at 37° C. Products were separated on 2% agarose gels. The presence of the A1864G mutation creates a second AciI site within the PCR product. Thus, the 360 bp PCR product is cleaved into fragments of 215 bp and 145 bp on the wild-type allele, but 185 bp, 145 bp and 30 bp on the mutant allele.

Detection of Mutation in FHA

Genotyping for the 693 variant was performed by PCR amplification of exon 14 followed by restriction enzyme digestion with EarI. PCR was carried out in a total volume of 80 μL with 1.5 mM MgCl$_2$, 187.5 nM of each dNTP, 2.5 U Taq polymerase and 20 μmol of each primer (forward primer in exon 14: 5'-CTT TCT GCG GGT GAT GAG CCG GTC AAT-3' (SEQ ID NO: 8); reverse primer in intron 14: 5'-CCT TAG CCC GTG TTG AGC TA-3' (SEQ ID NO: 9)). Following an initial denaturation of 3 minutes at 95° C., 35 cycles consisting of 95° C. 10 seconds, 55° C. 30 seconds, 72° C. 30 seconds were performed, with a final extension of 10 minutes at 72° C. Twenty microliters of PCR product was incubated with 4 U EarI in a total volume of 25 μL, for two hours at 37° C., and the fragments were separated on a 2% agarose gel. The presence of the 693 mutation destroys a restriction site for EarI, and thus the 297 bp PCR product will be cut into fragments of 151 bp, 59 bp, 48 bp and 39 bp in the presence of a wild-type allele, but only fragments of 210 bp, 48 bp and 39 bp in the presence of the deletion.

A 6 bp deletion encompassing nucleotides 5752-5757 (inclusive), was detected in exon 41 in the proband of family FHA-3 bp genomic sequencing using primers located within the introns flanking this exon. Genotyping of this mutation in family FHA-3 and controls was carried out by PCR with forward (5'-CCT GTA AAT GCA AAG CTA TCT CCT CT-3' (SEQ ID NO: 10)) and reverse primers (5'-CGT CAA CTC CTT GAT TTC TAA GAT GT (SEQ ID NO: 11)) located near the 5' and 3' ends of exon 41, respectively. Each PCR was carried out as for the genotyping of the 693 variant, but with annealing temperature of 58° C. Twenty microliters of PCR product was resolved on 3% agarose or 10% acrylamide gels. The wild type allele was detected as a 117 bp band and the mutant allele as a 111 bp band upon staining with ethidium bromide.

A C to T transition was detected at nucleotide 6504 in genomic DNA of the proband of family FHA-2. It was detectable as a double C and T peak in the genomic sequence of exon 48 of this individual, who is heterozygous for the alteration. This mutation, which creates a STOP codon that results in truncation of the last 118 amino acids of the ABC1 protein, also destroys an RsaI restriction site that is present in the wild type sequence. Genotyping of this mutation in family FHA-2 and controls was carried out by PCR with forward (5'-GGG TTC CCA GGG TTC AGT AT-3') (SEQ ID NO: 12)) and reverse (5'-GAT CAG GAA TTC AAG CAC CAA-3') (SEQ ID NO: 13)) primers directed to the intronic sequences flanking exon 48. PCR was done as for the 693 variant. Fifteen microliters of PCR product was digested with 5 Units of RsaI at 37° C. for two hours and the digestion products resolved on 1.5% agarose gels. The mutant allele is detected as an uncut 436 bp band. The normal sequence is cut by RsaI to produce 332 and 104 bp bands.

Cell Culture

Skin fibroblast cultures were established from 3.0 mm punch biopsies of the forearm of FHD patients and healthy control subjects as described (Marcil et al., Arterioscler. Thromb. Vasc. Biol. 19:159-169, 1999).

Cellular Cholesterol Labeling and Loading

The protocol for cellular cholesterol efflux experiments was described in detail elsewhere (Marcil et al., Arterioscler. Thromb. Vasc. Biol. 19:159-169, 1999). The cells were $^3$H-cholesterol labeled during growth and free cholesterol loaded in growth arrest.

Cholesterol Efflux Studies

Efflux studies were carried out from 0 to 24 hours in the presence of purified ApoAI (10 μg protein/mL medium).

Efflux was determined as a percent of free cholesterol in the medium after the cells were incubated for specified periods of time. All experiments were performed in triplicate, in the presence of cells from one control subject and the cells from the study subjects to be examined. All results showing an efflux defect were confirmed at least three times.

Oligonucleotide Synthesis

Eight phosphorothioate deoxyoligonucleotides complementary to various regions of the human ABC1 cDNA sequence were obtained from GIBCO BRL. The oligonucleotides were purified by HPLC. The sequences of the antisense oligonucleotides and their location are listed. One skilled in the art will recognize that other ABC1 antisense sequences can also be produced and tested for their ability to decrease ABC1-mediated cholesterol regulation.

| Name | Sequence (5'- 3') | mRNA target | % control |
|---|---|---|---|
| AN-1 | GCAGAGGGCATGGCTTTATTTG (SEQ ID NO: 3) | AUG codon | 46 |
| AN-2 | GTGTTCCTGCAGAGGGCATG (SEQ ID NO: 30) | AUG codon | 50 |
| AN-3 | CACTTCCAGTAACAGCTGAC (SEQ ID NO: 31) | 5'-Untranslated | 79 |
| AN-4 | CTTTGCGCATGTCCTTCATGC (SEQ ID NO: 32) | Coding | 80 |
| AN-5 | GACATCAGCCCTCAGCATCTT (SEQ ID NO: 33) | Coding | 120 |
| AN-6: | CAACAAGCCATGTTCCCTC (SEQ ID NO: 34) | Coding | |
| AN-7: | CATGTTCCCTCAGCCAGC (SEQ ID NO: 35) | Coding | |
| AN-8: | CAGAGCTCACAGCAGGGA C (SEQ ID NO: 36) | Coding | |

Cell Transfection with Antisense Oligonucleotides

Cells were grown in 35 mm culture dishes until 80% confluent, then washed once with DMEM medium (serum and antibiotics free). One milliliter of DMEM (serum and antibiotics free) containing 500 nM antisense oligonucleotides and 5 μg/ml or 7.5 μg/ml of lipofectin (GIBCO BRL) were added to each well according to the manufacturer's protocol. The cells were incubated at 37° C. for 4 hours, and then the medium was replaced by DMEM containing 10% FCS. Twenty-four hours after the transfection, the total cell RNA was isolated. Ten micrograms of total RNA was resolved on a 1% of agarose-formaldehyde gel and transferred to nylon membrane. The blot was hybridized with γ-$^{32}$P dCTP labeled human ABC1 cDNA overnight at 68° C. The membrane was subsequently exposed to x-ray film. The hybridizing bands were scanned by optical densitometry and standard to 28S ribosome RNA.

Cholesterol Efflux with Anti-ABC1 Oligonucleotides

Human skin fibroblasts were plated in 6-well plates. The cells were labeled with $^3$H-cholesterol (0.2 μCi/ml) in DMEM with 10% FBS for two days when the cell reached 50% confluence. The cells were then transfected with the antisense ABC1 oligonucleotides at 500 nM in DMEM (serum and antibiotic free) with 7.5 μg/ml Lipofectin (GIBCO BRL) according to the manufacturer's protocol. Following the transfection, and the cells were loaded with nonlipoprotein (20 μg/ml) for 12 hours in DMEM containing 2 mg/ml BSA without serum. The cellular cholesterol pools were then allowed to equilibrate for 6 hours in DMEM-BSA. The cholesterol efflux mediated by ApoAI (10 μg/ml, in DMEM-BSA) were then carried out which is 48 hours after transfection.

Radiolabeled cholesterol released into the medium is expressed as a percentage of total $^3$H-cholesterol per well (medium+cell). Results are the to mean+/−SD of triplicate dishes.

Determination of Genomic Structure of the ABC1 Gene

Most splice junction sequences were determined from genomic sequence generated from BAC clones spanning the ABC1 gene. More than 160 kb of genomic sequence were generated. Genomic sequences were aligned with cDNA sequences to identify intron/exon boundaries. In some cases, long distance PCR between adjacent exons was used to amplify intron/exon boundary sequences using amplification primers designed according to the cDNA sequence.

Functionality of the Newly-Discovered 60 Amino Acids at the N-Terminus

Antisense Experiments

Phosphorothioate antisense oligonucleotides were designed to be complementary to the regions of the cDNA near newly discovered translation start site. AN-6 and AN-7 both overlap the initiator methionine codon; this site is in the middle of oligonucleotide AN-6. AN-8 is complementary to the very 5' end of the ABC1 cDNA. Antisense oligonucleotide AN-1 is complementary to the region of the ABC1 cDNA corresponding to the site identified as the ABC1 initiator methionine in AJ012376. FIG. 7C shows that antisense oligonucleotide AN-6 interferes with cellular cholesterol efflux in normal fibroblasts to the same extent as does antisense oligonucleotide AN-1. Transfection with either of these antisense oligonucleotides results in a decrease in cellular cholesterol efflux almost as severe as that seen in FHA cells. In general, antisense oligonucleotides complementary to coding sequences, especially near the 5' end of a gene's coding sequence, are expected to be more effective in decreasing the effective amount of transcript than are oligonucleotides directed to more 3' sequences or to non-coding sequences. The observation that AN-6 depresses cellular cholesterol efflux as effectively as AN-1 implies that both of these oligonucleotides are complementary to ABC1 coding sequences, and that the amino terminal 60 amino acids are likely to be contained in ABC1 protein. In contrast, the ineffectiveness of AN-8 shows that it is likely to be outside the protein coding region of the transcript, as predicted by presence of an in-frame stop codon between the initiator methionine and the region targeted by AN-8.

Antibody Experiments

Polyclonal and monoclonal antibodies have been generated using peptides corresponding to discrete portions of the ABC1 amino acid sequence. One of these, 20-amino acid peptide #2 (Pep2: CSVRLSYPPYEQHECHFPNKA (SEQ ID NO: 37), in which the N-terminal cysteine was added to facilitate conjugation of the peptide) corresponds to a protein sequence within the 60 amino-terminal amino acids of the newly-discovered ABC1 protein sequence. The peptide was coupled to the KLH carrier protein and 300 μg injected at three intervals into two Balb/c mice over a four week period. The spleen was harvested from the mouse with the highest ELISA-determined immune response to free peptide, and the cells fused to NS-1 myeloma cells by standard monoclonal antibody generation methods. Positive hybridomas were selected first by ELISA and then further characterized by western blotting using cultured primary human fibroblasts. Monoclonal cell lines producing a high antibody titre and specifically recognizing the 245 kD human ABC1 protein were saved. The same size ABC1 protein product was detected by antibodies directed to four other discrete regions of the same protein. The 245 kD band could be eliminated in competition experiments with appropriate free peptide, indicating that it represents ABC1 protein (FIG. 13).

The foregoing experiments indicate that ABC1 protein is detected not only by antibodies corresponding to amino acid sequences within the previously-described ABC1 amino acid sequence, but also by the Pep2 monoclonal antibody that recognizes an epitope within the newly-discovered N-terminal 60 amino acids. The N-terminal 60 amino acid region is therefore coding, and is part of the ABC1 protein.

The epitope recognized by the Pep2 monoclonal antibody is also conserved among human, mouse, and chicken. Liver tissues from these three species employed in a Western blot produced an ABC1 band of 245 kD when probed with the Pep2 monoclonal antibody. This indicates that the 60 amino acid N-terminal sequence is part of the ABC1 coding sequence in humans, mice, and chickens. Presence of this region is therefore evolutionarily conserved and likely to be of important functional significance for the ABC1 protein.

Bioinformatic Analyses of ABC1 Protein Sequences

Transmembrane prediction programs indicate 13 transmembrane (TM) regions, the first one being between amino acids 26 and 42 (psort.nibb.ac.jp:8800/psort/helpwww2.ealom). The tentative number of TM regions for the threshold 0.5 is 13. (INTEGRAL Likelihood=−7.75 Transmembrane 26-42). The other 12 TM range in value between −0.64 and −12 (full results below). It is therefore very likely that the newly-discovered 60 amino acids contain a TM domain, and that the amino end of ABC1 may be on the opposite side of the membrane than originally thought.

ALOM: TM region allocation
Init position for calculation: 1
Tentative number of TMs for the threshold 0.5: 13
INTEGRAL Likelihood=−7.75 Transmembrane 26-42
INTEGRAL Likelihood=−3.98 Transmembrane 640-656
INTEGRAL Likelihood=−8.70 Transmembrane 690-706
INTEGRAL Likelihood=−9.61 Transmembrane 717-733
INTEGRAL Likelihood=−1.44 Transmembrane 749-765
INTEGRAL Likelihood=−0.64 Transmembrane 771-787
INTEGRAL Likelihood=−1.28 Transmembrane 1041-1057
INTEGRAL Likelihood=−12.79 Transmembrane 1351-1367
INTEGRAL Likelihood=−8.60 Transmembrane 1661-1677
INTEGRAL Likelihood=−6.79 Transmembrane 1708-1724
INTEGRAL Likelihood=−3.40 Transmembrane 1737-1753
INTEGRAL Likelihood=−1.49 Transmembrane 1775-1791
INTEGRAL Likelihood=−8.39 Transmembrane 1854-1870
PERIPHERAL Likelihood=0.69 (at 1643)
ALOM score: −12.79 (number of TMSs: 13)

There does not appear to be an obvious cleaved peptide, so this first 60 amino acid residues are not likely to be cleaved, and are therefore not specifically a signal/targeting sequence. No other signals (e.g., for targeting to specific organelles) are apparent.

Agonists and Antagonists

Useful therapeutic compounds include those which modulate the expression, activity, or stability of ABC1. To isolate such compounds, ABC1 expression, biological activity, or regulated catabolism is measured following the addition of candidate compounds to a culture medium of ABC1-expressing cells. Alternatively, the candidate compounds may be directly administered to animals (for example mice, pigs, or chickens) and used to screen for their effects on ABC1 expression.

In addition its role in the regulation of cholesterol, ABC1 also participates in other biological processes for which the development of ABC1 modulators would be useful. In one example, ABC1 transports interleukin-1β (IL-1β) across the cell membrane and out of cells. IL-1β is a precursor of the inflammatory response and, as such, inhibitors or antagonists of ABC1 expression or biological activity may be useful in the treatment of any inflammatory disorders, including but not limited to rheumatoid arthritis, systemic lupus erythematosis (SLE), hypo- or hyper-thyroidism, inflammatory bowel disease, and diabetes mellitus. In another example, ABC1 expressed in macrophages has been shown to be to engaged in the engulfment and clearance of dead cells. The ability of macrophages to ingest these apoptotic bodies is impaired after antibody-mediated blockade of ABC1. Accordingly, compounds that modulate ABC1 expression, stability, or biological activity would be useful for the treatment of these disorders.

ABC1 expression is measured, for example, by standard Northern blot analysis using an ABC1 nucleic acid sequence (or fragment thereof) as a hybridization probe, or by Western blot using an anti-ABC1 antibody and standard techniques. The level of ABC1 expression in the presence of the candidate molecule is compared to the level measured for the same cells, in the same culture medium, or in a parallel set of test animals, but in the absence of the candidate molecule. ABC1 activity can also be measured using the cholesterol efflux assay.

Transcriptional Regulation of ABC1 Expression

ABC1 mRNA is increased approximately 8-fold upon cholesterol loading. This increase is likely controlled at the transcriptional level. Using the promoter sequence described herein, one can identify transcription factors that bind to the promoter by performing, for example, gel shift assays, DNAse protection assays, or in vitro or in vivo reporter gene-based assays. The identified transcription factors are themselves drug targets. In the case of ABC1, drug compounds that act through modulation of transcription of ABC1 could be used for HDL modulation, atherosclerosis prevention, and the treatment of cardiovascular disease. For example, using a compound to inhibit a transcription factor that represses ABC1 would be expected to result in up-regulation of ABC1 and, therefore, HDL levels. In another example, a compound that increases transcription factor expression or activity would also increase ABC1 expression and HDL levels.

Transcription factors known to regulate other genes in the regulation of apolipoprotein genes or other cholesterol- or lipid-regulating genes are of particular relevance. Such factors include, but are not limited to, the steroid response element binding proteins (SREBP-1 and SREBP-2), the PPAR (peroxisomal proliferation-activated receptor) transcription factors. Several consensus sites for certain elements are present in the sequenced region 5' to is the ABC1 gene (FIG. 16) and are likely to modulate ABC1 expression. For example, PPARs may alter transcription of ABC1 by mechanisms including heterodimerization with retinoid X receptors (RXRs) and then binding to specific proliferator response elements (PPREs). Examples of such PPARs include PPARα, β, γ and δ. These distinct PPARs have been shown to have transcriptional regulatory effects on different genes. PPARα is expressed mainly in liver, whereas PPARγ is expressed in predominantly in adipocytes. Both PPARα and PPARγ are found in coronary and carotid artery atherosclerotic plaques and in endothelial cells, smooth muscle cells, monocytes and monocyte-derived macrophages. Activation of PPARα results in altered lipoprotein metabolism through PPARα's effect on genes such as lipoprotein lipase (LPL), apolipoprotein CIII (apo CIII) and apolipoprotein AI (apo AI) and AII (apo AII). PPARα activation results in overexpression of LPL and apoA-I and apoA-II, but inhibits the expression of apo CIII. PPARα activation also inhibits inflammation, stimulates lipid oxidation and increases the hepatic uptake and esterification of free fatty acids (FFA's). PPARα and PPARγ activation may inhibit nitric oxide (NO) synthase in macrophages and prevent interleukin-1 (IL-1) induced expression of IL-6 and cyclo-oxygenase-2 (COX-2) and thrombin induced endothelin-1 expression secondary to negative transcriptional regulation of NF-KB and activation of protein-1 signaling pathway. It has also been shown that PPARα induces apoptosis in monocyte-derived macrophages through the inhibition of NF-KB activity.

Activation of PPARα can be achieved by compounds such as fibrates, β-estradiol, arachidonic acid derivatives, WY-14,643 and LTB4 or 8(s)HETE. PPARγ activation can be achieved through compounds such as thiozolidinedione antidiabetic drugs, 9-HODE and 13-HODE. Additional compounds such as nicotinic acid or HMG CoA reductase inhibitors may also alter the activity of PPARs.

Compounds which alter activity of any of the PPARs (e.g., PPARα or PPARγ) may have an effect on ABC1 expression and thereby could affect HDL levels, atherosclerosis and risk of CAD. PPARs are also regulated by fatty acids (including modified fatty acids such as 3 thia fatty acids), leukotrienes such as leukotriene B4 and prostaglandin J2, which is a natural activator/ligand for PPARγ. Drugs that modulate PPARs may therefore have an important effect on modulating lipid levels (including HDL and triglyceride levels) and altering CAD risk. This effect could be achieved through the modulation of ABC1 gene expression. Drugs may also effect ABC1 gene expression and thereby HDL levels, by an indirect effect on PPARs via other transcriptional factors such as adipocyte differentiation and determination factor-1 (ADD-1) and sterol regulatory element binding protein-1 and 2 (SREBP-1 and 2). Drugs with combined PPARα and PPARγ agonist activity or PPARα and PPARγ agonists given in combination for example, may increase HDL levels even more.

A PPAR binding site (PPRE element) is found 5' to the ABC1 gene (nucleotides 2150 to 2169 of SEQ ID NO: 14). Like the PPRE elements found in the C-ACS, HD, CYP4A6 and ApoA-I genes, this PPRE site is a trimer related to the PPRE consensus sequence. Partly because of its similarity in the number and arrangement of repeats in this PPAR binding site, this element in particular is very likely to be of physiological relevance to the regulation of the ABC1 gene.

Additional transcription factors which may also have an effect in modulating ABC1 gene expression and thereby HDL levels, atherosclerosis and CAD risk include; REV-ERBα, SREBP-1 & 2, ADD-1, EBPα, CREB binding protein, P300, HNF 4, RAR, LXR, and RORα. Additional degenerate binding sites for these factors can be found through examination of the sequence in SEQ ID NO: 14.

Additional Utility of ABC1 Polypeptides, Nucleic Acids, and Modulators

ABC1 may act as a transporter of toxic proteins or protein fragments (e.g., APP) out of cells. Thus, ABC1 agonists/upregulators may be useful in the treatment of other disease areas, including Alzheimer's disease, Niemann-Pick disease, and Huntington's disease.

ABC transporters have been shown to increase the uptake of long chain fatty acids from the cytosol to peroxisomes and, moreover, to play a role in β-oxidation of very long chain fatty acids. Importantly, in x-linked adrenoleukodystrophy (ALD), fatty acid metabolism is abnormal, due to defects in the peroxisomal ABC transporter. Any agent that upregulates ABC transporter expression or biological activity may therefor be useful for the treatment of ALD or any other lipid disorder.

ABC1 is expressed in macrophages and is required for engulfment of cells undergoing programmed cell death. The apoptotic process itself, and its regulation, have important implications for disorders such as cancer, one mechanism of which is failure of cells to undergo cell death appropriately. ABC1 may facilitate apoptosis, and as such may represent an intervention point for cancer treatment. Increasing ABC1 expression or activity or otherwise up-regulating ABC1 by any method may constitute a treatment for cancer by increasing apoptosis and thus potentially decreasing the aberrant cellular proliferation characterized by this disease. Conversely, down-regulation of ABC1 by any method may provide opportunity for decreasing apoptosis and allowing increased proliferation of cells in conditions where cell growth is limited. Such disorders include but are not limited to neurodeficiencies and neurodegeneration, and growth disorders. ABC1 could, therefore, potentially be used as a method for identification of compounds for use in the treatment of cancer, or in the treatment of degenerative disorders.

Agents that have been shown to inhibit ABC1 include, for example, the anti-diabetic agents glibenclamide and glyburide, flufenamic acid, diphenylamine-2-carbonic acid, sulfobromophthalein, and DIDS.

Agents that upregulate ABC1 expression or biological activity include but is are not limited to protein kinase A, protein kinase C, vanadate, okadaic acid, and IBMX1.

Those in the art will recognize that other compounds can also modulate ABC1 biological activity, and these compounds are also in the spirit of the invention.

Drug Screens Based on the ABC1 Gene or Protein

The ABC1 protein and gene can be used in screening assays for identification of compounds which modulate its activity and may be potential drugs to regulate cholesterol levels. Useful ABC1 proteins include wild-type and mutant ABC1 proteins or protein fragments, in a recombinant form or endogenously expressed. Drug screens to identify compounds acting on the ABC1 expression product may employ any functional feature of the protein. In one example, the phosphorylation state or other post-translational modification is monitored as a measure of ABC1 biological activity. ABC1 has ATP binding sites, and thus assays may wholly or in part test the ability of ABC1 to bind ATP or to exhibit ATPase activity. ABC1, by analogy to similar proteins, is thought to be able to form a channel-like structure; drug screening assays could be based upon assaying for the ability of the protein to form a channel, or upon the ability to transport cholesterol or another molecule, or based upon the ability of other proteins bound by or regulated by ABC1 to form a channel. Alternatively, phospholipid or lipid transport can also be used as measures of ABC1 biological activity.

There is evidence that, in addition to its role as a regulator of cholesterol levels, ABC1 also transports anions. Functional assays could be based upon this property, and could employ drug screening technology such as (but not limited to) the ability of various dyes to change color in response to changes in specific ion concentrations in such assays can be performed in vesicles such as liposomes, or adapted to use whole cells.

Drug screening assays can also be based upon the ability of ABC1 or other ABC transporters to interact with other proteins. Such interacting proteins can be identified by a variety of methods known in the art, including, for example, radioimmunoprecipitation, co-immunoprecipitation, co-purification, and yeast two-hybrid screening. Such interactions can be further assayed by means including but not limited to fluorescence polarization or scintillation proximity methods. Drug screens can also be based upon functions of the ABC1 protein deduced upon X-ray crystallography of the protein and comparison of its 3-D structure to that of proteins with known functions. Such a crystal structure has been determined for the prokaryotic ABC family member H is P, histidine permease. Drug screens can be based upon a function or feature apparent upon creation of a transgenic or knockout mouse, or upon overexpression of the protein or protein fragment in mammalian cells in vitro. Moreover, expression of mammalian (e.g., human) ABC1 in yeast or C. elegans allows for screening of candidate compounds in wild-type and mutant backgrounds, as well as screens for mutations that enhance or suppress an ABC1-dependent phenotype. Modifier screens can also be performed in ABC1 transgenic or knock-out mice.

Additionally, drug screening assays can also be based upon ABC1 functions deduced upon antisense interference with the gene function. Intracellular localization of ABC1, or effects which occur upon a change in intracellular localization of the protein, can also be used as an assay for drug screening. Immunocytochemical methods will be used to determine the exact location of the ABC1 protein.

Human and rodent ABC1 protein can be used as an antigen to raise antibodies, including monoclonal antibodies. Such antibodies will be useful for a wide variety of purposes, including but not limited to functional studies and the development of drug screening assays and diagnostics. Monitoring the influence of agents (e.g., drugs, compounds) on the expression or biological activity of ABC1 can be applied not only in basic drug screening, but also in clinical trials. For example, the effectiveness of an agent determined by a screening assay as described herein to increase ABC1 gene expression, protein levels, or biological activity can be monitored in clinical trails of subjects exhibiting altered ABC1 gene expression, protein levels, or biological activity. Alternatively, the effectiveness of an agent determined by a screening assay to modulate ABC1 gene expression, protein levels, or biological activity can be monitored in clinical trails of subjects exhibiting decreased altered gene expression, protein levels, or biological activity. In such clinical trials, the expression or activity of ABC1 and, preferably, other genes that have been implicated in, for example, cardiovascular disease can be used to ascertain the effectiveness of a particular drug.

For example, and not by way of limitation, genes, including ABC1, that are modulated in cells by treatment with an agent (e.g., compound, drug or small molecule) that modulates ABC1 biological activity (e.g., identified in a screening assay as described herein) can be identified. Thus, to study the effect of agents on cholesterol levels or cardiovascular disease, for example, in a clinical trial, cells can be isolated and RNA prepared and analyzed for the levels of expression of ABC1 and other genes implicated in the disorder. The levels of gene expression can be quantified by Northern blot analysis or RT-PCR, or, alternatively, by measuring the amount of protein produced, by one of a number of methods known in the art, or by measuring the levels of biological activity of ABC1 or other genes. In this way, the gene expression can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an ABC1 protein, mRNA, or genomic DNA in the preadministration sample; (iii) obtaining one or more post-administration samples from the subject; (iv) detecting the level of expression or activity of the ABC1 protein, mRNA, or genomic DNA in the post-administration samples; (v) comparing the level of expression or activity of the ABC1 protein, mRNA, or genomic DNA in the pre-administration sample with the ABC1 protein, mRNA, or genomic DNA in the post administration sample or samples; and (vi) altering the administration of the agent to the subject accordingly. For example, increased administration of the agent may be desirable to increase the expression or activity of ABC1 to higher levels than detected, i.e., to increase the effectiveness of the agent. Alternatively, decreased administration of the agent may be desirable to decrease expression or activity of ABC1 to lower levels than detected.

The ABC1 gene or a fragment thereof can be used as a tool to express the protein in an appropriate cell in vitro or in vivo (gene therapy), or can be cloned into expression vectors which can be used to produce large enough amounts of ABC1 protein to use in in vitro assays for drug screening. Expression systems which may be employed include baculovirus, herpes virus, adenovirus, adeno-associated virus, bacterial systems, and eucaryotic systems such as CHO cells. Naked DNA and DNA-liposome complexes can also be used.

Assays of ABC1 activity includes binding to intracellular interacting proteins; interaction with a protein that up-regulates ABC1 activity; interaction with HDL particles or constituents; interaction with other proteins which facilitate interaction with HDL or its constituents; and measurement of cholesterol efflux. Furthermore, assays may be based upon the molecular dynamics of macromolecules, metabolites and ions by means of fluorescent-protein biosensors. Alternatively, the effect of candidate modulators on expression or activity may be measured at the level of ABC1 protein production using the same general approach in combination with standard immunological detection techniques, such as Western blotting or immunoprecipitation with an ABC1-specific antibody. Again, useful cholesterol-regulating or anti-CVD therapeutic modulators are identified as those which produce an change in ABC1 polypeptide production. Agonists may also affect ABC1 activity without any effect on expression level.

Candidate modulators may be purified (or substantially purified) molecules or may be one component of a mixture of compounds (e.g., an extract or supernatant obtained from cells). In a mixed compound assay, ABC1 expression is tested against progressively smaller subsets of the candidate compound pool (e.g., produced by standard purification techniques, e.g., HPLC or FPLC; Ausubel et al.) until a single compound or minimal compound mixture is demonstrated to modulate ABC1 expression.

Agonists, antagonists, or mimetics found to be effective at modulating the level of cellular ABC1 expression or activity may be confirmed as useful in animal models (for example, mice, pigs, rabbits, or chickens). For example, the compound may ameliorate the low HDL levels of mouse or chicken hypoalphalipoproteinemias.

A compound that promotes an increase in ABC1 expression or activity is considered particularly useful in the invention; such a molecule may be used, for example, as a therapeutic to increase the level or activity of native, cellular ABC1 and thereby treat a low HDL condition in an animal (for example, a human).

One method for increasing ABC biological activity is to increase the stabilization of the ABC protein or to prevent its degradation. Thus, it would be useful to identify mutations in an ABC polypeptide (e.g., ABC1) that lead to is increased protein stability. These mutations can be incorporated into any protein therapy or gene therapy undertaken for the treatment of low HDL-C or any other condition resulting from loss of ABC1 biological activity. Similarly, compounds that increase the stability of a wild-type ABC polypeptide or decrease its catabolism may also be useful for the treatment of low HDL-C or any other condition resulting from loss of ABC1 biological activity. Such mutations and compounds can be identified using the methods described herein.

In one example, cells expressing an ABC polypeptide having a mutation are transiently metabolically labeled during translation and the half-life of the ABC polypeptide is determined using standard techniques. Mutations that increase the half-life of an ABC polypeptide are ones that increase ABC protein stability. These mutations can then be assessed for ABC biological activity. They can also be used to identify proteins that affect the stability of ABC1 mRNA or protein. One can then assay for compounds that act on these factors or on the ability of these factors to bind ABC1.

In another example, cells expressing wild-type ABC polypeptide are transiently metabolically labeled during translation, contacted with a candidate compounds, and the half-life of the ABC polypeptide is determined using standard techniques. Compounds that increase the half-life of an ABC polypeptide are useful compounds in the present invention.

If desired, treatment with an agonist of the invention may be combined with any other HDL-raising or anti-CVD therapies.

It is understood that, while ABC1 is the preferred ABC transporter for the drug screens described herein, other ABC transporters can also be used. The replacement of ABC1 with another ABC transporter is possible because it is likely that ABC transporter family members, such as ABC2, ABCR, or ABC8 will have a similar mechanism of regulation.

Exemplary assays are described in greater detail below.

Protein-Based Assays

ABC1 polypeptide (purified or unpurified) can be used in an assay to determine its ability to bind another protein (including, but not limited to, proteins found to specifically interact with ABC1). The effect of a compound on that binding is then determined.

Protein Interaction Assays

ABC1 protein (or a polypeptide fragment thereof or an epitope-tagged form or fragment thereof) is harvested from a suitable source (e.g., from a prokaryotic expression system, eukaryotic cells, a cell-free system, or by immunoprecipitation from ABC1-expressing cells). The ABC1 polypeptide is then bound to a suitable support (e.g., nitrocellulose or an antibody or a metal agarose column in the case of, for example, a his-tagged form of ABC1). Binding to the support is preferably done under conditions that allow proteins associated with ABC1 polypeptide to remain associated with it. Such conditions may include use of buffers that minimize interference with protein-protein interactions. The binding step can be done in the presence and absence of compounds being tested for their ability to interfere with interactions between ABC1 and other molecules. If desired, other proteins (e.g., a cell lysate) are added, and allowed time to associate with the ABC polypeptide. The immobilized ABC1 polypeptide is then washed to remove proteins or other cell constituents that may be non-specifically associated with it the polypeptide or the support. The immobilized ABC1 polypeptide is then dissociated from its support, and so that proteins bound to it are released (for example, by heating), or, alternatively, associated proteins are released from ABC1 without releasing the ABC1 polypeptide from the support. The released proteins and other cell constituents can be analyzed, for example, by SDS-PAGE gel electrophoresis, Western blotting and detection with specific antibodies, phospho-amino acid analysis, protease digestion, protein sequencing, or isoelectric focusing. Normal and mutant forms of ABC1 can be employed in these assays to gain additional information about which part of ABC1 a given factor is binding to. In addition, when incompletely purified polypeptide is employed, comparison of the normal and mutant forms of the protein can be used to help distinguish true binding proteins.

The foregoing assay can be performed using a purified or semipurified protein or other molecule that is known to interact with ABC1. This assay may include the following steps.

1. Harvest ABC1 protein and couple a suitable fluorescent label to it;

2. Label an interacting protein (or other molecule) with a second, different fluorescent label. Use dyes that will produce different quenching patterns when they are in close proximity to each other vs. when they are physically separate (i.e., dyes that quench each other when they are close together but fluoresce when they are not in close proximity);

3. Expose the interacting molecule to the immobilized ABC1 in the presence or absence of a compound being tested for its ability to interfere with an interaction between the two; and 4. Collect fluorescent readout data.

Another assay is includes Fluorescent Resonance Energy Transfer (FRET) assay. This assay can be performed as follows.

1. Provide ABC1 protein or a suitable polypeptide fragment thereof and couple a suitable FRET donor (e.g., nitrobenzoxadiazole (NBD)) to it;

2. Label an interacting protein (or other molecule) with a FRET acceptor (e.g., rhodamine);

3. Expose the acceptor-labeled interacting molecule to the donor-labeled ABC1 in the presence or absence of a compound being tested for its ability to interfere with an interaction between the two; and 4. Measure fluorescence resonance energy transfer.

Quenching and FRET assays are related. Either one can be applied in a given case, depending on which pair of fluorophores is used in the assay.

Membrane Permeability Assay

The ABC1 protein can also be tested for its effects on membrane permeability. For example, beyond its putative ability to translocate lipids, ABC1 might affect the permeability of membranes to ions. Other related membrane proteins, most notably the cystic fibrosis transmembrane conductance regulator and the sulfonylurea receptor, are associated with and regulate ion channels.

ABC1 or a fragment of ABC1 is incorporated into a synthetic vesicle, or, alternatively, is expressed in a cell and vesicles or other cell sub-structures containing ABC1 are isolated. The ABC1-containing vesicles or cells are loaded with a reporter molecule (such as a fluorescent ion indicator whose fluorescent properties change when it binds a particular ion) that can detect ions (to observe outward movement), or alternatively, the external medium is loaded with such a molecule (to observe inward movement). A molecule which exhibits differential properties when it is inside the vesicle compared to when it is outside the vesicle is preferred. For example, a molecule that has quenching properties when it is at high concentration but not when it is at another low concentration would be suitable. The movement of the charged molecule (either its ability to move or the kinetics of its movement) in the presence or absence of a compound being tested for its ability to affect this process can be determined.

In another assay, membrane permeability is determined electro-physiologically by measuring ionic influx or efflux mediated by or modulated by ABC1 by standard electro-physiological techniques. A suitable control (e.g., TD cells or a cell line with very low endogenous ABC1 expression) can be used as a control in the assay to determine if the effect observed is specific to cells expressing ABC1.

In still another assay, uptake of radioactive isotopes into or out of a vesicle can be measured. The vesicles are separated from the extravesicular medium and the radioactivity in the vesicles and in the medium is quantitated and compared.

Nucleic Acid-Based Assays

ABC1 nucleic acid may be used in an assay based on the binding of factors necessary for ABC1 gene transcription. The association between the ABC1 DNA and the binding factor may be assessed by means of any system that discriminates between protein-bound and non-protein-bound DNA (e.g., a gel retardation assay). The effect of a compound on the binding of a factor to ABC1 DNA is assessed by means of such an assay. In addition to in vitro binding assays, in vivo assays in which the regulatory regions of the ABC1 gene are linked to reporter genes can also be performed.

Assays Measuring ABC1 Stability

A cell-based or cell-free system can be used to screen for compounds based on their effect on the half-life of ABC1 mRNA or ABC1 protein. The assay may employ labeled mRNA or protein. Alternatively, ABC1 mRNA may be detected by means of specifically hybridizing probes or a quantitative PCR assay. Protein can be quantitated, for example, by fluorescent antibody-based methods.

In Vitro mRNA Stability Assay

1. Isolate or produce, by in vitro transcription, a suitable quantity of ABC1 mRNA;
2. Label the ABC1 mRNA;
3. Expose aliquots of the mRNA to a cell lysate in the presence or absence of a compound being tested for its ability to modulate ABC1 mRNA stability;
4. Assess intactness of the remaining mRNA at suitable time points.

In Vitro Protein Stability Assay

1. Express a suitable amount of ABC1 protein;
2. Label the protein;
3. Expose aliquots of the labeled protein to a cell lysate in the presence or absence of a compound being tested for its ability to modulate ABC1 protein stability;
4. Assess intactness of the remaining protein at suitable time points In Vivo mRNA or Protein Stability Assay 1. Incubate cells expressing ABC1 mRNA or protein with a tracer (radiolabeled ribonucleotide or radiolabeled amino acid, respectively) for a very brief time period (e.g., five minutes) in the presence or absence of a compound being tested for its effect on mRNA or protein stability;
2. Incubate with unlabeled ribonucleotide or amino acid; and
3. Quantitate the ABC1 mRNA or protein radioactivity at time intervals beginning with the start of step 2 and extending to the time when the radioactivity in ABC1 mRNA or protein has declined by approximately 80%. It is preferable to separate the intact or mostly intact mRNA or protein from its radioactive breakdown products by a means such as gel electrophoresis in order to quantitate the mRNA or protein.

Assays Measuring Inhibition of Dominant Negative Activity

Mutant ABC1 polypeptides are likely to have dominant negative activity (i.e., activity that interferes with wild-type ABC1 function). An assay for a compound that can interfere with such a mutant may be based on any method of quantitating normal ABC1 activity in the presence of the mutant. For example, normal ABC1 facilitates cholesterol efflux, and a dominant negative mutant would interfere with this effect. The ability of a compound to counteract the effect of a dominant negative mutant may be based on cellular cholesterol efflux, or on any other normal activity of the wild-type ABC1 that was inhibitable by the mutant.

Assays Measuring Phosphorylation

The effect of a compound on ABC1 phosphorylation can be assayed by methods that quantitate phosphates on proteins or that assess the phosphorylation state of a specific residue of a ABC1. Such methods include but are not limited to $^{32}$P labelling and immunoprecipitation, detection with antiphospho-amino acid antibodies (e.g., antiphosphoserine antibodies), phosphoamino acid analysis on 2-dimensional TLC plates, and protease digestion fingerprinting of proteins followed by detection of $^{32}$P-labeled fragments.

Assays Measuring Other Post-Translational Modifications

The effect of a compound on the post-translational modification of ABC1 is based on any method capable of quantitating that particular modification. For example, effects of compounds on glycosylation may be assayed by treating ABC1 with glycosylase and quantitating the amount and nature of carbohydrate released.

Assays Measuring ATP Binding

The ability of ABC1 to bind ATP provides another assay to screen for compounds that affect ABC1. ATP binding can be quantitated as follows.

1. Provide ABC1 protein at an appropriate level of purity and reconstitute it in a lipid vesicle;
2. Expose the vesicle to a labeled but non-hydrolyzable ATP analog (such as gamma $^{35}$S-ATP) in the presence or absence of compounds being tested for their effect on ATP binding. Note that azido-ATP analogs can be used to allow covalent attachment of the azido-ATP to protein (by means of U.V. light), and permit easier quantitation of the amount of ATP bound to the protein.
3. Quantitate the amount of ATP analog associated with ABC1

Assays Measuring ATPase Activity

Quantitation of the ATPase activity of ABC1 can also be assayed for the effect of compounds on ABC1. This is preferably performed in a cell-free assay so as to separate ABC1 from the many other ATPases in the cell. An ATPase assay may be performed in the presence or absence of membranes, and with or without integration of ABC1 protein into a membrane. If performed in a vesicle-based assay, the ATP hydrolysis products produced or the ATP hydrolyzed may be measured within or outside of the vesicles, or both. Such an assay may be based on disappearance of ATP or appearance of ATP hydrolysis products.

For high-throughput screening, a coupled ATPase assay is preferable. For example, a reaction mixture containing pyruvate kinase and lactate dehydrogenase can be used. The mixture includes phosphoenolpyruvate (PEP), nicotinamide adenine dinucleotide (NAD+), and ATP. The ATPase activity of ABC1 generates ADP from ATP. The ADP is then converted back to ATP as part of the pyruvate kinase reaction. The product, pyruvate, is then converted to lactate. The latter reaction generates a colored quinone (NADH) from a colorless substrate (NAD+), and the entire reaction can be monitored by detection of the color change upon formation of NADH. Since ADP is limiting for the pyruvate kinase reaction, this coupled system precisely monitors the ATPase activity of ABC1.

Assays Measuring Cholesterol Efflux

A transport-based assay can be performed in vivo or in vitro. For to example, the assay may be based on any part of the reverse cholesterol transport process that is readily re-created in culture, such as cholesterol or phospholipid efflux. Alternatively, the assay may be based on net cholesterol transport in a whole organism, as assessed by means of a labeled substance (such as cholesterol).

For high throughput, fluorescent lipids can be used to measure ABC1-catalyzed lipid efflux. For phospholipids, a fluorescent precursor, C6-NBD-phosphatidic acid, can be used. This lipid is taken up by cells and dephosphorylated by phosphatidic acid phosphohydrolase. The product, NBD-diglyceride, is then a precursor for synthesis of glycerophospholipids like phosphatidylcholine. The efflux of NBD-phosphatidylcholine can be monitored by detecting fluorescence resonance energy transfer (FRET) of the NBD to a suitable acceptor in the cell culture medium. This acceptor can be rhodamine-labeled phosphatidylethanolamine, a phospholipid that is not readily taken up by cells. The use of short-chain precursors obviates the requirement for the phospholipid transfer protein in the media. For cholesterol, NBD-cholesterol ester can be reconstituted into LDL. The LDL can efficiently deliver this lipid to cells via the LDL receptor pathway. The NBD-cholesterol esters are hydrolyzed in the lysosomes, resulting in NBD-cholesterol that can now be transported back to the plasma membrane and efflux from the cell. The efflux can be monitored by the aforementioned FRET assay in which NBD transfers its fluorescence resonance energy to the rhodamine-phosphatidylethanoline acceptor.

Animal Model Systems

Compounds identified as having activity in any of the above-described assays are subsequently screened in any available animal model system, including, but not limited to, pigs, rabbits, and WHAM chickens. Test compounds are administered to these animals according to standard methods. Test compounds may also be tested in mice bearing mutations in the ABC1 gene. Additionally, compounds may be screened for their ability to enhance an interaction between ABC1 and any HDL particle constituent such as ApoAI, ApoAII, or ApoE.

The Cholesterol Efflux Assay as a Drug Screen

The cholesterol efflux assay measures the ability of cells to transfer cholesterol to an extracellular acceptor molecule and is dependent on ABC1 function. In this procedure, cells are loaded with radiolabeled cholesterol by any of several biochemical pathways (Marcil et al., Arterioscler. Thromb. Vasc. Biol. 19:159-169, 1999). Cholesterol efflux is then measured after incubation for various times (typically 0 to 24 hours) in the presence of HDL3 or purified ApoAI. Cholesterol efflux is determined as the percentage of total cholesterol in the culture medium after various times of incubation. ABC1 expression levels and/or biological activity are associated with increased efflux while decreased levels of ABC1 are associated with decreased cholesterol efflux.

This assay can be readily adapted to the format used for drug screening, which may consist of a multi-well (e.g., 96-well) format. Modification of the assay to optimize it for drug screening would include scaling down and streamlining the procedure, modifying the labeling method, using a different cholesterol acceptor, altering the incubation time, and changing the method of calculating cholesterol efflux. In all these cases, the cholesterol efflux assay remains conceptually the same, though experimental modifications may be made. A transgenic mouse overexpressing ABC1 would be expected to have higher than normal HDL levels.

Knock-Out Mouse Model

An animal, such as a mouse, that has had one or both ABC1 alleles inactivated (e.g., by homologous recombination) is likely to have low HDL-C levels, and thus is a preferred animal model for screening for compounds that raise HDL-C levels. Such an animal can be produced using standard techniques. In addition to the initial screening of test compounds, the animals having mutant ABC1 genes are useful for further testing of efficacy and safety of drugs or agents first identified using one of the other screening methods described herein. Cells taken from the animal and placed in culture can also be exposed to test compounds. HDL-C levels can be measured using standard techniques, such as those described herein.

WHAM Chickens: an Animal Model for Low HDL Cholesterol

Wisconsin Hypo-Alpha Mutant (WHAM) chickens arose by spontaneous mutation in a closed flock. Mutant chickens came to attention through their a Z-linked white shank and white beak phenotype referred to as 'recessive white skin' (McGibbon, 1981) and were subsequently found to have a profound deficiency of HDL (Poernama et al., 1990).

This chicken low HDL locus (Y) is Z-linked, or sex-linked. (In birds, females are ZW and males are ZZ). Genetic mapping placed the Y locus on the long arm of the Z chromosome (Bitgood, 1985), proximal to the ID locus (Bitgood, 1988). Examination of current public mapping data for the chicken genome mapping project, ChickMap (maintained by the Roslin Institute; www.ri.bbsrc.ac.uk/chickmap/ChickMapHomePage) showed that a region of synteny with human chromosome 9 lies on the long arm of the chicken Z chromosome (Zq) proximal to the ID locus. Evidence for this region of synteny is the location of the chicken aldolase B locus (ALDOB) within this region. The human ALDOB locus maps to chromosome 9q22.3 (The Genome Database, gdbwww.gdb.org/), not far from the location of human ABC1. This comparison of maps showed that the chicken Zq region near chicken ALDOB and the human 9q region near human ALDOB represent a region of synteny between human and chicken.

Since a low HDL locus maps to the 9q location in humans and to the Zq region in chickens, these low HDL loci are most probably located within the syntenic region. Thus we predicted that ABC1 is mutated in WHAM chickens. In support of this, we have identified an E_K mutation at a position that corresponds to amino acid 89 of human ABC1 (FIGS. 14 and 15). This non-conservative substitution is at a position that is conserved among human, mouse, and chicken, indicating that it is in a region of the protein likely to be of functional importance.

Discovery of the WHAM mutation in the amino-terminal portion of the ABC1 protein also establishes the importance of the amino-terminal region. This region may be critical because of association with other proteins required to carry out cholesterol efflux or related tasks. It may be an important regulatory region (there is a phosphorylation site for casein kinase near the mutated residue), or it may help to dictate a precise topological relationship with cellular membranes (the N-terminal 60 amino acid region contains a putative membrane-spanning or membrane-associated segment).

The amino-terminal region of the protein (up to the first 6-TM region at approximately amino acid 639) is an ideal tool for screening factors that affect ABC1 activity. It can be expressed as a truncated protein in ABC1 wild type cells in order to test for interference of the normal ABC1 function by the truncated protein. If the fragment acts in a dominant negative way, it could be used in immunoprecipitations to identify proteins that it may be competing away from the normal endogenous protein.

The C-terminus also lends itself to such experiments, as do the intracellular portions of the molecule, expressed as fragments or tagged or fusion proteins, in the absence of transmembrane regions.

Since it is possible that there are several genes in the human genome which affect cholesterol efflux, it is important to establish that any animal model to be used for a human genetic disease represents the homologous locus in that animal, and not a different locus with a similar function. The evidence above establishes that the chicken Y locus and the human chromosome 9 low HDL locus are homologous. WHAM chickens are therefore an important animal model for the identification of drugs that modulate cholesterol efflux.

The WHAM chickens' HDL deficiency syndrome is not, however, associated with an increased susceptibility to atherosclerosis in chickens. This probably reflects the shorter lifespan of the chicken rather than an inherent is difference in the function of the chicken ABC1 gene compared to the human gene. We propose the WHAM chicken as a model for human low HDL for the development and testing of drugs to raise HDL in humans. Such a model could be employed in several forms, through the use of cells or other derivatives of these chickens, or by the use of the chickens themselves in tests of drug effectiveness, toxicity, and other drug development purposes.

Therapy

Compounds of the invention, including but not limited to, ABC1 polypeptides, ABC1 nucleic acids, other ABC transporters, and any therapeutic agent that modulates biological activity or expression of ABC1 identified using any of the methods disclosed herein, may be administered with a pharmaceutically-acceptable diluent, carrier, or excipient, in unit dosage form. Conventional pharmaceutical practice may be employed to provide suitable formulations or compositions to administer such compositions to patients. Although intravenous administration is preferred, any appropriate route of administration may be employed, for example, perenteral, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspension; for oral administration, formulations may be in the form of tablets or capsules; and for intranasal formulations, in the form of powders, nasal drops, or aerosols.

Methods well known in the art for making formulations are found in, for example, *Remington: The Science and Practice of Pharmacy*, (19th ed.) ed. A. R. Gennaro A R., 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the invention include ethylenevinyl acetate copolymer particles, osmotic pumps, implantable infusion systems, and liposomes. Formulations for inhalation may contain excipients, or example, lactose, or may be aqueous solutions containing, for example, polyoxyethylene-9-lauryl ether, glycocholate and deoxycholate, or may be oily solutions for administration in the form of nasal drops, or as a gel.

Compounds

In general, novel drugs for the treatment of aberrant cholesterol levels and/or CVD are identified from large libraries of both natural product or synthetic (or semi-synthetic) extracts or chemical libraries according to methods known in the art. Those skilled in the field or drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their HDL-raising and anti-CVD activities should be employed whenever possible.

When a crude extract is found to have cholesterol-modulating or anti-CVD activities or both, further fractionation of the positive lead extract is necessary to isolate chemical constituent responsible for the observed effect. Thus, the goal of the extraction, fractionation, and purification process is the careful characterization and identification of a chemical entity within the crude extract having cholesterol-modulating or anti-CVD activities. The same in vivo and in vitro assays described herein for the detection of activities in mixtures of compounds can be used to purify the active component and to test derivatives thereof. Methods of fractionation and purification of such heterogeneous extracts are known in the art. If desired, compounds shown to be useful agents for the treatment of pathogenicity are chemically modified according to methods known in the art. Compounds identified as being of therapeutic value are subsequently analyzed using any standard animal model of diabetes or obesity known in the art.

It is understood that compounds that modulate activity of proteins that modulate or are modulated by ABC1 are useful compounds for modulating cholesterol levels. Exemplary compounds are provided herein; others are known to in the art.

Compounds that are structurally related to cholesterol, or that mimic ApoAI or a related apolipoprotein, and increase ABC1 biological activity are particularly useful compounds in the invention. Other compounds, known to act on the MDR protein, can also be used or derivatized and assayed for their ability to increase ABC1 biological activity. Exemplary MDR modulators are PSC833, bromocriptine, and cyclosporin A.

Screening Patients Having Low HDL-C

ABC1 expression, biological activity, and mutational analysis can each serve as a diagnostic tool for low HDL; thus determination of the genetic subtyping of the ABC1 gene sequence can be used to subtype low HDL individuals or families to determine whether the low HDL phenotype is related to ABC1 function. This diagnostic process can lead to the tailoring of drug treatments according to patient genotype, including prediction of side effects upon administration of HDL increasing drugs (referred to herein as pharmacogenomics). Pharmacogenomics allows for the selection of agents (e.g., drugs) for therapeutic or prophylactic treatment of an individual based on the genotype of the individual (e.g., the genotype of the individual is examined to determine the ability of the individual to respond to a particular agent).

Agents, or modulators which have a stimulatory or inhibitory effect on ABC1 biological activity or gene expression can be administered to individuals to treat disorders (e.g., cardiovascular disease or low HDL cholesterol) associated with aberrant ABC1 activity. In conjunction with such treatment, the pharmacogenomics (i.e., the study of the relationship between an individual's genotype and that individual's response to a foreign compound or drug) of the individual may be considered. Differences in efficacy of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of ABC1 protein, expression of ABC1 nucleic acid, or mutation content of ABC1 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons (Eichelbaum, M., Clin. Exp. Pharmacol. Physiol., 23:983-985, 1996; Linder, M. W., Clin. Chem., 43:254-266, 1997). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). Altered drug action may occur in a patient having a polymorphism (e.g., an single nucleotide polymorphism or SNP) in promoter, intronic, or exonic sequences of ABC1. Thus by determining the presence and prevalence of polymorphisms allow for prediction of a patient's response to a particular therapeutic agent. In particular, polymorphisms in the promoter region may be critical in determining the risk of HDL deficiency and CVD.

In addition to the mutations in the ABC1 gene described herein, we have detected polymorphisms in the human ABC1 gene (FIG. 11). These polymorphisms are located in promoter, intronic, and exonic sequence of ABC1. Using standard methods, such as direct sequencing, PCR, SSCP, or any other polymorphism-detection system, one could easily ascertain whether these polymorphisms are present in a patient prior to the establishment of a drug treatment regimen for a patient having low HDL, cardiovascular disease, or any other ABC1-mediated condition. It is possible that some these polymorphisms are, in fact, weak mutations. Individuals harboring such mutations may have an increased risk for cardiovascular disease; thus, these polymorphisms may also be useful in diagnostic assays.

Association Studies of ABC1 Gene Variants and HDL Levels or Cardiovascular Disease The following polymorphisms have been examined for their effect on cholesterol regulation and the predisposition for the development of cardiovascular disease.

Substitution of G for A at nucleotide −1045 [G(−1045)A]. This variant is in complete linkage disequilibrium with the variant at −738 in the individuals we have sequenced, and thus any potential phenotypic effects currently attributed to the variant at −738 may at least in part be due to changes at this site.

Substitution of G for A at nucleotide −738 [G(−738)A]. This variant has been found at very high frequencies in populations selected for low HDL cholesterol or premature coronary artery disease.

Insertion of a G nucleotide at position −4 [G ins (−4)]. This variant has been associated with less coronary artery disease in its carriers than in non-carriers.

Substitution of a C for G at nucleotide −57 [G(−57)C]. This variant is in complete linkage disequilibrium with the variant at −4 in the individuals we have sequenced, and thus the phenotypic effects currently attributed to the variant at 4 may at least in part be due to changes at this site.

Substitution of A for G at nucleotide 730 (R219K). We have found carriers to have significantly less cardiovascular disease.

Substitution of C for T at nucleotide 1270 (V399A). Within the French Canadian population, this variant has only been found in individuals from the low HDL population. It has also been seen in individuals with low HDL or premature coronary artery disease in individuals of Dutch ancestry.

Substitution of A for G at nucleotide 2385 (V771M). This variant has been found at an increased frequency in a Dutch population selected for low HDL and at an increased frequency in a population selected for premature coronary artery disease compared to a control Dutch population, indicating carriers of this variant may have reduced HDL and an increased susceptibility to coronary artery disease.

Substitution of C for A at nucleotide 2394 (T774P). This variant has been seen at lower frequencies in populations with coronary artery disease or low HDL than in individuals without.

Substitution of C for G at nucleotide 2402 (K776N). This variant has been found at a significantly lower frequency (0.56% vs. 2.91%, p=0.02) in a coronary artery disease population vs. a control population of similar Dutch background.

Substitution of C for G at nucleotide 3590 (E1172D). This variant is seen at lower frequencies in individuals with low HDL and in some populations with premature coronary artery disease.

Substitution of A for G at nucleotide 4384 (R1587K). This variant has been found at decreased frequencies in the ⅓ of individuals with the highest HDL levels in our large Dutch coronary artery disease population (p=0.036), at increased frequencies in those with HDL cholesterol <0.9 mmol/L (p<0.0001) and at decreased frequencies in the cohorts with HDL cholesterol >1.4 mmol/L in both this population (p=0.02) and the Dutch control population (p=0.003).

Substitution of G for C at nucleotide 5266 (S1731C). Two FHA individuals who have this variant on the other allele have much lower HDL cholesterol (0.155±0.025) than the FHA individuals in the family who do not have this variant is on the other allele (0.64±0.14, p=0.0009). This variant has also been found in one general population French Canadian control with HDL at the 8th percentile (0.92) and one French Canadian individual from a population selected for low HDL and coronary disease (0.72).

Substitution of G for A at nucleotide −1113 [A(−1113)G]. This variant has been seen at varying frequencies in populations distinguished by their HDL levels.

Additional polymorphisms that may be associated with altered risk for cardiovascular disease or altered cholesterol levels are as follows:

Substitution of G for A at nucleotide 2723 (I883M). This variant has been seen at a much higher frequency in individuals of Dutch ancestry with premature coronary artery disease.

Insertion of 4 nucleotides (CCCT) at position −1181.

Substitution of C for A at nucleotide −479 (linkage disequilibrium with −518).

Substitution of G for A at nucleotide −380.

Other Embodiments

All publications mentioned in this specification are herein incorporated by reference to the same extent as if each independent publication was specifically and individually indicated to be incorporated by reference.

While the invention has been described in connection with specific embodiments thereof, it will be understood that it is capable of further modifications. This application is intended to cover any variations, uses, or adaptations following, in general, the principles of the invention and including such departures from the present disclosure within known or customary practice is within the art to which the invention pertains and may be applied to the essential features hereinbefore set forth.

---

What is claimed is:

1. An isolated polynucleotide comprising a nucleotide sequence, wherein said nucleotide sequence encodes a polypeptide comprising the amino acid sequence of SEQ ID NO: 1.

2. The isolated polynucleotide of claim 1 wherein said isolated polynucleotide comprises the nucleotide sequence of nucleotides 75-6858 of SEQ ID NO: 2.

3. The isolated polynucleotide of claim 1 wherein said isolated polynucleotide comprises the nucleotide sequence of nucleotides 75 to 254 of SEQ ID NO: 2.

4. The isolated polynucleotide of claim 1 wherein said isolated polynucleotide comprises the nucleotide sequence of nucleotides 255 to 6858 of SEQ ID NO: 2.

5. An isolated cell transformed with a vector comprising the isolated polynucleotide of claim 1.

6. A method of making an ATP Binding Cassette 1 (ABC1) polypeptide comprising the amino acid sequence of SEQ ID NO: 1, comprising expressing said polypeptide from the isolated cell of claim 5.

7. The isolated polynucleotide of claim 1 wherein said isolated polynucleotide is a cDNA.

8. An isolated polynucleotide comprising the complement of the isolated polynucleotide of claim 1.

9. An isolated cell transformed with a vector comprising the isolated polynucleotide of claim 8.

* * * * *